United States Patent
Takahashi et al.

(10) Patent No.: US 9,206,173 B2
(45) Date of Patent: Dec. 8, 2015

(54) HETEROCYCLIC COMPOUNDS FOR THE TREATMENT OF STRESS-RELATED CONDITIONS

(75) Inventors: Akira Takahashi, Osaka (JP); Masaki Suzuki, Osaka (JP); Yuichi Nakamura, Osaka (JP); Yohji Sakurai, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/322,399

(22) PCT Filed: May 27, 2010

(86) PCT No.: PCT/JP2010/059405
§ 371 (c)(1),
(2), (4) Date: Nov. 23, 2011

(87) PCT Pub. No.: WO2010/137738
PCT Pub. Date: Dec. 2, 2010

(65) Prior Publication Data
US 2012/0065189 A1 Mar. 15, 2012

(30) Foreign Application Priority Data
May 28, 2009 (JP) .................. 2009-129002

(51) Int. Cl.
*A01N 43/00* (2006.01)
*A61K 31/00* (2006.01)
*C07D 471/04* (2006.01)
*A61K 31/519* (2006.01)
*C07D 491/048* (2006.01)
*C07D 491/056* (2006.01)
*C07D 495/04* (2006.01)
*C07D 519/00* (2006.01)

(52) U.S. Cl.
CPC ............ *C07D 471/04* (2013.01); *A61K 31/519* (2013.01); *C07D 491/048* (2013.01); *C07D 491/056* (2013.01); *C07D 495/04* (2013.01); *C07D 519/00* (2013.01)

(58) Field of Classification Search
CPC ............... A61K 31/519; C07D 471/04; C07D 491/048; C07D 491/056; C07D 495/04; C07D 519/00
USPC ........... 514/211.05, 228.5, 230.5, 234.2, 249, 514/250, 252.16, 264.11; 540/490; 544/52, 544/61, 92, 117, 279
See application file for complete search history.

(56) References Cited

U.S. PATENT DOCUMENTS

| 6,383,764 | B1 | 5/2002 | Civelli et al. |
| 8,232,282 | B2 * | 7/2012 | Nakamura et al. ......... 514/264.1 |
| 2004/0216177 | A1 | 10/2004 | Jordan et al. |
| 2005/0059823 | A1 | 3/2005 | McNaughton-Smith et al. |
| 2007/0249631 | A1 | 10/2007 | Oberboersch et al. |
| 2009/0176811 | A1 | 7/2009 | Oberborsch et al. |

FOREIGN PATENT DOCUMENTS

| WO | WO 2004/014909 A1 | 2/2004 |
| WO | WO 2005/105759 A1 | 11/2005 |
| WO | WO 2006/100520 A1 | 9/2006 |

OTHER PUBLICATIONS

STN CAPLUS Accession No. 1991:408706, 1991.*
International Search Report from the European Patent Office in International Application No. PCT/JP2010/059405 mailed Aug. 31, 2010.
Hinuma et al.; "A Prolactin-Releasing Peptide in the Brain", Nature, vol. 393, pp. 272-276, (1998).
Hinuma et al.; "A Prolactin-Releasing Peptide in the Brain", Nature, vol. 394, pp. 302, (1998).
Ibata et al.; "Morphological Survey of Prolactin-Releasing Peptide and Its Receptor With Special Reference to Their Functional Roles in the Brain", Neuroscience Research, vol. 38, pp. 223-230, (2000).
Matsumoto et al.; "Stimulation of Corticotropin-Releasing Hormone-Mediated Adrenocorticotropin Secretion by Central Administration of Prolactin-Releasing Peptides in Rats", Neuroscience Letters, vol. 285, pp. 234-238, (2000).
Maruyama et al.; "Prolactin-Releasing Peptide As a Novel Stress Mediator in the Central Nervous System", Endocrinology, vol. 142, No. 5, pp. 2032-2038, (2001).
Watanabe et al.; "Altered Emotional Behaviors in the Diabetes Mellitus OLETF Type 1 Congenic Rat", Brain Research, vol. 1178, pp. 114-124, (2007).

* cited by examiner

*Primary Examiner* — Wu-Cheng Winston Shen
*Assistant Examiner* — Jean Cornet
(74) *Attorney, Agent, or Firm* — Finnegan, Henderson, Farabow, Garrett & Dunner, L.L.P.

(57) ABSTRACT

The present invention provides a novel heterocyclic compound. A heterocyclic compound represented by general formula (1) wherein, $R_1$ and $R_2$, each independently represent hydrogen; a phenyl lower alkyl group that may have a substituent(s) selected from the group consisting of a lower alkyl group and the like on a benzene ring and/or a lower alkyl group; or a cyclo C3-C8 alkyl lower alkyl group; or the like; $R_3$ represents a lower alkynyl group or the like; $R_4$ represents a phenyl group that may have a substituent(s) selected from the group consisting of a 1,3,4-oxadiazolyl group that may have e.g., halogen or a heterocyclic group selected from pyridyl group and the like; the heterocyclic group may have at least one substituent(s) selected from a lower alkoxy group and the like or a salt thereof.

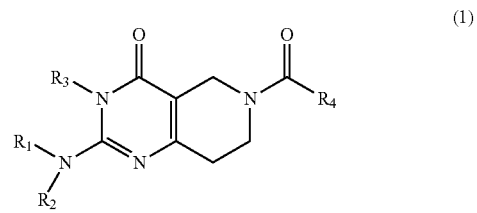

(1)

12 Claims, No Drawings

HETEROCYCLIC COMPOUNDS FOR THE TREATMENT OF STRESS-RELATED CONDITIONS

TECHNICAL FIELD

The present invention relates to a novel heterocyclic compound.

BACKGROUND ART

In the modern society, people are exposed to various physical or psychosocial stresses in living environments and complicated human relations. It is known that when such stress is build up to the extent that an individual person cannot cope with, the homeostatic function of the body and mind is destroyed and an extremely wide variety of diseases thus develop, including a neurotic disorder such as depression, panic disorder, post-traumatic stress disorder and anxiety disorder; an eating disorder such as bulimia and anorexia; gastric and duodenal ulcer, irritable bowel syndrome, hypertension, ischemic heart disease, hyperventilation (hyperventilation syndrome), asthma, urticaria, alopecia areata, frequent urination, ringing in the ears and dizziness.

The hypothalamus-pituitary gland-adrenal system (HPA-axis) or the sympathetic nerve-adrenal medulla system is activated by stress stimuli. Likewise, the neuroendocrine system responds to stress.

It has been elucidated that a biological reaction to stress is controlled by stress hormones represented by corticotropin releasing hormone (CRH), neurotransmitters such as noradrenaline, serotonin and dopamine, and other various neuropeptides. Of them, CRH is a main stress hormone mediating a stress response through the HPA-axis. Clinical studies have been conducted on a CRH receptor antagonist in expectation of a therapeutic effect on various stress-related diseases; however, a sufficient therapeutic effect has not yet been observed.

A prolactin-releasing peptide (PrRP) was identified as an endogenous ligand of orphan G-protein coupled receptor, GPR10 (Nature 393 (1998) 272-276). PrRP is expressed primarily in the hypothalamus of the brain, the medulla oblongata and the intestine, and PrRP-producing nerve cells are present in the solitary nucleus of the medulla oblongatas, the ventrolateral reticular formation of the medulla oblongata and the hypothalamus. A PrRP receptor, GPR10, is present in the area postrema, the amygdala, the paraventricular nucleus and the supraoptic nucleus of hypothalamus in large amounts. Based on the nerve function of the sites at which GPR10 is expressed, it is suggested that a receptor antagonist may be useful as a therapeutic agent for various disorders including stress-related disorders (U.S. Pat. No. 6,383,764 B1). The PrRP nerve cells of the medulla oblongata are A1 and A2 noradrenaline nerve cells and it is suggested that the CRH nerve cells and oxytocin nerve cells are activated by projecting the PrRP nerve cells in the paraventricular nucleus (Neuroscience Research 38 (2000) 223-230). When PrRP is administered into the cerebral ventricle, the CRH nerve cells of the paraventricular nucleus are activated (Neuroscience Letter 285 (2000) 234-238) and release of adrenocorticotropic hormone (ACTH) and oxytocin from the pituitary gland is accelerated. Furthermore, the PrRP nerve cells of the medulla oblongata and the hypothalamus are activated by stress stimuli (Endocrinology 142 (2001) 2032-2038). These suggest that PrRP is deeply involved in the stress response of the neuroendocrine system. On the other hand, in extensive wide-genome quantitative trait loci (QTL) analysis of the obesity, dyslipemia and diabetes model rat, namely, OLETF rat (Otsuka•Long-Evans•Tokushima fatty•rat), Dmo 1 was identified as one of the gene loci significantly related to pathologic phenotypes. As a result of detailed analysis, a GPR10 gene was found. It was found that a part of the GPR10 gene was mutated in the OLETF rat and the mutation was related to obesity and dyslipemia in the obese diabetic strain rat. In order to analyze the function of the GPR10 gene, a congenic BN (Brown-Norway) rat was prepared by introducing a mutant GPR10 domain, which is defective in PrRP signal transmission, to a normal BN rat background. The mutant GPR10 congenic rat did not exhibit obesity or dyslipemia as compared to the normal BN rat, while the mutant rat expressed a resistant phenotype to stress and anxiety. The anti-stress and anti-anxiety-like behaviors of the mutant GPR10 congenic rat support involvement of the GPR10 receptor in stress response, which is estimated from the aforementioned histochemical analysis, and also supports the possibility that a GPR10 antagonist serves as a therapeutic agent for depression, anxiety disorder or various types of stress-related disorders (US 2004216177 A1, Brain Research 1178 (2007) 114-124).

SUMMARY OF THE INVENTION

Problem to be Solved by the Invention

An object of the present invention is to provide a therapeutic agent for various types of stress-related disorders having a novel mechanism of action for suppressing an excessive stress response in a central nervous system, having few adverse drug reactions compared to known antidepressants and anxiolytic drugs, and being excellent in safety.

Means for Solving the Problems

The present inventors have repeatedly conducted intensive studies with a view toward solving the aforementioned problem. As a result, they succeeded in synthesizing a novel compound having a GPR10 receptor antagonist effect. The present invention was accomplished based on this finding.

The present invention provides a heterocyclic compound shown in the following Items or a salt thereof and a method for producing the same.

Item 1. A heterocyclic compound represented by general formula (1)

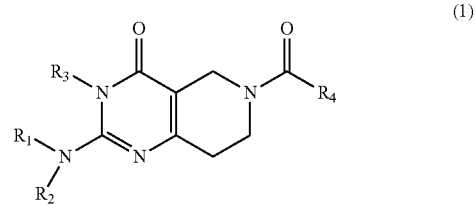

wherein, $R_1$ and $R_2$ each independently represent hydrogen; a phenyl lower alkyl group that may have a substituent(s) selected from the group consisting of a lower alkyl group, a lower alkoxy group, a halogen atom, a halogen-substituted lower alkyl group, a halogen-substituted lower alkoxy group, a cyclo C3-C8 alkyl group and a cyano group, on a benzene ring and/or a lower alkyl group; a cyclo C3-C8 alkyl lower alkyl group; a cyclo C3-C8 alkyl group that may have a halophenyl group(s); or $R_1$ and $R_2$ may form a pyrrolidine ring together with nitrogen adjacent to $R_1$ and $R_2$, and the pyrrolidine ring may have a substituent(s) selected from the group consisting of a halophenyl group and a phenyl group having a halogen-substituted lower alkyl group(s);

$R_3$ represents a lower alkynyl group; an amino group that may have a lower alkyl group(s); a lower alkoxy group; a piperazinyl group that may have a lower alkyl group(s); a phenyloxy group; a morpholinyl group or a pyrrolidinyl group;

$R_4$ represents any one of groups represented by the following (1) to (91):
(1) a phenyl group
(2) a naphthyl group
(3) a dihydroindenyl group
(4) a phenyl lower alkyl group
(5) a pyridyl group
(6) a pyridazinyl group
(7) a triazolyl group
(8) a pyrimidinyl group
(9) an imidazolyl group
(10) a dihydropyridyl group
(11) a quinolyl group
(12) an isoquinolyl group
(13) a tetrahydroquinolyl group
(14) a dihydroquinolyl group
(15) an imidazopyridyl group
(16) a pyrazolopyridyl group
(17) an indolinyl group
(18) a naphthyridinyl group
(19) a benzoimidazolyl group
(20) an indolizinyl group
(21) a thienyl group
(22) a benzothienyl group
(23) a benzodioxolyl group
(24) a benzofuryl group
(25) a thienopyridyl group
(26) a thienopyrrolyl group
(27) a dihydrobenzothiazinyl group
(28) an isoxazolyl group
(29) a tetrahydrobenzoxazepinyl group
(30) an indolyl group
(31) a benzothiazolyl group
(32) a dihydrothienodioxinyl group
(33) a pyrrolidinyl group
(34) a dihydrobenzoxazinyl group
(35) a tetrahydroquinazolinyl group
(36) a tetrahydroquinoxalinyl group
(37) a dihydrobenzodioxinyl group
(38) a chromanyl group
(39) a dihydropyridooxazinyl group
(40) a tetrahydronaphthyl group
(41) a dihydrobenzofuryl group
(42) a dihydrobenzoxazolyl group
(43) a tetrahydrobenzothienyl group
(44) a tetrahydrocyclopentapyrazolyl group
(45) a benzotriazolyl group
(46) a dihydrobenzoimidazolyl group
(47) a dihydrobenzothiazolyl group
(48) an isoindolinyl group
(49) a tetrahydrobenzodiazepinyl group
(50) a dihydrobenzodioxepinyl group
(51) a quinoxalinyl group
(52) an indazolyl group
(53) a cinnolinyl group
(54) a dihydrophthalazinyl group
(55) a dihydronaphthyridinyl group
(56) a hexahydroquinolinyl group
(57) a furopyrrolyl group
(58) a thienopyrazinyl group
(59) an imidazothiazolyl group
(60) a xanthenyl group
(61) a piperidinyl group
(62) a pyrrolyl group
(63) a pyrazolyl group
(64) a thiazolyl group
(65) a furyl group
(66) a pyrazinyl group
(67) a dihydropyrazolyl group
(68) a thiazolidinyl group
(69) a tetrahydrofuranyl group
(70) a tetrahydropyranyl group
(71) a thiadiazolyl group
(72) a dihydropyridazinyl group
(73) a thienyl lower alkyl group
(74) a cyclo C3-C8 alkyl group
(75) a lower alkyl group
(76) a benzodioxolyloxy group
(77) a phenylthio lower alkyl group
(78) a phenylcyclo C3-C8 alkyl group
(79) a phenoxy lower alkyl group
(80) a phenyl lower alkenyl group
(81) a cyclo C3-C8 alkyl lower alkenyl group
(82) a pyridyl lower alkyl group
(83) a benzofuryl lower alkenyl group
(84) a dihydrobenzofuryl lower alkenyl group
(85) a dihydrobenzodioxinyl lower alkenyl group
(86) a dihydrobenzodioxinyloxy lower alkyl group
(87) an oxazolyl group
(88) a dihydroindenyloxy lower alkyl group
(89) a dihydropyrimidinyl group
(90) a pyridyloxy lower alkyl group
(91) a lower alkoxy lower alkyl group;
wherein on the lower alkyl group, cycloalkyl ring, aromatic ring or heterocyclic ring, one or more substituent(s) selected from the following (1-1) to (1-46) may be present:
(1-1) a halogen atom
(1-2) a lower alkyl group
(1-3) a lower alkanoyl group
(1-4) a halogen-substituted lower alkyl group
(1-5) a halogen-substituted lower alkoxy group
(1-6) a cyano group
(1-7) a lower alkoxy group
(1-8) a lower alkylthio group
(1-9) an imidazolyl group that may have a lower alkyl group(s)
(1-10) an oxazolyl group
(1-11) an oxadiazolyl group that may have a lower alkyl group(s)
(1-12) a triazolyl group
(1-13) a benzoyl group
(1-14) a pyridyl group
(1-15) an oxo group
(1-16) a phenyl group that may have a substituent(s) selected from the group consisting of a lower alkyl group, a halogen-substituted lower alkoxy group, a halogen-substituted lower alkyl group and a halogen atom
(1-17) a thienyl group
(1-18) a furyl group
(1-19) a thiazolyl group
(1-20) a triazolyl lower alkyl group
(1-21) a cyclo C3-C8 alkyloxy group
(1-22) a phenyl lower alkyl group
(1-23) a phenoxy group
(1-24) a cyclo C3-C8 alkyl group (1-25) a pyrazolyl group
(1-26) a pyrrolyl group
(1-27) a lower alkenyl group
(1-28) a pyrrolidinyl group that may have an oxo group(s)
(1-29) a dihydropyrazolyl group that may have a substituent(s) selected from the group consisting of an oxo group and a lower alkyl group
(1-30) a hydroxy group
(1-31) a tetrazolyl group
(1-32) a morpholinyl group
(1-33) a pyrimidinyl group
(1-34) a homo-piperazinyl group that may have a lower alkyl group(s)
(1-35) a lower alkanoylamino group
(1-36) a cyclo C3-C8 alkylcarbonylamino group
(1-37) a phenoxy lower alkyl group
(1-38) a thiomorpholino group
(1-39) a piperidinyl group
(1-40) a lower alkoxy lower alkyl group
(1-41) an amino group that may have a substituent(s) selected from the group consisting of a lower alkyl group, a lower alkanoyl group and a cyclo C3-C8 alkyl group
(1-42) a morpholinyl lower alkyl group
(1-43) a piperidinyl lower alkyl group
(1-44) a lower alkylsulfonyl group
(1-45) an adamantyl lower alkyl group
(1-46) a carbamoyl group that may have a lower alkyl group(s)
or a salt thereof.

Item 2. The heterocyclic compound according to (1) represented by general formula (1), wherein, $R_1$ and $R_2$ each independently represent hydrogen; a phenyl lower alkyl group that may have 1 to 3 substituent(s) selected from the group consisting of a lower alkyl group, a lower alkoxy group, a halogen atom, a halogen-substituted lower alkyl group, a halogen-substituted lower alkoxy group, a cyclo C3-C8 alkyl group and a cyano group, on a benzene ring and/or a lower alkyl group; a cyclo C3-C8 alkyl lower alkyl group; a cyclo C3-C8 alkyl group that may have a single halophenyl group; or $R_1$ and $R_2$ may form a pyrrolidine ring together with nitrogen adjacent to $R_1$ and $R_2$, and the pyrrolidine ring may have a single substituent selected from the group consisting of a halophenyl group and a phenyl group having a single halogen-substituted lower alkyl group;

$R_3$ represents a lower alkynyl group; an amino group that may have 1 to 2 lower alkyl group(s); a lower alkoxy group; a piperazinyl group that may have a single lower alkyl group; a phenyloxy group; a morpholinyl group or a pyrrolidinyl group;

$R_4$ represents any one of groups represented by the following (1) to (91):
(1) a phenyl group
(2) a naphthyl group
(3) a dihydroindenyl group
(4) a phenyl lower alkyl group
(5) a pyridyl group
(6) a pyridazinyl group
(7) a triazolyl group
(8) a pyrimidinyl group
(9) an imidazolyl group
(10) a dihydropyridyl group
(11) a quinolyl group
(12) an isoquinolyl group
(13) a tetrahydroquinolyl group
(14) a dihydroquinolyl group
(15) an imidazopyridyl group
(16) a pyrazolopyridyl group
(17) an indolinyl group
(18) a naphthyridinyl group
(19) a benzoimidazolyl group
(20) an indolizinyl group
(21) a thienyl group
(22) a benzothienyl group
(23) a benzodioxolyl group
(24) a benzofuryl group
(25) a thienopyridyl group
(26) a thienopyrrolyl group
(27) a dihydrobenzothiazinyl group
(28) an isoxazolyl group
(29) a tetrahydrobenzoxazepinyl group
(30) an indolyl group
(31) a benzothiazolyl group
(32) a dihydrothienodioxinyl group
(33) a pyrrolidinyl group
(34) a dihydrobenzoxazinyl group
(35) a tetrahydroquinazolinyl group
(36) a tetrahydroquinoxalinyl group
(37) a dihydrobenzodioxinyl group
(38) a chromanyl group
(39) a dihydropyridooxazinyl group
(40) a tetrahydronaphthyl group
(41) a dihydrobenzofuryl group
(42) a dihydrobenzoxazolyl group
(43) a tetrahydrobenzothienyl group
(44) a tetrahydrocyclopentapyrazolyl group
(45) a benzotriazolyl group
(46) a dihydrobenzoimidazolyl group
(47) a dihydrobenzothiazolyl group
(48) an isoindolinyl group
(49) a tetrahydrobenzodiazepinyl group
(50) a dihydrobenzodioxepinyl group
(51) a quinoxalinyl group
(52) an indazolyl group
(53) a cinnolinyl group
(54) a dihydrophthalazinyl group
(55) a dihydronaphthyridinyl group
(56) a hexahydroquinolinyl group
(57) a furopyrrolyl group
(58) a thienopyrazinyl group
(59) an imidazothiazolyl group
(60) a xanthenyl group
(61) a piperidinyl group
(62) a pyrrolyl group
(63) a pyrazolyl group
(64) a thiazolyl group
(65) a furyl group
(66) a pyrazinyl group
(67) a dihydropyrazolyl group
(68) a thiazolidinyl group
(69) a tetrahydrofuranyl group
(70) a tetrahydropyranyl group
(71) a thiadiazolyl group
(72) a dihydropyridazinyl group
(73) a thienyl lower alkyl group
(74) a cyclo C3-C8 alkyl group
(75) a lower alkyl group
(76) a benzodioxolyloxy group
(77) a phenylthio lower alkyl group
(78) a phenylcyclo C3-C8 alkyl group
(79) a phenoxy lower alkyl group
(80) a phenyl lower alkenyl group
(81) a cyclo C3-C8 alkyl lower alkenyl group
(82) a pyridyl lower alkyl group
(83) a benzofuryl lower alkenyl group

(84) a dihydrobenzofuryl lower alkenyl group
(85) a dihydrobenzodioxinyl lower alkenyl group
(86) a dihydrobenzodioxinyloxy lower alkyl group
(87) an oxazolyl group
(88) a dihydroindenyloxy lower alkyl group
(89) a dihydropyrimidinyl group
(90) a pyridyloxy lower alkyl group
(91) a lower alkoxy lower alkyl group;

wherein, on the lower alkyl group, cycloalkyl ring, aromatic ring or heterocyclic ring, 1 to 4 substituent(s) selected from the following (1-1) to (1-46) may be present:
(1-1) a halogen atom
(1-2) a lower alkyl group
(1-3) a lower alkanoyl group
(1-4) a halogen-substituted lower alkyl group
(1-5) a halogen-substituted lower alkoxy group
(1-6) a cyano group
(1-7) a lower alkoxy group
(1-8) a lower alkylthio group
(1-9) an imidazolyl group that may have a single lower alkyl group
(1-10) an oxazolyl group
(1-11) an oxadiazolyl group that may have a single lower alkyl group
(1-12) a triazolyl group
(1-13) a benzoyl group
(1-14) a pyridyl group
(1-15) an oxo group
(1-16) a phenyl group that may have a single substituent selected from the group consisting of a lower alkyl group, a halogen-substituted lower alkoxy group, a halogen-substituted lower alkyl group and a halogen atom
(1-17) a thienyl group
(1-18) a furyl group
(1-19) a thiazolyl group
(1-20) a triazolyl lower alkyl group
(1-21) a cyclo C3-C8 alkyloxy group
(1-22) a phenyl lower alkyl group
(1-23) a phenoxy group
(1-24) a cyclo C3-C8 alkyl group
(1-25) a pyrazolyl group that may have a single lower alkyl group
(1-26) a pyrrolyl group
(1-27) a lower alkenyl group
(1-28) a pyrrolidinyl group that may have a single oxo group
(1-29) a dihydropyrazolyl group that may have 1 to 2 substituent(s) selected from the group consisting of an oxo group and a lower alkyl group
(1-30) a hydroxy group
(1-31) a tetrazolyl group
(1-32) a morpholinyl group
(1-33) a pyrimidinyl group
(1-34) a homo-piperazinyl group that may have a single lower alkyl group
(1-35) a lower alkanoylamino group
(1-36) a cyclo C3-C8 alkylcarbonylamino group
(1-37) a phenoxy lower alkyl group
(1-38) a thiomorpholino group
(1-39) a piperidinyl group
(1-40) a lower alkoxy lower alkyl group
(1-41) an amino group that may have 1 to 2 substituent(s) selected from the group consisting of a lower alkyl group, a lower alkanoyl group and a cyclo C3-C8 alkyl group
(1-42) a morpholinyl lower alkyl group
(1-43) a piperidinyl lower alkyl group
(1-44) a lower alkylsulfonyl group
(1-45) an adamantyl lower alkyl group
(1-46) a carbamoyl group that may have 1 to 2 lower alkyl group(s)
or a salt thereof.

Item 3. The heterocyclic compound according to (2) represented by general formula (1), wherein, $R_1$ and $R_2$ each independently represent hydrogen; a phenyl lower alkyl group that may have 1 to 2 substituent(s) selected from the group consisting of a lower alkoxy group, a halogen atom and a halogen-substituted lower alkyl group on a benzene ring and/or a lower alkyl group; a cyclo C3-C8 alkyl lower alkyl group; a cyclo C3-C8 alkyl group that may have a single monohalophenyl group; or $R_1$ and $R_2$ may form a pyrrolidine ring together with nitrogen adjacent to $R_1$ and $R_2$, and the pyrrolidine ring may have a single substituent selected from the group consisting of a halophenyl group and a phenyl group having a single halogen-substituted lower alkyl group;

$R_3$ represents a lower alkynyl group; an amino group that may have 1 to 2 lower alkyl group(s); a lower alkoxy group; a morpholinyl group or a pyrrolidinyl group;

$R_4$ represents any one of groups represented by the following (1) to (90):
(1) a phenyl group
(4) a phenyl lower alkyl group
(5) a pyridyl group
(11) a quinolyl group
(12) a isoquinolyl group
(13) a tetrahydroquinolyl group
(16) a pyrazolopyridyl group
(19) a benzoimidazolyl group
(21) a thienyl group
(22) a benzothienyl group
(23) a benzodioxolyl group
(24) a benzofuryl group
(25) a thienopyridyl group
(30) an indolyl group
(37) a dihydrobenzodioxinyl group
(40) a tetrahydronaphthyl group
(57) a furopyrrolyl group
(63) a pyrazolyl group
(65) a furyl group
(77) a phenylthio lower alkyl group
(79) a phenoxy lower alkyl group
(80) a phenyl lower alkenyl group
(88) a dihydroindenyloxy lower alkyl group
(90) a pyridyloxy lower alkyl group;

wherein, on the lower alkyl group, cycloalkyl ring, aromatic ring or heterocyclic ring, 1 to 3 substituent(s) selected from the following (1-1) to (1-46) may be present:
(1-1) a halogen atom
(1-2) a lower alkyl group
(1-5) a halogen-substituted lower alkoxy group
(1-6) a cyano group
(1-7) a lower alkoxy group
(1-9) an imidazolyl group that may have a single lower alkyl group
(1-10) an oxazolyl group
(1-15) an oxo group
(1-17) a thienyl group
(1-27) a lower alkenyl group
(1-46) a carbamoyl group that may have 1 to 2 lower alkyl group(s)
or a salt thereof.

Item 4. The heterocyclic compound according to (3) represented by general formula (1), wherein, $R_4$ represents any one of groups (1) to (90) below:
(1) a phenyl group that may have 1 to 3 substituent(s) selected from the group consisting of a halogen atom, a lower alkyl group, a halogen-substituted lower alkoxy group, a cyano group, a lower alkoxy group, a lower alkenyl group, an oxazolyl group, a carbamoyl group that may have 1 to 2 lower alkyl group(s) and an imidazolyl group
(4) a phenyl lower alkyl group that may have a single halogen atom
(5) a pyridyl group that may have 1 to 2 substituent(s) selected from the group consisting of a cyano group and a lower alkoxy group
(11) a quinolyl group that may have a single halogen atom
(13) a tetrahydroquinolyl group that may have 1 to 2 substituent(s) selected from the group consisting of a lower alkyl group and an oxo group.
(16) a pyrazolopyridyl group
(19) a benzimidazolyl group that may have 1 to 2 substituent(s) selected from the group consisting of a halogen atom and a lower alkyl group
(21) a thienyl group that may have a single substituent selected from the group consisting of a lower alkyl group, a lower alkoxy group and a halogen atom
(22) a benzothienyl group
(23) a benzodioxolyl group
(24) a benzofuryl group that may have a single substituent selected from the group consisting of a halogen atom and a lower alkoxy group
(25) a thienopyridyl group
(30) an indolyl group that may have 1 to 2 substituent(s) selected from the group consisting of a halogen atom and a lower alkyl group
(37) a dihydrobenzodioxinyl group
(40) a tetrahydronaphthyl group
(57) a furopyrrolyl group that may have a single lower alkyl group
(63) a pyrazolyl group that may have 1 to 2 substituent(s) selected from the group consisting of a thienyl group and a lower alkyl group
(65) a furyl group that may have a single halogen atom
(77) a phenylthio lower alkyl group that may have a single halogen atom
(79) a phenoxy-lower alkyl group that may have 1 to 2 substituent(s) selected from the group consisting of a halogen atom and a cyano group
(80) a phenyl lower alkenyl group that may have a single halogen atom
(88) a dihydroindenyloxy lower alkyl group
(90) a pyridyloxy lower alkyl group
or a salt thereof.

Item 5. Use of the heterocyclic compound according to any one of (1) to (4) represented by general formula (1) or a salt thereof as a pharmaceutical agent.

Item 6. Use of the heterocyclic compound according to any one of (1) to (4) or a salt thereof for the manufacture of a medicament for preventing or treating stress-related diseases.

Item 7. Use of the heterocyclic compound according to any one of (1) to (4) represented by general formula (1) or a salt thereof as a GPR10 antagonist.

Item 8. A method of treating or preventing stress-related diseases, comprising administering to a human or animal the heterocyclic compound according to any one of (1) to (4) represented by general formula (1) or a salt thereof.

Item 9. A pharmaceutical composition comprising the heterocyclic compound according to any one of (1) to (4) or a salt thereof as an active ingredient and a pharmaceutically acceptable carrier.

Item 10. The pharmaceutical composition according to (9) for preventing or treating stress-related diseases.

Item 11. The pharmaceutical composition according to (10) for preventing or treating stress-related diseases selected from the group consisting of respiratory system disorders, gastrointestinal disorders, cardiovascular system disorders, endocrine and metabolic disorders, nervous system disorders, eating disorders, done and muscle disorders, dermatopathy, urinary system disorders, otorhinolaryngological disorders, oral cavity disorders, ophthalmic disorders and gynecologic disorders.

Item 12. The pharmaceutical composition according to (11) for treating or preventing eating disorders.

Item 13. A method of producing a pharmaceutical composition, comprising blending the heterocyclic compound according to any one of (1) to (4) represented by general formula (1) or a salt thereof and a pharmaceutically acceptable carrier.

Item 14. The heterocyclic compound according to any one of (1) to (4) or a salt thereof for preventing or treating stress-related diseases.

Item 15. A method of producing a heterocyclic compound represented by general formula (1)

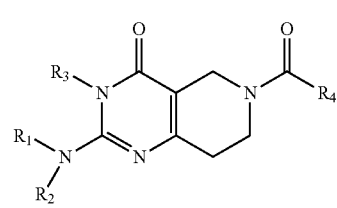

wherein $R_1$, $R_2$, $R_3$ and $R_4$ are the same as those in formula (1) of claim 1 or a salt thereof, comprising reacting a compound (2) or a reactive derivative thereof represented by general formula (2)

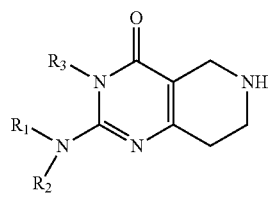

wherein $R_1$, $R_2$ and $R_3$ are the same as those in formula (1) of claim 1, or a salt thereof with a compound (3) or a reactive derivative thereof represented by general formula (3)

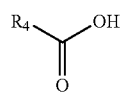

wherein $R_4$ is the same as that in formula (1) of claim 1, or a salt thereof.

Specific examples of individual groups shown in the general formula are as follows. The term "lower" is intended to mean a group having 1 to 6 (preferably 1 to 4, more preferably 1 to 3) carbon atom(s), unless otherwise provided.

Examples of the lower alkyl group include, unless otherwise specified, a straight or branched alkyl groups having 1 to 6 carbon atoms (preferably, 1 to 4 carbon atoms), and more specifically, include methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl and 3-methylpentyl groups, etc.

Examples of the lower alkoxy group include, unless otherwise specified, straight or branched alkoxy groups having 1 to 6 carbon atoms (preferably, 1 to 4 carbon atoms), and more specifically, include methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy and 3-methylpentyloxy groups, etc.

Examples of the halogen atom include, unless otherwise specified, a fluorine atom, a chlorine atom, a bromine atom and an iodine atom.

Examples of the halogen-substituted lower alkyl group include, unless otherwise specified, the lower alkyl groups exemplified above that are substituted with 1 to 7, more preferably, 1 to 3 halogen atoms, and more specifically, include fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl and perfluorohexyl groups, etc.

Examples of the cyclo C3-C8 alkyl group may include, unless otherwise specified, such as cyclopropyl, cyclobutyl, cyclopentyl, cyclohexyl, cycloheptyl and cyclooctyl groups, etc.

Examples of the phenyl lower alkyl group include, unless otherwise specified, the lower alkyl groups exemplified above (straight or branched alkyl groups having preferably 1 to 6 carbon atoms (more preferably, 1 to 4 carbon atoms)) having 1 to 3 phenyl groups, preferably a single phenyl group; and more specifically, include benzyl, phenethyl, 3-phenylpropyl, benzhydryl, trityl, 4-phenylbutyl, 5-phenylpentyl and 6-phenylhexyl groups, etc.

Examples of the lower alkynyl group may include, unless otherwise specified, straight or branched alkynyl groups having 2 to 6 carbon atoms (preferably, 2 to 4 carbon atoms), and more specifically, include ethynyl, 2-propynyl, 2-butynyl, 3-butynyl, 1-methyl-2-propynyl, 2-pentynyl, 2-hexynyl, and 3,3-dimethyl-1-butynyl groups, etc.

Examples of the lower alkanoyl group may include, unless otherwise specified, straight or branched alkanoyl groups having 1 to 6 carbon atoms (preferably, 1 to 4 carbon atoms), and more specifically, include formyl, acetyl, propionyl, butyryl, isobutyryl, pentanoyl, tert-butyl carbonyl and hexanoyl groups, etc.

Examples of the halogen-substituted lower alkoxy group may include, unless otherwise specified, the lower alkoxy groups exemplified above and substituted with 1 to 7, preferably, 1 to 3 halogen atoms, and more specifically, include fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentoxy, 5-chloropentoxy, 6,6,6-trifluorohexyloxy and 6-chlorohexyloxy groups, etc.

Examples of the halophenyl group may include, unless otherwise specified, a phenyl group substituted with 1 to 5 halogen atoms, preferably 1 to 3 halogen atoms, and further preferably, a single halogen atom.

Examples of the lower alkylthio group may include, unless otherwise specified, thio groups substituted with straight or branched alkyl having 1 to 6 carbon atoms (preferably, 1 to 4 carbon atoms), and more specifically, include, methylthio, ethylthio, n-propylthio, isopropylthio, n-butylthio, isobutylthio, tert-butylthio, sec-butylthio, n-pentylthio, 1-ethylpropylthio, isopentylthio, neopentylthio, n-hexylthio, 1,2,2-trimethylpropylthio, 3,3-dimethylbutylthio, 2-ethylbutylthio, isohexylthio and 3-methylpentylthio groups.

Examples of the lower alkenyl group may include, unless otherwise specified, a straight or branched alkenyl group having 2 to 6 carbon atoms (preferably, 2 to 4 carbon atoms) and having 1 to 3 double bonds, which includes both trans-form and cis-form; and more specifically include, vinyl, 1-propenyl, 2-propenyl, 1-methyl-1-propenyl, 2-methyl-1-propenyl, 2-methyl-2-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-yl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl and 1,4-hexadienyl groups, etc.

Examples of the dihydroindenyl group may include a (1-, 2-, 4-, or 5-)-1,2-dihydroindenyl group, etc.

Examples of the triazolyl group may include 1,2,4-triazolyl, 1,3,5-triazolyl and 1,2,3-triazolyl groups, etc.

Examples of the imidazolyl group may include a (1-, 2-, 4-, or 5-)imidazolyl group, etc.

Examples of the dihydropyridyl group may include 1,2-dihydropyridyl, 1,4-dihydropyridyl, 3,4-dihydropyridyl, 5,6-dihydropyridyl and 3,6-dihydropyridyl groups, etc.

Examples of the quinolyl group may include 2-quinolyl, 3-quinolyl, 4-quinolyl, 5-quinolyl, 6-quinolyl, 7-quinolyl and 8-quinolyl groups, etc.

Examples of the isoquinolyl group may include 1-isoquinolyl, 3-isoquinolyl, 4-isoquinolyl, 5-isoquinolyl, 6-isoquinolyl, 7-isoquinolyl and 8-isoquinolyl groups, etc.

Examples of the tetrahydroquinolyl group may include a (1-, 2-, 4-, 5-, 6-, or 8-)(1,2,3,4-tetrahydroquinolyl group, etc.

Examples of the dihydroquinolyl group may include 1,2-dihydroquinolyl, 3,4-dihydroquinolyl, 1,4-dihydroquinolyl, 4a,8a-dihydroquinolyl, 5,6-dihydroquinolyl, 7,8-dihydroquinolyl and 5,8-dihydroquinolyl groups, etc.

Examples of the imidazopyridyl group may include imidazo[1,2-a]pyridyl and imidazo[1,5a]pyridyl groups, etc.

Examples of the pyrazolopyridyl group may include a pyrazolo[1,5a]pyridyl group.

Examples of the indolinyl group may include a (1-, 2-, 3-, 4-, 5-, 6- or 7-)indolinyl group.

Examples of the naphthyridinyl group may include 1,8-naphthyridinyl, 1,7-naphthyridinyl, 1,6-naphthyridinyl, 1,5-naphthyridinyl, 2,7-naphthyridinyl, 2,6-naphthyridinyl and 2,5-naphthyridinyl groups.

Examples of the benzoimidazolyl group may include 1H-benzo[d]imidazolyl, 2H-benzo[d]imidazolyl and 3aH-benzo[d]imidazolyl groups.

Examples of the benzothienyl group may include benzo[b]thienyl and benzo[c]thienyl groups.

Examples of the benzodioxolyl group may include benzo[d][1,3]dioxolyl and 3H-benzo[c][1,2]dioxolyl groups.

Examples of the benzofuryl group may include a (2-, 3-, 4-, 5-, 6- or 7-)benzofuryl group.

Examples of the thienopyridyl group may include thieno[2,3-b]pyridyl, thieno[2,3-c]pyridyl, thieno[3,2-b]pyridyl, thieno[3,4-b]pyridyl and thieno[3,4-c]pyridyl groups, etc.

Examples of the thienopyrrolyl group may include 4H-thieno[3,2-b]pyrrolyl, 6H-thieno[2,3-b]pyrrolyl, 4H-thieno[2,3-b]pyrrolyl, 4H-thieno[2,3-c]pyrrolyl, 6aH-thieno[2,3-b]pyrrolyl, 3H-thieno[3,4-b]pyrrolyl, 4H-thieno[3,4-c]pyrrolyl and 1H-thieno[3,4-b]pyrrolyl groups, etc.

Examples of the dihydrobenzothiazinyl group may include 3,4-dihydro-2H-benzo[b][1,4]thiazinyl, 3,4-dihydro-2H-benzo[e][1,2]thiazinyl, 3,4-dihydro-2H-benzo[e][1,3]thiazinyl, 3,4-dihydro-1H-benzo[d][1,2]thiazinyl, 2,4-dihydro-1H-benzo[d][1,3]thiazinyl and 3,4-dihydro-1H-benzo[c][1,2]thiazinyl groups, etc.

Examples of the isoxazolyl group may include a (3-, 4-, or 5-)isoxazolyl group.

Examples of the tetrahydrobenzoxazepinyl group may include 1,2,3,5-tetrahydrobenzo[e][1,4]oxazepinyl, 1,3,4,5-tetrahydrobenzo[c][1,2]oxazepinyl and 1,2,4,5-tetrahydrobenzo[d][1,3]oxazepinyl, etc.

Examples of the indolyl group may include a 1H-indolyl and 3H-indolyl groups.

Examples of the benzothiazolyl group may include a benzo[d]thiazolyl group.

Examples of the dihydrothienodioxinyl group may include 2,3-dihydrothieno[3,4-b][1,4]dioxinyl, 3,4-dihydrothieno[3,4-c][1,2]dioxinyl, 2,3-dihydrothieno[3,4-b][1,4]dioxinyl, 2,3-dihydrothieno[3,2-b][1,4]dioxinyl, 3,4-dihydrothieno[3,2-c][1,2]dioxinyl and 3,4-dihydrothieno[2,3-c][1,2]dioxinyl groups, etc.

Examples of the pyrrolidinyl group may include a (1-, 2- or 3-)pyrrolidinyl group.

Examples of the dihydrobenzoxazinyl group may include (2-, 3-, 4-, 5-, 6-, 7-, or 8-)3,4-dihydro-2H-benzo[b][1.4]oxazinyl and (1-, 2-, 4-, 5-, 6-, 7-, or 8-)2,4-dihydro-1H-benzo[d][1.3]oxazinyl groups, etc.

Examples of the tetrahydroquinazolinyl group may include (1-, 2-, 3-, 4-, 5-, 6-, 7-, or 8-)1,2,3,4-tetrahydroquinazolinyl and (1-, 2-, 3-, 4-, 5-, 6-, 7-, or 8-)5,6,7,8-tetrahydroquinazolinyl groups, etc.

Examples of the tetrahydroquinoxalinyl group may include (1-, 2-, 5-, or 6-)1,2,3,4-tetrahydroquinoxalinyl and (1-, 2-, 5-, or 6-)5,6,7,8-tetrahydroquinoxalinyl groups, etc.

Examples of the dihydrobenzodioxinyl group may include 2,3-dihydrobenzo[b][1,4]dioxinyl and 3,4-dihydrobenzo[c][1,2]dioxinyl groups, etc.

Examples of the dihydropyridodioxinyl group may include 3,4-dihydro-2H-pyrido[3,2-b][1,4]oxazinyl, 3,4-dihydro-1H-pyrido[2,3-c][1,2]oxazinyl, 6,8-dihydro-5H-pyrido[3,2-d][1,4]oxazinyl, 7,8-dihydro-5H-pyrido[2,3-b][1,2]oxazinyl and 3,4-dihydro-2H-pyrido[2,3-e][1,3]oxazinyl groups, etc.

Examples of the tetrahydronaphthyl group may include a (1- or 2-)1,2,3,4-tetrahydronaphthyl group, etc.

Examples of the dihydrobenzofuryl group may include a 2,3-dihydro-(2-, 3-, 4-, 5-, 6-, or 7-)benzofuryl group, etc.

Examples of the dihydrobenzoxazolyl group may include a (2-, 3-, 4-, 5-, 6-, or 7-)2,3-dihydrobenzoxazolyl group, etc.

Examples of the tetrabenzothienyl group may include 4,5,6,7-tetrabenzo[c]thienyl and 4,5,6,7-tetrabenzo[b]thienyl groups, etc.

Examples of the tetrahydrocyclopentapyrazolyl group may include 1,4,5,6-tetrahydrocyclopenta[c]pyrazolyl and 2,4,5,6-tetrahydrocyclopenta[c]pyrazolyl groups.

Examples of the benzotriazolyl group may include a 1H-benzo[d][1,2,3]triazolyl group.

Examples of the dihydrobenzoimidazolyl group may include a (1-, 2-, 4-, or 5-)2,3-dihydro-1H-benzoimidazolyl group, etc.

Examples of the dihydrobenzothiazolyl group may include a (2-, 3-, 4-, 5-, 6-, or 7-)2,3-dihydrobenzothiazolyl group, etc.

Examples of the tetrahydrobenzodiazepinyl group may include (1-, 2-, 3-, 4-, 5-, 6-, 7-, 8-, or 9-)2,3,4,5-tetrahydro-1H-benzo[b][1.4]diazepinyl and (1-, 2-, 3-, 4-, 5-, 6-, 7-, 8-, or 9-)2,3,4,5-tetrahydro-1H-benzo[e][1.4]diazepinyl groups, etc.

Examples of the dihydrobenzodioxepinyl may include 3,4-dihydro-2H-1,5-benzodioxepinyl, 4,5-dihydro-3H-1,2-benzodioxepinyl and 3,5-dihydro-2H-1,4-benzodioxepinyl groups, etc.

Examples of the indazolyl group may include a (1-, 3-, 4-, 5-, 6-, or 7-)indazolyl group, etc.

Examples of the dihydrophthalazinyl group may include 1,2-dihydrophthalazinyl, 1,4-dihydrophthalazinyl and 3,4-dihydrophthalazinyl groups, etc.

Examples of the dihydronaphthylidyl group may include 7,8-dihydro-1,8-naphthyridinyl, 5,6-dihydro-1,8-naphthyridinyl, 5,8-dihydro-1,8-naphthyridinyl, 1,4-dihydro-1,7-naphthyridinyl, 3,4-dihydro-1,7-naphthyridinyl, 1,2-dihydro-1,7-naphthyridinyl, 5,6-dihydro-1,5-naphthyridinyl, 5,8-dihydro-1,5-naphthyridinyl, and 7,8-dihydro-1,5-naphthyridinyl groups, etc.

Examples of the hexahydroquinolinyl group may include a 1,2,5,6,7,8-hexahydroquinolinyl group, a 1,4,5,6,7,8-hexahydroquinolinyl group, a 1,5,6,7,8,8a-hexahydroquinolinyl group, a 1,4,6,7,8,8a-hexahydroquinolinyl group, a 1,4,4a,7,8,8a-hexahydroquinolinyl group, a 1,4,4a,5,8,8a-hexahydroquinolinyl group, a 1,4,4a,5,6,8a-hexahydroquinolinyl group and a 1,4,4a,5,6,7-hexahydroquinolinyl group, etc.

Examples of the furopyrrolyl group may include a 4H-furo[3,2-b]pyrrolyl group, a 5H-furo[2,3-c]pyrrolyl group and a 6H-furo[2,3-b]pyrrolyl group, etc.

Examples of the thienopyrazinyl group may include a thieno[3,2-b]pyrazinyl group, a thieno[3,4-b]pyrazinyl group and a thieno[2,3-b]pyrazinyl group, etc.

Examples of the imidazothiazolyl group may include a (2-, 3-, 5-, or 6-)imidazo[2,1-b]thiazolyl group, etc.

Examples of the xanthenyl group may include a (1-, 2-, 3- or 4-)9H-xanthenyl group, etc.

Examples of the piperidinyl group may include a (1-, 2-, 3- or 4-)piperidinyl group.

Examples of the pyrrolyl group may include a (1-, 2- or 3-)pyrrolyl group.

Examples of the pyrazolyl group may include a 1H-pyrazolyl group, a 3H-pyrazolyl group and a 4H-pyrazolyl group.

Examples of the thiazolyl group may include a (2-, 4-, or 5-)thiazolyl group.

Examples of the furyl group may include a (2- or 3-)furyl group.

Examples of the pyrazinyl group may include a 2-pyrazinyl group.

Examples of the dihydropyrazolyl group may include a 2,3-dihydropyrazolyl group or a 4,5-dihydro pyrazolyl group.

Examples of the thiazolidinyl group may include a (2-, 3-, 4-, or 5-)thiazolidinyl group.

Examples of the tetrahydrofuranyl group may include 2-tetrahydrofuranyl and 3-tetrahydrofuranyl groups.

Examples of the tetrahydropyranyl group may include a tetrahydro-2H-pyranyl group.

Examples of the thiadiazolyl group may include 1,2,3-thiadiazolyl, 1,2,4-thiadiazolyl, 1,2,5-thiadiazolyl or 1,3,4-thiadiazolyl group.

Examples of the dihydropyridazinyl group may include 1,6-dihydropyridazinyl, 1,4-dihydropyridazinyl or 4,5-dihydropyridazinyl group.

Examples of the thienyl lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 thienyl groups (preferably a single thienyl group); and more specifically include (2- or 3-)thienylmethyl, 2-[(2- or 3-)thienyl]ethyl, 1-[(2- or 3-)thienyl]ethyl, 3-[(2- or 3-)thienyl]propyl, 4-[(2- or 3-)thienyl]butyl, 5-[(2- or 3-)thienyl]pentyl, 6-[(2- or 3-)thienyl]hexyl, 1,1-dimethyl-2-[(2- or 3)-thienyl]ethyl and 2-methyl-3-[(2- or 3-)thienyl]propyl groups, etc.

Examples of the benzodioxolyloxy group may include benzo[d][1,3]dioxolyloxy and 3H-benzo[c][1,2]dioxolyloxy groups, etc.

Examples of the phenylthio lower alkyl group may include, unless otherwise specified, a lower alkyl group as exemplified above (straight or branched alkyl groups having 1 to 6 carbon atoms (more preferably, 1 to 4 carbon atoms, and most preferably 1 to 3 carbon atoms)) having 1 to 2 phenylthio groups (preferably a single phenylthio group).

Examples of the phenylcyclo C3-C8 alkyl group may include, unless otherwise specified, C3-C8 alkyl group as exemplified above having 1 to 2 phenyl groups (preferably a single phenyl group); and more specifically include phenylcyclopropyl, phenylcyclobutyl, phenylcyclopentyl, phenylcyclohexyl, phenylcycloheptyl and phenylcyclooctyl groups, etc.

Examples of the phenoxy lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 3 phenoxy groups (preferably a single phenoxy group); and more specifically include, phenoxymethyl, 1-phenoxyethyl, 2-phenoxyethyl, 3-phenoxypropyl, 2-phenoxypropyl, 4-phenoxybutyl, 5-phenoxypentyl, 4-phenoxypentyl, 6-phenoxyhexyl, 2-methyl-3-phenoxypropyl and 1,1-dimethyl-2-phenoxyethyl, etc.

Examples of the phenyl lower alkenyl group may include, unless otherwise specified, a lower alkenyl group as exemplified above (more preferably a straight or branched alkyl group having 2 to 6 carbon atoms (most preferably 2 to 4-carbon atoms) having 1 to 3 phenyl groups (preferably a single phenyl group); and more specifically include, styryl, 3-phenyl-2-propenyl (trivial name: cinnamyl), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl and 6-phenyl-1,3,5-hexatrienyl groups, etc.

Examples of the cyclo C3-C8 alkyl lower alkenyl group may include, unless otherwise specified, a lower alkenyl group as exemplified above (more preferably a straight or branched alkyl group having 2 to 6 carbon atoms (most preferably 2 to 4-carbon atoms) having 1 to 3 cyclo C3-C8 alkyl groups (preferably a single cyclo C3-C8 alkyl group); and more specifically include, 2-cyclopropylethenyl, 1-cyclobutylethenyl, 3-cyclopentylpropenyl, 4-cyclohexylbutenyl, 5-cycloheptylpentenyl and 6-cyclooctylhexenyl groups, etc.

Examples of the pyridyl lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 pyridyl groups (preferably a single pyridyl group); and more specifically include (2-, 3-, or 4-)pyridylmethyl, 2-[(2-, 3-, or 4-)pyridyl]ethyl, 1-[(2-, 3-, or 4-)pyridyl]ethyl, 3-[(2-, 3-, or 4-)pyridyl]propyl, 4-[(2-, 3-, or 4-)pyridyl]butyl, 1,1-dimethyl-2-[(2-, 3-, or 4-)pyridyl]ethyl, 5-[(2-, 3-, or 4-)pyridyl]pentyl, 6-[(2-, 3-, or 4-)pyridyl]hexyl, 1-[(2-, 3-, or 4-)pyridyl]isopropyl and 2-methyl-3-[(2-, 3-, or 4-)pyridyl]propyl groups, etc.

Examples of the benzofuryl lower alkenyl group may include, unless otherwise specified, a lower alkenyl group as exemplified above (more preferably a straight or branched alkyl group having 2 to 6 carbon atoms (most preferably 2 to 4-carbon atoms) having 1 to 2 benzofuryl groups (preferably a single benzofuryl group); and more specifically include, 2-(4-benzofuryl)ethenyl, 1-(4-benzofuryl)ethenyl, 3-(4-benzofuryl)propenyl, 4-(4-benzofuryl)butenyl, 5-(4-benzofuryl)pentenyl and 6-(4-benzofuryl)hexenyl groups, etc.

Examples of the dihydrobenzofuryl lower alkenyl group may include, unless otherwise specified, a lower alkenyl group as exemplified above (more preferably a straight or branched alkyl group having 2 to 6 carbon atoms (most preferably 2 to 4-carbon atoms) having 1 to 2 dihydrobenzofuryl groups (preferably a single dihydrobenzofuryl group); and more specifically include, a 2-(2,3-dihydrobenzofuryl)vinyl group, a 1-(2,3-dihydrobenzofuryl)vinyl group, a 3-(2,3-dihydrobenzofuryl)propenyl group, a 4-(2,3-dihydrobenzofuryl)butenyl group, a 5-(2,3-dihydrobenzofuryl)pentenyl group and a 6-[2,3-dihydrobenzofuryl)hexenyl group, etc.

Examples of the dihydrobenzodioxinyl lower alkenyl group may include, unless otherwise specified, a lower alkenyl group as exemplified above (more preferably a straight or branched alkyl group having 2 to 6 carbon atoms (most preferably 2 to 4-carbon atoms) having 1 to 2 dihydrobenzodioxinyl groups (preferably a single dihydrobenzodioxinyl group); and more specifically include a 2-(2,3-dihydrobenzo[b][1,4]dioxinyl)vinyl group, a 1-(2,3-dihydrobenzo[b][1,4]dioxinyl)vinyl group, a 3-(2,3-dihydrobenzo[b][1,4]dioxinyl)propenyl group, a 4-(2,3-dihydrobenzo[b][1,4]dioxinyl)butenyl group, a 5-(2,3-dihydrobenzo[b][1,4]dioxinyl)pentenyl group and a 6-(2,3-dihydrobenzo[b][1,4]dioxinyl)hexenyl group, etc.

Examples of the dihydrobenzodioxinyloxy group may include, unless otherwise specified, the dihydrobenzodioxinyl group exemplified above that are substituted with oxy groups; and more specifically include 2,3-dihydrobenzo[b][1,4]dioxinyloxy and 3,4-dihydrobenzo[c][1,2]dioxinyloxy groups, etc.

Examples of the dihydrobenzodioxinyloxy lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 dihydrobenzodioxinyloxy groups (preferably a single dihydrobenzodioxinyloxy group); and more specifically include (2,3-dihydrobenzo[b][1,4]dioxinyloxy)methyl, 2-(2,3-dihydrobenzo[b][1,4]dioxinyloxy)ethyl, 3-(2,3-dihydrobenzo[b][1,4]dioxinyloxy)propyl, 2-(2,3-dihydrobenzo[b][1,4]dioxinyloxy)propyl, 4-(2,3-dihydrobenzo[b][1,4]dioxinyloxy)butyl, 5-(2,3-dihydrobenzo[b][1,4]dioxinyloxy)pentyl and 6-(2,3-dihydrobenzo[b][1,4]dioxinyloxy)hexyl groups, etc.

Examples of the oxazolyl group may include a (2-, 4- or 5-)oxazolyl group.

Examples of the dihydroindenyloxy group may include, unless otherwise specified, the dihydroindenyl group exemplified above that are substituted with oxy groups; and more specifically include a (1-, 2-, 4- or 5-)-1,2-dihydroindenyloxy group.

Examples of the dihydroindenyloxy lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 dihydroindenyloxy groups (preferably a single dihydroindenyloxy group); and more specifically include (2,3-dihydro-1H-indenyloxy)methyl, 2-(2,3-dihydro-1H-indenyloxy)ethyl, 3-(2,3-dihydro-1H-indenyloxy)propyl, 4-(2,3-dihydro-1H-indenyloxy)butyl, 5-(2,3-dihydro-1H-indenyloxy)pentyl and 6-(2,3-dihydro-1H-indenyloxy)hexyl groups, etc.

Examples of the dihydropyrimidinyl group may include 2,3-dihydropyrimidinyl, 4,5-dihydropyrimidinyl and 2,5-dihydropyrimidinyl groups, etc.

Examples of the pyridyloxy lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 pyridyloxy groups (preferably a single pyridyloxy group); and more specifically include (pyridyloxy)methyl, 2-(pyridyloxy)ethyl, 1-(pyridyloxy)ethyl, 3-(pyridyloxy)propyl, 4-(pyridyloxy)butyl, 5-(pyridyloxy)pentyl and 6-(pyridyloxy)hexyl groups, etc.

Examples of the lower alkoxy lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 3 (preferably a single lower alkoxy group) lower alkoxy group as exemplified above groups (preferably a straight or branched alkyl group having 1 to 6 carbon atoms); and more specifically include methoxymethyl, 2-methoxyethyl, 1-ethoxyethyl, 2-ethoxyethyl, 2-isobutoxyethyl, 2,2-dimethoxyethyl, 2-methoxy-1-methylethyl, 2-methoxy-1-ethylethyl, 3-methoxypropyl, 3-ethoxypropyl, 3-isobutoxypropyl, 3-n-butoxypropyl, 4-n-propoxybutyl, 1-methyl-3-isobutoxypropyl, 1,1-dimethyl-2-n-pentyloxyethyl, 5-n-hexyloxypentyl, 6-methoxyhexyl, 1-ethoxyisopropyl and 2-methyl-3-methoxypropyl groups.

Examples of the imidazolyl group that may have a lower alkyl group may include an imidazolyl group that may have 1 to 2 lower alkyl groups as exemplified above (preferably a single lower alkyl group); and more specifically include 2-methyl-1H-imidazolyl, 2-ethyl-1H-imidazolyl, 2-propyl-1H-imidazolyl, 2-butyl-1H-imidazolyl, 2-pentyl-1H-imidazolyl and 2-hexyl-1H-imidazolyl groups, etc.

Examples of the oxadiazolyl group that may have a lower alkyl group may include an oxadiazolyl group that may have 1 to 2 lower alkyl groups as exemplified above (preferably a single lower alkyl group); and more specifically include 5-methyl-1,3,4-oxadiazolyl, 5-ethyl-1,3,4-oxadiazolyl, 5-propyl-1,3,4-oxadiazolyl, 5-butyl-1,3,4-oxadiazolyl, 5-pentyl-1,3,4-oxadiazolyl and 5-hexyl-1,3,4-oxadiazolyl groups, etc.

Examples of a triazolyl lower alkyl group may include, unless otherwise specified, a lower alkyl group (preferably a straight or branched alkyl group having 1 to 6 chain atoms) as exemplified above and having a 1 to 2 (preferably 1) triazolyl groups as exemplified above; and more specifically include [1,2,4-triazol-(3- or 5-)yl]methyl, [1,2,3-triazol-(4- or 5-)yl]methyl, 2-[1,2,4-triazol-(3- or 5-)yl]ethyl, 1-[1,2,4-triazol-(3- or 5-)yl]ethyl, 3-[1,2,4-triazol-(3- or 5-)yl]propyl, 4-[1,2,4-triazol-(3- or 5-)yl]butyl, 1,1-dimethyl-2-[1,2,4-triazol-(3- or 5-)yl]ethyl, 5-[1,2,4-triazol-(3- or 5-)yl]pentyl, 6-[1,2,4-triazol-(3- or 5-)yl]hexyl, 1-[1,2,4-triazol-(3- or 5-)yl]isopropyl and 2-methyl-3-[1,2,4-triazol-(3- or 5)-yl]propyl groups, etc.

Examples of the cyclo C3-C8 alkyloxy group may include, unless otherwise specified, cyclopropyloxy, cyclobutyloxy, cyclopentyloxy, cyclohexyloxy, cycloheptyloxy and cyclooctyloxy groups, etc.

Examples of the pyrrolidinyl group that may have an oxo group may include, unless otherwise specified, a pyrrolidinyl group having 1 to 2 (preferably 1) oxo groups; and more specifically may include (1-, 2-, or 3-)pyrrolidinyl, (2- or 3-)oxo-1-pyrrolidinyl, (3-, 4-, or 5-)oxo-2-pyrrolidinyl and (2-, 4-, or 5-)oxo-3-pyrrolidinyl groups.

Examples of the dihydropyrazolyl group that may have a substituent selected from the group consisting of an oxo group and a lower alkyl group may include, unless otherwise specified, dihydropyrazolyl group having 2 to 3 substituent groups (preferably 2 substituent groups) selected from the group consisting of an oxo group and a lower alkyl group (preferably a straight or branched alkyl group having 1 to 6 carbon atoms (more preferably 1 to 4 carbon atoms, and most preferably 1 to 3 carbon atoms); and more specifically include a 3-methyl-5-oxo-4,5-dihydro-1H-pyrazolyl group, a 3-ethyl-5-oxo-4,5-dihydro-1H-pyrazolyl group, a 5-oxo-3-propyl-4,5-dihydro-1H-pyrazolyl group, a 3-butyl-5-oxo-4,5-dihydro-1H-pyrazolyl group, a 5-oxo-3-pentyl-4,5-dihydro-1H-pyrazolyl group and a 3-hexyl-5-oxo-4,5-dihydro-1H-pyrazolyl group, etc.

Examples of the tetrazolyl group may include a (1- or 5-)tetrazolyl group.

Examples of the homopiperazinyl group that may have a lower alkyl group may include, unless otherwise specified, a homopiperazinyl group having 1 to 2 (preferably a single lower alkyl group) lower alkyl group as exemplified above (preferably a straight or branched alkyl group having 1 to 6 carbon atoms (more preferably 1 to 4 carbon atoms, and most preferably 1 to 3 carbon atoms) groups; and more specifically include, a 1-homopiperazinyl group, a 2-homopiperazinyl group, a 3-homopiperazinyl group, a 4-homopiperazinyl group, a 5-homopiperazinyl group, a 6-homopiperazinyl group, a 7-homopiperazinyl group, a 4-methyl-1-homopiperazinyl group, a 4-ethyl-1-homopiperazinyl group, a 4-n-propyl-1-homo piperazinyl group, a 4-tert-butyl-1-homopiperazinyl group, a 4-n-pentyl-1-homopiperazinyl group and a 4-n-hexyl-1-homopiperazinyl group.

Examples of the lower alkanoyl amino group may include, unless otherwise specified, a amino group that are substituted with lower alkanoyl group as exemplified above (straight or branched lower alkanoyl groups having 1 to 6 carbon atoms (more preferably, 1 to 4 carbon atoms, and most preferably 1 to 3 carbon atoms)); and more specifically include, acetylamino, propionylamino, butyrylamino, pentanoylamino, 2-methylpropionylamino and hexanoylamino groups, etc.

Examples of the cycloC3-C8alkyl carbonyl amine group may include, unless otherwise specified, a amino group having cycloC3-C8alkyl carbonyl groups as exemplified above (preferably a single cycloC3-C8alkyl carbonyl group); and more specifically include, cyclopropylcarbonylamino, cyclobutylcarbonylamino, cyclopentylcarbonylamino, cyclohexylcarbonylamino, cycloheptylcarbonylamino and cyclooctylcarbonylamino, etc.

Examples of the morpholinyl lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 morpholinyl groups (preferably a single morpholinyl); and more specifically include 2-morpholinylmethyl, 3-morpholinylmethyl, 4-morpholinylmethyl, 2-(2-morpholinyl)ethyl, 2-(3-morpholinyl)ethyl, 2-(4-morpholinyl)ethyl, 1-(2-morpholinyl)ethyl, 1-(3-morpholinyl)ethyl, 1-(4-morpholinyl)ethyl, 3-(2-morpholinyl)propyl, 3-(3-morpholinyl)propyl, 3-(4-morpholinyl)propyl, 4-(2-morpholinyl)butyl, 4-(3-morpholinyl)butyl, 4-(4-morpholinyl)butyl, 5-(2-morpholinyl)pentyl, 5-(3-morpholinyl)pentyl, 5-(4-morpholinyl)pentyl, 6-(2-morpholinyl)hexyl, 6-(3-morpholinyl)hexyl, 6-(4-morpholinyl)hexyl, 3-methyl-3-(2-morpholinyl)propyl, 3-methyl-3-(3-morpholinyl)propyl, 3-methyl-3-(4-morpholinyl)propyl, 1,1-dimethyl-2-(2-morpholinyl)ethyl, 1,1-dimethyl-2-(3-morpholinyl)ethyl and 1,1-dimethyl-2-(4-morpholinyl)ethyl groups.

Examples of the piperidinyl lower alkyl group may include, unless otherwise specified, a lower alkyl group as exemplified above (preferably a straight or branched alkyl group having 1 to 6 carbon atoms (more preferably 1 to 4 carbon atoms, and most preferably 1 to 3 carbon atoms) having 1 to 2 piperidinyl groups (preferably a single piperidinyl); and more specifically include [(1, 2, 3 or 4-)piperidinyl] methyl, 2-[(1, 2, 3 or 4-)piperidinyl]ethyl, 1-[(1, 2, 3 or 4-)piperidinyl]ethyl, 3-(1, 2, 3 or 4-)piperidinyl]propyl, 4-[(1, 2, 3 or 4-)piperidinyl]butyl, 5-[(1, 2, 3 or 4-)piperidinyl]pentyl, 6-[(1, 2, 3 or 4-)piperidinyl]hexyl, 1,1-dimethyl-2-[(1, 2, 3 or 4-)piperidinyl]ethyl and 2-methyl-3-[(1, 2, 3 or 4-)piperidinyl]propyl.

Examples of the lower alkylsulfonyl group may include unless otherwise specified, a sulfonyl group having lower alkyl group as exemplified above (preferably a straight or branched alkyl group having 1 to 6 carbon atoms (more preferably 1 to 4 carbon atoms, and most preferably 1 to 3 carbon atoms) groups; and more specifically include, sulfonyl group having a lower alkyl group (preferably a straight or branched alkyl group having 1 to 6 carbon atoms (more preferably 1 to 4 carbon atoms)) having an lower alkyl moiety as exemplified above; and more specifically include methylsulfonyl, ethylsulfonyl, n-propylsulfonyl, isopropylsulfonyl, n-butylsulfonyl, isobutylsulfonyl, tert-butylsulfonyl, sec-butylsulfonyl, n-pentylsulfonyl, isopentylsulfonyl, neopentylsulfonyl, n-hexylsulfonyl, isohexylsulfonyl and 3-methylpentylsulfonyl groups, etc.

Examples of the adamantyl lower alkyl group may include unless otherwise specified, a lower alkyl group (preferably a straight or branched alkyl group having 1 to 6 carbon atoms (more preferably 1 to 4 carbon atoms)) as exemplified above and having 1 to 3 (preferably 1) adamantyl groups.

Examples of the cyclo C3-C8 alkyl lower alkyl group may include, unless otherwise specified, a lower alkyl group as exemplified above (straight or branched alkyl groups having 1 to 6 carbon atoms (more preferably, 1 to 4 carbon atoms, and most preferably 1 to 3 carbon atoms)) having 1 to 3 cyclo C3-C8 alkyl groups (preferably a single cyclo C3-C8 alkyl group), and more specifically include cyclopropylmethyl, cyclohexylmethyl, 2-cyclopropylethyl, 1-cyclobytylethyl, cyclopentylmethyl, 3-cyclopentylpropyl, cyclohexylmethyl, 2-cyclohexylethyl, 3-cyclohexylpropyl, 4-cyclohexylbutyl, 5-cycloheptylpentyl, 6-cyclooctylhexyl, 1,1-dimethyl-2-cyclohexylethyl and 2-methyl-3-cyclopropylpropyl, etc.

A heterocyclic compound represented by the general formula (1) is produced by various methods, for example, produced in accordance with the following reaction formulas-1 and 2.

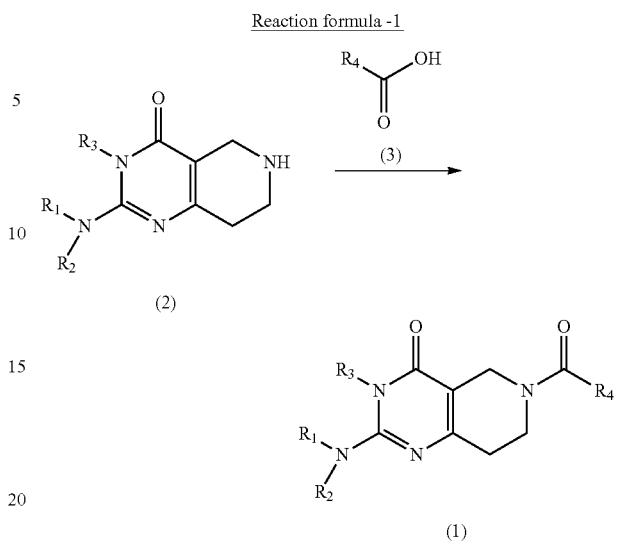

Reaction formula -1

[in the formula, $R_1$, $R_2$, $R_3$, $R_4$ are the same as defined above.]

A compound (1) is produced by reacting a compound (3) or a reactive derivative thereof modified at the carboxy group and a compound (2) or a reactive derivative thereof modified at the imino group.

Examples of a preferable reactive derivative of the compound (3) modified at the carboxy group include an acid halide, an acid anhydride, an activated amide and an activated ester, etc. As a preferable example of the reactive derivative, mention may be made of an acid chloride; an acid azide; a mixed anhydride with an acid such as a substituted phosphoric acid, such as dialkylphosphoric acid, phenylphosphoric acid, diphenylphosphoric acid, dibenzylphosphoric acid and halogenated phosphoric acid, dialkylphosphorous acid, sulfurous acid, thiosulfuric acid, sulfuric acid, a sulfonic acid such as methanesulfonic acid, an aliphatic carboxylic acid such as acetic acid, propionic acid, butyric acid, isobutyric acid, pivalic acid, pentane acid, isopentane acid, 2-ethylbutyric acid and trichloro acetic acid or an aromatic carboxylic acid such as benzoic acid; a symmetric anhydride; an activated amide with imidazole, 4-substituted imidazole, dimethylpyrazole, triazole or tetrazole; or activated ester such as cyanomethyl ester, methoxymethyl ester, dimethyliminomethyl ester, vinyl ester, propargyl ester, p-nitrophenyl ester, 2,4-dinitrophenyl ester, trichlorophenyl ester, pentachlorophenyl ester and mesylphenyl ester, or an ester with an N-hydroxy compound such as N,N-dimethylhydroxylamine, 1-hydroxy-2-(1H)-pyridone, N-hydroxysuccinimide, N-hydroxyphthalimide and 1-hydroxy-1H-benzotriazole, etc. These reactive derivatives can be arbitrarily selected from the above examples depending upon the compound (3) to be used.

In the aforementioned reaction, when the compound (3) is used in the form of a free acid or a salt thereof, the reaction is desirably conducted in the presence of a condensing agent. As the condensing agent, a wide variety of condensing agents known in this field can be used. Examples thereof include N,N'-dicyclohexyl carbodiimide; N-cyclohexyl-N'-morpholinoethyl carbodiimide; N-cyclohexyl-N'-(4-diethylaminocyclohexyl)carbodiimide; N,N'-diethyl carbodiimide; N,N'-diisopropyl carbodiimide; N-ethyl-N'-(3-dimethylaminopropyl)carbodiimide or a hydrochloride thereof; N,N-carbonylbis(2-methylimidazole); pentamethyleneketene-N-cyclohexylimine; diphenylketene-N-cyclohexylimine;

ethoxyacetylene, 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate such as ethyl chloroformate and isopropyl chloroformate; triphenyl phosphine; 2-ethyl-7-hydroxybenzisoxazolium salt; 2-ethyl-5-(m-sulfophenyl)isoxazolium hydroxide internal salt; benzotriazol-1-yloxy-tris(dimethylamino)phosphonium hexafluorophosphate; 1-(p-chlorobenzenesulfonyloxy)-6-chloro-1H-benzotriazole; and a so-called Vilsmeier reagent prepared by the reaction between N,N-dimethyl formamide and thionyl chloride, phosgene, trichloromethyl chloroformate, phosphorus oxychloride or the like. Furthermore, the reaction is further desirably conducted in the copresence of the condensing agent and an esterification activating agent such as N-hydroxysuccinimide and N-hydroxyphthalimide and 1-hydroxy-1H-benzotriazole, etc.

Examples of a preferable reactive derivative of a compound (2) modified at the imino group include a Schiff base imino, which is produced by the reaction between a compound (2) and a carbonyl compound such as aldehyde, ketone or an enamine tautomer; a silyl derivative, which is produced by the reaction between a compound (2) and a silyl compound such as bis(trimethylsilyl)acetamide, mono(trimethylsilyl)acetamide, bis(trimethylsilyl)urea; and a derivative which is produced by the reaction between a compound (2) and phosphorus trichloride, phosgene or the like.

This reaction is usually conducted in a customary solvent having no adverse effect on the reaction. As the solvent, for example, mention is made of water; an alcohol solvent such as methanol, ethanol, isopropanol, n-butanol, trifluoroethanol and ethylene glycol; a ketone solvent such as acetone and methylethyl ketone; an ether solvent such as tetrahydrofuran, dioxane, diethylether, diisopropyl ether and diglyme; an ester solvent such as methyl acetate and ethyl acetate; a nonprotonic polar solvent such as acetonitrile, N,N-dimethylformamide and dimethylsulfoxide; a hydrocarbon solvent such as n-pentane, n-hexane, n-heptane and cyclohexane; a halogenated hydrocarbon solvent such as methylene chloride and ethylene chloride; or an organic solvent other than these, or solvent mixtures of these, etc.

This reaction may be conducted in the presence of a base. As the base, a wide variety of inorganic bases and organic bases known in the art can be used. Examples of the inorganic base include an alkali metal (e.g., sodium, potassium), a hydrogen carbonate of an alkali metal (e.g., lithium hydrogen carbonate, sodium hydrogen carbonate, potassium hydrogen carbonate), a hydroxide of an alkali metal (e.g., lithium hydroxide, sodium hydroxide, potassium hydroxide, cesium hydroxide), a carbonate of an alkali metal (e.g., lithium carbonate, sodium carbonate, potassium carbonate, cesium carbonate), a lower alkoxide of an alkali metal (e.g., sodium methoxide, sodium ethoxide) and a hydride of an alkali metal (e.g., sodium hydride, potassium hydride). Examples of the organic base include a trialkylamine (e.g., trimethylamine, triethylamine, N-ethyldiisopropylamine), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), etc. Furthermore, when these bases are in a liquid state, they can be also used as a solvent. These bases are used singly or as a mixture of two or more types. The amount of the base(s) to be used is usually 0.1 to 10 moles and preferably 0.1 to 3 moles based on 1 mole of a compound (3).

With respect to the ratio of a compound (3) relative to a compound (2) used in reaction formula 2 above, the former is usually used in an amount of at least 1 mole and preferably about 1 to 5 moles relative to 1 mole of the latter.

The reaction temperature is not particularly limited; however, the reaction is conducted usually under any one of cooling, room temperature and heating. Preferably, the reaction is conducted under temperature conditions of room temperature to 100° C. for 30 minutes to 30 hours, preferably, for 30 minutes to 5 hours.

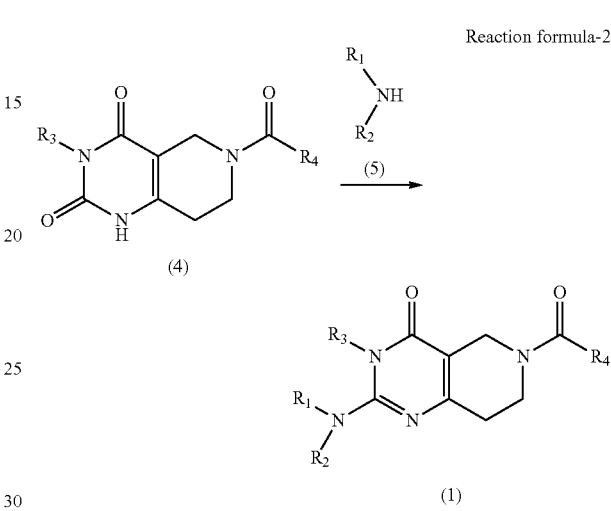

Reaction formula-2

[in the formula, $R_1$, $R_2$, $R_3$, $R_4$ are the same as defined above.]

A compound (1) can be produced by the reaction between a compound (4) and a compound (5). The reaction is conducted in the absence of a solvent or in an inert solvent, in the presence or absence of a basic compound and in the presence of a condensing agent.

Examples of the inert solvent may include water; ethers such as dioxane, tetrahydrofuran, diethylether, diethylene glycol methyl ether and ethylene glycol dimethyl ether; aromatic hydrocarbons such as benzene, toluene and xylene; lower alcohols such as methanol, ethanol and isopropanol; ketones such as acetone and methyl ethyl ketone; and polar solvents such as N,N-dimethyl formide (DMF), dimethylsulfoxide (DMSO), hexamethylphosphoric acid triamide and acetonitrile, etc.

As the basic compound, a wide variety of basic compounds known in the art can be used. Examples thereof may include a hydroxide of an alkali metal such as sodium hydroxide, potassium hydroxide, cesium hydroxide and lithium hydroxide, a carbonate of an alkali metal such as sodium carbonate, potassium carbonate, cesium carbonate and lithium carbonate; an alkali metal such as sodium and potassium; an inorganic base such as sodium amide, sodium hydride and potassium hydride, and alkali metal alcoholates such as sodium methoxide, sodium ethoxide, potassium methoxide and potassium ethoxide; an organic base such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazacyclo[4.3.0]nonene-5 (DBN), 1,8diazabicyclo[5.4.0]undecene-7 (DBU) and 1,4-diazabicyclo[2.2.2]octane (DABCO), etc.

These basic compounds are used singly or as a mixture of two or more types.

The amount of the basic compound(s) to be used, usually 0.5 to 10 fold by mole of a compound represented by the general formula (4), and preferably, 0.5 to 6 fold by mole.

The reaction may be conducted by adding, if necessary, an alkali metal iodide such as potassium iodide and sodium iodide as a reaction accelerator.

With respect to the ratio of a compound of the general formula (4) relative to a compound of the general formula (5) in reaction formula 3 above, the latter may be used at least 0.5 fold by mole, preferably, about 0.5 to 5 fold by mole relative to the former.

The reaction is usually conducted under temperature conditions of 0° C. to 200° C., preferably, room temperature to 150° C., and generally completed in about 1 to 30 hours.

As the condensing agent, for example, hexafluoro phosphoric acid benzotriazol-1-yloxy-tris(dimethylamino)phosphonium and bromotriphenylpyrrolidinophosphonium hexafluorophosphate are mentioned.

A compound of the general formula (2) to be used as a starting material is produced, for example, through the step of the following reaction formula-3→4→5→6, and a compound of the general formula (4) is produced, for example, through the step of the following reaction formula-3→4→7→8 or through the step of the following reaction formula-9→10→11, respectively.

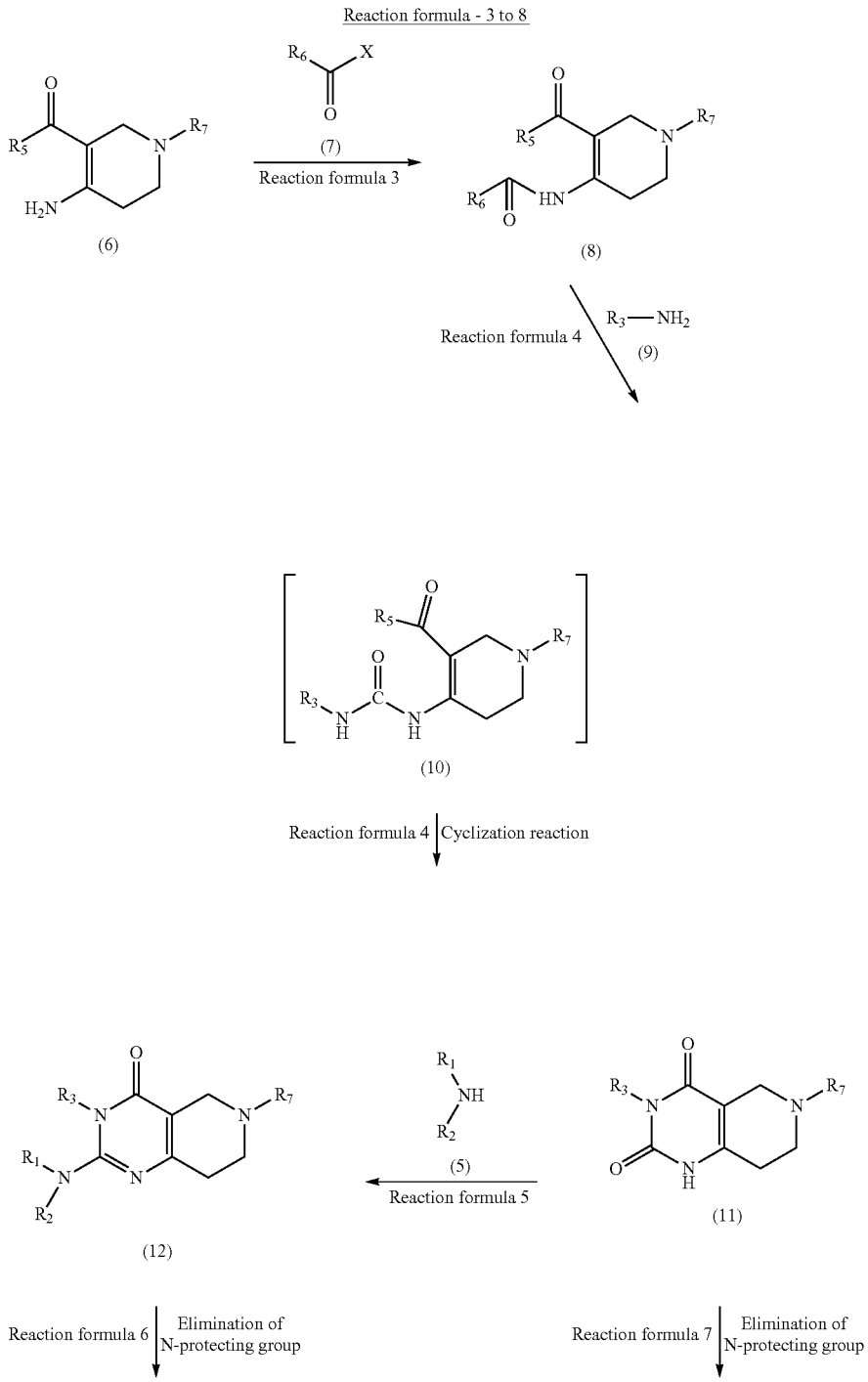

Reaction formula - 3 to 8

-continued
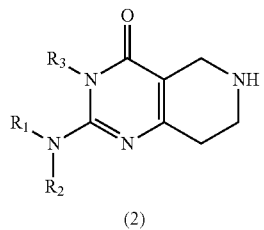
(2)
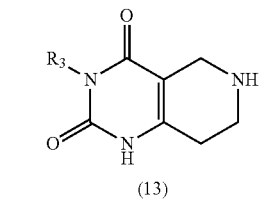
(13)
Reaction formula 8
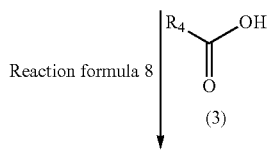
(3)
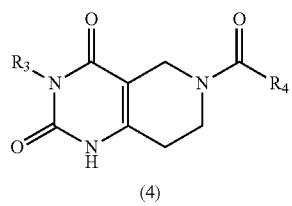
(4)
Reaction formula - 9 to 11
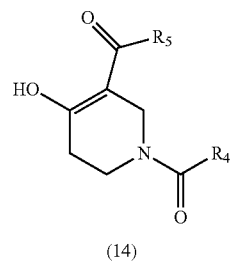
(14)
Reaction formula 9 | Amination
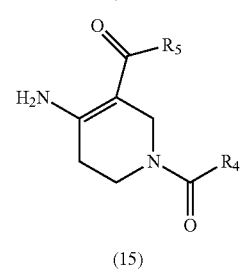
(15)
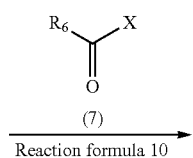
(7)
Reaction formula 10
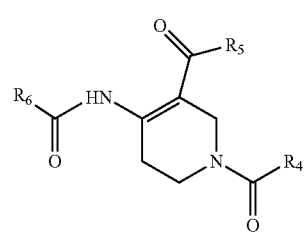
(16)
Reaction formula 11 | $H_2N-R_3$
(9)
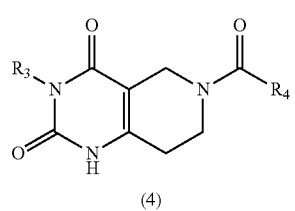
(4)
Cyclization reaction
Reaction formula 11
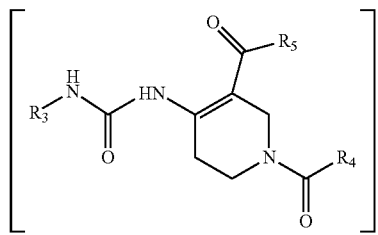
(17)

In reaction formulas 3 to 11, $R_1$, $R_2$, $R_3$ and $R_4$ are the same as defined above, $R_5$ represents a lower alkoxy, $R_6$ phenoxy, $R_7$ an N-protecting group and X a halogen atom, etc. The lower alkoxy group represented by $R_5$ and the halogen atom represented by X are the same as defined above.

Examples of the N-protecting group may include a lower alkoxycarbonyl group, a lower alkanoyl group and an aryl-substituted lower alkyl group, etc.

Examples of the lower alkoxycarbonyl group include a straight or branched alkoxycarbonyl group having 1 to 6 carbon atoms. Specific examples thereof may include methoxycarbonyl, ethoxycarbonyl, propoxycarbonyl, butoxycarbonyl, tert-butoxycarbonyl, pentyloxycarbonyl and hexyloxycarbonyl groups, etc.

Examples of the lower alkanoyl group include straight or branched alkanoyl group having 1 to 6 carbon atoms. Specific examples thereof include formyl, acetyl, propionyl, butyryl, isobutyryl, pentanoyl, tert-butyl carbonyl and hexanoyl groups, etc.

Examples of the aryl-substituted lower alkyl group may include a straight or branched alkyl group having 1 to 6 carbon atoms that is substituted with 1 to 3 phenyl groups, such as benzyl, 2-phenylethyl, 1-phenylethyl, 3-phenylpropyl, 4-phenylbutyl, 5-phenylpentyl, 6-phenylhexyl, diphenylmethyl and trityl, etc. As the substituents on the phenyl group, mention can be made of a straight or branched alkyl group having 1 to 6 carbon atoms and optionally having 1 to 3 groups selected from the group consisting of a halogen atom and a hydroxy group as substituents, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl and 3-hydroxy-2-chloropropyl group; a straight or branched alkoxy group having 1 to 6 carbon atoms and optionally having 1 to 3 groups selected from the group consisting of a halogen atom and a hydroxy group as substituents, such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy and 3-hydroxy-2-chloropropoxy groups; and halogen atoms such as a fluorine atom, a bromine atom, a chlorine atom and an iodine atom, etc. When the number of substituents is 2 or more, these substituents may be of the same or different types.

The individual reaction formulas will be more specifically described below.

Reaction Formula 3

A compound (8) can be produced by the reaction between a compound (6) and a compound (7). The reaction is conducted in the absence of a solvent or in an inert solvent and in the presence or absence of a basic compound.

Examples of the inert solvent may include, water; ethers such as dioxane, tetrahydrofuran, diethylether, diethylene glycol methyl ether and ethylene glycol dimethyl ether; aromatic hydrocarbons such as benzene, toluene and xylene; lower alcohols such as methanol, ethanol and isopropanol; ketones such as acetone and methyl ethyl ketone; and polar solvents such as N,N-dimethyl formide (DMF), dimethylsulfoxide (DMSO), hexamethylphosphoric acid triamide and acetonitrile, etc.

As the basic compound, a wide variety of basic compounds known in the art can be used. Examples thereof may include a hydroxide of an alkali metal such as sodium hydroxide, potassium hydroxide, cesium hydroxide and lithium hydroxide, a carbonate of an alkali metal such as sodium carbonate, potassium carbonate, cesium carbonate and lithium carbonate; an alkali metal such as sodium and potassium; an inorganic base such as sodium amide, sodium hydride and potassium hydride, and alkali metal alcoholates such as sodium methoxide, sodium ethoxide, potassium methoxide and potassium ethoxide; an organic base such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazacyclo[4.3.0]nonene-5 (DBN), 1,8diazabicyclo[5.4.0]undecene-7 (DBU) and 1,4-diazabicyclo[2.2.2]octane (DABCO), etc.

These basic compounds are used singly or as a mixture of two or more types.

The amount of the basic compound(s) to be used, usually 0.5 to 10 fold by mole of a compound represented by the general formula (6), and preferably, 0.5 to 6 fold by mole.

The reaction may be conducted by adding, if necessary, an alkali metal iodide such as potassium iodide and sodium iodide as a reaction accelerator.

With respect to the ratio of a compound of the general formula (6) relative to a compound of the general formula (7) in reaction formula 4 above, the latter may be used at least 0.5 fold by mole of the former, preferably, about 0.5 to 5 fold by mole.

The reaction is usually conducted under temperature conditions of 0° C. to 200° C., preferably, room temperature to 150° C. and generally completed in about 1 to 30 hours.

Reaction Formula 4

A compound (11) can be produced by reacting a compound (8) and a compound (9) to obtain a compound (10) and subjecting the compound (10) to a cyclization reaction. The reaction is conducted in the absence of a solvent or in an inert solvent and in the presence or absence of a basic compound.

Examples of the inert solvent may include, water; ethers such as dioxane, tetrahydrofuran, diethylether, diethylene glycol methyl ether and ethylene glycol dimethyl ether; aromatic hydrocarbons such as benzene, toluene and xylene; lower alcohols such as methanol, ethanol and isopropanol; ketones such as acetone and methyl ethyl ketone; and polar solvents such as N,N-dimethyl formide (DMF), dimethylsulfoxide (DMSO), hexamethylphosphoric acid triamide and acetonitrile, etc.

As the basic compound, a wide variety of basic compounds known in the art can be used. Examples thereof may include a hydroxide of an alkali metal such as sodium hydroxide, potassium hydroxide, cesium hydroxide and lithium hydroxide, a carbonate of an alkali metal such as sodium carbonate, potassium carbonate, cesium carbonate and lithium carbonate; an alkali metal such as sodium and potassium; an inorganic base such as sodium amide, sodium hydride and potassium hydride, and alkali metal alcoholates such as sodium methoxide, sodium ethoxide, potassium methoxide and potassium ethoxide; an organic base such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazacyclo[4.3.0]nonene-5 (DBN), 1,8diazabicyclo[5.4.0]undecene-7 (DBU) and 1,4-diazabicyclo[2.2.2]octane (DABCO), etc.

These basic compounds are used singly or as a mixture of two or more types.

The amount of the basic compound(s) to be used, usually 0.5 to 10 fold by mole of a compound of the general formula (8), and preferably, 0.5 to 6 fold by mole.

The reaction may be conducted by adding, if necessary, an alkali metal iodide such as potassium iodide and sodium iodide as a reaction accelerator.

With respect to the ratio of a compound of the general formula (8) relative to a compound of the general formula (9) in reaction formula 3 above, the latter may be used at least 0.5 fold by mole of the former, preferably, about 0.5 to 5 fold by mole.

The reaction is usually conducted under temperature conditions of 0° C. to 200° C., preferably, room temperature to 150° C. and generally completed in about 1 to 30 hours.

Reaction Formula 5

A compound (12) can be produced by reacting a compound (11) and a compound (5). The reaction is conducted in the same reaction conditions as in reaction formula 2 above.

Reaction Formula 6

The compound (2) can be produced by subjecting compound (12) to a reaction of eliminating an N-protecting group.

To the elimination reaction of an N-protecting group, a customary method such as hydrolysis and hydrogenolysis can be applied.

The elimination reaction is usually conducted in a customary solvent having no adverse effect on the reaction. As the solvent, for example, mention is made of water; an alcohol solvent such as methanol, ethanol, isopropanol, n-butanol, trifluoroethanol and ethylene glycol; a ketone solvent such as acetone and methylethyl ketone; an ether solvent such as tetrahydrofuran, dioxane, diethylether, dimethoxyethane and diglyme; an ester solvent such as methyl acetate and ethyl acetate; a nonprotonic polar solvent such as acetonitrile, N,N-dimethylformamide, dimethylsulfoxide and N-methylpyrrolidone; a halogenated hydrocarbon solvent such as methylene chloride and ethylene chloride; or an organic solvent other than these, etc.

(i) Hydrolysis:

Hydrolysis is preferably performed in the presence of a base or an acid (including Lewis acid).

As the base, a wide variety of inorganic bases and organic bases known in the art can be used. As the inorganic base preferably used, for example, mention is made of an alkali metal (e.g., sodium, potassium), an alkaline-earth metal (e.g., magnesium, calcium), hydroxides, carbonates or hydrogen carbonates of these. As the organic base preferably used, for example, mention is made of trialkyl amine (e.g., trimethylamine, triethylamine), picoline and 1,5-diazabicyclo[4,3,0]non-5-ene, etc.

As the acid, a wide variety of inorganic acids and organic acids known in the art can be used. As the inorganic acid preferably used, for example, mention is made of a fatty acid such as formic acid, acetic acid and propionic acid; and a trihaloacetic acid such as trichloroacetic acid and trifluoroacetic acid, etc. As the inorganic base preferably used, for example, mention is made of hydrochloric acid, hydrobromic acid, sulfuric acid, hydrogen chloride and hydrogen bromide.

As the Lewis acid, for example, mention is made of a boron trifluoride ether complex, boron tribromide, aluminum chloride and ferric chloride, etc.

When a trihaloacetic acid or a Lewis acid is used as the acid, hydrolysis is preferably performed in the presence of a cation trapping agent (e.g., anisole, phenol).

The amount of the base or acid to be used is not particularly limited as long as it is required for hydrolysis.

The reaction temperature is usually 0 to 120° C., preferably, room temperature to 100° C., and more preferably room temperature to 80° C. The reaction time is usually 30 minutes to 24 hours, preferably, 30 minutes to 12 hours, and more preferably, 1 to 8 hours.

(ii) Hydrogenolysis:

To hydrogenolysis, a wide variety of hydrogenolysis methods known in the art can be applied. As the hydrogenolysis method, for example, chemical reduction and catalytic reduction are mentioned.

Examples of the reducing agent preferably used for chemical reduction include a hydride (e.g., hydrogen iodide, hydrogen sulfide, lithium aluminum hydride, sodium boron hydride, sodium cyanoborohydride) or a combination of a metal (e.g., tin, zinc, iron) or a metal compound (e.g., chromium chloride, chromium acetate) and an organic acid or an inorganic acid (e.g., formic acid, acetic acid, propionic acid, trifluoroacetic acid, p-toluenesulfonic acid, hydrochloric acid, hydrobromic acid).

Examples of the catalyst preferably used for catalytic reduction include a platinum catalyst (e.g., platinum plate, spongy platinum, platinum black, colloidal platinum, platinum oxide, platinum wire), a palladium catalyst (e.g., spongy palladium, palladium black, palladium oxide, palladium carbon, palladium/barium sulfate, palladium/barium carbonate), a nickel catalyst (e.g., reduced nickel, nickel oxide, Raney nickel), a cobalt catalyst (e.g., reduced cobalt, Raney cobalt) and an iron catalyst (e.g., reduced iron), etc.

Note that the aforementioned acids to be used in chemical reduction are in a liquid state, they can be also used as a solvent.

The amount of the reducing agent to be used for chemical reduction and the amount of the catalyst to be used as catalytic reduction are not particularly limited and the amounts usually used may be employed.

The reaction temperature is usually 0 to 120° C., preferably, room temperature to 100° C., and more preferably room temperature to 80° C. The reaction time is usually 30 minutes to 24 hours, preferably, 30 minutes to 10 hours, and more preferably, 30 minutes to 4 hours.

Furthermore, the elimination reaction of the N-protecting group mentioned above is not limited to the aforementioned reaction conditions, for example, the reaction described in T. W. Green, P. G. M. Wuts, "Protective Groups in Organic Synthesis", the 4th edition and John Wiley & Sons; New York, 1991, P. 309 can be also applied to the step of the elimination reaction.

Reaction Formula 7

The compound (13) can be produced by subjecting a compound (11) to a reaction of eliminating an N-protecting group. The elimination reaction can be conducted in the same reaction conditions as in the reaction represented by the above reaction formula-6.

Reaction Formula 8

The compound (4) is produced by reacting a compound (3) or its reactive derivative modified at a carboxy group and a compound (13) or its reactive derivative modified at an imino group. The reaction is conducted in the same reaction conditions as in the reaction represented by the above reaction formula-1.

Reaction Formula 9

The compound (15) is produced by amination of a compound (14). The reaction is conducted in the same reaction conditions as in the reaction of Reference Example 21 (described later).

Reaction Formula 10

The compound (16) can be produced by the reaction between a compound (15) and a compound (7). The reaction can be conducted in the same reaction conditions as in the reaction of reaction formula-3.

Reaction Formula 11

The compound (4) can be produced by obtaining a compound (17) formed through the reaction between a compound (16) and a compound (9) and subjecting the compound (17) to a cyclization reaction. The reaction is conducted in the same reaction conditions as in the reaction of reaction formula-4.

The raw material compounds used in each of the reaction formulas may be a salt preferably used, and a desired compound obtained in each reaction may form also a salt preferably used. Examples of the salt preferably used include preferable salts of the compound (1) as exemplified below.

A preferable salt of the compound (1) is a pharmacologically acceptable salt. Examples thereof include a metal salt such as an alkali metal salt (e.g., sodium salt, potassium salt), an alkaline-earth metal salt (e.g., a calcium salt, a magnesium salt), a salt of an inorganic base such as an ammonium salt, a carbonate of an alkali metal (e.g., lithium carbonate, potassium carbonate, sodium carbonate, cesium carbonate), a hydrogen carbonate of an alkali metal (e.g., lithium hydrogen carbonate, sodium hydrogen carbonate, potassium hydrogen carbonate), a hydroxide of an alkali metal (e.g., lithium hydroxide, sodium hydroxide, potassium hydroxide, cesium hydroxide); a salt of an organic base such as tri(lower)alkylamine (e.g., trimethylamine, triethylamine, N-ethyldiisopropylamine), pyridine, quinoline, piperidine, imidazole, picoline, dimethylaminopyridine, dimethylaniline, N-(lower)alkyl-morpholine (e.g., N-methylmorpholine), 1,5-diazabicyclo[4.3.0]nonene-5 (DBN), 1,8-diazabicyclo[5.4.0]undec-7-ene (DBU) and 1,4-diazabicyclo[2.2.2]octane (DABCO); a salt of an inorganic acid such as hydrochloride, hydrobromide, hydroiodide, sulfate, nitrate and phosphate; and a salt of an organic acid such as formic acid, acetate, propionate, oxalate, malonate, succinate, fumarate, maleate, lactate, malate, citrate, tartrate, carbonate, picrate, methanesulfonate, ethanesulfonate, p-toluenesulfonate and glutamate, etc.

Furthermore, compounds formed by adding a solvate (e.g., hydrate, ethanolate) to a raw material and a desired compound shown in each reaction formula are also included in each of the general formulas. As a preferable solvate, a hydrate is mentioned.

The desired compound obtained in each of the reaction formulas above can be isolated from a reaction mixture and purified, for example, by cooling the reaction mixture, subjecting it to an isolation operation such as filtration, concentration and extraction to separate a crude reaction product and subjecting to a customary purification operation such as column chromatography and recrystallization.

The compounds represented by the general formula (1) of the present invention, as a matter of course, include isomers such as a geometric isomer, a stereoisomer and an optical isomer.

Furthermore, the present invention may include an isotope-labeled compound, which is identical with a compound represented by the general formula (1) except that one or more atoms are substituted with one or more atoms having a specific atomic mass or mass number. Examples of the isotope to be integrated into a compound according to the present invention may include hydrogen, carbon, nitrogen, oxygen, sulfur, fluorine and chlorine isotopes such as $^2H$, $^3H$, $^{13}C$, $^{14}C$, $^{15}N$, $^{18}O$, $^{17}O$, $^{18}F$ and $^{36}Cl$, respectively. A compound according to the present invention labeled with a specific isotope, which includes the aforementioned isotopes and/or other isotopes of other atoms, for example, a compound according to the present invention labeled with a radio isotope such as $^3H$ and $^{14}C$, is useful in a drug tissue-distribution assay and/or a substrate tissue-distribution assay. Tritiated (that is, $^3H$) isotope and carbon-14 (that is $^{14}C$) isotope are particularly preferable since it is easily prepared and detected. Furthermore, if a heavier isotope such as heavy hydrogen (that is, $^2H$) is used in place, metabolic stability is improved, for example, in-vivo half time is increased or a requisite dose is reduced. Due to these, specific therapeutic benefits can be expected. An isotope labeled compound according to the present invention generally can be prepared in accordance with the aforementioned reaction formula and/or the method disclosed in Examples below by replacing a non-isotope labeled reagent with an easily available isotope-labeled reagent.

A compound of the general formula (1) and a salt thereof are used in the form of a general pharmaceutical preparation. The preparation is prepared using a diluent or an excipient usually used such as a filler, an extending agent, a binder, a moisturizing agent, a disintegrator, a surfactant and a lubricant. The dosage form of the pharmaceutical preparation can be selected from various forms depending upon the purpose of therapy. Typical examples thereof include a tablet, a pill, a powder, a liquid, a suspension, an emulsion, a grain, a capsule, a suppository and an injection (liquid, suspension, etc.), etc.

When the preparation is formed into a tablet, a wide variety of carriers conventionally known in this field can be used. Examples thereof that can be used may include an excipient such as lactose, white sugar, sodium chloride, glucose, urea, starch, calcium carbonate, kaolin, crystal cellulose and silica, a binder such as water, ethanol, propanol, simple syrup, a glucose solution, a starch solution, a gelatin solution, carboxymethylcellulose, shellac, methylcellulose, potassium phosphate and polyvinyl pyrrolidone, a disintegrator such as dry starch, sodium alginate, powdered agar, powdered laminaran, sodium hydrogen carbonate, calcium carbonate, a polyoxyethylene sorbitan fatty acid ester, sodium lauryl sulfate, stearic acid monoglyceride, starch and lactose, a disintegration suppressing agent such as white sugar, stearin, cacao butter and hydrogenated oil, an absorption promoter such as a quaternary ammonium base and sodium lauryl sulfate, a moisturizing agent such as glycerin and starch, an adsorbent such as starch, lactose, kaolin, bentonite, colloidal silica, and a lubricant such as purified talc, a stearate, powdered boric acid and polyethylene glycol. Furthermore, a tablet may be coated with a film usually used and formed into a sugar coating tablet, gelatin encapsulated tablet, an enteric coated tablet, a film coated tablet, or a double-layer tablet and a multi-layer tablet, etc.

When a preparation is formed into a pill, a wide variety of carriers conventionally known in this field can be used. For example, an excipient such as glucose, lactose, starch, cacao butter, hydrogenated vegetable oil, kaolin and talc, a binder such as powdered gum Arabic, powdered tragacanth, gelatin and ethanol, and a disintegrator such as laminaran and agar, can be used.

When a preparation is formed into a suppository, a wide variety of carriers conventionally known in this field can be used. As examples thereof, polyethylene glycol, cacao butter, a higher alcohol, an ester of a higher alcohol, gelatin and a semi-synthesized glyceride may be mentioned.

A capsule can be prepared usually by mixing an active-ingredient compound with a carrier as exemplified above and filling a capsule such as a hard gelatin capsule and a soft capsule with the mixture in accordance with a customary method.

When a preparation is prepared as an injection, a liquid, an emulsion and a suspension are preferably sterilized and rendered isotonic with blood. When a preparation is formed into these forms, all diluents customarily used in this field can be used. For example, water, ethyl alcohol, macrogol, propylene glycol, ethoxylated isostearyl alcohol, polyoxylated isostearyl alcohol and polyoxyethylene sorbitan fatty acid ester can be used.

Note that, in this case, a sufficient amount of salt, glucose or glycerin for preparing an isotonic solution may be contained in a pharmaceutical preparation or a general solubilization agent, a buffer and a soothing agent, etc. may be added. Furthermore, if necessary, a colorant, a preservative, a flavor and a sweetener, etc. and other medical drugs may be contained in a pharmaceutical preparation.

The amount of the compound of the general formula (1) or a salt thereof to be contained in a pharmaceutical preparation of the present invention is not particularly limited and may be appropriately selected from a broad range; however, it is usually about 1 to 70 wt %, and preferably, about 1 to 30 wt % in a preparation composition.

The method for administering a pharmaceutical preparation of the present invention is not particularly limited. The preparation is administered by a method selected in accordance with the dosage form, the age and gender of the patient, other conditions and the extent of the disease. For example, in the case of a tablet, a pill, a liquid, a suspension, an emulsion, a grain and a capsule, the preparation is orally administered. In the case of an injection, the preparation is intravenously injected singly or as a mixture with a fluid replacement usually used such as glucose and amino acid. Further, if necessary, the preparation is singly injected intramuscularly, subcutaneously, or intraperitoneally. In the case of a suppository, the preparation is administered intrarectally.

The dose of the pharmaceutical preparation of the present invention is appropriately selected depending upon the dosage form, the age and gender of the patient, other conditions and the extent of the disease; however, it may be usually about 0.1 to 10 mg per weight (kg) per day in terms of amount of active-ingredient compound. Furthermore, it is desirable to contain an active-ingredient compound in an amount within the range of about 1 to 200 mg in a dose unit of a preparation.

A compound according to the present invention can be used in combination with a medical drug (hereinafter, simply referred to as a concomitant drug) such as a therapeutic agent for diabetes, a therapeutic agent for a diabetic complication, a hypolipidemic agent, an antihypertensive agent, an anti-obesity agent and a diuretic agent for augmentation of the effect. The time for administrating a compound according to the present invention and a concomitant drug is not limited and they may be administered to a subject to be administered at the same time and at a time interval. Furthermore, a compound according to the present invention and a concomitant drug may be integrated into a combination drug. The dose of the concomitant drug can be appropriately selected based on the clinical dosage. Furthermore, the blending ratio of a compound according to the present invention and a concomitant drug can be appropriately selected depending upon the subject to be administered, administration route, target disease, symptom and combination, etc. For example, when a human is a subject to be administered, a concomitant drug may be used in an amount of 0.01 to 100 parts by weight based on the compound according to the present invention (1 part by weight).

Note that examples of the therapeutic agent for diabetes include an insulin preparation (e.g., an animal insulin preparation extracted from bovine and swine pancreas, human insulin preparation synthesized in a genetic engineering process using *Escherichia coli* or a yeast), an insulin-resistance improving agent (e.g., pioglitazone or a hydrochloride thereof, troglitazone, rosiglitazone or a maleate thereof, GI-262570, JTT-501, MCC-555, YM-440, KRP-297, CS-011), an α-glucosidase inhibitor (e.g., voglibose, acarbose, miglitol, emiglitate), a biguanide agent (e.g., metformin), an insulin-secretion accelerating agent (e.g., a sulfonylurea agent such as tolbutamide, glibenclamide, gliclazide, chlorpropamide, tolazamide, acetohexamide, glyclopyramide and glimepiride; repaglinide, senaglinide, nateglinide, mitiglinide), a dipeptidylpeptidase IV (DPP-IV) inhibitor (e.g., sitagliptin or a phosphate thereof, vildagliptin, alogliptin or a benzoate thereof, denagliptin or a tosyl acid salt), GLP-1, a GLP-1 analogue (exenatide, liraglutide, SUN-E7001, AVE010, BIM-51077, CJC1131), a protein tyrosine phosphate inhibitor (e.g., vanadium acid), and a β3 agonist (e.g., GW-427353B, N5984).

Examples of the therapeutic agent for a diabetic complication include an aldose reductase inhibitor (e.g., tolrestat, epalrestat, zenarestat, zopolrestat, minarestat, fidarestat, ranirestat, SK-860, CT-112); a neurotrophic factor (e.g., NGF, NT-3, BDNF), a PKC inhibitor (e.g., LY-333531), an AGE inhibitor (e.g., ALT946, pimagedine, piratoxathin, N-phenacylthiazolium bromide (ALT766)), an active oxygen eliminating agent (e.g., thioctic acid) and a cerebral vasodilator (e.g., tiapride, mexiletine). Examples of the hypolipidemic agent include a HMG-CoA reductase inhibitor (e.g., pravastatin, simvastatin, lovastatin, atorvastatin, fluvastatin, itavastatin or sodium salts thereof), a squalene synthase inhibitor and an ACAT inhibitor. Examples of the antihypertensive agent include an angiotensin-converting enzyme inhibitor (e.g., captopril, enalapril, alacepril, delapril, lisinopril, imidapril, benazepril, cilazapril, temocapril, trandolapril), an angiotensin II antagonist (e.g., olmesartan, medoxomil, candesartan, cilexetil, losartan, eprosartan, valsartan, telmisartan, irbesartan, tasosartan), a calcium antagonist (e.g., nicardipine hydrochloride, manidipine hydrochloride, nisoldipine, nitrendipin, nilvadipine, amlodipine).

Examples of the anti-obesity agent include a centrally-acting anti-obesity agent (e.g., phentermine, sibutramine, amfepramone, dexamfetamin, mazindol, SR-141716A), a pancreatic lipase inhibitor (e.g., orlistat), a peptidic appetite suppressor (e.g., leptin, CNTF (ciliary body neurotrophic factor)), a cholecystokinin agonist (e.g., lintitript, FPL-15849). Examples of the diuretic agent include a xanthine derivative (e.g., theobromine sodium salicylate, theobromine calcium salicylate), a thiazide preparation (e.g., ethiazide, cyclopenthiazide, trichlormethiazide, hydrochlorthiazide, hydroflumethiazide, bentyl hydrochlorothiazide, penflutizide, polythiazide, methyclothiazide), an antialdosterone preparation (e.g., spironolactone, triamterene), a carbonic anhydrase inhibitor (e.g., acetazolamide), a chlorobenzene sulfoneamide preparation (e.g., chlorthalidone, mefruside, indapamide), azosemide, isosorbide, ethacrynic acid, piretanide, bumetanide and furosemide.

Preferable examples of the concomitant drug include GLP-1, a GLP-1 analogue, an α-glucosidase inhibitor, a biguanide agent, an insulin-secretion accelerating agent and an insulin-resistance improver. The concomitant drugs may be used in appropriate combination of two or more.

When a compound according to the present invention is used in combination with a concomitant drug, the dose of these medical drugs can be reduced within the safe range in view of adverse drug reactions of the medical drugs. Particularly, the biguanide agent can be reduced than a general dose. Accordingly, adverse drug reactions that will be caused by these medical drugs can be safely prevented. In addition, the dosages of e.g., a diabetic complication agent, a hypolipidemic agent, an antihypertensive agent can be reduced. As a result, adverse drug reactions that will be caused by these medical drugs can be effectively prevented.

Advantages of the Invention

The compound of the present invention has a human GPR10 receptor antagonist effect.

The compound of the present invention has a strong suppression effect on stress-induced defecation in a restraint stress-induced defecation rat, which is used as a model of irritable bowel syndrome known as one of the stress-related diseases. Furthermore, the compound of the present invention, has a strong suppression effect on stress-induced eating behavior in a tale-pinch stress induced eating behavior rat used as a model of a stress induced bulimia.

The compound of the present invention effectively works on a stress-related disease caused by excessive stress load, for example, including a disorder of the respiratory system (e.g., bronchial asthma; hyperventilation syndrome), a gastrointestinal disorder (e.g., irritable bowel syndrome; gastric atony; gastric ulcer; duodenum ulcer; gastritis; ulcerative colitis), a cardiovascular system disorder (e.g., essential hypertension; orthostatic hypotension; arrhythmia; myocardial infarction; angina pectoris), an endocrine/metabolic disorder (e.g., obesity; diabetes; hyperthyroidism), a nervous system disorder (e.g., major depression; generalized anxiety disorder; panic disorder; obsessive-compulsive disorder; phobia; conversion disorder; dissociative disorder; posttraumatic stress syndrome; migraine headache; autonomic dysregulation), an eating disorder (e.g., bulimia nervosa; anorexia nervosa), a bone/muscle disorder (e.g., chronic rheumatoid arthritis; systemic myalgia; spinal irritation; tic syndrome; traumatic neurosis), dermatopathy (e.g., atopic dermatitis; chronic urticaria; alopecia areata; cutaneous pruritus), a urinary system disorder (e.g., enuresis; impotency; hypersensitive cystitis), an otorhinolaryngological disorder (e.g., Meniere syndrome; pharyngolaryngeal paresthesia; hearing loss; ringing in the ears; loss of voice; stutter), an oral cavity disorder (stomatitis; oral dysodia; abnormal salivation; dental prothesis neurotic disorder), an ophthalmic disorder (e.g., primary glaucoma; eyestrain; eyelid twitching) and a gynecologic disorder (e.g., dysmenorrhea; amenorrhea; menstrual disorder; menopausal disorder; frigidity).

EXAMPLES

For a better understanding of the present invention, Reference Examples, Examples and Pharmacological Tests will be described below.

Reference Example 1

Synthesis of ethyl-4-phenoxycarbonylamino-1-tert-butoxycarbonyl-1,2,5,6-tetrahydropyridine-3-carboxylate

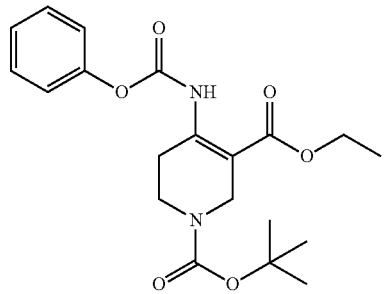 [SMILES: CCOC(=O)C1=C(NC(=O)Oc2ccccc2)CCN(C(=O)OC(C)(C)C)C1]

Ethyl-4-amino-1-tert-butoxycarbonyl-1,2,5,6-tetrahydropyridine-3-carboxylate (23.6 g) was dissolved in methylene chloride (460 ml), and pyridine (13 ml) and phenyl chlorocarbonate (15 ml) were added under ice cooling and the resultant mixture was stirred for one hour at the same temperature. To the reaction solution, water was added and the mixture was extracted with methylene chloride. After the organic layer was washed sequentially with 1 N hydrochloric acid and saturated saline solution in this order, the organic layer was dried over sodium sulfate, filtrated and concentrated under reduced pressure. To the resultant residue, diethyl ether was added to obtain a precipitate by filtration. The titled compound (10.57 g) was obtained as a colorless solid substance. Furthermore, the filtrate was concentrated under reduced pressure. Thereafter, the resultant residue was purified by medium-pressure silica gel column (solvent; ethyl acetate:hexane=10:90 to 50:50). The resultant crude crystal was washed with a solvent mixture of diethyl ether-hexane to obtain the titled compound (11.10 g) as a slightly yellow solid substance.

$^1$H-NMR (CDCl$_3$) δ ppm: 1.32 (t, J=7.1 Hz, 3H), 1.48 (s, 9H), 3.02 (t, J=5.9 Hz, 2H), 3.52 (t, J=5.9 Hz, 2H), 4.18 (brs, 2H), 4.24 (q, J=7.1 Hz, 2H), 7.13 (t, J=7.8 Hz, 2H), 7.19-7.25 (m, 1H), 7.37 (t, J=7.8 Hz, 2H), 11.36 (s, 1H).

Reference Example 2

Synthesis of 6-(tert-butoxycarbonyl)-3-propargyl-5,6,7,8-tetrahydropyrido[4,3-d]pyrimidine-2,4-dione

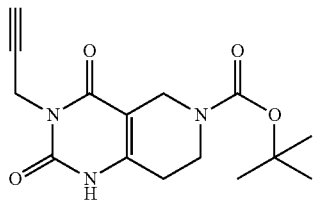 [SMILES: C#CCn1c(=O)[nH]c2c(c1=O)CN(C(=O)OC(C)(C)C)CC2]

Ethyl-4-phenoxycarbonylamino-1-tert-butoxycarbonyl-1,2,5,6-tetrahydropyridine-3-carboxylate (5.0 g) was dissolved in THF (50 ml), and propargylamine (1.32 ml) and 1,8-diazabicyclo[5.4.0]-7-undecene (DBU) (0.2 ml) were added and the resultant mixture was stirred at room temperature for 2 hours. After production of an intermediate (urea) was confirmed by TLC, a 5 N aqueous sodium hydroxide solution (5 ml) was added and the resultant mixture was further stirred at room temperature for 2 hours. To the reaction solution, 6 N hydrochloric acid was added to neutralize and the resultant mixture was then concentrated. To the residue, water was added and the mixture was extracted with ethyl acetate. After the organic layer was washed with a saturated saline solution, the organic layer was dried over sodium sulfate, filtrated and concentrated under reduced pressure. A precipitate was obtained by filtration. The titled compound (3.78 g) was obtained as a white powder.

$^1$H-NMR (CDCl$_3$) δ ppm: 1.48 (s, 9H), 2.18 (t, J=2.4 Hz, 1H), 2.54 (t, 5.7 Hz, 2H), 3.68 (t, J=5.7 Hz, 2H), 4.24 (s, 2H), 4.69 (d, J=2.4 Hz, 2H), 9.82 (brs, 1H).

Reference Example 3

Synthesis of 6-(tert-butoxycarbonyl)-2-(S)-{1-[4-(trifluoromethyl)phenyl]ethylamino}-3-propargyl-5,6,7,8-tetrahydropyrido[4,3-d]pyrimidine-4-(3H)-one

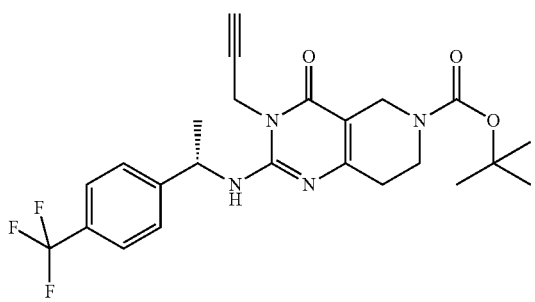 [SMILES: C#CCn1c(N[C@@H](C)c2ccc(C(F)(F)F)cc2)nc2c(c1=O)CN(C(=O)OC(C)(C)C)CC2]

6-(tert-Butoxycarbonyl)-3-propargyl-5,6,7,8-tetrahydropyrido[4,3-d]pyrimidine-2,4-dione (1.0 g) was dissolved in tetrahydrofuran (20 ml) and 1H-benzotriazol-1-yloxytris(dimethylamino)phosphonium hexafluorophosphate (BOP) (2.17 g) and 1,8-diazabicyclo[5.4.0]-7-undecene (DBU) (0.76 ml) were added and the resultant mixture was stirred at room temperature. At 10 minutes later, (S)-1-[4-(trifluoromethyl)phenyl]ethylamine (0.93 ml) was added and the resultant mixture was stirred at room temperature overnight. The reaction solution was concentrated under reduced pressure and a saturated aqueous sodium hydrogen carbonate solution was added to the residue and the mixture was extracted with ethyl acetate. The organic layer was washed with a saturated saline solution and thereafter dried over sodium sulfate, filtrated and concentrated under reduced pressure. The resultant residue was purified by medium-pressure silica gel column (solvent; ethyl acetate:hexane=20:80 to 90:10). The titled compound (520 mg) was obtained as a colorless amorphous substance.

$^1$H-NMR (CDCl$_3$) δ ppm: 1.46 (s, 9H), 1.60 (d, J=6.7 Hz, 3H), 2.30-2.61 (m, 3H), 3.44-3.71 (m, 2H), 4.15-4.36 (m, 2H), 4.88 (d, J=2.6 Hz, 2H), 5.21-5.40 (m, 2H), 7.48 (d, J=8.2 Hz, 2H), 7.60 (d, J=8.2 Hz, 2H).

Reference Example 4

Synthesis of 6-(tert-butoxycarbonyl)-3-propargyl-2-(S)-[1-(4-chlorophenyl)ethylamino]-5,6,7,8-tetrahydropyrido[4,3-d]pyrimidin-4-(3H)-one

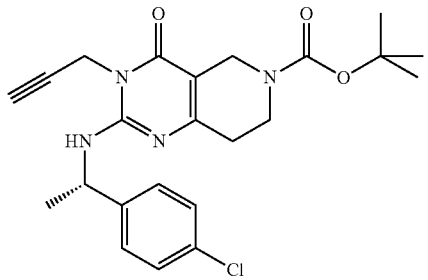 [SMILES: C#CCn1c(N[C@@H](C)c2ccc(Cl)cc2)nc2c(c1=O)CN(C(=O)OC(C)(C)C)CC2]

Synthesis was performed in the same manner as in Reference Example 3.

Colorless Amorphous $^1$H-NMR (CDCl$_3$) δ ppm: 1.47 (s, 9H), 1.57 (d, J=6.9 Hz, 3H), 2.35-2.60 (m, 3H), 3.50-3.70 (m, 2H), 4.15-4.35 (m, 2H), 4.85 (d, J=2.5H, 2H), 5.20-5.25 (m, 2H), 7.31 (s, 4H).

Reference Example 5

Synthesis of 6-(tert-butoxycarbonyl)-3-dimethylamino-5,6,7,8-tetrahydropyrido[4,3-d]pyrimidine-2,4-dione

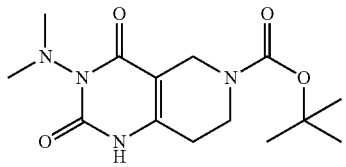 [SMILES: CN(C)n1c(=O)[nH]c2c(c1=O)CN(C(=O)OC(C)(C)C)CC2]

Ethyl-4-phenoxycarbonylamino-1-tert-butoxycarbonyl-1,2,5,6-tetrahydropyridine-3-carboxylate (5.0 g) was dissolved in THF (50 ml) and dimethyl hydrazine (1.46 ml) and DBU (0.2 ml) were added and the resultant mixture was stirred at room temperature for 2 hours. Dimethylhydrazine (0.73 ml) and DBU (0.2 ml) were added and the resultant mixture was further stirred at room temperature for 2 hours. After production of an intermediate (urea) was confirmed by TLC, a 5 N aqueous sodium hydroxide solution (5 ml) was added and the resultant mixture was further stirred at room temperature overnight. To the reaction solution, 6 N hydrochloric acid was added to neutralize and the resultant mixture was then concentrated. To the residue, water was added and the mixture was extracted with ethyl acetate. After the organic layer was washed with a saturated saline solution, the organic layer was dried over sodium sulfate, filtrated and concentrated. The resultant residue was purified by medium-pressure silica gel column chromatography (solvent; ethyl acetate:hexane=50:50 to 100:0). To the resultant amorphous substance, diethyl ether was added to obtain a precipitate by filtration. The titled compound (3.34 g) was obtained as a white powder.

$^1$H-NMR (CDCl$_3$) δ ppm: 1.48 (s, 9H), 2.48 (t, J=5.7 Hz, 2H), 2.97 (s, 6H), 3.65 (t, J=5.7 Hz, 2H), 4.21 (s, 2H), 9.20 (brs, 1H).

Reference Example 6

Synthesis of 6-(tert-butoxycarbonyl)-2-(S)-{1-[4-(trifluoromethyl)phenyl]ethylamino}-3-dimethylamino-5,6,7,8-tetrahydropyrido[4,3-d]pyrimidin-4-(3H)-one

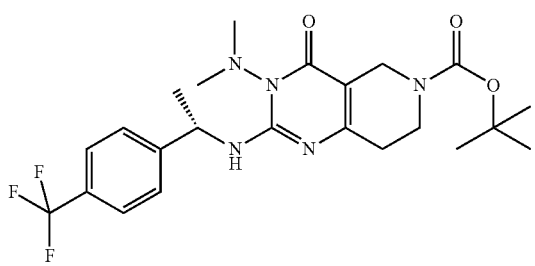 [SMILES: C[C@H](Nc1nc2c(c(=O)n1N(C)C)CN(C(=O)OC(C)(C)C)CC2)c1ccc(C(F)(F)F)cc1]

6-(tert-Butoxycarbonyl)-3-dimethylamino-5,6,7,8-tetrahydropyrido[4,3-d]pyrimidine-2,4-dione (1.0 g) was dissolved in tetrahydrofuran (20 ml) and 1H-benzotriazol-1-yloxytris(dimethylamino)phosphonium hexafluorophosphate (BOP) (2.17 g) and 1,8-diazabicyclo[5.4.0]-7-undecene (DBU) (0.76 ml) were added and the resultant mixture was stirred at room temperature. At 10 minutes later, (S)-1-[4-(trifluoromethyl)phenyl]ethylamine (0.93 ml) was added and the resultant mixture was further stirred at room temperature overnight. The reaction solution was distilled away under reduced pressure. To the residue, a saturated aqueous sodium hydrogen carbonate solution was added and the mixture was extracted with ethyl acetate. After the organic layer was washed with a saturated saline solution, the organic layer was dried over sodium sulfate, filtrated and concentrated. The resultant residue was purified by medium-pressure silica gel column chromatography (solvent; ethyl acetate:hexane=20:80 to 70:30). The titled compound (990 mg) was obtained as a colorless amorphous substance.

$^1$H-NMR (CDCl$_3$) δ ppm: 1.46 (s, 9H), 1.56 (d J=7.0 Hz, 3H), 2.30-2.57 (m, 2H), 2.93-3.11 (m, 6H), 3.45-3.70 (m, 2H), 4.10-4.30 (m, 2H), 5.11-5.28 (m, 1H), 6.85 (d, J=8.0 Hz, 1H), 7.44 (d, J=8.1 Hz, 2H), 7.59 (d, J=8.1 Hz, 21-1).

Reference Example 7

Synthesis of 6-(tert-butoxycarbonyl)-3-dimethylamino-2-[3-fluoro-4-(trifluoromethyl)benzylamino]-5,6,7,8-tetrahydropyrido[4,3-d]pyrimidin-4-(3H)-one

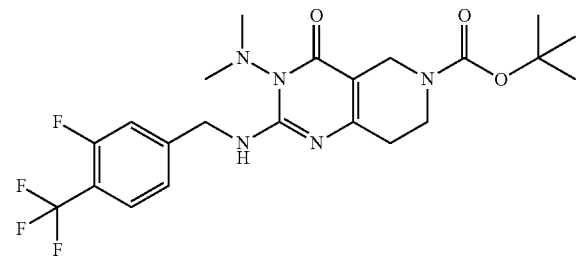 [SMILES: CN(C)n1c(NCc2ccc(C(F)(F)F)c(F)c2)nc2c(c1=O)CN(C(=O)OC(C)(C)C)CC2]

Synthesis was performed in the same manner as in Reference Example 6.

Colorless Amorphous.

$^1$H-NMR (CDCl$_3$) δ ppm: 1.48 (s, 9H), 2.40-2.52 (m, 2H), 3.02 (s, 6H), 3.59 (t, J=5.7 Hz, 2H), 4.20-4.25 (m, 2H), 4.63 (d, J=6.2 Hz, 2H), 7.01 (t, J=6.2 Hz, 1H), 7.15-7.19 (m, 2H), 7.57 (t, J=7.6 Hz, 1H).

Reference Example 8

Synthesis of 6-(tert-butoxycarbonyl)-2-(S)-[1-(4-chlorophenyl)ethylamino]-3-dimethylamino-5,6,7,8-tetrahydropyrido[4,3-d]pyrimidin-4-(3H)-one

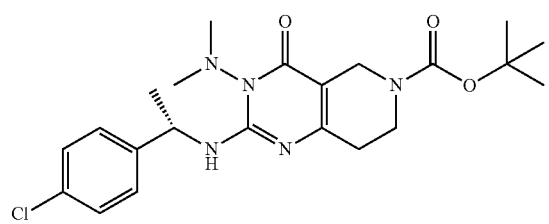 [SMILES: C[C@H](Nc1nc2c(c(=O)n1N(C)C)CN(C(=O)OC(C)(C)C)CC2)c1ccc(Cl)cc1]

Synthesis was performed in the same manner as in Reference Example 6.

Colorless Amorphous.

$^1$H-NMR (CDCl$_3$) δ ppm: 1.47 (s, 9H), 1.53 (d, J=6.9 Hz, 3H), 2.41-2.51 (m, 2H), 2.98 (s, 3H), 3.02 (s, 3H), 3.50-3.60 (m, 2H), 4.18-4.25 (m, 2H), 5.11-5.15 (m, 1H), 6.79 (d, J=8.1 Hz, 1H), 7.25-7.32 (m, 4H).

Reference Example 9

Synthesis of 6-(tert-butoxycarbonyl)-3-methoxy-5,6,7,8-tetrahydropyrido[4,3-d]pyrimidine-2,4-dione

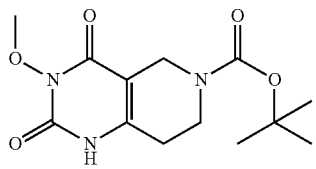 [SMILES: COn1c(=O)[nH]c2c(c1=O)CN(C(=O)OC(C)(C)C)CC2]

Ethyl-4-phenoxycarbonylamino-1-tert-butoxycarbonyl-1,2,5,6-tetrahydropyridine-3-carboxylate (3.0 g) was dissolved in THF (30 ml) and O-methylhydroxylamine hydrochloride (3.2 g), triethylamine (5.35 ml) and DBU (0.3 ml) were added to the solvent, and the resultant mixture was stirred at room temperature overnight. O-methylhydroxylamine hydrochloride (3.2 g) and triethylamine (5.35 ml) were added and the resultant mixture was further stirred at room temperature for 6 hours. After production of an intermediate (urea) was confirmed by TLC, a 5 N sodium hydroxide solution (5 ml) was added and the resultant mixture was further stirred at room temperature overnight. To the reaction solution, 6 N hydrochloric acid was added, and the resultant mixture was neutralized and concentrated to obtain a precipitate by filtration. The resultant crude crystal was dissolved in methylene chloride-methanol and ethyl acetate was added to obtain a precipitate by filtration. The resultant crude crystal was purified by medium-pressure silica gel column chromatography (solvent; methanol:ethyl acetate=0:100 to 10:90). The titled compound (2.21 g) was obtained as a white powder.

$^1$H-NMR (CDCl$_3$) δ ppm: 1.48 (s, 9H), 2.53 (t, J=5.7 Hz, 2H), 3.67 (t, J=5.7 Hz, 2H), 4.00 (s, 3H), 4.25 (s, 2H), 9.56 (brs, 1H).

Reference Example 10

Synthesis of 6-(tert-butoxycarbonyl)-2-(S)-{1-[4-(trifluoromethyl)phenyl]ethylamino}-3-methoxy-5,6,7,8-tetrahydropyrido[4,3-d]pyrimidin-4-(3H)-one

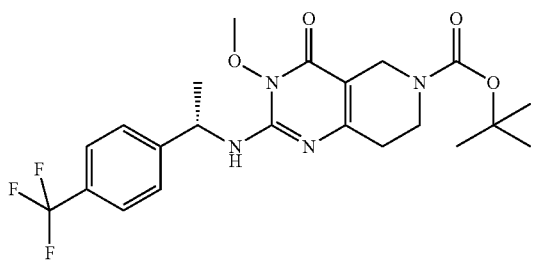 [SMILES: COn1c(N[C@@H](C)c2ccc(C(F)(F)F)cc2)nc2c(c1=O)CN(C(=O)OC(C)(C)C)CC2]

6-(tert-Butoxycarbonyl)-3-methoxy-5,6,7,8-tetrahydropyrido[4,3-d]pyrimidine-2,4-dione (1.0 g) was dissolved in tetrahydrofuran (20 ml) and 1H-benzotriazol-1-yloxytris(dimethylamino)phosphonium hexafluorophosphate (BOP) (2.17 g), and 1,8-diazabicyclo[5.4.0]-7-undecene (DBU) (0.76 ml) were added and the resultant mixture was stirred at room temperature. At 10 minutes later, (S)-1-[4-(trifluoromethyl)phenyl]ethylamine (0.93 ml) was added and the resultant mixture was further stirred at room temperature overnight. The reaction solution was distilled away under reduced pressure, a saturated aqueous sodium hydrogen carbonate solution was added to the residue and the mixture was extracted with ethyl acetate. After the organic layer was washed with a saturated saline solution, the organic layer was dried over sodium sulfate, filtrated and concentrated. The resultant residue was purified by medium-pressure silica gel column chromatography (solvent; ethyl acetate:hexane=20:80 to 90:10). The titled compound (788 mg) was obtained as a slightly yellow amorphous substance.

$^1$H-NMR (CDCl$_3$) δ ppm: 1.43 (s, 9H), 1.61 (d, J=7.0 Hz, 3H), 2.31-2.60 (m, 2H), 3.39-3.64 (m, 2H), 3.85-4.40 (m, 5H), 5.13-5.31 (m, 1H), 5.61-6.00 (m, 1H), 7.40-7.58 (m, 2H), 7.61 (d, J=8.3 Hz, 2H).

Reference Example 11

Synthesis of 6-(tert-butoxycarbonyl)-3-methoxy-2-(S)-[1-(4-chlorophenyl)ethylamino]-5,6,7,8-tetrahydropyrido[4,3-d]pyrimidin-4-(3H)-one

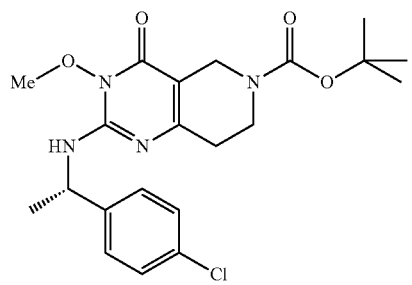 [SMILES: COn1c(N[C@@H](C)c2ccc(Cl)cc2)nc2c(c1=O)CN(C(=O)OC(C)(C)C)CC2]

Synthesis was performed in the same manner as in Reference Example 10.

Colorless Amorphous.

$^1$H-NMR (CDCl$_3$) δ ppm: 1.47 (s, 9H), 1.57 (d, J=6.9 Hz, 3H), 2.35-2.60 (m, 2H), 3.50-3.70 (m, 2H), 4.04 (s, 3H), 4.15-4.35 (m, 2H), 5.15-5.25 (m, 1H), 5.55-5.75 (m, 1H), 7.20-7.40 (m, 4H).

Reference Example 12

Synthesis of 2-(S)-{1-[4-(trifluoromethyl)phenyl]ethylamino}-3-dimethylamino-5,6,7,8-tetrahydropyrido[4,3-d]pyrimidin-4-(3H)-one

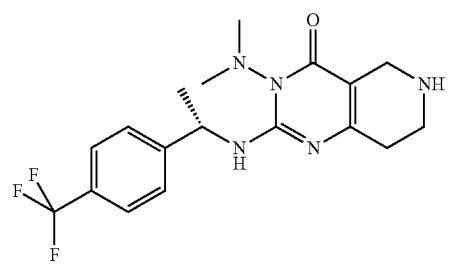 [SMILES: C[C@H](Nc1nc2c(c(=O)n1N(C)C)CNCC2)c1ccc(C(F)(F)F)cc1]

6-(tert-Butoxycarbonyl)-2-(S)-{1-[4-(trifluoromethyl) phenyl]ethylamino}-3-dimethylamino-5,6,7,8-tetrahydropyrido[4,3-D]pyrimidin-4-(3H)-one (990 mg) was dissolved in methylene chloride (10 ml), trifluoroacetic acid (3 ml) was added under ice cooling and the resultant mixture was stirred at room temperature overnight. Under ice cooling, the reaction mixture was alkalified with sodium hydroxide solution, and the mixture was extracted with methylene chloride. After the organic layer was washed with a saturated saline solution, the organic layer was dried over sodium sulfate, filtrated and concentrated to obtain the titled compound (733 mg) as a colorless amorphous substance. The resultant compound was used in a next reaction without further purifying.

$^1$H-NMR (CDCl$_3$) δ ppm: 1.56 (d, J=7.0 Hz, 3H), 2.25-2.50 (m, 2H), 2.92-3.12 (m, 8H), 3.57-3.73 (m, 2H), 5.12-5.29 (m, 2H), 6.83 (d, J=8.0 Hz, 1H), 7.45 (d, J=8.2 Hz, 2H), 7.59 (d, J=8.2 Hz, 2H).

Reference Example 13

Synthesis of 2-(S)-{1-[4-(trifluoromethyl)phenyl] ethylamino}-3-methoxy-5,6,7,8-tetrahydropyrido[4,3-d]pyrimidin-4-(3H)-one

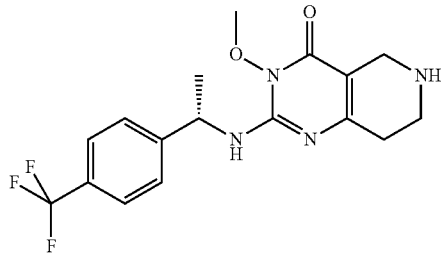 [SMILES: COn1c(N[C@@H](C)c2ccc(C(F)(F)F)cc2)nc2c(c1=O)CNCC2]

6-(tert-Butoxycarbonyl)-2-(S)-{1-[4-(trifluoromethyl) phenyl]ethylamino}-3-methoxy-5,6,7,8-tetrahydropyrido[4,3-d]pyrimidin-4-(3H)-one (788 mg) was dissolved in methylene chloride (5 ml), trifluoroacetic acid (2 ml) was added under ice cooling and the resultant mixture was stirred at room temperature overnight. Under ice cooling, the reaction mixture was alkalified with sodium hydroxide solution, and the mixture was extracted with methylene chloride. After the organic layer was washed with a saturated saline solution, the organic layer was dried over sodium sulfate, filtrated and concentrated to obtain the titled compound (310 mg) as a colorless amorphous substance. The resultant compound was used in a next reaction without further purifying.

$^1$H-NMR (CDCl$_3$) δ ppm: 1.60 (d, J=7.0 Hz, 3H), 2.28-2.42 (m, 2H), 2.93-3.11 (m, 2H), 3.60-3.80 (m, 2H), 4.06 (s, 3H), 5.18-5.35 (m, 1H), 5.61 (d, J=7.7 Hz, 1H), 7.47 (d, J=8.2 Hz, 2H), 7.61 (d, J=8.2 Hz, 2H). Amine H was not observed.

Reference Example 14

Synthesis of tert-butyl-2,4-dioxo-3-(pyrrolidin-1-yl)-1,2,3,4,7,8-hexahydropyrido[4,3-d]pyrimidine-6(5H)-carboxylate

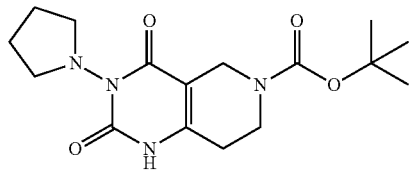 [SMILES: CC(C)(C)OC(=O)N1CCc2[nH]c(=O)n(N3CCCC3)c(=O)c2C1]

Under nitrogen, 1-tert-butyl 3-ethyl 4-(phenoxycarbonylamino)-5,6-dihydropyridine-1,3(2H)-dicarboxylate (6.14 g) was dissolved in THF (50 ml) and 1-aminopyrrolidine hydrochloride (2.31 g), triethylamine (6.58 ml) and 1,8-diazabicyclo[5.4.0]und-7-ene (0.24 ml) were added, and the resultant mixture was stirred at room temperature for 2 hours. Thereafter, the reaction solution was stirred at 50° C. for 2 hours and 68° C. for 3 hours. After consumption of the raw materials was confirmed by TLC or LC/MS, to the reaction mixture 2 N sodium hydroxide solution (15.7 ml) was added at 0° C., and the resultant mixture was stirred at room temperature for two days. Thereafter, the solution was stirred at 50° C. for 3 hours and further 2 N sodium hydroxide solution (10 ml) was added at the same temperature. The reaction mixture was stirred at 68° C. for 2 hours. After the completion of the reaction was confirmed by TLC or LC/MS, the solution was cooled to room temperature, 2 N hydrochloric acid (30 ml) and a saturated ammonium chloride solution were added, the resultant mixture was extracted with ethyl acetate and dried over sodium sulfate. The solution was filtrated, concentrated and purified by silica gel chromatography to obtain desired tert-butyl-2,4-dioxo-3-(pyrrolidin-1-yl)-1,2,3,4,7,8-hexahydropyrido[4,3-d]pyrimidine-6(5H)-carboxylate in an amount of 3.19 g (yield 60%).

$^1$H-NMR (DMSO-d$_6$) δ ppm: 11.10 (brs, 1H), 4.02 (brs, 2H), 3.50 (brt, J=5.68 Hz, 4H), 3.11 (brt, J=6.52 Hz, 2H), 2.37 (brt, J=5.68 Hz, 2H), 1.84 (m, 4H), 1.41 (s, 9H).

Reference Example 15

Synthesis of 2-(S)-{1-[4-(trifluoromethyl)phenyl] ethylamino}-3-propargyl-5,6,7,8-tetrahydropyrido[4,3-d]pyrimidin-4-(3H)-one

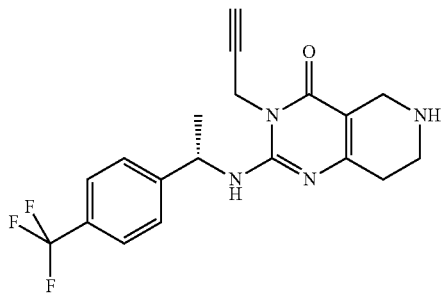 [SMILES: C#CCn1c(N[C@@H](C)c2ccc(C(F)(F)F)cc2)nc2c(c1=O)CNCC2]

6-(tert-Butoxycarbonyl)-2-(S)-{1-[4-(trifluoromethyl) phenyl]ethylamino}-3-propargyl-5,6,7,8-tetrahydropyrido

[4,3-d]pyrimidin-4-(3H)-one (520 mg) was dissolved in methylene chloride (10 ml), trifluoroacetic acid (3 ml) was added under ice cooling and the resultant mixture was stirred at room temperature overnight. Under ice cooling, the reaction mixture was alkalified with sodium hydroxide solution, and the mixture was extracted with methylene chloride. After the organic layer was washed with saturated saline solution, the organic layer was dried over sodium sulfate, filtrated and concentrated to obtain the titled compound (402 mg) as a colorless amorphous substance. The resultant compound was used in a next reaction without further purifying.

$^1$H-NMR (CDCl$_3$) δ ppm: 1.60 (d, J=6.8 Hz, 3H), 2.30-2.57 (m, 3H), 2.96-3.18 (m, 2H), 3.63-3.79 (m, 2H), 4.87 (d, J=2.4 Hz, 2H), 5.18-5.41 (m, 2H), 7.48 (d, J=8.0 Hz, 2H), 7.59 (d, J=8.0 Hz, 2H). Amine H was not observed.

Reference Example 16

Synthesis of 3-propargyl-5,6,7,8-tetrahydropyrido[4,3-d]pyrimidine-2,4-dione hydrochloride

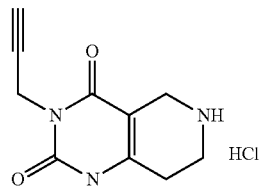

6-(tert-Butoxycarbonyl)-3 propargyl-5,6,7,8-tetrahydropyrido[4,3-d]pyrimidine-2,4-dione (1.0 g) was suspended in 4 N hydrochloric acid in ethyl acetate (10 ml) and the resultant mixture was stirred at room temperature for 3 hours. A precipitate was obtained by filtration and dissolved in ethanol and the solvent was distilled away under reduced pressure. This was repeated three times to obtain the titled compound (790 mg) as a colorless amorphous substance. The resultant compound was subjected to a next reaction without further purifying.

$^1$H-NMR (DMSO-d$_6$) δ ppm: 2.60-2.74 (m, 2H), 3.08-3.11 (m, 1H), 3.21-3.35 (m, 2H), 3.77 (s, 2H), 4.41-4.52 (m, 2H), 9.38 (brs, 2H), 11.61 (s, 1H).

Reference Example 17

Synthesis of 6-(4-chlorobenzoyl)-3-propargyl-5,6,7,8-tetrahydropyrido[4,3-d]pyrimidine-2,4-dione

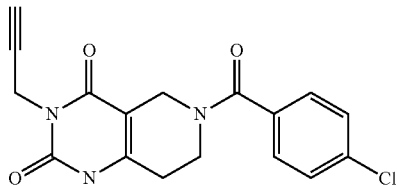 [SMILES: C#CCn1c(=O)[nH]c2c(c1=O)CN(C(=O)c1ccc(Cl)cc1)CC2]

3-propargyl-5,6,7,8-tetrahydropyrido[4,3-d]pyrimidine-2,4-dione hydrochloride (790 mg) was suspended in methylene chloride, triethylamine (0.95 ml) and 4-chlorobenzoyl chloride (0.42 ml) were added under ice cooling and the resultant mixture was stirred at the same temperature for 30 minutes. To the reaction solution, water was added and the resultant mixture was concentrated. To the residue, diethyl ether was added and insoluble matter was separated by filtration to obtain the titled compound (894 mg) as a white powder. The resultant compound was used in a next reaction without further purifying.

$^1$H-NMR (DMSO-d$_6$) δ ppm: 2.46-2.60 (m, 2H), 2.90-3.12 (m, 1H), 3.41-3.92 (m, 2H), 3.94-4.38 (m, 2H), 4.38-4.64 (m, 2H), 7.43-7.58 (m, 4H), 11.41 (brs, 1H).

Reference Example 18

Synthesis of 3-methoxy-5,6,7,8-tetrahydropyrido[4,3-d]pyrimidine-2,4-dione hydrochloride

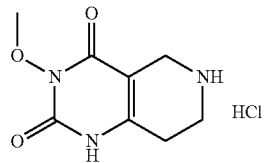

6-(tert-Butoxycarbonyl)-3-methoxy-5,6,7,8-tetrahydropyrido[4,3-d]pyrimidine-2,4-dione (1.0 g) was suspended in 4 N hydrochloric acid in ethyl acetate (10 ml) and the resultant mixture was stirred at room temperature for 3 hours. The reaction solution was distilled away under reduced pressure. To the residue, methanol was added and the solvent was distilled away under reduced pressure. This was repeated three times to obtain the titled compound (790 mg) as a white powder. The resultant compound was used in a next reaction without further purifying.

$^1$H-NMR (DMSO-d$_6$) δ ppm: 2.62-2.72 (m, 2H), 3.22-3.35 (m, 2H), 3.68-3.79 (m, 2H), 3.81 (s, 3H), 9.56 (brs, 2H), 11.72 (brs, 1H).

Reference Example 19

Synthesis of 6-(4-chlorobenzoyl)-3-methoxy-5,6,7,8-tetrahydropyrido[4,3-d]pyrimidine-2,4-dione

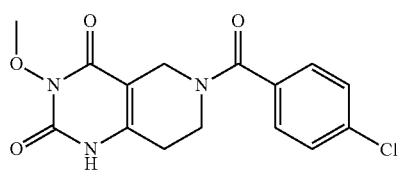 [SMILES: COn1c(=O)[nH]c2c(c1=O)CN(C(=O)c1ccc(Cl)cc1)CC2]

3-Methoxy-5,6,7,8-tetrahydropyrido[4,3-d]pyrimidine-2,4-dione hydrochloride (790 mg) was suspended in methylene chloride, and triethylamine (1.17 ml) and 4-chlorobenzoyl chloride (0.43 ml) were added under ice cooling and the resultant mixture was stirred at the same temperature for 1.5 hours. To the reaction solution, water was added and the resultant mixture was concentrated. To the residue, diethyl ether was added and insoluble matter was obtained by filtration. The titled compound (684 mg) was obtained as a white powder. The resultant compound was used in a next reaction without further purifying.

$^1$H-NMR (DMSO-d$_6$) δ ppm: 2.40-2.55 (m, 2H), 3.39-3.92 (m, 5H), 3.92-4.40 (m, 2H), 7.48 (d J=8.5 Hz, 2H), 7.54 (d, J=8.5 Hz, 2H), 11.45 (brs, 1H).

Reference Example 20

Synthesis of ethyl 1-(4-chlorobenzoyl)-4-piperidone-3-carboxylate

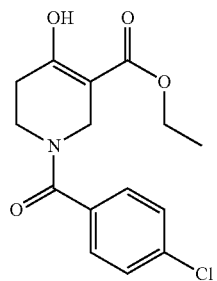 [SMILES: CCOC(=O)C1=C(O)CCN(C(=O)c2ccc(Cl)cc2)C1]

Ethyl 4-piperidone-3-carboxylate hydrochloride (10 g) was suspended in methylene chloride (250 ml), triethylamine (16 ml) and 4-chlorobenzoyl chloride (7.2 ml) were added and the resultant mixture was stirred one hour under ice cooling. To the reaction solution, water was added and the mixture was extracted with methylene chloride. After the organic layer was washed with a saturated saline solution, the organic layer was dried over sodium sulfate, filtrated and concentrated. The resultant residue was purified by medium-pressure silica gel column chromatography (solvent; ethyl acetate:hexane=33:67 to 50:50). The titled compound (15.95 g) was obtained as a colorless solid substance.
$^1$H-NMR (CDCl$_3$) δ ppm: 1.20-1.40 (m, 3H), 2.30-2.71 (m, 2H), 3.42-4.00 (m, 2H), 4.00-4.51 (m, 4H), 7.29-7.48 (m, 4H), 12.1 (s, 1H).

Reference Example 21

Synthesis of ethyl-4-amino-1-(4-chlorobenzoyl)-1,2,5,6-tetrahydropyridine-3-carboxylate

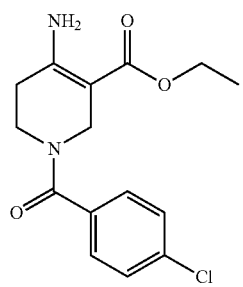 [SMILES: CCOC(=O)C1=C(N)CCN(C(=O)c2ccc(Cl)cc2)C1]

Ethyl 1-(4-chlorobenzoyl)-4-piperidone-3-carboxylate (15.9 g) was dissolved in toluene (200 ml), ammonium acetate (12.0 g) and acetic acid (3.0 ml) were added and the resultant mixture was heated to reflux for 5 hours by use of Dean-Stark apparatus. To the reaction solution, a saturated aqueous sodium hydrogen carbonate solution was added and the mixture was extracted with ethyl acetate. After the organic layer was washed with a saturated saline solution, the organic layer was dried over sodium sulfate, filtrated and concentrated. The resultant residue was subjected to medium-pressure column fractionation (solvent; ethyl acetate:hexane=33:67 to 50:50). A crude crystal was washed with diethyl ether to obtain the titled compound (13.97 g) as a white powder.
$^1$H-NMR (CDCl$_3$) δ ppm: 1.07-1.36 (m, 3H), 2.25-2.52 (m, 2H), 3.31-3.98 (m, 2H), 4.01-4.49 (m, 4H), 7.30-7.48 (m, 4H). Amine H was not observed.

Reference Example 22

Synthesis of ethyl-4-phenoxycarbonylamino-1-(4-chlorobenzoyl)-1,2,5,6-tetrahydropyridine-3-carboxylate

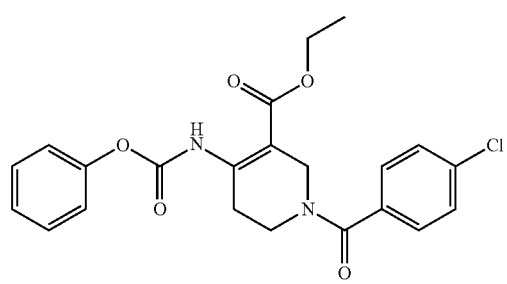 [SMILES: CCOC(=O)C1=C(NC(=O)Oc2ccccc2)CCN(C(=O)c2ccc(Cl)cc2)C1]

Ethyl-4-amino-1-(4-chlorobenzoyl)-1,2,5,6-tetrahydropyridine-3-carboxylate (7.0 g) was dissolved in methylene chloride (140 ml), pyridine (6.0 ml) and phenyl chlorocarbonate (6.0 ml) were added under ice cooling, and the resultant mixture was stirred at room temperature for 2 hours. To the reaction solution, water was added and the mixture was extracted with methylene chloride. After the organic layer was washed with citric acid solution and a saturated saline solution, the organic layer was dried over sodium sulfate, filtrated and concentrated. The resultant residue was subjected to medium-pressure column fractionation (solvent; ethyl acetate:hexane=20:80 to 60:40). The titled compound (8.35 g) was obtained as a white powder.
$^1$H-NMR (CDCl$_3$) δ ppm: 1.20-1.44 (m, 3H), 2.98-3.23 (m, 2H), 3.38-3.94 (m, 2H), 4.06-4.54 (m, 4H), 7.13 (d, J=5.5 Hz, 2H), 7.20-7.25 (m, 1H), 7.29-7.47 (m, 6H), 11.4 (brs, 1H).

Reference Example 23

Synthesis of 6-(4-chlorobenzoyl)-3-dimethylamino-5,6,7,8-tetrahydropyrido[4,3-d]pyrimidine-2,4-dione

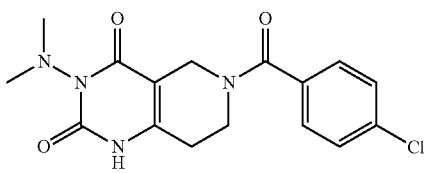 [SMILES: CN(C)n1c(=O)[nH]c2c(c1=O)CN(C(=O)c1ccc(Cl)cc1)CC2]

Ethyl-4-phenoxycarbonylamino-1-(4-chlorobenzoyl)-1,2,5,6-tetrahydropyridine-3-carboxylate (200 mg) was dissolved in THF (2 ml), N,N-dimethylhydrazine (142 μl) and DBU (10 μl) were added and the resultant mixture was shaken at 50° C. for 3 hours. 5 N sodium hydroxide solution (200 μl) was added and the resultant mixture was further shaken at 50° C. overnight. To the reaction solution, acetic acid (300 μl) was added to neutralize, and the reaction solution was then concentrated. The resultant residue was subjected to medium-pressure column fractionation (solvent; methanol:methylene chloride=0:100 to 7:93). The titled compound (105 mg) was obtained as a white powder.

$^1$H-NMR (CDCl$_3$) δ ppm: 2.47-2.69 (m, 2H), 2.94 (s, 6H), 3.53-4.02 (m, 2H), 4.04-4.51 (m, 2H), 7.29-7.46 (m, 4H), 9.03 (brs, 1H).

Reference Example 24

Synthesis of (S)-tert-butyl-4-oxo-3-(pyrrolidin-1-yl)-2-{1-[4-(trifluoromethyl)phenyl]ethylamino}-3,4,7,8-tetrahydropyrido[4,3-d]pyrimidine-6(5H)-carboxylate

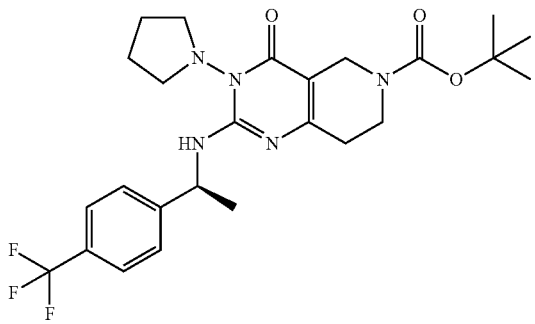 [SMILES: C[C@H](Nc1nc2c(c(=O)n1N1CCCC1)CN(C(=O)OC(C)(C)C)CC2)c1ccc(C(F)(F)F)cc1]

Under nitrogen, tert-butyl 2,4-dioxo-3-(pyrrolidin-1-yl)-1,2,3,4,7,8-hexahydropyrido[4,3-d]pyrimidine-6(5H)-carboxylate (1.5 g) was dissolved in THF (50 ml), and 1,8-diazabicyclo[5.4.0]unde-7-ene (1 ml) and benzotriazol-1-yloxy-tris-(dimethylamino)phosphonium hexafluorophosphate (2.96 g) were added at room temperature. After the reaction solution was stirred at room temperature for a while, (S)-1-(4-trichlorophenyl)ethylamine (1.25 ml) was added. The reaction solution was stirred at room temperature. Saturated sodium hydrogen carbonate solution was added, and the resultant mixture was extracted with ethyl acetate, washed with a saturated saline solution, dried over sodium sulfate, filtrated, concentrated and purified by silica gel column chromatography (hexane:ethyl acetate=1:1) to obtain a desired compound (1.91 g, yield 84%).

$^1$H-NMR (DMSO-d$_6$) δ ppm: 7.60 (d, J=8.24 Hz, 2H), 7.45 (d, J=8.24 Hz, 2H), 6.88 (d, J=8.24 Hz, 1H), 5.22 (dt, J=8.24, 7.00 Hz, 1H), 4.22-4.15 (m, 2H), 3.63-3.48 (m, 4H), 3.14-3.07 (m, 2H), 2.45 (m, 2H), 2.20 (m, 2H), 1.87 (m, 2H), 1.57 (d, J=7.00 Hz, 3H), 1.46 (s, 9H).

Reference Example 25

Synthesis of 3-(pyrrolidin-1-yl)-5,6,7,8-tetrahydropyrido[4,3-d]pyrimidine-2,4-(1H,5H)-dione hydrochloride

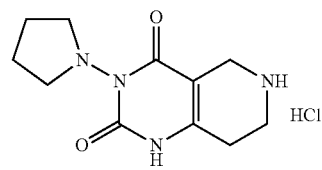 [SMILES: O=c1[nH]c2c(c(=O)n1N1CCCC1)CNCC2 ; Cl]

tert-Butyl 2,4-dioxo-3-(pyrrolidin-1-yl)-1,2,3,4,7,8-hexahydropyrido[4,3-d]pyrimidine-6(5H)-carboxylate (1.690 g) was dissolved in methylene chloride (50 ml), 4 N HCl in ethyl acetate (10 ml) was added and the resultant mixture was stirred under room temperature, overnight. A solid substance was precipitated, filtrated off, dried to quantitatively obtain the desired compound.

$^1$H-NMR (DMSO-d$_6$) δ ppm: 11.40 (brs, 1H), 9.30 (brs, 2H), 4.00-3.50 (br, 2H), 3.28 (br, 2H), 3.12 (brt, J=6.54 Hz, 4H), 2.62 (br, 2H), 1.85 (m, 4H).

Reference Example 26

Synthesis of 6-(4-chlorobenzoyl)-3-(pyrrolidin-1-yl)-5,6,7,8-tetrahydropyrido[4,3-d]pyrimidine-2,4-(1H,3H)-dione

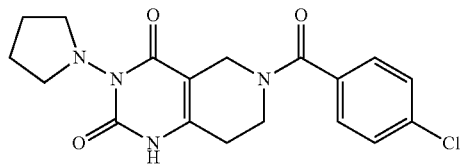 [SMILES: O=C(c1ccc(Cl)cc1)N1CCc2[nH]c(=O)n(N3CCCC3)c(=O)c2C1]

Under nitrogen, 3-(pyrrolidin-1-yl)-5,6,7,8-tetrahydropyrido[4,3-d]pyrimidine-2,4-(1H,5H)-dione hydrochloride (1.370 g) was dissolved in methylene chloride (20 ml), and pyridine (1 ml) and 4-chlorobenzoyl chloride (0.64 ml) were added at 0° C. After the solution was stirred at 0° C. for 45 minutes, the temperature was raised up to room temperature and the solution was stirred for one hour and a half. Methylene chloride (10 ml) and pyridine (1 ml) were added and the resultant mixture was stirred overnight at room temperature. Thereafter, the reaction solution was cooled to 0° C. and pyridine (1 ml) and 4-chlorobenzoyl chloride (0.6 ml) were added, and the resultant mixture was stirred at the same temperature for 2 hours for 50 minutes, and heated to reflux further one hour. After consumption of the raw materials was confirmed by TLC and LC/MS, water was added. The mixture was extracted with methylene chloride. The organic layer was dried over sodium sulfate, filtrated and concentrated. Thereafter, the resultant solid substance was washed with diethyl ether and ethyl acetate. The solid substance was recovered and dried to obtain a desired compound in an amount of 1.03 g (yield 55%).

$^1$H-NMR (DMSO-d$_6$) δ ppm: 11.2 (s, 1H), 7.54 (d, J=8.36 Hz, 2H), 7.48 (d, J=8.36 Hz, 2H), 4.24 (br, 1H), 4.04 (br, 1H), 3.79 (br, 1H), 3.46 (br, 1H), 3.10 (br, 4H), 2.50 (br, 2H), 1.84 (br, 4H).

Reference Example 27

Synthesis of tert-butyl 3-ethoxy-2,4-dioxo-1,2,3,4,7,8-hexahydropyrido[4,3-d]pyrimidine-6(5H)-carboxylate

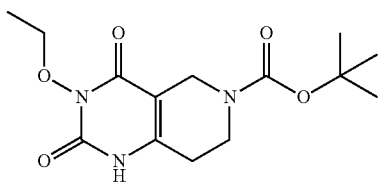 [SMILES: CCOn1c(=O)[nH]c2c(c1=O)CN(C(=O)OC(C)(C)C)CC2]

The titled compound was obtained in the same manner as in Reference Example 14.

¹H-NMR (DMSO-d$_6$) δ ppm: 11.6-11.4 (brs, 1H), 4.03 (q, J=7.08 Hz, 2H), 4.02 (br, 2H), 3.50 (t, J=5.68 Hz, 2H), J=5.68 Hz, 2H), 1.41 (s, 9H), 1.22 (t, J=7.08 Hz, 3H).

Reference Example 28

Synthesis of (S)-tert-butyl 3-ethoxy-4-oxo-2-{1-[4-(trifluoromethyl)phenyl]ethylamino}-3,4,7,8-tetrahydropyrido[4,3-d]pyrimidine-6(5H)-carboxylate

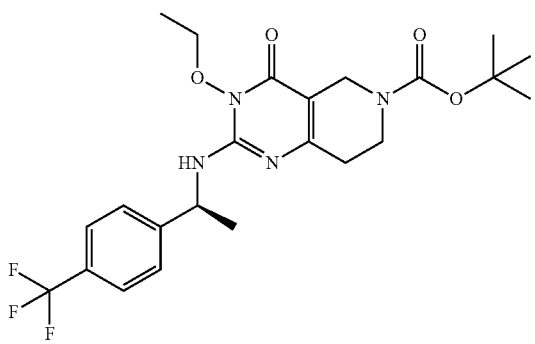 [SMILES: CCOn1c(N[C@@H](C)c2ccc(C(F)(F)F)cc2)nc2c(c1=O)CN(C(=O)OC(C)(C)C)CC2]

The titled compound was obtained in the same manner as in Reference Example 24.

¹H-NMR (DMSO-d$_6$) δ ppm: 7.61 (d, J=8.16 Hz, 2H), 7.46 (d, J=8.16 Hz, 2H), 5.62 (d, J=7.68 Hz, 1H), 5.25 (dt, J=7.68, 5.36 Hz, 1H), 4.34 (m, 2H), 4.24 (q, J=7.14 Hz, 2H), 3.60-3.49 (m, 2H), 2.52-2.40 (m, 2H), 3.11 (d, J=5.36 Hz, 1H), 1.61 (d, J=5.36 Hz, 3H), 1.47 (s, 9H), 1.41 (t, J=7.14 Hz, 3H).

Reference Example 29

Synthesis of 3-ethoxy-5,6,7,8-tetrahydropyrido[4,3-d]pyrimidine-2,4-(1H,5H)-dione hydrochloride

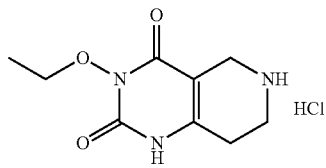

The titled compound was obtained in the same manner as in Reference Example 25.

¹H-NMR (DMSO-d$_6$) δ ppm: 9.20 (brs, 2H), 4.05 (q, J=7.04 Hz, 2H), 3.78 (brs, 2H), 3.29 (t, J=5.92 Hz, 2H), 2.64 (brt, J=5.92 Hz, 2H), 1.23 (t, J=7.04 Hz, 3H). Amine H was not observed.

Reference Example 30

Synthesis of 3-dimethylamino-2-(3-fluoro-4-trifluoromethylbenzylamino)-5,6,7,8-tetrahydropyrido[4,3-d]pyrimidin-4-(3H)-one

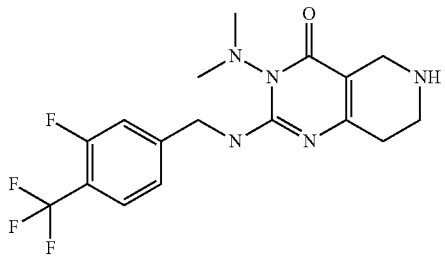 [SMILES: CN(C)n1c(NCc2ccc(C(F)(F)F)c(F)c2)nc2c(c1=O)CNCC2]

The titled compound was obtained in the same manner as in Reference Example 12. Colorless amorphous ¹H-NMR (CDCl$_3$) δ ppm: 2.41-2.45 (m, 2H), 3.03 (s, 6H), 3.04-3.06 (m, 3H), 3.68-3.69 (m, 2H), 4.63 (d, J=6.2 Hz, 2H), 6.98 (t, J=6.0 Hz, 1H), 7.16-7.20 (m, 2H), 7.57 (t, J=8.0 Hz, 1H).

Reference Example 31

Synthesis of 2-(S)-[1-(4-chlorophenyl)ethylamino]-3-dimethylamino-5,6,7,8-tetrahydropyrido[4,3-d]pyrimidin-4-(3H)-one

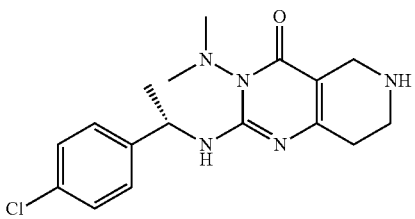 [SMILES: C[C@H](Nc1nc2c(c(=O)n1N(C)C)CNCC2)c1ccc(Cl)cc1]

The titled compound was obtained in the same manner as in Reference Example 12. Colorless amorphous ¹H-NMR (CDCl$_3$) δ ppm: 1.53 (d, J=6.9 Hz, 3H), 2.35-2.48 (m, 3H), 2.96 (s, 3H), 3.00 (s, 3H), 3.03-3.09 (m, 2H), 3.63-3.72 (m, 2H), 5.09-5.17 (m, 1H), 6.78 (d, J=8.1 Hz, 1H), 7.26-7.31 (m, 4H).

Reference Example 32

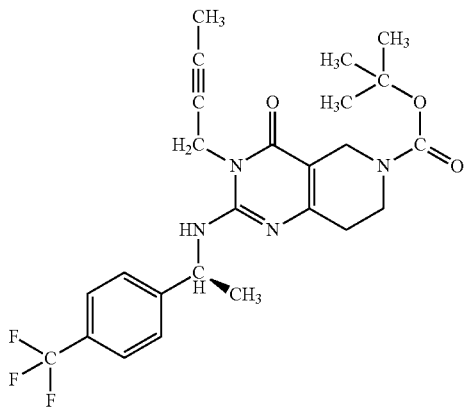 [SMILES: CC#CCn1c(N[C@@H](C)c2ccc(C(F)(F)F)cc2)nc2c(c1=O)CN(C(=O)OC(C)(C)C)CC2]

3-(2-Butynyl)-4-oxo-2-[(S)-1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 7.43 (d, J=8.22 Hz, 2H), 7.49 (d, J=8.22 Hz, 2H), 5.45 (d, J=6.84 Hz, 1H), 5.35 (qd, J=6.92, 6.84 Hz, 1H), 4.91 (dd, J=17.6, 2.42 Hz, 1H), 4.71 (dd, J=17.6, 2.42 Hz, 1H), 4.28 (d, J=17.12 Hz, 1H), 4.20 (d, J=17.12 Hz, 1H), 3.60 (br, 1H), 3.53 (m, 1H), 2.47 (brm, 2H), 1.80 (t, J=2.42 Hz, 3H), 1.60 (d, J=6.92 Hz, 3H), 1.46 (s, 9H).

Reference Example 33

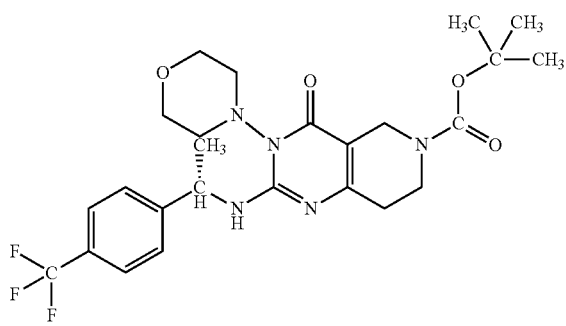 [SMILES: C[C@H](Nc1nc2c(c(=O)n1N1CCOCC1)CN(C(=O)OC(C)(C)C)CC2)c1ccc(C(F)(F)F)cc1]

3-Morpholin-4-yl-4-oxo-2-[(S)-1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.48 (s, 9H), 1.57 (d, J=7.0 Hz, 3H), 2.32-2.56 (m, 2H), 2.66-2.83 (m, 2H), 3.45-3.76 (m, 4H), 3.95-4.04 (m, 2H), 4.17-4.35 (m, 4H), 5.13-5.24 (m, 1H), 6.89 (d, J=8.0 Hz, 1H), 7.42 (d, J=8.0 Hz, 2H), 7.61 (d, J=8.0 Hz, 2H).

Reference Example 34

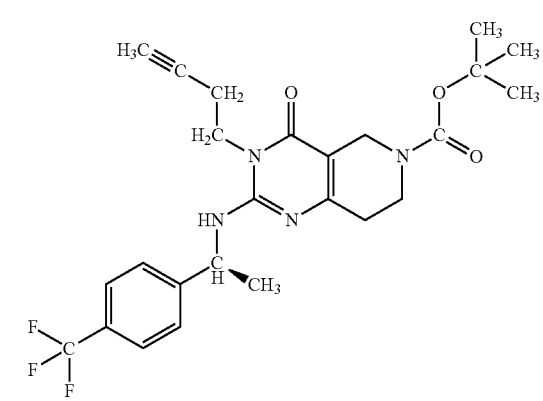 [SMILES: C#CCCn1c(N[C@@H](C)c2ccc(C(F)(F)F)cc2)nc2c(c1=O)CN(C(=O)OC(C)(C)C)CC2]

3-(3-Butynyl)-4-oxo-2-[(S)-1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 7.59 (d, J=8.24 Hz, 2H), 7.49 (d, J=8.24 Hz, 2H), 5.46 (d, J=6.0 Hz, 1H), 5.29 (m, 1H), 4.30-4.05 (m, 4H), 3.63 (br, 1H), 3.57-3.50 (m, 1H), 2.73-2.68 (m, 2H), 2.60-2.40 (br, 2H), 1.98 (t, J=2.66 Hz, 1H), 1.57 (d, J=6.36 Hz, 3H), 1.47 (s, 9H),

Reference Example 35

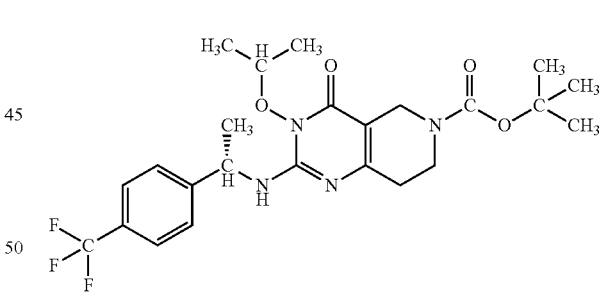

3-Isopropoxy-4-oxo-2-[(S)-1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.31 (d, J=6.5 Hz, 3H), 1.37 (d, J=6.5 Hz, 3H), 1.47 (s, 9H), 1.59 (d, J=7.0 Hz, 3H), 2.35-2.58 (m, 2H), 3.47-3.68 (m, 2H), 4.15-4.32 (m, 2H), 4.84-4.97 (m, 1H), 5.17-5.30 (m, 1H), 5.62 (d, J=7.5 Hz, 1H), 7.46 (d, J=8.5 Hz, 2H), 7.61 (d, J=8.5 Hz, 2H).

Reference Example 36

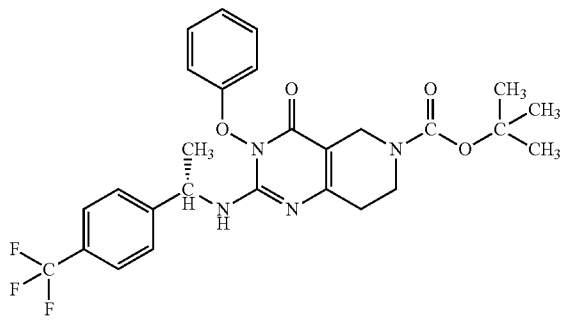 [SMILES: C[C@H](Nc1nc2c(c(=O)n1Oc1ccccc1)CN(C(=O)OC(C)(C)C)CC2)c1ccc(C(F)(F)F)cc1]

4-Oxo-3-phenoxy-2-[(S)-1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.46 (s, 9H), 1.52 (d, J=7.0 Hz, 3H), 2.38-2.62 (m, 2H), 3.46-3.69 (m, 2H), 4.14-4.32 (m, 2H), 5.16-5.32 (m, 1H), 5.55 (d, J=7.5 Hz, 1H), 7.00 (d, J=8.0 Hz, 2H), 7.17 (dd, J=7.0 Hz, 7.0 Hz, 1H), 7.27-7.43 (m, 4H), 7.54 (d, J=8.0 Hz, 2H).

Reference Example 37

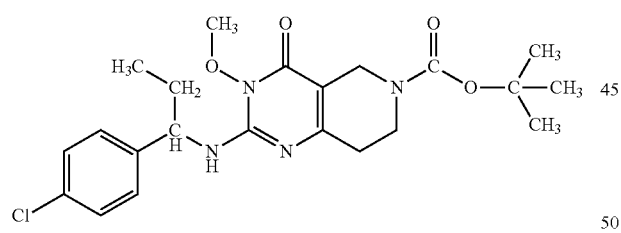

2-[1-(4-Chloro-phenyl)-propylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.94 (t, J=7.4 Hz, 3H), 1.47 (s, 9H), 1.84-1.94 (m, 2H), 2.35-2.58 (m, 2H), 3.47-3.69 (m, 2H), 4.05 (s, 3H), 4.11-4.30 (m, 2H), 4.89-4.96 (m, 1H), 5.62 (d, J=8.0 Hz, 1H), 7.24-7.33 (m, 4H).

Reference Example 38

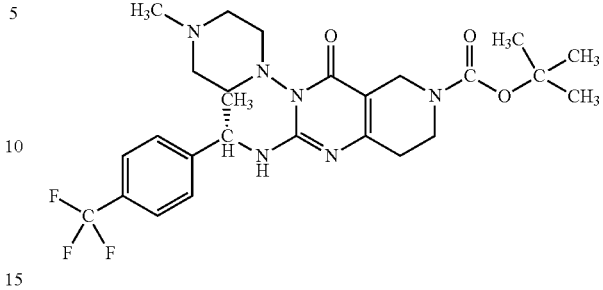

3-(4-Methyl-piperazin-1-yl)-4-oxo-2-[(S)-1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.46 (s, 9H), 1.56 (d, J=7.0 Hz, 3H), 2.13-2.26 (m, 2H), 2.34 (s, 3H), 2.37-2.54 (m, 2H), 2.68-2.86 (m, 2H), 2.88-2.95 (m, 2H), 3.43-3.65 (m, 2H), 4.12-4.27 (m, 4H), 5.10-5.22 (m, 1H), 6.95 (d, J=8.0 Hz, 1H), 7.42 (d, J=8.0 Hz, 2H), 7.61 (d, J=8.0 Hz, 2H).

Reference Example 39

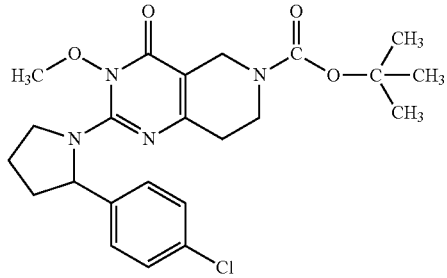 [SMILES: COn1c(N2CCCC2c2ccc(Cl)cc2)nc2c(c1=O)CN(C(=O)OC(C)(C)C)CC2]

2-[2-(4-Chloro-phenyl)-pyrrolidin-1-yl]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.46 (s, 9H), 1.78-2.02 (m, 2H), 2.06-2.14 (m, 1H), 2.23-2.45 (m, 2H), 2.46-2.60 (m, 1H), 3.40-3.57 (m, 1H), 3.58-3.69 (m, 1H), 3.71-3.86 (m, 4H), 3.90-4.00 (m, 1H), 4.15-4.37 (m, 2H), 5.12-5.21 (m, 1H), 7.17-7.32 (m, 4H).

Reference Example 40

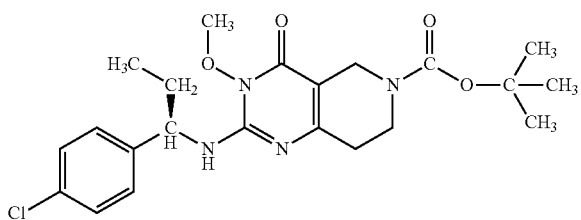 [SMILES: CC[C@@H](Nc1nc2c(c(=O)n1OC)CN(C(=O)OC(C)(C)C)CC2)c1ccc(Cl)cc1]

2-[(R)-1-(4-Chloro-phenyl)-propylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.94 (t, J=7.4 Hz, 3H), 1.47 (s, 9H), 1.84-1.94 (m, 2H), 2.35-2.58 (m, 2H), 3.47-3.69 (m, 2H), 4.05 (s, 3H), 4.11-4.30 (m, 2H), 4.89-4.96 (m, 1H), 5.62 (d, J=8.0 Hz, 1H), 7.24-7.33 (m, 4H).

Reference Example 41

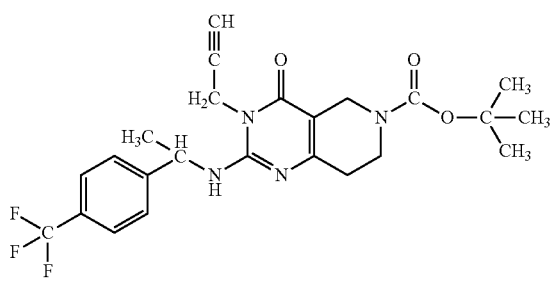 [SMILES: C#CCn1c(NC(C)c2ccc(C(F)(F)F)cc2)nc2c(c1=O)CN(C(=O)OC(C)(C)C)CC2]

4-Oxo-3-(2-propynyl)-2-[1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.46 (s, 9H), 1.60 (d, J=6.7 Hz, 3H), 2.30-2.61 (m, 3H), 3.44-3.71 (m, 2H), 4.15-4.36 (m, 2H), 4.88 (d, J=2.6 Hz, 2H), 5.21-5.40 (m, 2H), 7.48 (d, J=8.2 Hz, 2H), 7.60 (d, J=8.2 Hz, 2H).

Reference Example 42

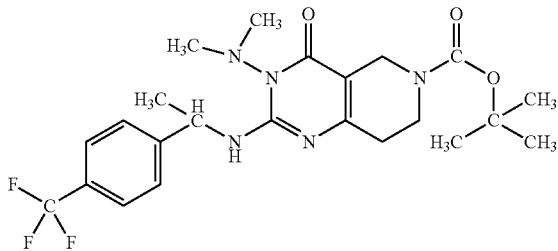 [SMILES: CC(Nc1nc2c(c(=O)n1N(C)C)CN(C(=O)OC(C)(C)C)CC2)c1ccc(C(F)(F)F)cc1]

3-Dimethylamino-4-oxo-2-[1-(4-trifluoromethyl-phenyl)-ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.46 (s, 9H), 1.56 (d J=7.0 Hz, 3H), 2.30-2.57 (m, 2H), 2.93-3.11 (m, 6H), 3.45-3.70 (m, 2H), 4.10-4.30 (m, 2H), 5.11-5.28 (m, 1H), 6.85 (d, J=8.0 Hz, 1H), 7.44 (d, J=8.1 Hz, 2H), 7.59 (d, J=8.1 Hz, 2H).

Reference Example 43

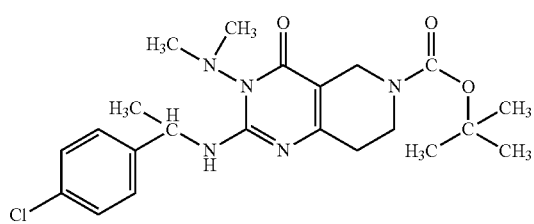 [SMILES: CC(Nc1nc2c(c(=O)n1N(C)C)CN(C(=O)OC(C)(C)C)CC2)c1ccc(Cl)cc1]

2-[1-(4-Chloro-phenyl)-ethylamino]-3-dimethylamino-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.47 (s, 9H), 1.53 (d, J=6.9 Hz, 3H), 2.41-2.51 (m, 2H), 2.98 (s, 3H), 3.02 (s, 3H), 3.50-3.60 (m, 2H), 4.18-4.25 (m, 2H), 5.11-5.15 (m, 1H), 6.79 (d, J=8.1 Hz, 1H), 7.25-7.32 (m, 4H)

Reference Example 44

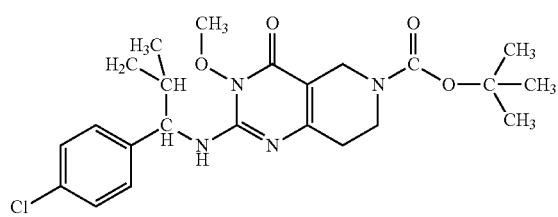 [SMILES: COn1c(NC(c2ccc(Cl)cc2)C(C)C)nc2c(c1=O)CN(C(=O)OC(C)(C)C)CC2]

2-[1-(4-Chloro-phenyl)-2-methyl-propylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.87 (d, J=6.7 Hz, 3H), 1.03 (d, J=6.7 Hz, 3H), 1.46 (s, 9H), 2.00-2.14 (m, 1H), 2.27-2.53 (m, 2H), 3.40-3.69 (m, 2H), 4.07 (s, 3H), 4.10-4.30 (m, 2H), 4.77 (dd, J=7.7, 7.7 Hz, 1H), 5.71 (d, J=8.6 Hz, 1H), 7.12-7.35 (m, 4H).

Reference Example 45

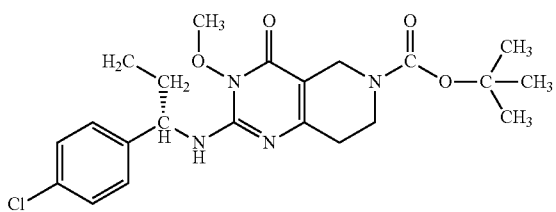 [SMILES: CC[C@H](Nc1nc2c(c(=O)n1OC)CN(C(=O)OC(C)(C)C)CC2)c1ccc(Cl)cc1]

2-[(S)-1-(4-Chloro-phenyl)-propylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.94 (t, J=7.4 Hz, 3H), 1.47 (s, 9H), 1.84-1.94 (m, 2H), 2.35-2.58 (m, 2H), 3.47-3.69 (m, 2H), 4.05 (s, 3H), 4.11-4.30 (m, 2H), 4.89-4.96 (m, 1H), 5.62 (d, J=8.0 Hz, 1H), 7.24-7.33 (m, 4H).

Reference Example 46

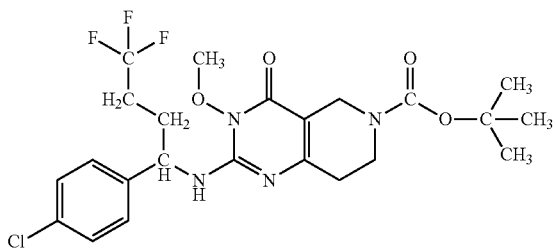 [SMILES: COn1c(NC(CCC(F)(F)F)c2ccc(Cl)cc2)nc2c(c1=O)CN(C(=O)OC(C)(C)C)CC2]

2-[1-(4-Chloro-phenyl)-4,4,4-trifluoro-butylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.47 (s, 9H), 2.00-2.28 (m, 4H), 2.35-2.56 (m, 2H), 3.44-3.63 (m, 2H), 4.04 (s, 3H), 4.16-4.32 (m, 2H), 5.01-5.15 (m, 1H), 5.65 (d, 8.1 Hz, 1H), 7.20-7.38 (m, 4H).

Reference Example 47

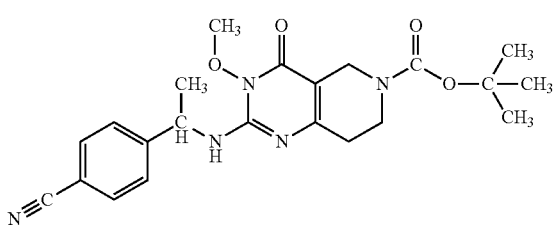 [SMILES: COn1c(NC(C)c2ccc(C#N)cc2)nc2c(c1=O)CN(C(=O)OC(C)(C)C)CC2]

2-[1-(4-Cyano-phenyl)-ethylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.47 (s, 9H), 1.61 (d, J=7.0 Hz, 3H), 2.30-2.53 (m, 2H), 3.42-3.63 (m, 2H), 4.05 (s, 3H), 4.07-4.24 (m, 2H), 5.15-5.29 (m, 1H), 5.80 (bs, 1H), 7.48 (d, J=8.3 Hz, 2H), 7.63 (d, 8.3 Hz, 2H).

Reference Example 48

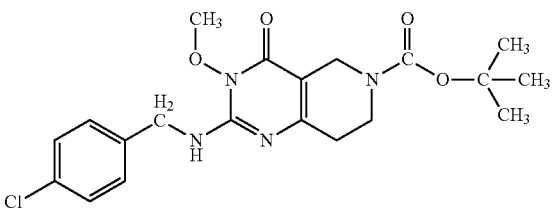 [SMILES: COn1c(NCc2ccc(Cl)cc2)nc2c(c1=O)CN(C(=O)OC(C)(C)C)CC2]

2-(4-Chloro-benzylamino)-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.48 (s, 9H), 2.54 (brt, J=5.5 Hz, 2H), 3.61 (t, J=6.0 Hz, 2H), 4.04 (s, 3H), 4.27 (s, 2H), 4.58 (d, J=6.0 Hz, 2H), 5.75 (brt, J=6.0 Hz, 1H), 7.26-7.35 (m, 4H).

Reference Example 49

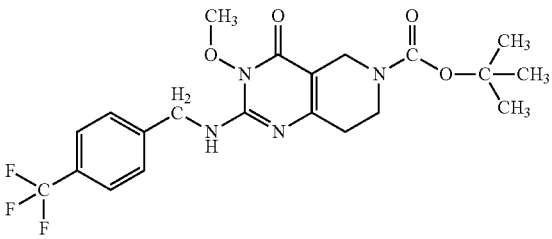 [SMILES: COn1c(NCc2ccc(C(F)(F)F)cc2)nc2c(c1=O)CN(C(=O)OC(C)(C)C)CC2]

3-Methoxy-4-oxo-2-(4-trifluoromethyl-benzylamino)-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.48 (s, 9H), 2.53 (t, J=6.0 Hz, 2H), 3.61 (t, J=6.0 Hz, 2H), 4.07 (s, 3H), 4.28 (s, 2H), 4.69 (d, J=6.0 Hz, 2H), 5.83 (t, J=6.0 Hz, 1H), 7.46 (d, J=8.0 Hz, 2H), 7.62 (d, J=8.0 Hz, 2H).

Reference Example 50

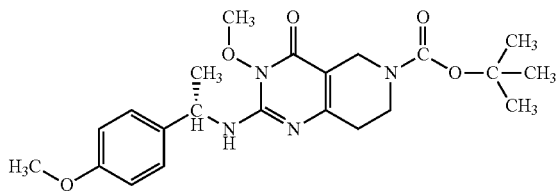 [SMILES: COc1ccc([C@H](C)Nc2nc3c(c(=O)n2OC)CN(C(=O)OC(C)(C)C)CC3)cc1]

3-Methoxy-2-[(S)-1-(4-methoxy-phenyl)-ethylamino]-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.47 (s, 9H), 1.58 (d, J=7.0 Hz, 3H), 2.41-2.59 (m, 2H), 3.49-3.68 (m, 2H), 3.80 (s, 3H), 4.00 (s, 3H), 4.14-4.30 (m, 2H), 5.11-5.23 (m, 1H), 5.60 (d, J=8.0 Hz, 1H), 6.86-6.91 (m, 2H), 7.28-7.32 (m, 2H).

Reference Example 51

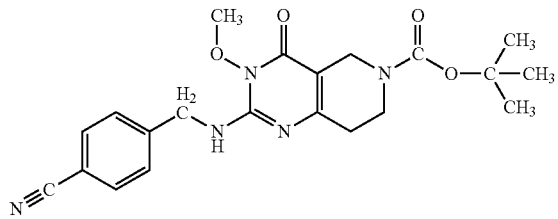 [SMILES: COn1c(NCc2ccc(C#N)cc2)nc2c(c1=O)CN(C(=O)OC(C)(C)C)CC2]

2-(4-Cyano-benzylamino)-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 1.47 (s, 9H), 2.50 (t, J=5.5 Hz, 2H), 3.59 (t, J=5.5 Hz, 2H), 4.06 (s, 3H), 4.26 (s, 2H), 4.70 (d, J=6.0 Hz, 2H), 6.18 (t, J=6.0 Hz, 1H), 7.46 (d, J=8.0 Hz, 2H), 7.63 (d, J=8.0 Hz, 2H).

Reference Example 52

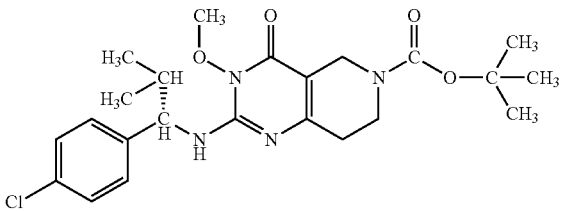 [SMILES: COn1c(N[C@H](c2ccc(Cl)cc2)C(C)C)nc2c(c1=O)CN(C(=O)OC(C)(C)C)CC2]

2-[(S)-1-(4-Chloro-phenyl)-2-methyl-propylamino]-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.87 (d, J=6.6 Hz, 3H), 1.03 (d, J=6.6 Hz, 3H), 1.46 (s, 9H), 2.00-2.17 (m, 1H), 2.29-2.55 (m, 2H), 3.40-3.69 (m, 2H), 4.07 (s, 3H), 4.10-4.30 (m, 2H), 4.77 (dd, J=7.7, 7.7 Hz, 1H), 5.71 (d, J=8.4 Hz, 1H), 7.14-7.37 (m, 4H).

Reference Example 53

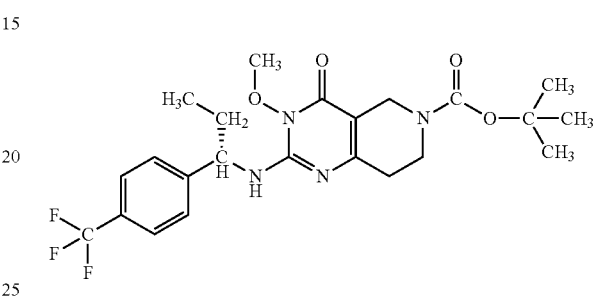

3-Methoxy-4-oxo-2-[(S)-1-(4-trifluoromethyl-phenyl)-propylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.97 (t, J=7.3 Hz, 3H), 1.46 (s, 9H), 1.79-2.00 (m, 2H), 2.24-2.56 (m, 2H), 3.36-3.62 (m, 2H), 4.07 (s, 3H), 4.10-4.33 (m, 2H), 4.90-5.07 (m, 1H), 5.69 (d, J=7.8 Hz, 1H), 7.43 (d, J=8.1 Hz, 2H), 7.60 (d, J=8.0 Hz, 2H).

Reference Example 54

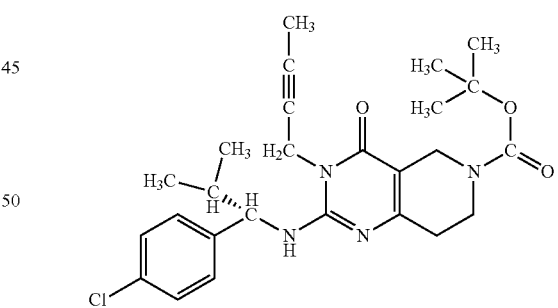

3-(2-Butynyl)-2-[(S)-1-(4-chloro-phenyl)-2-methyl-propylamino]-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.91 (d, J=6.7 Hz, 3H), 1.03 (d, J=6.7 Hz, 3H), 1.45 (s, 9H), 1.84 (s, 3H), 1.95-2.16 (m, 1H), 2.26-2.52 (m, 2H), 3.39-3.65 (m, 2H), 4.07-4.36 (m, 2H), 4.78-4.84 (m, 2H), 4.92 (dd, J=7.3, 7.3 Hz, 1H), 5.58 (d, J=7.4 Hz, 1H), 7.16-7.32 (m, 4H).

Reference Example 55

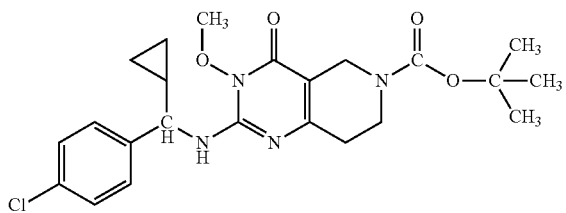 [SMILES: COn1c(NC(c2ccc(Cl)cc2)C2CC2)nc2c(c1=O)CN(C(=O)OC(C)(C)C)CC2]

2-{[(4-Chloro-phenyl)-cyclopropyl-methyl]-amino}-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.
$^1$H-NMR (CDCl$_3$) δ ppm: 0.37-0.56 (m, 2H), 0.58-0.71 (m, 2H), 1.41-1.27 (m, 1H), 1.47 (s, 9H), 2.29-2.52 (m, 2H), 3.42-3.66 (m, 2H), 4.08 (s, 3H), 4.12-4.31 (m, 2H), 4.37-4.46 (m, 1H), 5.85 (d, J=7.5 Hz, 1H), 7.26-7.38 (m, 4H).

Reference Example 56

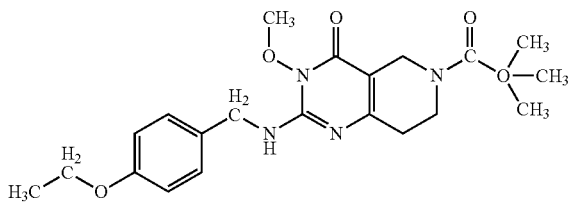

2-(4-Ethoxy-benzylamino)-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.
$^1$H-NMR (CDCl$_3$) δ ppm: 1.39-1.43 (m, 3H), 1.48 (s, 9H), 2.56 (bs, 2H), 3.54-3.67 (m, 2H), 3.96-4.06 (m, 5H), 4.23-4.33 (m, 2H), 4.48-4.53 (m, 2H), 5.56-5.65 (m, 1H), 6.88 (d, J=5.2 Hz, 2H), 7.26 (d, J=5.2 Hz, 2H).

Reference Example 57

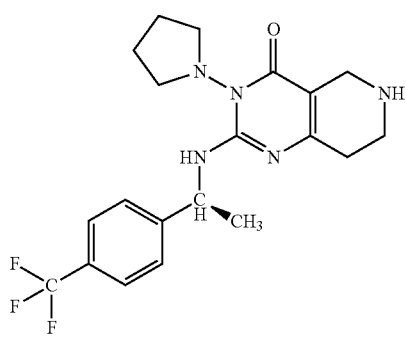 [SMILES: C[C@H](Nc1nc2c(c(=O)n1N1CCCC1)CNCC2)c1ccc(C(F)(F)F)cc1]

3-Pyrrolidin-1-yl-2-[(S)-1-(4-trifluoromethylphenyl)ethylamino]-5,6,7,8-tetrahydro-3H-pyrido[4,3-d]pyrimidin-4-one The titled compound was obtained in the same manner as in Reference Example 12.
$^1$H-NMR (CDCl$_3$) δ ppm: 7.59 (d, J=8.26 Hz, 2H), 7.45 (d, J=8.26 Hz, 2H), 6.85 (d, J=8.16 Hz, 1H), 5.22 (m, 1H), 3.70-3.50 (m, 4H), 3.16-2.96 (m, 5H), 2.46-2.31 (m, 2H), 2.24-2.10 (m, 2H), 1.89-1.80 (m, 2H), 1.57 (d, J=7.0 Hz, 3H).

Reference Example 58

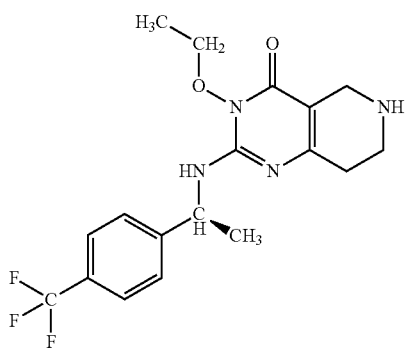 [SMILES: CCOn1c(N[C@@H](C)c2ccc(C(F)(F)F)cc2)nc2c(c1=O)CNCC2]

3-Ethoxy-2-[(S)-1-(4-trifluoromethylphenyl)ethylamino]-5,6,7,8-tetrahydro-3H-pyrido[4,3-d]pyrimidin-4-one The titled compound was obtained in the same manner as in Reference Example 12.
$^1$H-NMR (CDCl$_3$) δ ppm: 7.61 (d, J=8.32 Hz, 2H), 7.46 (d, J=8.32 Hz, 2H), 5.59 (d, J=7.72 Hz, 1H), 5.25 (m, 1H), 4.33 (q, J=7.6 Hz, 2H), 3.70 (m, 2H), 3.05-3.00 (m, 2H), 2.44-2.37 (m, 2H), 1.41 (t, J=7.16 Hz, 3H), 1.60 (d, J=6.96 Hz, 3H).

Reference Example 59

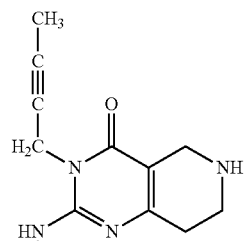

3-(2-Butynyl)-2-[(S)-1-(4-trifluoromethylphenyl)ethylamino]-5,6,7,8-tetrahydro-3H-pyrido[4,3-d]pyrimidin-4-one The titled compound was obtained in the same manner as in Reference Example 12.

¹H-NMR (CDCl₃) δ ppm: 7.59 (d, J=8.16 Hz, 2H), 7.49 (dd, J=8.16, 2.44 Hz, 2H), 5.42 (dd, J=6.8, 2.44 Hz, 1H), 5.32 (m, 1H), 4.90 (d, J=17.3 Hz, 1H), 4.71 (d, J=17.3 Hz, 1H), 3.72 (d, J=16.1 Hz, 1H), 3.67 (d, J=16.1 Hz, 1H), 3.03 (m, 2H), 2.48-2.33 (m, 2H), 1.80 (t, J=2.44 Hz, 3H), 1.60 (d, J=6.8 Hz, 3H).

Reference Example 60

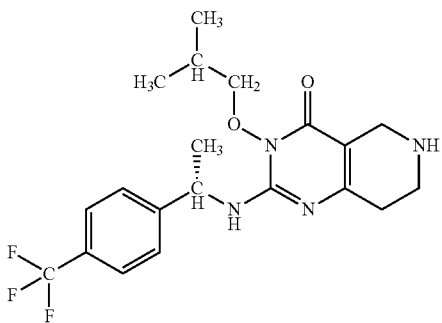 [SMILES: CC(C)COn1c(N[C@@H](C)c2ccc(C(F)(F)F)cc2)nc2c(c1=O)CNCC2]

3-Isobutoxy-2-[(S)-1-(4-trifluoromethylphenyl)ethylamino]-5,6,7,8-tetrahydro-3H-pyrido[4,3-d]pyrimidin-4-one The titled compound was obtained in the same manner as in Reference Example 12.

¹H-NMR (CDCl₃) δ ppm: 1.05 (d, J=6.7 Hz, 6H), 1.59 (d, J=6.9 Hz, 3H), 2.08-2.23 (m, 1H), 2.28-2.52 (m, 2H), 2.95-3.10 (m, 2H), 3.64-3.77 (m, 2H), 3.90-4.08 (m, 2H), 5.16-5.28 (m, 1H), 5.60 (d, J=7.6 Hz, 1H), 7.46 (d, J=8.3 Hz, 2H), 7.61 (d, J=8.3 Hz, 2H).

Reference Example 61

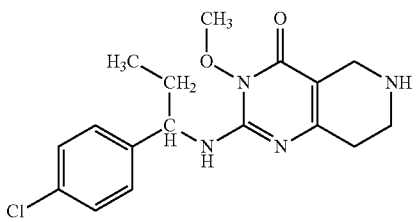 [SMILES: CCC(Nc1nc2c(c(=O)n1OC)CNCC2)c1ccc(Cl)cc1]

2-[1-(4-Chlorophenyl)propylamino]-3-methoxy-5,6,7,8-tetrahydro-3H-pyrido[4,3-d]pyrimidin-4-one The titled compound was obtained in the same manner as in Reference Example 12.

¹H-NMR (CDCl₃) δ ppm: 0.94 (t, J=7.3 Hz, 3H), 1.78-2.00 (m, 2H), 2.28-2.44 (m, 2H), 2.90-3.10 (m, 2H), 3.55-3.77 (m, 2H), 4.05 (s, 3H), 4.82-5.03 (m, 1H), 5.50-5.61 (m, 1H), 7.18-7.38 (m, 4H).

Reference Example 62

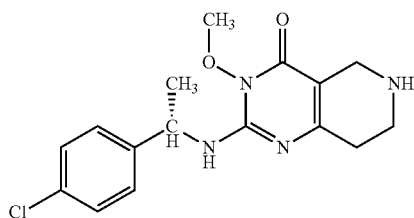 [SMILES: COn1c(N[C@@H](C)c2ccc(Cl)cc2)nc2c(c1=O)CNCC2]

2-[(S)-1-(4-Chlorophenyl)ethylamino]-3-methoxy-5,6,7,8-tetrahydro-3H-pyrido[4,3-d]pyrimidin-4-one The titled compound was obtained in the same manner as in Reference Example 12.

¹H-NMR (CDCl₃) δ ppm: 1.58 (d, J=6.9 Hz, 3H), 2.32-2.53 (m, 2H), 2.95-3.13 (m, 2H), 3.61-3.80 (m, 2H), 4.03 (s, 3H), 5.11-5.26 (m, 1H), 5.56 (d, J=7.8 Hz, 1H), 7.26-7.40 (m, 4H).

Reference Example 63

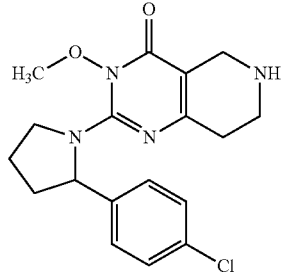 [SMILES: COn1c(N2CCCC2c2ccc(Cl)cc2)nc2c(c1=O)CNCC2]

2-[2-(4-Chlorophenyl)pyrrolidin-1-yl]-3-methoxy-5,6,7,8-tetrahydro-3H-pyrido[4,3-d]pyrimidin-4-one The titled compound was obtained in the same manner as in Reference Example 12.

MS [M+H]⁺=361

Reference Example 64

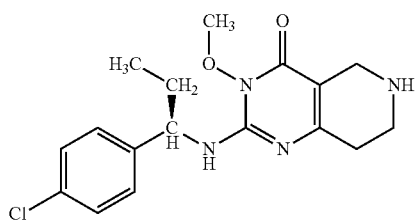 [SMILES: CC[C@@H](Nc1nc2c(c(=O)n1OC)CNCC2)c1ccc(Cl)cc1]

2-[(R)-1-(4-Chlorophenyl)propylamino]-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.94 (t, J=7.4 Hz, 3H), 1.78-2.00 (m, 2H), 2.29-2.52 (m, 2H), 2.91-3.11 (m, 2H), 3.59-3.79 (m, 2H), 4.04 (s, 3H), 4.88-4.99 (m, 1H), 5.59 (d, J=8.0 Hz, 1H), 7.18-7.37 (m, 4H).

Reference Example 65

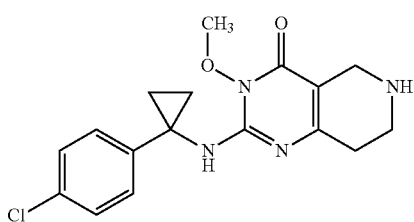 [SMILES: COn1c(NC2(c3ccc(Cl)cc3)CC2)nc2c(c1=O)CNCC2]

2-[1-(4-Chlorophenyl)cyclopropylamino]-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 1.30-1.39 (m, 4H), 2.44 (t, J=5.9 Hz, 2H), 3.03 (t, J=5.9 Hz, 2H), 3.70 (s, 2H), 4.03 (s, 3H), 6.08 (s, 1H), 7.20-7.31 (m, 4H).

Reference Example 66

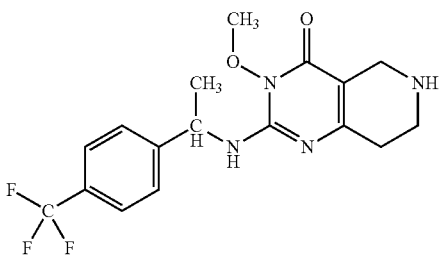 [SMILES: COn1c(NC(C)c2ccc(C(F)(F)F)cc2)nc2c(c1=O)CNCC2]

3-Methoxy-2-[1-(4-trifluoromethylphenyl)ethylamino]-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 1.60 (d, J=7.0 Hz, 3H), 2.28-2.42 (m, 2H), 2.93-3.11 (m, 2H), 3.60-3.80 (m, 2H), 4.06 (s, 3H), 5.18-5.35 (m, 1H), 5.61 (d, J=7.7 Hz, 1H), 7.47 (d, J=8.2 Hz, 2H), 7.61 (d, J=8.2 Hz, 2H).

Reference Example 67

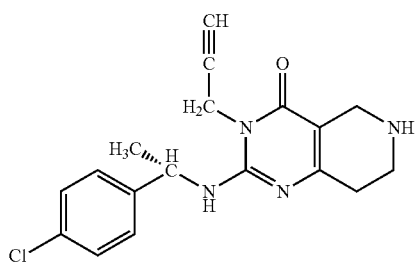

2-[(S)-1-(4-Chlorophenyl)ethylamino]-3-(2-propynyl)-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 1.57 (d, J=6.5 Hz, 3H), 2.37-2.70 (m, 3H), 3.02-3.20 (m, 2H), 3.68-3.85 (m, 2H), 4.84 (d, J=2.2 Hz, 2H), 5.17-5.32 (m, 2H), 7.28-7.37 (m, 4H).

Reference Example 68

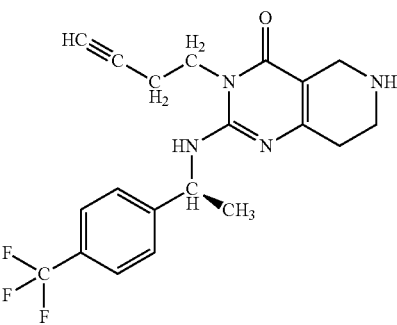 [SMILES: C#CCCn1c(N[C@@H](C)c2ccc(C(F)(F)F)cc2)nc2c(c1=O)CNCC2]

3-(3-Butynyl)-2-[(S)-1-(4-trifluoromethylphenyl)ethylamino]-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 1.57 (d, J=6.9 Hz, 3H), 1.92-1.98 (m, 1H), 2.28-2.54 (m, 2H), 2.57-2.77 (m, 2H), 2.92-3.08 (m, 2H), 3.57-3.74 (m, 2H), 3.97-4.19 (m, 2H), 5.17-5.32 (m, 1H), 5.40 (d, J=6.0 Hz, 1H), 7.41-7.63 (m, 4H).

Reference Example 69

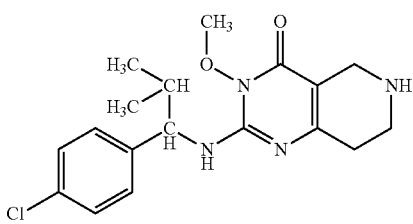 [SMILES: COn1c(NC(c2ccc(Cl)cc2)C(C)C)nc2c(c1=O)CNCC2]

2-[1-(4-Chlorophenyl)-2-methylpropylamino]-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.87 (d, J=6.7 Hz, 3H), 1.03 (d, J=6.7 Hz, 3H), 2.00-2.17 (m, 1H), 2.25-2.52 (m, 2H), 2.90-3.10 (m, 2H), 3.60-3.78 (m, 2H), 4.06 (s, 3H), 4.78 (dd, J=8.3, 8.3 Hz, 1H), 5.69 (d, J=8.5 Hz, 1H), 7.11-7.34 (m, 4H).

Reference Example 70

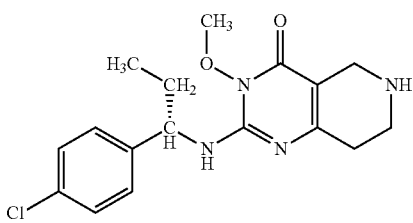 [SMILES: CC[C@H](Nc1nc2c(c(=O)n1OC)CNCC2)c1ccc(Cl)cc1]

2-[(S)-1-(4-Chlorophenyl)propylamino]-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.94 (t, J=7.4 Hz, 3H), 1.78-2.01 (m, 2H), 2.27-2.52 (m, 2H), 2.90-3.11 (m, 2H), 3.59-3.76 (m, 2H), 4.04 (s, 3H), 4.85-4.99 (m, 1H), 5.60 (d, J=8.0 Hz, 1H), 7.18-7.36 (m, 4H).

Reference Example 71

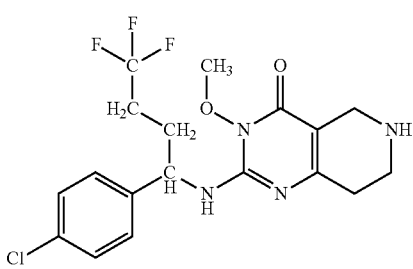 [SMILES: COn1c(NC(CCC(F)(F)F)c2ccc(Cl)cc2)nc2c(c1=O)CNCC2]

2-[1-(4-Chlorophenyl)-4,4,4-trifluorobutylamino]-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 1.91-2.29 (m, 4H), 2.29-2.53 (m, 2H), 2.90-3.10 (m, 2H), 3.58-3.77 (m, 2H), 4.02 (s, 3H), 5.01-5.16 (m, 1H), 5.58 (d, 8.3 Hz, 1H), 7.16-7.41 (m, 4H).

Reference Example 72

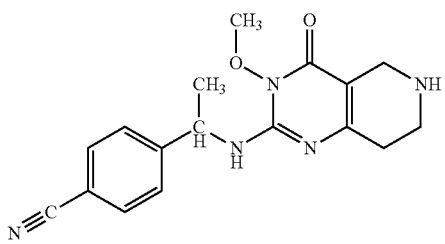 [SMILES: COn1c(NC(C)c2ccc(C#N)cc2)nc2c(c1=O)CNCC2]

4-[1-(3-Methoxy-4-oxo-3,4,5,6,7,8-hexahydropyrido[4,3-d]pyrimidin-2-ylamino)ethyl]-benzonitrile The titled compound was obtained in the same manner as in Reference Example 12.

$^1$H-NMR (CDCl$_3$) δ ppm: 1.59 (d, J=7.0 Hz, 3H), 2.21-2.51 (m, 2H), 3.58-3.76 (m, 2H), 4.07 (s, 3H), 4.27-4.45 (m, 2H), 5.14-5.28 (m, 1H), 5.56-5.72 (m, 1H), 7.40-7.50 (m, 2H), 7.54-7.70 (m, 2H).

Reference Example 73

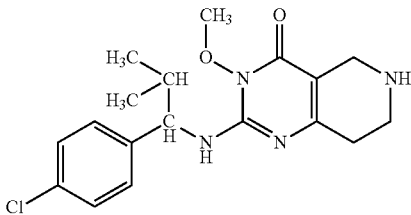 [SMILES: COn1c(NC(c2ccc(Cl)cc2)C(C)C)nc2c(c1=O)CNCC2]

2-[(S)-1-(4-Chlorophenyl)-2-methylpropylamino]-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.87 (d, J=6.7 Hz, 3H), 1.03 (d, J=6.7 Hz, 3H), 1.97-2.16 (m, 1H), 2.24-2.48 (m, 2H), 2.88-3.08 (m, 2H), 3.57-3.77 (m, 2H), 4.06 (s, 3H), 4.78 (dd, J=8.3, 8.3 Hz, 1H), 5.69 (d, J=8.5 Hz, 1H), 7.11-7.35 (m, 4H).

Reference Example 74

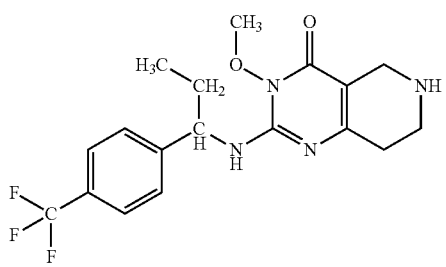 [SMILES: CCC(Nc1nc2c(c(=O)n1OC)CNCC2)c1ccc(C(F)(F)F)cc1]

3-Methoxy-2-[(S)-1-(4-trifluoromethylphenyl)propylamino]-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.97 (t, J=7.3 Hz, 3H), 1.81-2.00 (m, 2H), 2.22-2.52 (m, 2H), 2.88-3.11 (m, 2H), 3.60-3.75 (m, 2H), 4.06 (s, 3H), 4.92-5.08 (m, 1H), 5.64 (d, J=7.7 Hz, 1H), 7.43 (d, J=8.0 Hz, 2H), 7.60 (d, J=8.0 Hz, 2H).

Reference Example 75

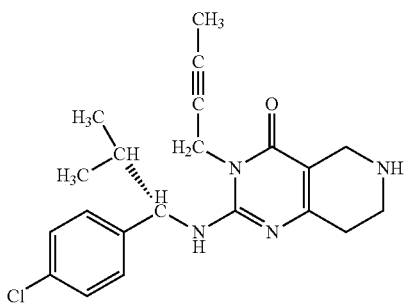

3-(2-Butynyl)-2-[(S)-1-(4-chlorophenyl)-2-methylpropylamino]-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.91 (d, J=6.7 Hz, 3H), 1.02 (d, J=6.7 Hz, 3H), 1.84 (s, 3H), 2.00-2.17 (m, 1H), 2.17-2.47 (m, 2H), 2.87-3.06 (m, 2H), 3.54-3.73 (m, 2H), 4.77-4.86 (m, 2H), 4.93 (dd, J=7.3, 7.3 Hz, 1H), 5.54 (d, J=7.1 Hz, 1H), 7.16-7.34 (m, 4H).

Reference Example 76

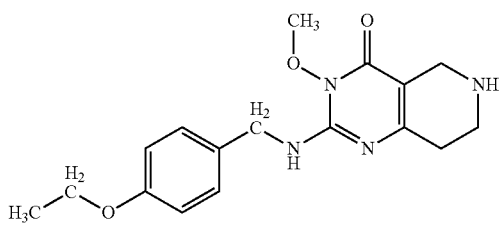 [SMILES: CCOc1ccc(CNc2nc3c(c(=O)n2OC)CNCC3)cc1]

2-(4-Ethoxybenzylamino)-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 1.42 (t, J=7.0 Hz, 3H), 2.42-2.60 (m, 2H), 2.96-3.13 (m, 2H), 3.74 (s, 2H), 3.94-4.11 (m, 5H), 4.52 (d, J=5.4 Hz, 2H), 5.50-5.65 (m, 1H), 6.80-6.92 (m, 2H), 7.18-7.32 (m, 2H).

Reference Example 77

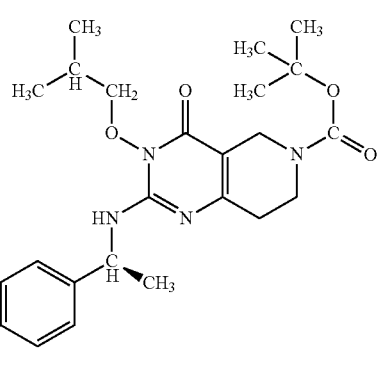

3-Isobutoxy-4-oxo-2-[(S)-1-(4-trifluoromethylphenyl)ethylamino]-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 7.61 (d, J=8.26 Hz, 2H), 7.45 (d, J=8.26 Hz, 2H), 5.63 (d, J=7.6 Hz, 1H), 5.23 (dq, J=7.6, 6.92 Hz, 1H), 4.24 (q, J=17.3 Hz, 2H), 4.07-3.98 (m, 2H), 3.61-3.45 (m, 2H), 2.60-2.45 (m, 2H), 2.19-2.12 (m, 1H), 1.59 (d, J=6.92 Hz, 3H), 1.46 (s, 9H), 1.07 (d, J=6.06 Hz, 6H).

Reference Example 78

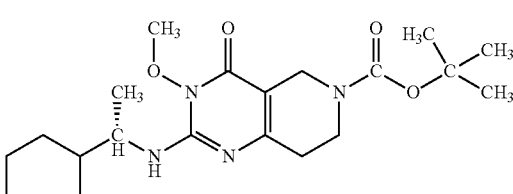

2-((S)-1-Cyclohexylethylamino)-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.88-1.31 (m, 9H), 1.48 (s, 9H), 1.62-1.85 (m, 5H), 2.45-2.60 (m, 2H), 3.60 (t, J=5.7 Hz, 2H), 3.90-4.02 (m, 1H), 4.06 (s, 3H), 4.26 (s, 2H), 5.22 (d, J=9.0 Hz, 1H).

Reference Example 79

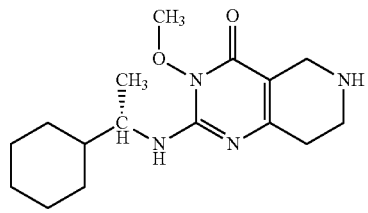 [SMILES: COn1c(N[C@@H](C)C2CCCCC2)nc2c(c1=O)CNCC2]

2-((S)-1-Cyclohexylethylamino)-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.90-1.55 (m, 9H), 1.64-2.00 (m, 5H), 2.47 (t, J=5.8 Hz, 2H), 3.07 (t, J=5.8 Hz, 2H), 3.73 (s, 2H), 3.90-4.01 (m, 1H), 4.03 (s, 3H), 5.21 (d, J=8.9 Hz, 1H).

Reference Example 80

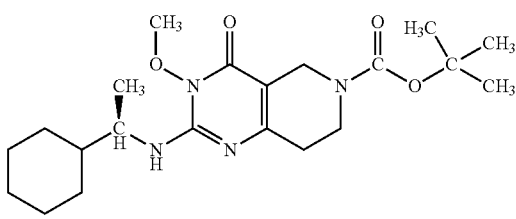 [SMILES: COn1c(N[C@H](C)C2CCCCC2)nc2c(c1=O)CN(C(=O)OC(C)(C)C)CC2]

2-((R)-1-Cyclohexylethylamino)-3-methoxy-4-oxo-3,5,7,8-tetrahydro-4H-pyrido[4,3-d]pyrimidine-6-carboxylic acid tert-butyl ester Synthesis was performed in the same manner as in Reference Example 10.

$^1$H-NMR (CDCl$_3$) δ ppm: 0.88-1.31 (m, 9H), 1.48 (s, 9H), 1.62-1.85 (m, 5H), 2.45-2.60 (m, 2H), 3.60 (t, J=5.7 Hz, 2H), 3.90-4.02 (m, 1H), 4.06 (s, 3H), 4.26 (s, 2H), 5.22 (d, J=9.0 Hz, 1H).

Reference Example 81

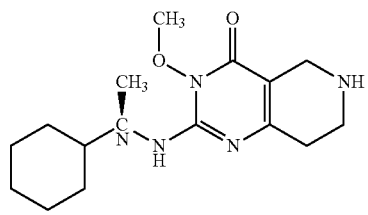

2-((R)-1-Cyclohexylethylamino)-3-methoxy-5,6,7,8-tetrahydro-3H-pyrido[4,3-d]pyrimidin-4-one The titled compound was obtained in the same manner as in Reference Example 12.

$^1$H-NMR (CDCl$_3$) δ ppm: 0.90-1.55 (m, 9H), 1.64-2.00 (m, 5H), 2.47 (t, J=5.8 Hz, 2H), 3.07 (t, J=5.8 Hz, 2H), 3.73 (s, 2H), 3.90-4.01 (m, 1H), 4.03 (s, 3H), 5.21 (d, J=8.9 Hz, 1H).

Reference Example 82

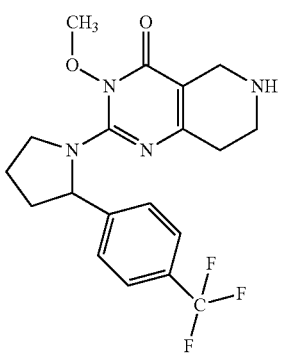 [SMILES: COn1c(N2CCCC2c2ccc(C(F)(F)F)cc2)nc2c(c1=O)CNCC2]

3-Methoxy-2-[2-(4-trifluoromethylphenyl)pyrrolidin-1-yl]-5,6,7,8-tetrahydro-3H-pyrido[4,3-d]pyrimidin-4-one The titled compound was obtained in the same manner as in Reference Example 12.
MS [M+H]+=359

Example 1

Synthesis of 6-(4-cyano-2-fluorobenzoyl)-3-propargyl-2-(S)-{1-[4-(trifluoromethyl)phenyl]ethylamino}-5,6,7,8-tetrahydropyrido[4,3-d]pyrimidin-4-(3H)-one hydrochloride

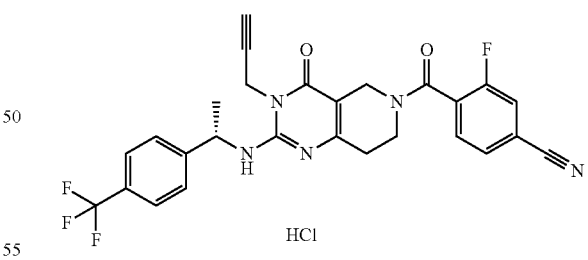

Under nitrogen atmosphere, 4-cyano-2-fluoro benzoate (658 mg) was dissolved in DMF (20 ml), and to the solution 1-ethyl-3-(3-dimethylaminopropyl)carbodiimide hydrochloride (WSC) (930 mg) and 1-hydroxybenzotriazole (637.8 mg) were added at 0° C. After the reaction solution was stirred at 0° C. for a while, 2-(S)-{1-[4-(trifluoromethyl)phenyl]ethylamino}-3-propargyl-5,6,7,8-tetrahydropyrido[4,3-d]pyrimidin-4-(3H)-one (1 g) was added. The temperature was raised to room temperature and the resultant mixture was stirred for 5 hours. Water was added to the reaction solution and the mixture was extracted with ethyl acetate. The organic layer was washed with water and dried over sodium sulfate. Thereafter, filtration and concentration were performed and purification was performed by column chromatography (hexane:ethyl acetate=1:1). The purified substance was dissolved in methylene chloride (5 ml), 1 N hydrogen chloride in ethanol (2 ml) was added, and the resultant mixture was concentrated. The residue was washed with diethyl ether:methylene chloride (1:1) to obtain the titled compound in an amount of 902.5 mg (yield 61%) as a white solid substance. The melting point: 136-138° C.

Example 2

Synthesis of 6-(4-chlorobenzoyl)-3-propargyl-2-(S)-{1-[4-(trifluoromethyl)phenyl]ethylamino}-5,6,7,8-tetrahydropyrido[4,3-d]pyrimidin-4-(3H)-one hydrochloride

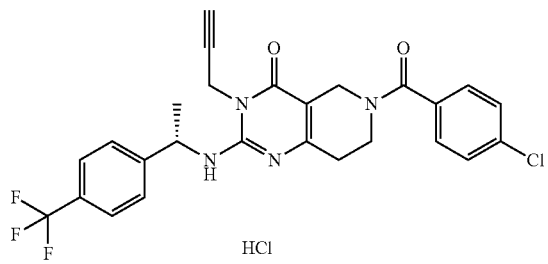 [SMILES: C#CCn1c(N[C@@H](C)c2ccc(C(F)(F)F)cc2)nc2c(c1=O)CN(C(=O)c1ccc(Cl)cc1)CC2 ; Cl]

Under nitrogen atmosphere, 2-(S)-{1-[4-(trifluoromethyl)phenyl]ethylamino}-3-propargyl-5,6,7,8-tetrahydropyrido[4,3-d]pyrimidin-4-(3H)-one (830 mg) was dissolved in methylene chloride (40 ml) at 0° C. To the solution, triethylamine (0.46 ml) and 4-chlorobenzoyl chloride (0.28 ml) were added. After stirred at 0° C. for 30 minutes, water and saturated sodium hydrogen carbonate solution were added and the resultant mixture was extracted with methylene chloride and dried over sodium sulfate. After filtration and concentration were performed, the residue was purified by silica gel column chromatography (hexane:ethyl acetate=1:1). The purified substance was dissolved in methylene chloride (10 ml), 1 N hydrogen chloride in ethanol (2 ml) was added and the resultant mixture was concentrated. The residue was washed with diethyl ether:methylene chloride (1:1) to obtain the titled compound in an amount of 755.9 mg (67%) as a white solid substance. The melting point: 173-174° C.

Example 3

Synthesis of 6-(4-chlorobenzoyl)-3-propargyl-2-(S)-{1-[4-chloro phenyl]ethylamino}-5,6,7,8-tetrahydropyrido[4,3-d]pyrimidin-4-(3H)-one

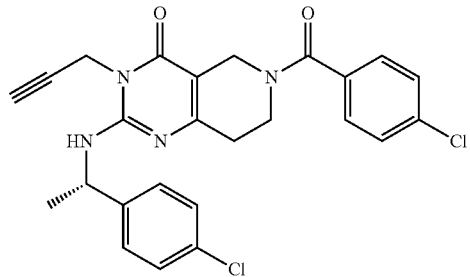 [SMILES: C#CCn1c(N[C@@H](C)c2ccc(Cl)cc2)nc2c(c1=O)CN(C(=O)c1ccc(Cl)cc1)CC2]

Colorless Amorphous $^1$H-NMR (CDCl$_3$) δ ppm: 1.57 (d, J=1.8 Hz, 3H), 2.35-2.75 (m, 3H), 3.45-4.70 (m, 4H), 4.75-4.95 (m, 2H), 5.20-5.30 (m, 2H), 7.20-7.50 (m, 8H).

Example 4

Synthesis of 6-(4 chlorobenzoyl)-2-(3-fluoro-4-trifluorobenzylamino)-3-propargyl-5,6,7,8-tetrahydropyrido[4,3-d]pyrimidin-4-(3H)-one

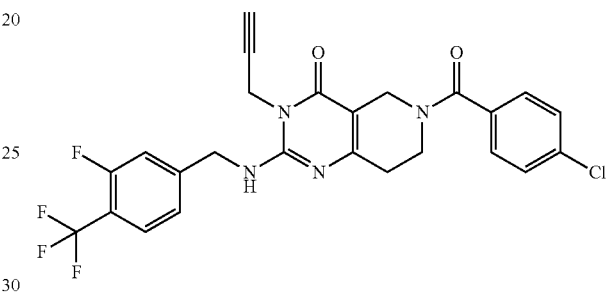

6-(4-Chlorobenzoyl)-3-propargyl-5,6,7,8-tetrahydropyrido[4,3-d]pyrimidine-2,4-dione (800 mg) was dissolved in tetrahydrofuran (16 ml), 1H-benzotriazol-1-yloxytris(dimethylamino)phosphonium hexafluorophosphate (BOP) (1.85 g) and 1,8-diazabicyclo[5.4.0]-7-undecene (DBU) (0.71 ml) were added and the resultant mixture was stirred at room temperature. At 10 minutes later, 3-fluoro-4-trifluoromethylbenzylamine (0.90 ml) was added and the resultant mixture was further stirred at room temperature overnight. The reaction solution was concentrated under reduced pressure. To the residue, saturated sodium hydrogen carbonate solution was added and the mixture was extracted with ethyl acetate. The organic layer was washed with saturated saline solution and thereafter dried over sodium sulfate, filtrated and concentrated. The resultant residue was purified by medium-pressure silica gel column chromatography (solvent; ethyl acetate:hexane=50:50 to 80:20) to obtain a colorless amorphous substance (460 mg). A substance (860 mg) separately synthesized was combined and dissolved in ethanol (15 ml) and 1 N hydrochloric acid in ethanol (2.50 ml) was added. After concentration, diisopropyl ether was added to the resultant residue to form a crystal. The resultant crude crystal was recrystallized from isopropyl alcohol. The titled compound (367 mg) was obtained as a white powder.

$^1$H-NMR (CDCl$_3$) δ ppm: 2.36-2.46 (m, 1H), 2.46-2.75 (m, 2H), 3.35-4.06 (m, 2H), 4.16-4.66 (m, 2H), 4.72-4.76 (m, 2H), 4.85 (brs, 2H), 5.39-5.57 (m, 1H), 7.11-7.25 (m, 2H), 7.39 (s, 4H), 7.59 (t, 7.6 Hz, 1H).

Example 5

Synthesis of 6-(4-cyano-2-fluorobenzoyl)-3-dimethylamino-2-(S)-{1-[4-(trifluoromethyl)phenyl]ethylamino}-5,6,7,8-tetrahydropyrido[4,3-d]pyrimidin-4-(3H)-one hydrochloride

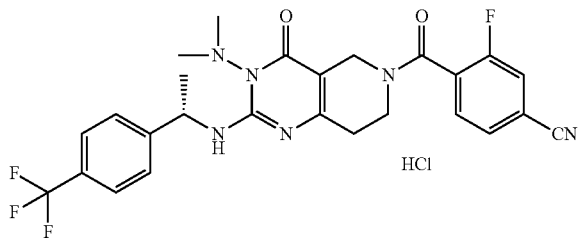 [SMILES: C[C@H](Nc1nc2c(c(=O)n1N(C)C)CN(C(=O)c1ccc(C#N)cc1F)CC2)c1ccc(C(F)(F)F)cc1 ; Cl]

$^1$H-NMR (DMSO-$d_6$) δ ppm: 1.52 (d, J=6.9 Hz, 3H), 2.27-2.67 (m, 2H), 2.85-2.95 (m, 6H), 3.33-3.37 (m, 1H), 3.58-4.10 (m, 2H), 4.16-4.44 (m, 1H), 5.01-5.36 (m, 1H), 7.56-7.73 (m, 5H), 7.76-7.86 (m, 1H), 7.96-7.86 (m, 1H), 8.06-8.17 (m, 1H). HCl was not observed.

Example 6

Synthesis of 6-(4-chlorobenzoyl)-3-dimethylamino-2-(S)-{1-[4-(trifluoromethyl)phenyl]ethylamino}-5,6,7,8-tetrahydropyrido[4,3-d]pyrimidin-4-(3H)-one hydrochloride

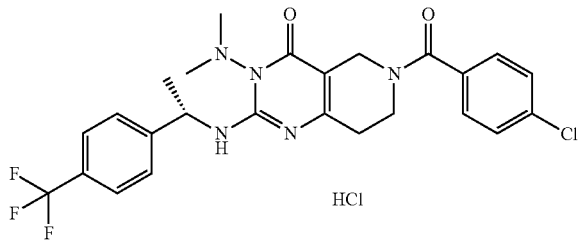 [SMILES: C[C@H](Nc1nc2c(c(=O)n1N(C)C)CN(C(=O)c1ccc(Cl)cc1)CC2)c1ccc(C(F)(F)F)cc1 ; Cl]

Slightly yellow powder, melting point 116-118° C. (ether-ethyl acetate)

$^1$H-NMR (DMSO-$d_6$) δ ppm: 1.54 (d, J=7.0 Hz, 3H), 2.33-2.52 (m, 2H), 2.86 (s, 3H), 2.93 (s, 3H), 3.35-3.50 (m, 1H), 3.70-3.85 (m, 1H), 4.00-4.15 (m, 1H), 4.25-4.40 (m, 1H), 5.25-5.50 (m, 1H), 7.45-7.53 (m, 4H), 7.63 (d, J=8.3 Hz, 2H), 7.70 (d, J=8.3 Hz, 2H), 8.20-8.40 (m, 1H). HCl was not observed.

Example 7

Synthesis of 6-(4-chlorobenzoyl)-3-dimethylamino-2-(3-fluoro-4-trifluoromethylbenzylamino)-5,6,7,8-tetrahydropyrido[4,3-d]pyrimidin-4-(3H)-one hydrochloride

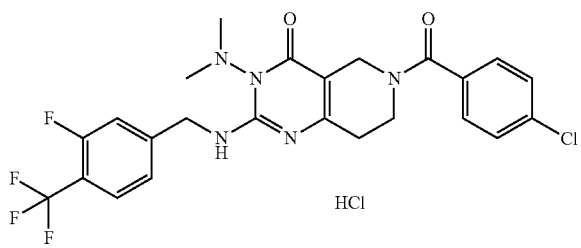 [SMILES: CN(C)n1c(NCc2ccc(C(F)(F)F)c(F)c2)nc2c(c1=O)CN(C(=O)c1ccc(Cl)cc1)CC2 ; Cl]

Slightly yellow powder, melting point 122-124° C. (ether-ethyl acetate)

$^1$H-NMR (DMSO-$d_6$) δ ppm: 2.40-2.55 (m, 2H), 2.87 (s, 3H), 2.95 (s, 3H), 3.40-3.60 (m, 1H), 3.70-3.80 (m, 1H), 4.00-4.20 (m, 1H), 4.25-4.40 (m, 1H), 4.65-4.80 (m, 2H), 7.38 (d, J=8.0 Hz, 1H), 7.46-7.58 (m, 5H), 7.74 (t, J=7.9 Hz, 1H), 8.70-9.00 (m, 1H). HCl was not observed.

Example 8

Synthesis of 6-(4-chlorobenzoyl)-2-(S)-[1-(4-chlorophenyl)ethylamino]-3-dimethylamino-5,6,7,8-tetrahydropyrido[4,3-d]pyrimidin-4-(3H)-one hydrochloride

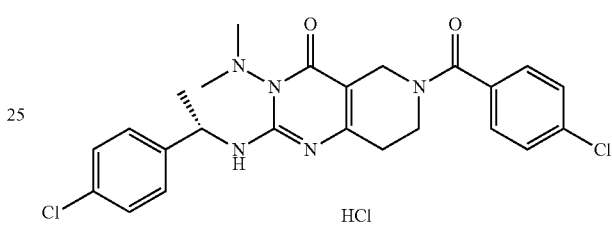

Slightly yellow powder, melting point 121-123° C. (ether-ethyl acetate)

$^1$H-NMR (DMSO-$d_6$) δ ppm: 1.50 (d, J=7.0 Hz, 3H), 2.37-2.55 (m, 2H), 2.85 (s, 3H), 2.91 (s, 3H), 3.35-3.50 (m, 1H), 3.70-3.85 (m, 1H), 4.00-4.15 (m, 1H), 4.25-4.40 (m, 1H), 5.20-5.30 (m, 1H), 7.37-7.39 (m, 2H), 7.44-7.58 (m, 6H), 8.10-8.40 (m, 1H). HCl was not observed.

Example 9

Synthesis of 6-(4-chlorobenzoyl)-3-methoxy-2-(S)-[1-(4-chlorophenyl)ethylamino]-5,6,7,8-tetrahydropyrido[4,3-d]pyrimidin-4-(3H)-one

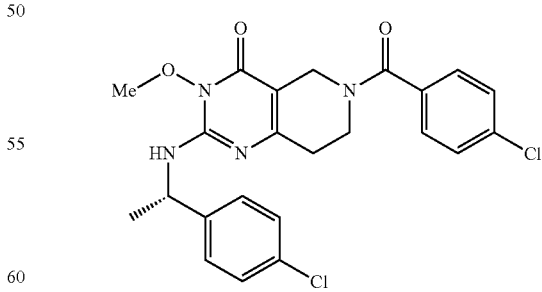

Colorless Amorphous $^1$H-NMR (CDCl$_3$) δ ppm: 1.56 (d, J=1.8 Hz, 3H), 2.35-2.75 (m, 2H), 3.45-4.70 (m, 7H) 5.10-5.30 (m, 1H), 5.55-5.70 (m, 1H), 7.20-7.50 (m, 8H).

Example 10

Synthesis of 6-(4-chlorobenzoyl)-3-methoxy-2-(S)-{1-[4-(trifluoromethyl)phenyl]ethylamino}-5,6,7,8-tetrahydropyrido[4,3-d]pyrimidin-4-(3H)-one hydrochloride

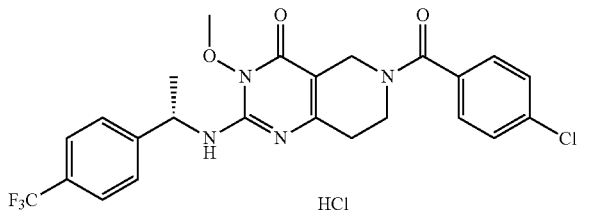 [SMILES: COn1c(N[C@@H](C)c2ccc(C(F)(F)F)cc2)nc2c(c1=O)CN(C(=O)c1ccc(Cl)cc1)CC2 ; Cl]

Under nitrogen atmosphere, 3-methoxy-2-(S)-{1-[4-(trifluoromethyl)phenyl]ethylamino}-5,6,7,8-tetrahydropyrido[4,3-d]pyrimidin-4-(3H)-one (0.75 g) was dissolved in methylene chloride (7 ml), and diisopropylmethylamine (0.45 ml) and 4-chlorobenzoyl chloride (0.32 ml) were added while stirring under ice cooling. The reaction mixture was stirred under nitrogen atmosphere at room temperature for 18 hours. To the reaction solution, saturated saline solution was added and the mixture was extracted with methylene chloride. The organic layer was dried over sodium sulfate, filtrated and concentrated. The resultant residue was subjected to medium-pressure silica gel column chromatography (solvent; ethyl acetate:hexane=0:100 to 50:50) to obtain a white amorphous substance (0.57 g).

The resultant compound was dissolved in ethanol and 1 N hydrochloric acid in ethanol (1.5 ml) was added and the resultant mixture was concentrated. The resultant residue was dissolved in a small amount of ethanol and ether was added to form a crystal. The titled compound (0.49 g) was obtained as a white powdery crystal.

Melting point 123 to 126° C.
$^1$H-NMR (DMSO-$d_6$) δ ppm: 1.54 (d, J=7.0 Hz, 3H), 2.24-2.52 (m, 2H), 3.34-3.50 (m, 1H), 3.61-3.97 (m, 5H), 4.00-4.13 (m, 1H), 5.19-5.33 (m, 1H), 7.46 (d, J=8.5 Hz, 2H), 7.52 (d, J=8.5 Hz, 2H), 7.63 (d, J=8.5 Hz, 2H), 7.70 (d, J=8.5 Hz, 2H), 8.21 (d, J=8.5 Hz, 1H). HCl was not observed.

Example 11

Synthesis of 6-(4-cyano-2-fluorobenzoyl)-3-methoxy-2-(S)-{1-[4-(trifluoromethyl)phenyl]ethylamino}-5,6,7,8-tetrahydropyrido[4,3-d]pyrimidin-4-(3H)-one hydrochloride

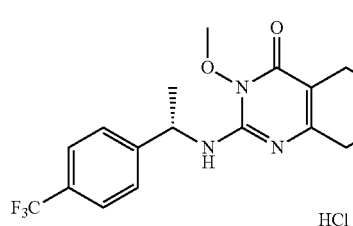

Under nitrogen atmosphere, to 3-methoxy-2-(S)-{1-[4-(trifluoromethyl)phenyl]ethylamino}-5,6,7,8-tetrahydropyrido[4,3-d]pyrimidin-4-(3H)-one (0.75 g) and 4-cyano-2-fluoro benzoate (0.40 g) in DMF (7 ml), diisopropylmethylamine (0.45 ml) was added. Under ice cooling while stirring, O-(7-azabenzotriazol-1-yl)-N,N,N',N'-tetra methyluronium hexafluorophosphate (HATU) (0.92 g) was added. The reaction mixture was stirred under nitrogen atmosphere at room temperature for 18 hours. Water was added and the mixture was extracted with ethyl acetate. The organic layer was dried over Na2SO4, filtrated and concentrated. The resultant residue was purified by medium-pressure silica gel column chromatography (solvent; ethyl acetate:hexane=0:100 to 50:50). A white amorphous substance (1.04 g) was obtained.

The resultant compound was dissolved in ethanol, 1 N hydrochloric acid in ethanol (2.5 ml) was added and the resultant mixture was concentrated. The resultant residue was dissolved in a small amount of ethanol and ether was added to form a crystal. The titled compound (0.85 g) was obtained as a white powdery crystal. Melting point 120 to 122° C.
$^1$H-NMR (DMSO-$d_6$) δ ppm: 1.54 (d, J=7.0 Hz, 3H), 2.24-2.45 (m, 2H), 3.30-3.39 (m, 1H), 3.67-3.91 (m, 2H), 3.94 (s, 3H), 4.27-4.39 (m, 1H), 5.20-5.33 (m, 1H), 7.58-7.72 (m, 5H), 7.76-7.84 (m, 1H), 7.97-8.50 (m, 1H), 8.24 (d, J=8.5 Hz, 1H). HCl was not observed.

Appropriate corresponding starting materials were used to produce compounds of Examples 12-2384 shown in the following table in the same manner as the above Reference Examples and the above Examples.

TABLE 1

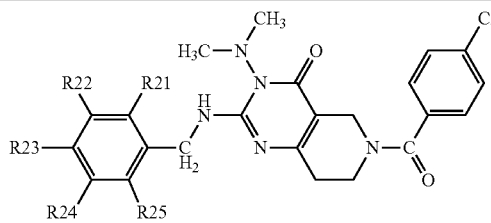

| Example | R21 | R22 | R23 | R24 | R25 | MS(M + 1) |
|---|---|---|---|---|---|---|
| 12 | —H | —H | —OCH$_3$ | —H | —H | 468 |
| 13 | —H | —H | —Cl | —H | —H | 472 |
| 14 | —H | —H | —CF$_3$ | —H | —H | 506 |
| 15 | —H | —H | —CN | —H | —H | 463 |
| 16 | —H | —H | —OCF$_3$ | —H | —H | 522 |
| 17 | —H | —H | —CH$_3$ | —H | —H | 452 |
| 18 | —H | —H | —F | —H | —H | 456 |
| 19 | —H | —F | —CF$_3$ | —H | —H | 524 |
| 20 | —H | —Cl | —Cl | —H | —H | 506 |

TABLE 2

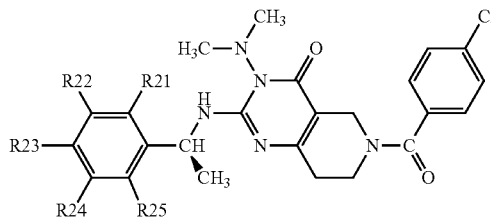

| Example | R21 | R22 | R23 | R24 | R25 | MS(M + 1) |
|---|---|---|---|---|---|---|
| 21 | —H | —H | —Cl | —H | —H | 486 |
| 22 | —H | —H | —CF$_3$ | —H | —H | 520 |
| 23 | —H | —H | —CH$_3$ | —H | —H | 466 |
| 24 | —H | —H | —OCH$_3$ | —H | —H | 482 |

TABLE 2-continued

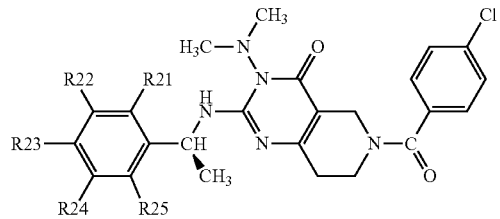

| Example | R21 | R22 | R23 | R24 | R25 | MS(M + 1) |
|---|---|---|---|---|---|---|
| 25 | —H | —H | —F | —H | —H | 470 |
| 26 | —H | —H | —OCF₃ | —H | —H | 536 |

TABLE 3

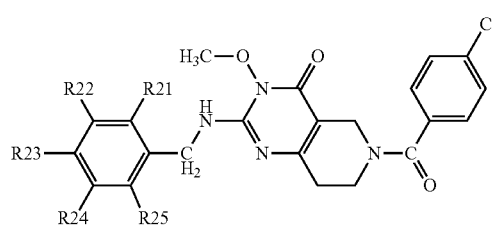

| Example | R21 | R22 | R23 | R24 | R25 | MS(M + 1) |
|---|---|---|---|---|---|---|
| 27 | —H | —H | —Cl | —H | —H | 459 |
| 28 | —H | —H | —CF₃ | —H | —H | 493 |
| 29 | —H | —H | —OCF₃ | —H | —H | 509 |
| 30 | —H | —H | —CH₃ | —H | —H | 439 |
| 31 | —H | —H | —F | —H | —H | 443 |
| 32 | —H | —F | —CF₃ | —H | —H | 511 |

TABLE 4

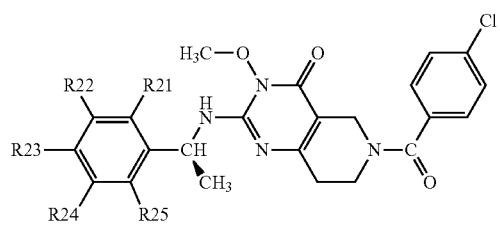

| Example | R21 | R22 | R23 | R24 | R25 | MS(M + 1) |
|---|---|---|---|---|---|---|
| 33 | —H | —H | —Cl | —H | —H | 473 |
| 34 | —H | —H | —CF₃ | —H | —H | 507 |
| 35 | —H | —H | —CH₃ | —H | —H | 453 |
| 36 | —H | —H | —OCH₃ | —H | —H | 469 |
| 37 | —H | —H | —F | —H | —H | 457 |
| 38 | —H | —H | —OCF₃ | —H | —H | 523 |

TABLE 5

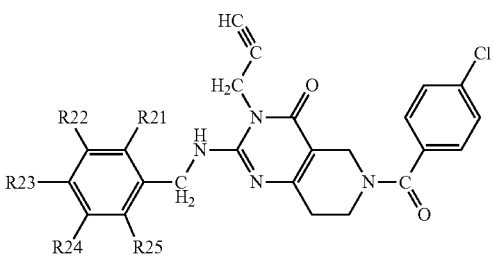

| Example | R21 | R22 | R23 | R24 | R25 | MS(M + 1) |
|---|---|---|---|---|---|---|
| 39 | —H | —H | —Cl | —H | —H | 467 |
| 40 | —H | —H | —CF₃ | —H | —H | 501 |
| 41 | —H | —H | —OCF₃ | —H | —H | 517 |
| 42 | —H | —H | —CH₃ | —H | —H | 447 |
| 43 | —H | —H | —F | —H | —H | 451 |
| 44 | —H | —F | —CF₃ | —H | —H | 519 |

TABLE 6

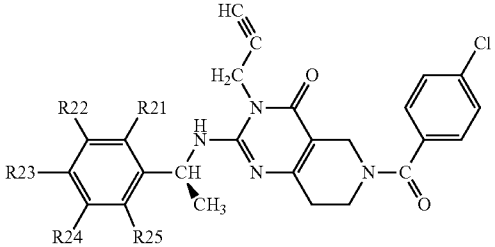

| Example | R21 | R22 | R23 | R24 | R25 | MS(M + 1) |
|---|---|---|---|---|---|---|
| 45 | —H | —H | —Cl | —H | —H | 481 |
| 46 | —H | —H | —CF₃ | —H | —H | 515 |
| 47 | —H | —H | —CH₃ | —H | —H | 461 |
| 48 | —H | —H | —OCH₃ | —H | —H | 477 |
| 49 | —H | —H | —F | —H | —H | 465 |
| 50 | —H | —H | —OCF₃ | —H | —H | 531 |

TABLE 7

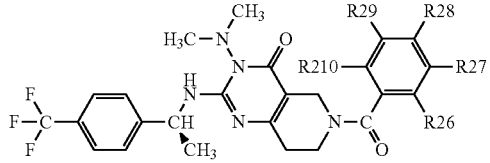

| Example | R26 | R27 | R28 | R29 | R210 | MS(M + 1) |
|---|---|---|---|---|---|---|
| 51 | —H | —H | —CN | —H | —H | 511 |
| 52 | —F | —H | —CN | —H | —H | 529 |
| 53 | —H | —H | —CH₃ | —H | —H | 500 |
| 54 | —H | —H | —COCH₃ | —H | —H | 528 |
| 55 | —H | —H | —CF₃ | —H | —H | 554 |
| 56 | —H | —H | —OCF₃ | —H | —H | 570 |
| 57 | —H | —H | 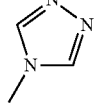 | —H | —H | 553 |

TABLE 8

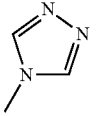

| Example | R26 | R27 | R28 | R29 | R210 | MS(M + 1) |
|---|---|---|---|---|---|---|
| 58 | —H | —H | —CN | —H | —H | 498 |
| 59 | —F | —H | —CN | —H | —H | 516 |
| 60 | —H | —H | —CH₃ | —H | —H | 487 |
| 61 | —H | —H | —COCH₃ | —H | —H | 515 |
| 62 | —H | —H | —CF₃ | —H | —H | 541 |
| 63 | —H | —H | —OCF₃ | —H | —H | 557 |
| 64 | —H | —H | 4-methyl-1,2,4-triazol-3-yl | —H | —H | 540 |

TABLE 9

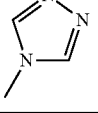

| Example | R26 | R27 | R28 | R29 | R210 | MS(M + 1) |
|---|---|---|---|---|---|---|
| 65 | —H | —H | —CN | —H | —H | 506 |
| 66 | —F | —H | —CN | —H | —H | 524 |
| 67 | —H | —H | —CH₃ | —H | —H | 495 |
| 68 | —H | —H | —COCH₃ | —H | —H | 523 |
| 69 | —H | —H | —CF₃ | —H | —H | 549 |
| 70 | —H | —H | —OCF₃ | —H | —H | 565 |
| 71 | —H | —H | 4-methyl-1,2,4-triazol-3-yl | —H | —H | 548 |

TABLE 10

| Example | R211 | R212 | MS(M + 1) |
|---|---|---|---|
| 72 | 6-methylnaphthalen-2-yl | —N(CH₃)₂ | 536 |
| 73 | 6-methylnaphthalen-2-yl | —CH₂C≡CH | 531 |

TABLE 10-continued

| Example | R211 | R212 | MS(M + 1) |
|---|---|---|---|
| 74 | 5-methylbenzo[b]thiophen-2-yl | —CH₂C≡CH | 537 |
| 75 | 6-methylnaphthalen-2-yl | —OCH₃ | 523 |
| 76 | 5-methylbenzo[b]thiophen-2-yl | —OCH₃ | 529 |
| 77 | 2,5-dimethylthiophen-3-yl | —N(CH₃)₂ | 506 |
| 78 | 2,5-dimethylthiophen-3-yl | —CH₂C≡CH | 501 |
| 79 | 2,5-dimethylthiophen-3-yl | —OCH₃ | 493 |

TABLE 11

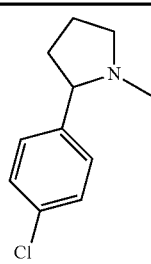

| Example | R212 | R213 | MS(M + 1) |
|---|---|---|---|
| 80 | —N(CH₃)₂ | 2-(4-chlorophenyl)-1-methylpyrrolidin-2-yl | 512 |

TABLE 11-continued

| Example | R212 | R213 | MS(M + 1) |
|---|---|---|---|
| 81 | —CH₂C≡CH | (1-methylpyrrolidin-2-yl)(4-chlorophenyl) | 507 |
| 82 | —OCH₃ | (1-methylpyrrolidin-2-yl)(4-chlorophenyl) | 499 |
| 83 | —OCH₃ | 1-(4-chlorophenyl)-1-(N-methylamino)cyclopropyl | 485 |

TABLE 12

| Example | R26 | R27 | R28 | R29 | R210 | MS(M + 1) |
|---|---|---|---|---|---|---|
| 84 | —H | —H | —H | —H | —H | 487 |
| 85 | —H | —H | —CH₃ | —H | —H | 501 |
| 86 | —H | —H | —Cl | —H | —H | 521 |
| 87 | —H | —H | —F | —H | —H | 505 |
| 88 | —H | —H | —OCH₃ | —H | —H | 517 |
| 89 | —H | —H | —CF₃ | —H | —H | 555 |
| 90 | —H | —Cl | —H | —H | —H | 521 |
| 91 | —H | —CH₃ | —H | —H | —H | 501 |
| 92 | —H | —H | —CN | —H | —H | 512 |
| 93 | —H | —CH₃ | —CH₃ | —H | —H | 515 |
| 94 | —H | —H | —OCF₃ | —H | —H | 571 |
| 95 | —F | —H | —CN | —H | —H | 530 |
| 96 | —H | —CH₃ | —Cl | —H | —H | 535 |
| 97 | —H | —Cl | —CH₃ | —H | —H | 535 |
| 98 | —H | —H | —OC₂H₅ | —H | —H | 531 |
| 99 | —H | —H | —SCH₃ | —H | —H | 533 |
| 100 | —H | —H | —OCH(CH₃)₂ | —H | —H | 545 |

TABLE 13

| Example | R26 | R27 | R28 | R29 | R210 | MS(M + 1) |
|---|---|---|---|---|---|---|
| 101 | —H | —H | 1-methyl-1,2,4-triazol-3-yl | —H | —H | 554 |
| 102 | —H | —H | 1-methylimidazol-2-yl | —H | —H | 553 |
| 103 | —H | —H | 4-methyl-1,2,4-triazol-3-yl | —H | —H | 554 |
| 104 | —H | —H | 5-methyloxazol-2-yl | —H | —H | 554 |
| 105 | —H | —H | 2,5-dimethyl-1,3,4-oxadiazol-yl | —H | —H | 569 |

TABLE 14

| Example | R211 | MS(M + 1) |
|---|---|---|
| 106 | naphthalen-2-yl | 537 |
| 107 | naphthalen-1-yl | 537 |
| 108 | benzo[d][1,3]dioxol-5-yl (methyl-substituted) | 531 |

TABLE 14-continued
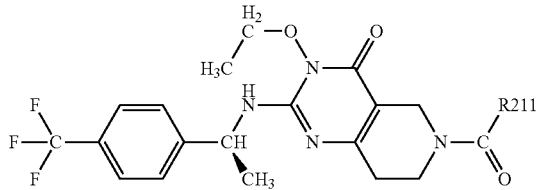
| Example | R211 | MS(M + 1) |
|---|---|---|
| 109 | 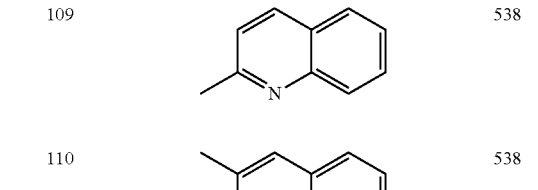 | 538 |
| 110 | 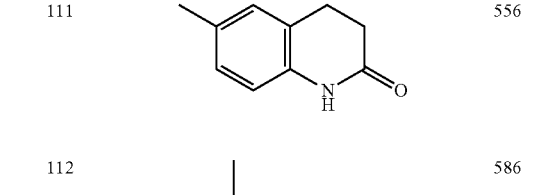 | 538 |
| 111 | 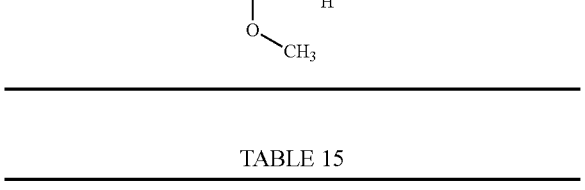 | 556 |
| 112 | 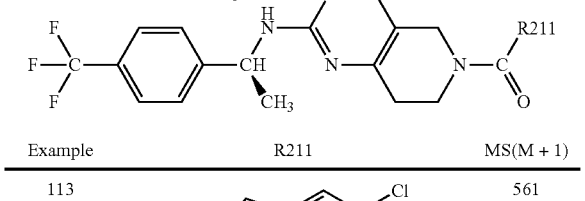 | 586 |
TABLE 15
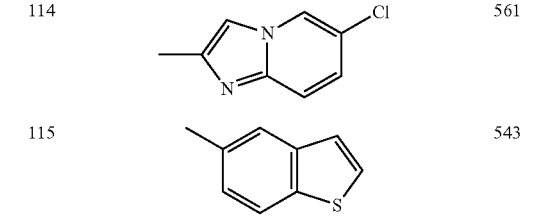
| Example | R211 | MS(M + 1) |
|---|---|---|
| 113 |  | 561 |
| 114 | 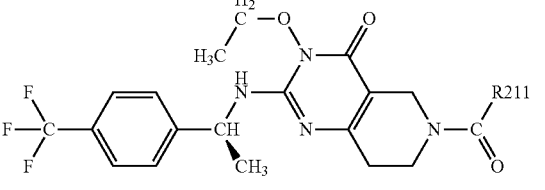 | 561 |
| 115 | 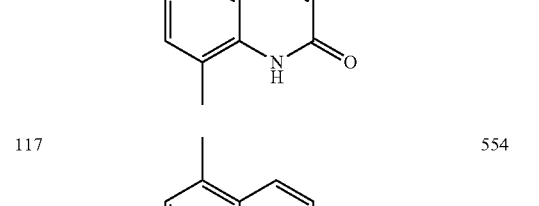 | 543 |
TABLE 15-continued
| Example | R211 | MS(M + 1) |
|---|---|---|
| 116 | 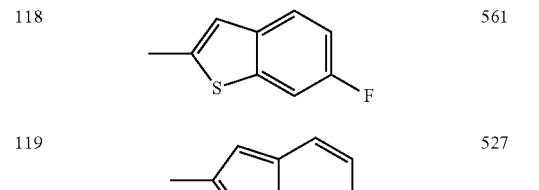 | 554 |
| 117 | 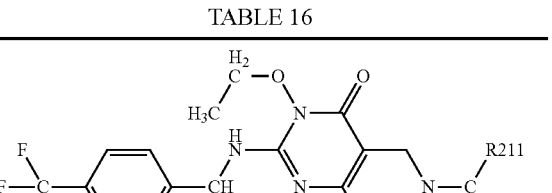 | 554 |
| 118 | 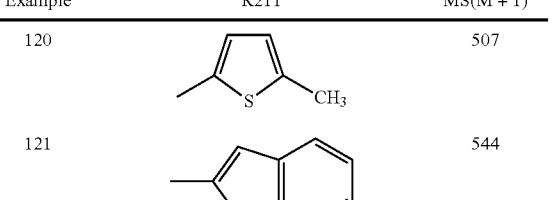 | 561 |
| 119 | 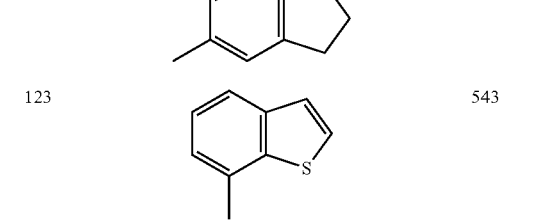 | 527 |
TABLE 16
| Example | R211 | MS(M + 1) |
|---|---|---|
| 120 |  | 507 |
| 121 | | 544 |
| 122 | | 527 |
| 123 | | 543 |

TABLE 16-continued
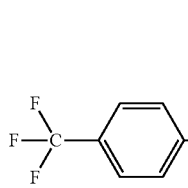
| Example | R211 | MS(M + 1) |
|---|---|---|
| 124 | 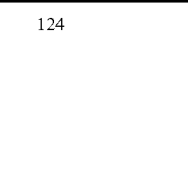 | 554 |
| 125 |  | 489 |
| 126 | 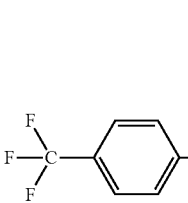 | 538 |
TABLE 17
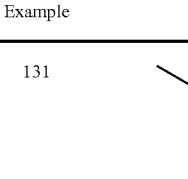
| Example | R211 | MS(M + 1) |
|---|---|---|
| 127 | 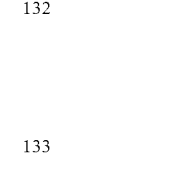 | 570 |
| 128 | 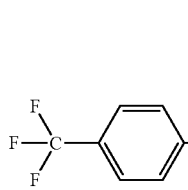 | 572 |
| 129 | 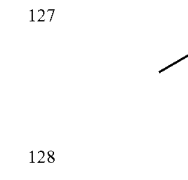 | 478 |
| 130 | 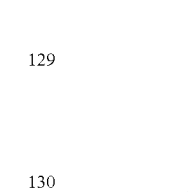 | 542 |
TABLE 17-continued
| Example | R211 | MS(M + 1) |
|---|---|---|
| 131 |  | 556 |
| 132 |  | 489 |
| 133 | 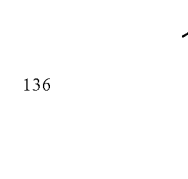 | 540 |
TABLE 18
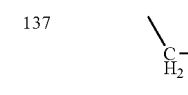
| Example | R211 | MS(M + 1) |
|---|---|---|
| 134 |  | 502 |
| 135 |  | 502 |
| 136 |  | 523 |
| 137 |  | 526 |

TABLE 18-continued

[Structure: ethoxy-N, trifluoromethylphenyl-CH(CH3)-NH, pyrimidinone fused piperidine with R211-C(=O)-N]

| Example | R211 | MS(M + 1) |
|---------|------|-----------|
| 138 | 5-fluoro-8-methylnaphthalenyl | 555 |
| 139 | 2-methyl-1H-benzimidazolyl | 527 |
| 140 | 5-methyl-4H-thieno[3,2-b]pyrrolyl | 532 |

TABLE 19

[Same core structure]

| Example | R211 | MS(M + 1) |
|---------|------|-----------|
| 141 | methyl-thieno-dioxine | 551 |
| 142 | methyl-1,8-naphthyridinyl | 539 |
| 143 | 5-methyl-indolin-2-one | 542 |
| 144 | 6-methyl-indolin-2-one | 542 |

TABLE 19-continued

| Example | R211 | MS(M + 1) |
|---------|------|-----------|
| 145 | 2-methylpyrimidinyl | 489 |
| 146 | 6-methyl-4-methyl-2H-benzo[b][1,4]thiazin-3(4H)-one | 588 |
| 147 | 7-methylquinolinyl | 538 |

TABLE 20

[Same core structure]

| Example | R211 | MS(M + 1) |
|---------|------|-----------|
| 148 | 2-methylbenzothiazolyl | 544 |
| 149 | 8-methylquinolinyl | 538 |

TABLE 20-continued

| Example | R211 | MS(M + 1) |
|---|---|---|
| 150 | 2-methylindolizinyl | 526 |
| 151 | 5-methyl-1H-imidazolyl | 477 |
| 152 | 1-benzoyl-3-methylpyrrolidinyl | 584 |
| 153 | 1,3-dimethyl-2-oxo-1,2-dihydropyridinyl | 518 |
| 154 | 1,5-dimethyl-2-oxo-1,2-dihydropyridinyl | 518 |

TABLE 21

| Example | R26 | R27 | R28 | R29 | R210 | MS(M + 1) |
|---|---|---|---|---|---|---|
| 155 | —H | —H | —H | —H | —H | 512 |
| 156 | —H | —H | —CH₃ | —H | —H | 526 |
| 157 | —H | —H | —Cl | —H | —H | 546 |
| 158 | —H | —H | —F | —H | —H | 530 |
| 159 | —H | —H | —OCH₃ | —H | —H | 542 |
| 160 | —H | —H | —CF₃ | —H | —H | 580 |
| 161 | —H | —Cl | —H | —H | —H | 546 |
| 162 | —H | —CH₃ | —H | —H | —H | 526 |
| 163 | —H | —H | —CN | —H | —H | 537 |
| 164 | —H | —CH₃ | —CH₃ | —H | —H | 540 |
| 165 | —H | —H | —OCF₃ | —H | —H | 596 |
| 166 | —F | —H | —CN | —H | —H | 555 |
| 167 | —H | —CH₃ | —Cl | —H | —H | 560 |
| 168 | —H | —Cl | —CH₃ | —H | —H | 560 |
| 169 | —H | —H | —OC₂H₅ | —H | —H | 556 |
| 170 | —H | —H | —SCH₃ | —H | —H | 558 |
| 171 | —H | —H | —OCH(CH₃)₂ | —H | —H | 570 |

TABLE 22
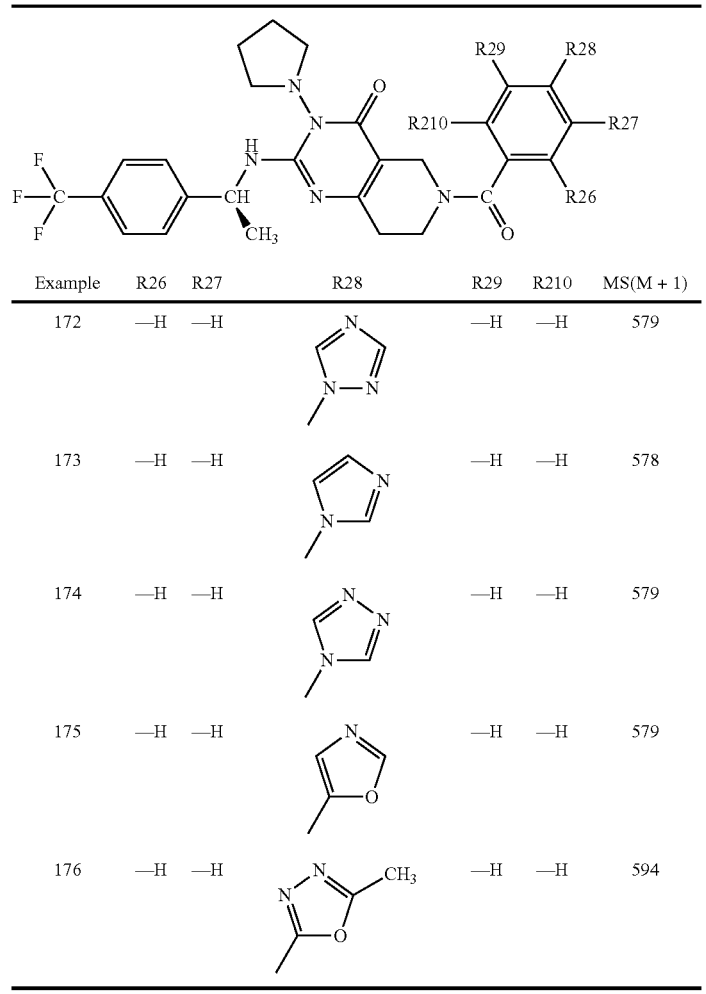
| Example | R26 | R27 | R28 | R29 | R210 | MS(M + 1) |
|---|---|---|---|---|---|---|
| 172 | —H | —H | (1-methyl-1,2,4-triazol-3-yl) | —H | —H | 579 |
| 173 | —H | —H | (1-methylimidazol-2-yl) | —H | —H | 578 |
| 174 | —H | —H | (4-methyl-1,2,4-triazol-3-yl) | —H | —H | 579 |
| 175 | —H | —H | (oxazol-5-yl) | —H | —H | 579 |
| 176 | —H | —H | (2,5-dimethyl-1,3,4-oxadiazol-yl) | —H | —H | 594 |
TABLE 23
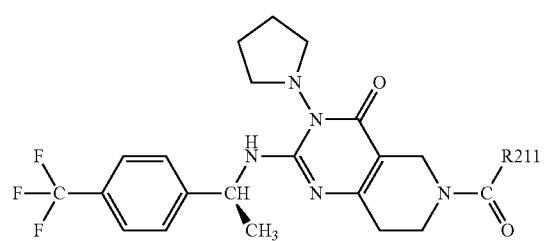
| Example | R211 | MS(M + 1) |
|---|---|---|
| 177 | 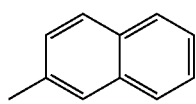 | 562 |
| 178 | 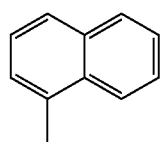 | 562 |
TABLE 23-continued
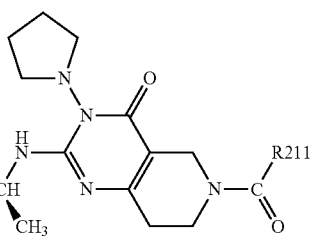
| Example | R211 | MS(M + 1) |
|---|---|---|
| 179 | 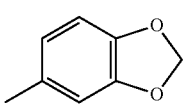 | 556 |
| 180 | 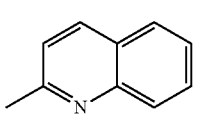 | 563 |

TABLE 23-continued

| Example | R211 | MS(M + 1) |
|---|---|---|
| 181 | 3-methylquinoline | 563 |
| 182 | 6-methyl-3,4-dihydroquinolin-2(1H)-one | 581 |
| 183 | 5-methyl-8-methoxy-3,4-dihydroquinolin-2(1H)-one | 611 |

TABLE 24

| Example | R211 | MS(M + 1) |
|---|---|---|
| 184 | 5-chloro-2-methylbenzofuran | 586 |
| 185 | 6-chloro-2-methylimidazo[1,2-a]pyridine | 586 |
| 186 | 5-methylbenzothiophene | 568 |
| 187 | 8-methylquinolin-2(1H)-one | 579 |

TABLE 24-continued

| Example | R211 | MS(M + 1) |
|---|---|---|
| 188 | 5-methylquinolin-2(1H)-one | 579 |
| 189 | 6-fluoro-2-methylbenzothiophene | 586 |
| 190 | 2-methylpyrazolo[1,5-a]pyridine | 552 |

TABLE 25

| Example | R211 | MS(M + 1) |
|---|---|---|
| 191 | 2,5-dimethylthiophene | 532 |
| 192 | 2-methylthieno[2,3-b]pyridine | 569 |
| 193 | 5-methylindane | 564 |
| 194 | 7-methylbenzothiophene | 552 |

TABLE 25-continued
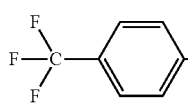
| Example | R211 | MS(M + 1) |
|---|---|---|
| 195 | 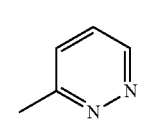 | 568 |
| 196 | 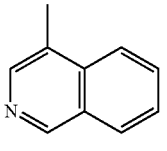 | 579 |
| 197 | 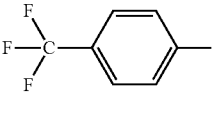 | 514 |
TABLE 26
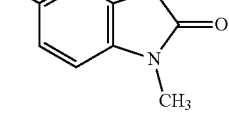
| Example | R211 | MS(M + 1) |
|---|---|---|
| 198 | 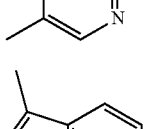 | 563 |
| 199 | 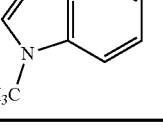 | 595 |
| 200 | 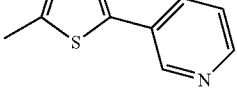 | 597 |
TABLE 26-continued
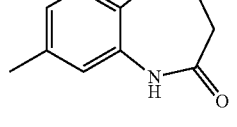
| Example | R211 | MS(M + 1) |
|---|---|---|
| 201 | 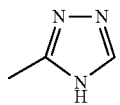 | 567 |
| 202 | 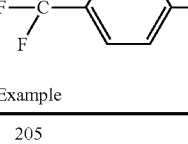 | 581 |
| 203 | 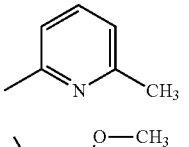 | 514 |
| 204 | 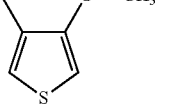 | 565 |
TABLE 27
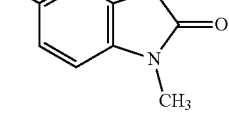
| Example | R211 | MS(M + 1) |
|---|---|---|
| 205 | | 527 |
| 206 | | 527 |
| 207 | | 548 |

TABLE 27-continued

| Example | R211 | MS(M + 1) |
|---|---|---|
| 208 | 4-cyanobenzyl (CH2-C6H4-CN) | 551 |
| 209 | 5-fluoro-8-methylnaphthalenyl | 580 |
| 210 | 2-methylbenzimidazolyl | 552 |
| 211 | 5-methylthieno-pyrrole | 557 |

TABLE 28

| Example | R211 | MS(M + 1) |
|---|---|---|
| 212 | 2-methyl-thieno[3,4-b][1,4]dioxine | 576 |
| 213 | 7-methyl-1,8-naphthyridinyl | 564 |
| 214 | 5-methyl-2-oxoindolinyl | 567 |

TABLE 28-continued

| Example | R211 | MS(M + 1) |
|---|---|---|
| 215 | 6-methyl-2-oxoindolinyl | 567 |
| 216 | 2-methylpyrimidinyl | 514 |
| 217 | 4,6-dimethyl-3-oxo-benzothiazinyl | 613 |
| 218 | 7-methylquinolinyl | 563 |

TABLE 29

| Example | R211 | MS(M + 1) |
|---|---|---|
| 219 | 2-methylbenzothiazolyl | 569 |
| 220 | 5-methylquinolinyl | 563 |
| 221 | 2-methylindolizinyl | 551 |

TABLE 29-continued

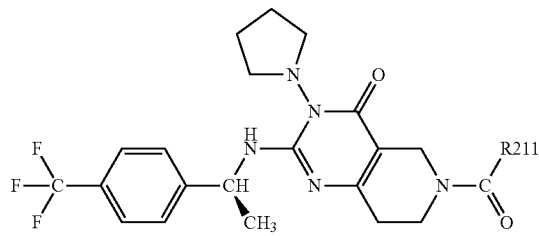

| Example | R211 | MS(M + 1) |
|---|---|---|
| 222 | (4-methylimidazole) | 502 |
| 223 | (3-methylpyrrolidine benzoyl) | 609 |
| 224 | (1,3-dimethylpyridin-2(1H)-one) | 543 |
| 225 | (1,5-dimethylpyridin-2(1H)-one) | 543 |

TABLE 30

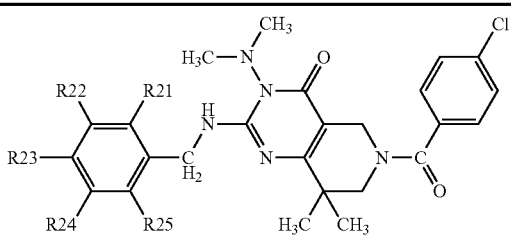

| Example | R21 | R22 | R23 | R24 | R25 | MS(M + 1) |
|---|---|---|---|---|---|---|
| 226 | —H | —H | —H | —H | —H | 466 |
| 227 | —H | —H | —CH₃ | —H | —H | 480 |
| 228 | —H | —H | —OCH₃ | —H | —H | 496 |
| 229 | —H | —H | —CN | —H | —H | 490 |
| 230 | —H | —H | —CF₃ | —H | —H | 534 |
| 231 | —H | —H | —Cl | —H | —H | 500 |
| 232 | —H | —H | —OCF₃ | —H | —H | 550 |
| 233 | —H | —Cl | —Cl | —H | —H | 536 |
| 234 | —H | —F | —CF₃ | —H | —H | 552 |

TABLE 31

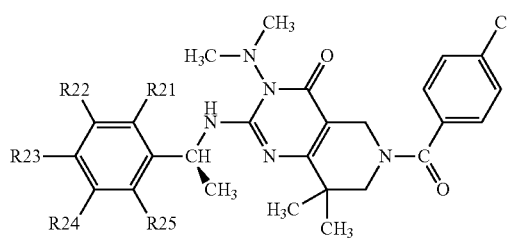

| Example | R21 | R22 | R23 | R24 | R25 | MS(M + 1) |
|---|---|---|---|---|---|---|
| 235 | —H | —H | —F | —H | —H | 498 |
| 236 | —H | —H | —Cl | —H | —H | 514 |
| 237 | —H | —H | —CF₃ | —H | —H | 548 |
| 238 | —H | —H | —OCH₃ | —H | —H | 510 |
| 239 | —H | —CF₃ | —H | —CF₃ | —H | 616 |

TABLE 32

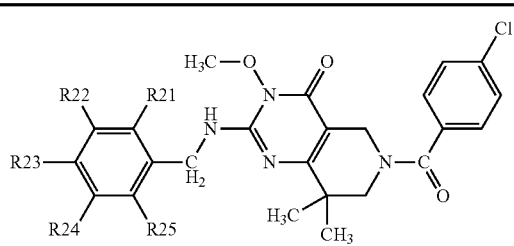

| Example | R21 | R22 | R23 | R24 | R25 | MS(M + 1) |
|---|---|---|---|---|---|---|
| 240 | —H | —H | —H | —H | —H | 453 |
| 241 | —H | —H | —CH₃ | —H | —H | 467 |
| 242 | —H | —H | —OCH₃ | —H | —H | 483 |
| 243 | —H | —H | —CN | —H | —H | 478 |
| 244 | —H | —H | —CF₃ | —H | —H | 521 |
| 245 | —H | —H | —Cl | —H | —H | 487 |
| 246 | —H | —H | —OCF₃ | —H | —H | 537 |
| 247 | —H | —Cl | —Cl | —H | —H | 523 |
| 248 | —H | —F | —CF₃ | —H | —H | 539 |

TABLE 33

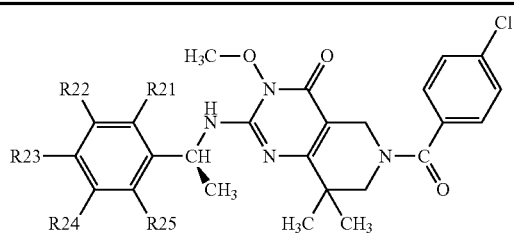

| Example | R21 | R22 | R23 | R24 | R25 | MS(M + 1) |
|---|---|---|---|---|---|---|
| 249 | —H | —H | —F | —H | —H | 485 |
| 250 | —H | —H | —Cl | —H | —H | 501 |
| 251 | —H | —H | —CF₃ | —H | —H | 535 |
| 252 | —H | —H | —OCH₃ | —H | —H | 497 |
| 253 | —H | —CF₃ | —H | —CF₃ | —H | 603 |

TABLE 34

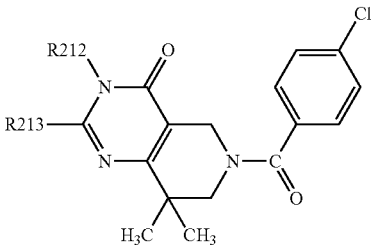

| Example | R21 | R22 | R23 | R24 | R25 | MS(M + 1) |
|---|---|---|---|---|---|---|
| 254 | —H | —H | —H | —H | —H | 461 |
| 255 | —H | —H | —CH₃ | —H | —H | 475 |
| 256 | —H | —H | —OCH₃ | —H | —H | 491 |
| 257 | —H | —H | —CN | —H | —H | 486 |
| 258 | —H | —H | —CF₃ | —H | —H | 529 |
| 259 | —H | —H | —Cl | —H | —H | 495 |
| 260 | —H | —H | —OCF₃ | —H | —H | 545 |
| 261 | —H | —Cl | —Cl | —H | —H | 531 |
| 262 | —H | —F | —CF₃ | —H | —H | 547 |

TABLE 35

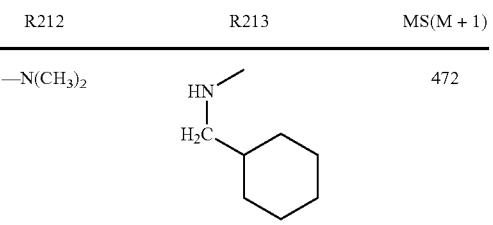

| Example | R21 | R22 | R23 | R24 | R25 | MS(M + 1) |
|---|---|---|---|---|---|---|
| 263 | —H | —H | —F | —H | —H | 493 |
| 264 | —H | —H | —Cl | —H | —H | 509 |
| 265 | —H | —H | —CF₃ | —H | —H | 543 |
| 266 | —H | —H | —OCH₃ | —H | —H | 505 |
| 267 | —H | —CF₃ | —H | —CF₃ | —H | 611 |

TABLE 36

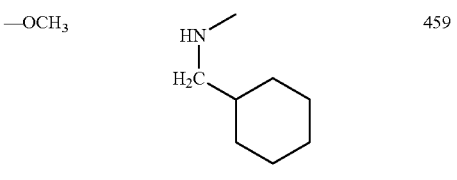

| Example | R212 | R213 | MS(M + 1) |
|---|---|---|---|
| 268 | —CH₂C≡CH | 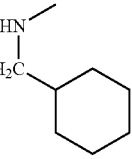 | 467 |

TABLE 36-continued

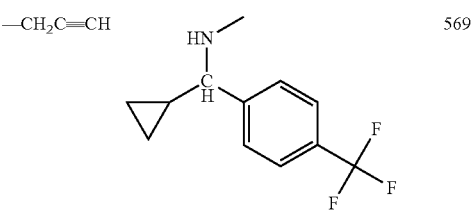

| Example | R212 | R213 | MS(M + 1) |
|---|---|---|---|
| 269 | —N(CH₃)₂ | (N-methylaminomethyl cyclohexyl) | 472 |
| 270 | —OCH₃ | (N-methylaminomethyl cyclohexyl) | 459 |
| 271 | —CH₂C≡CH | 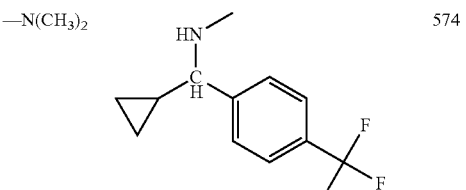 | 569 |
| 272 | —N(CH₃)₂ | 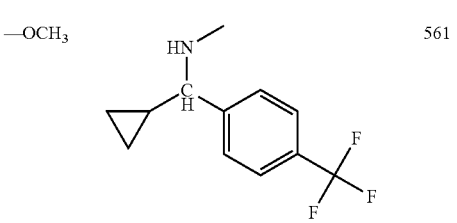 | 574 |
| 273 | —OCH₃ | (N-methyl-α-cyclopropyl-4-trifluoromethylbenzylamine) | 561 |

TABLE 37

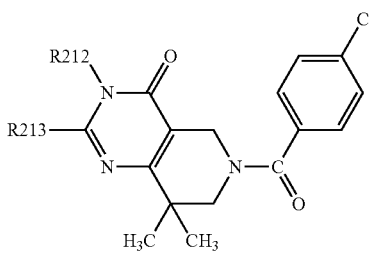

| Example | R212 | R213 | MS (M + 1) |
|---|---|---|---|
| 274 | —CH₂C≡CH | HN-CH₃, CH(CH₂-CH(CH₃)₂)-(4-Cl-C₆H₄) | 551 |
| 275 | —OCH₃ | HN-CH₃, CH(CH₂-CH(CH₃)₂)-(4-Cl-C₆H₄) | 543 |
| 276 | —CH₂C≡CH | HN-CH₃, CH(cyclopropyl)-(4-Cl-C₆H₄) | 535 |
| 277 | —N(CH₃)₂ | HN-CH₃, CH(cyclopropyl)-(4-Cl-C₆H₄) | 540 |
| 278 | —OCH₃ | HN-CH₃, CH(cyclopropyl)-(4-Cl-C₆H₄) | 527 |
| 279 | —CH₂C≡CH | HN-CH₃, CH(CH₂-CH(CH₃)₂)-(4-OCF₃-C₆H₄) | 601 |

TABLE 38

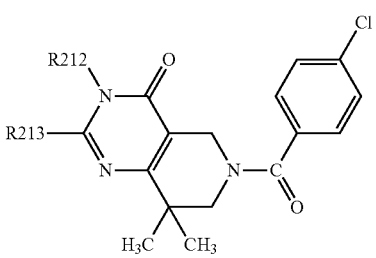

| Example | R212 | R213 | MS (M + 1) |
|---|---|---|---|
| 280 | —N(CH₃)₂ | HN-CH₃, CH(CH₂-CH(CH₃)₂)-(4-OCF₃-C₆H₄) | 606 |
| 281 | —OCH₃ | HN-CH₃, CH(CH₂-CH(CH₃)₂)-(4-OCF₃-C₆H₄) | 593 |
| 282 | —CH₂C≡CH | HN-CH₃, CH(CH(CH₃)₂)-(4-Cl-C₆H₄) | 537 |
| 283 | —N(CH₃)₂ | HN-CH₃, CH(CH(CH₃)₂)-(4-Cl-C₆H₄) | 542 |
| 284 | —OCH₃ | HN-CH₃, CH(CH(CH₃)₂)-(4-Cl-C₆H₄) | 529 |

TABLE 39
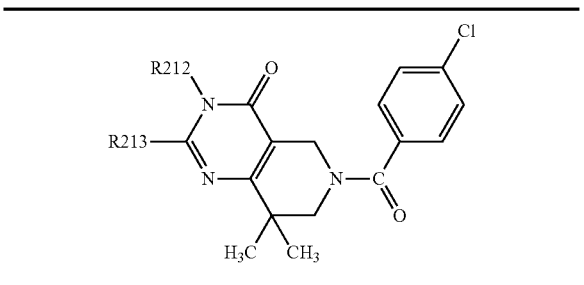
| Example | R212 | R213 | MS(M + 1) |
|---|---|---|---|
| 285 | —CH₂C≡CH | 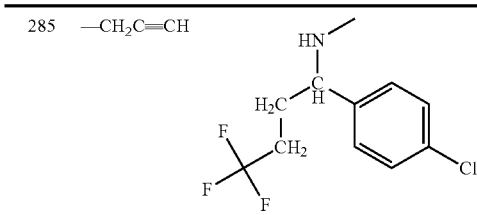 | 591 |
| 286 | —CH₂C≡CH | 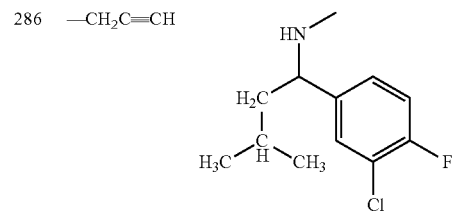 | 569 |
| 287 | —N(CH₃)₂ | 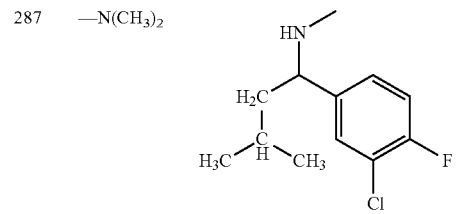 | 574 |
| 288 | —OCH₃ | 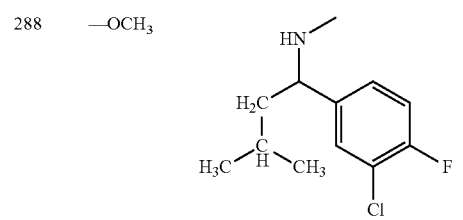 | 561 |
TABLE 39-continued
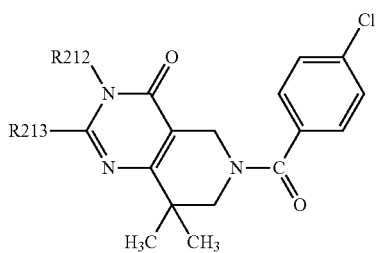
| Example | R212 | R213 | MS(M + 1) |
|---|---|---|---|
| 289 | —CH₂C≡CH | 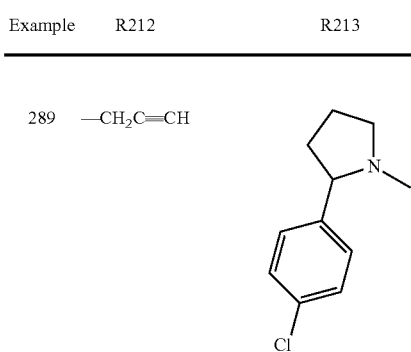 | 535 |
TABLE 40
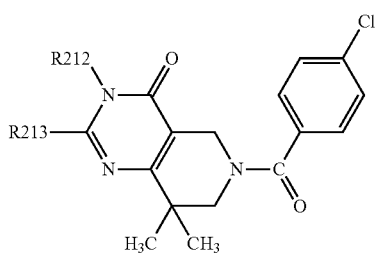
| Example | R212 | R213 | MS(M + 1) |
|---|---|---|---|
| 290 | —N(CH₃)₂ | 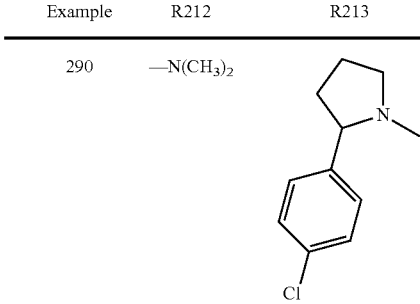 | 540 |
| 291 | —OCH₃ | 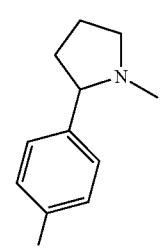 | 527 |

TABLE 41
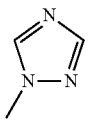
| Example | R26 | R27 | R28 | R29 | R210 | MS(M + 1) |
|---|---|---|---|---|---|---|
| 292 | —H | —H | —H | —H | —H | 515 |
| 293 | —H | —H | —CH₃ | —H | —H | 529 |
| 294 | —H | —H | —Cl | —H | —H | 549 |
| 295 | —H | —H | —F | —H | —H | 533 |
| 296 | —H | —H | —OCH₃ | —H | —H | 545 |
| 297 | —H | —H | —CF₃ | —H | —H | 583 |
| 298 | —H | —Cl | —H | —H | —H | 549 |
| 299 | —H | —CH₃ | —H | —H | —H | 529 |
| 300 | —H | —H | —CN | —H | —H | 540 |
| 301 | —H | —H | —OCF₃ | —H | —H | 599 |
| 302 | —F | —H | —CN | —H | —H | 558 |
| 303 | —H | —CH₃ | —Cl | —H | —H | 563 |
| 304 | —H | —Cl | —CH₃ | —H | —H | 563 |
| 305 | —H | —H | —OC₂H₅ | —H | —H | 559 |
| 306 | —H | —H | —SCH₃ | —H | —H | 561 |
| 307 | —H | —H | —OCH(CH₃)₂ | —H | —H | 573 |
| 308 | —H | —H | 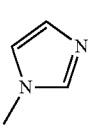 | —H | —H | 582 |
| 309 | —H | —H | 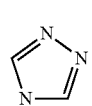 | —H | —H | 581 |
| 310 | —H | —H | 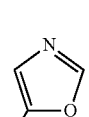 | —H | —H | 582 |
| 311 | —H | —H | 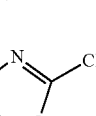 | —H | —H | 582 |
| 312 | —H | —H |  | —H | —H | 597 |

TABLE 42

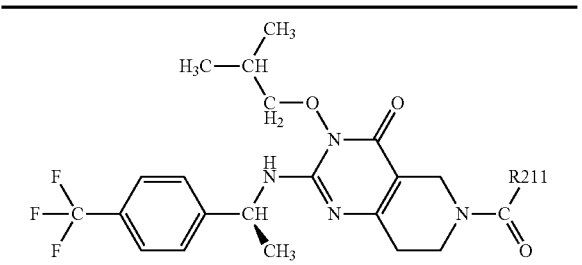

| Example | R211 | MS(M + 1) |
|---|---|---|
| 292 | 2-methylnaphthalene | 565 |
| 293 | 8-methylnaphthalene | 565 |
| 294 | 5-methylbenzo[d][1,3]dioxole | 559 |
| 295 | 2-methylquinoline | 566 |
| 296 | 3-methylquinoline | 566 |
| 297 | 6-methyl-3,4-dihydroquinolin-2(1H)-one | 584 |
| 298 | 5-methyl-8-methoxy-3,4-dihydroquinolin-2(1H)-one | 614 |
| 299 | 5-chloro-2-methylbenzofuran | 589 |
| 300 | 6-chloro-2-methylimidazo[1,2-a]pyridine | 589 |
| 301 | 5-methylbenzo[b]thiophene | 571 |

TABLE 42-continued

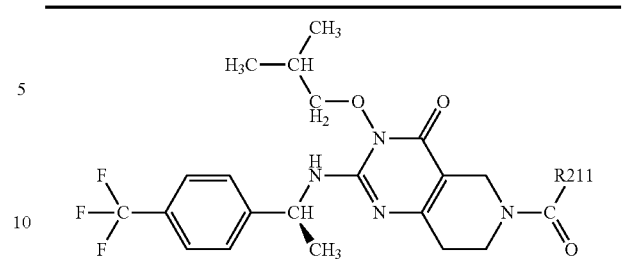

| Example | R211 | MS(M + 1) |
|---|---|---|
| 302 | 8-methylquinolin-2(1H)-one | 582 |
| 303 | 5-methylquinolin-2(1H)-one | 582 |
| 304 | 6-fluoro-2-methylbenzo[b]thiophene | 589 |
| 305 | 2-methylpyrazolo[1,5-a]pyridine | 555 |
| 306 | 2,5-dimethylthiophene | 535 |
| 307 | 2-methylthieno[2,3-b]pyridine | 572 |
| 308 | 3-methylquinoxaline | 567 |
| 309 | 6-methyl-2,3-dihydro-1H-indene | 555 |
| 310 | 7-methylbenzo[b]thiophene | 571 |
| 311 | 5-methyl-3-phenylisoxazole | 582 |

TABLE 42-continued

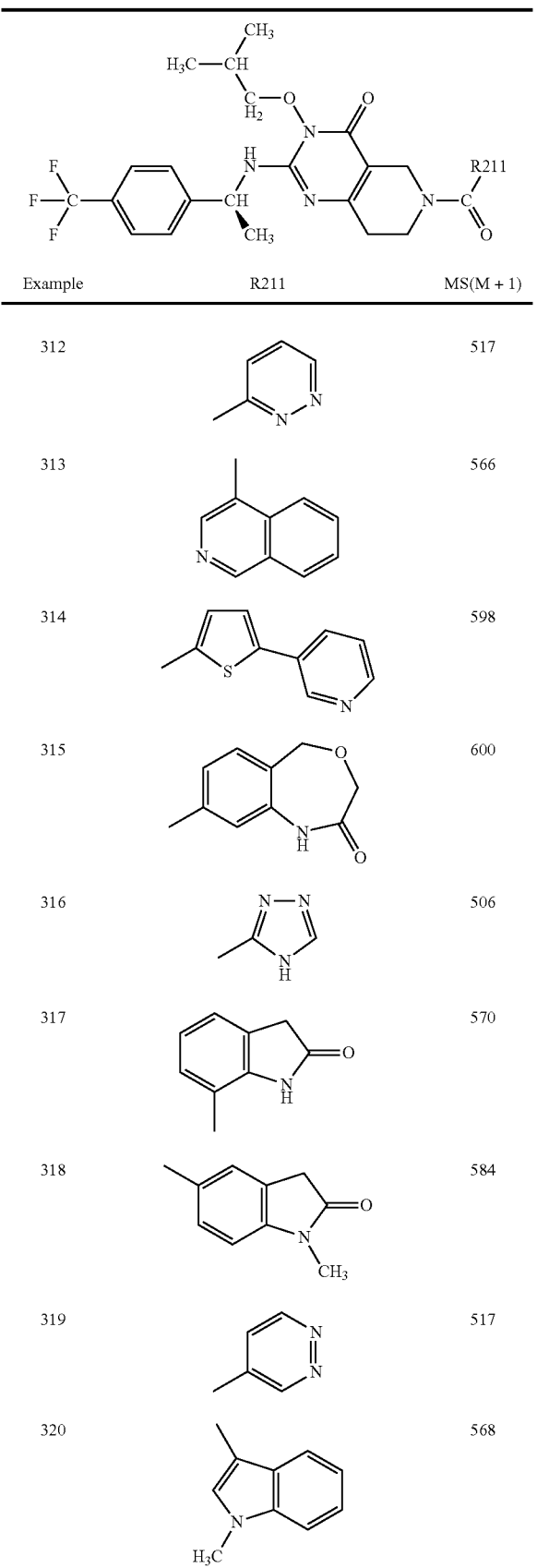

| Example | R211 | MS(M + 1) |
|---|---|---|
| 312 | 3-methylpyridazine | 517 |
| 313 | 4-methylisoquinoline | 566 |
| 314 | 5-methyl-2-(pyridin-3-yl)thiophene | 598 |
| 315 | 7-methyl-2,3-dihydrobenzo[f][1,4]oxazepin-3(5H)-one | 600 |
| 316 | 5-methyl-1H-1,2,4-triazole | 506 |
| 317 | 7-methylindolin-2-one | 570 |
| 318 | 1,5-dimethylindolin-2-one | 584 |
| 319 | 4-methylpyridazine | 517 |
| 320 | 1,3-dimethyl-1H-indole | 568 |

TABLE 42-continued

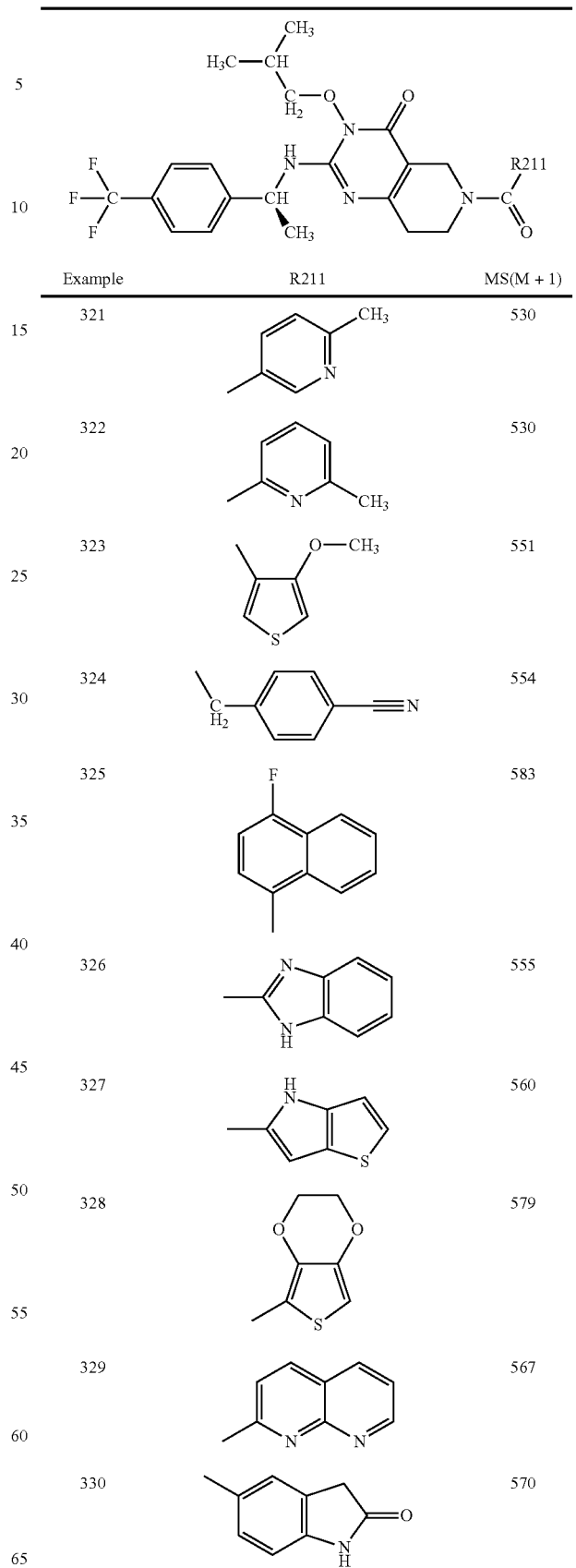

| Example | R211 | MS(M + 1) |
|---|---|---|
| 321 | 2,5-dimethylpyridine | 530 |
| 322 | 2,6-dimethylpyridine | 530 |
| 323 | 3-methoxy-4-methylthiophene | 551 |
| 324 | 4-cyanobenzyl | 554 |
| 325 | 5-fluoro-8-methylnaphthalene | 583 |
| 326 | 2-methyl-1H-benzimidazole | 555 |
| 327 | 5-methyl-4H-thieno[3,2-b]pyrrole | 560 |
| 328 | methyl-dioxinothiophene | 579 |
| 329 | 7-methyl-1,8-naphthyridine | 567 |
| 330 | 5-methylindolin-2-one | 570 |

TABLE 42-continued
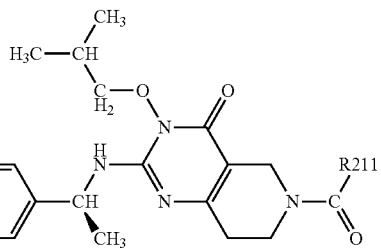
| Example | R211 | MS(M + 1) |
|---|---|---|
| 331 | 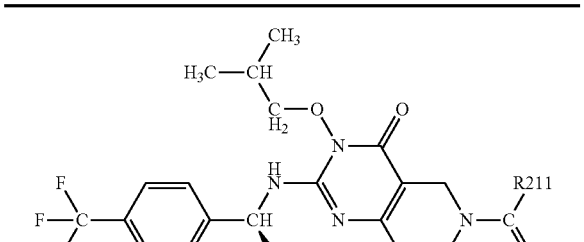 | 570 |
| 332 | 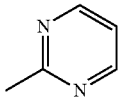 | 517 |
| 333 | 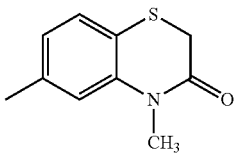 | 616 |
| 334 | 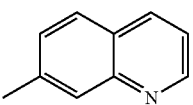 | 566 |
| 335 | 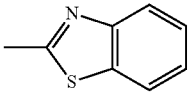 | 572 |
| 336 | 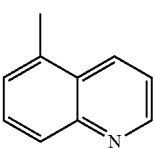 | 566 |
TABLE 42-continued
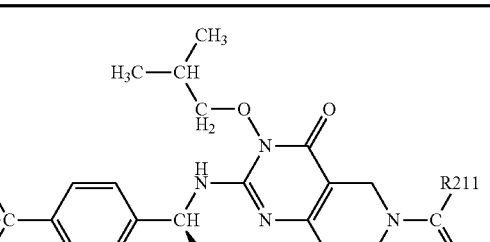
| Example | R211 | MS(M + 1) |
|---|---|---|
| 337 | 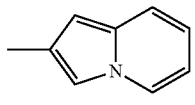 | 554 |
| 338 | 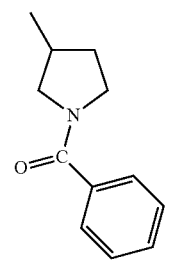 | 505 |
| 339 | 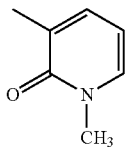 | 612 |
| 340 | 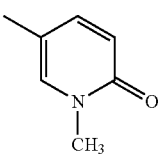 | 546 |
| 341 |  | 546 |

TABLE 43

| Example | R26 | R27 | R28 | R29 | R210 | MS(M + 1) |
|---|---|---|---|---|---|---|
| 363 | —H | —H | —H | —H | —H | 495 |
| 364 | —H | —H | —CH₃ | —H | —H | 509 |
| 365 | —H | —H | —Cl | —H | —H | 529 |
| 366 | —H | —H | —F | —H | —H | 513 |
| 367 | —H | —H | —OCH₃ | —H | —H | 525 |
| 368 | —H | —H | —CF₃ | —H | —H | 563 |
| 369 | —H | —Cl | —H | —H | —H | 529 |
| 370 | —H | —CH₃ | —H | —H | —H | 509 |
| 371 | —H | —H | —CN | —H | —H | 520 |
| 372 | —H | —CH₃ | —CH₃ | —H | —H | 523 |
| 373 | —H | —H | —OCF₃ | —H | —H | 579 |
| 374 | —F | —H | —CN | —H | —H | 538 |
| 375 | —H | —CH₃ | —Cl | —H | —H | 543 |
| 376 | —H | —Cl | —CH₃ | —H | —H | 543 |
| 377 | —H | —H | —OC₂H₅ | —H | —H | 539 |
| 378 | —H | —H | —SCH₃ | —H | —H | 541 |
| 379 | —H | —H | —OCH(CH₃)₂ | —H | —H | 553 |
| 380 | —H | —H | 1-methyl-1,2,4-triazol-3-yl | —H | —H | 562 |
| 381 | —H | —H | 1-methylimidazol-2-yl | —H | —H | 561 |
| 382 | —H | —H | 4-methyl-1,2,4-triazol-3-yl | —H | —H | 562 |
| 383 | —H | —H | 5-methyloxazol-2-yl | —H | —H | 562 |
| 384 | —H | —H | 2,5-dimethyl-1,3,4-oxadiazol-... | —H | —H | 577 |

TABLE 44

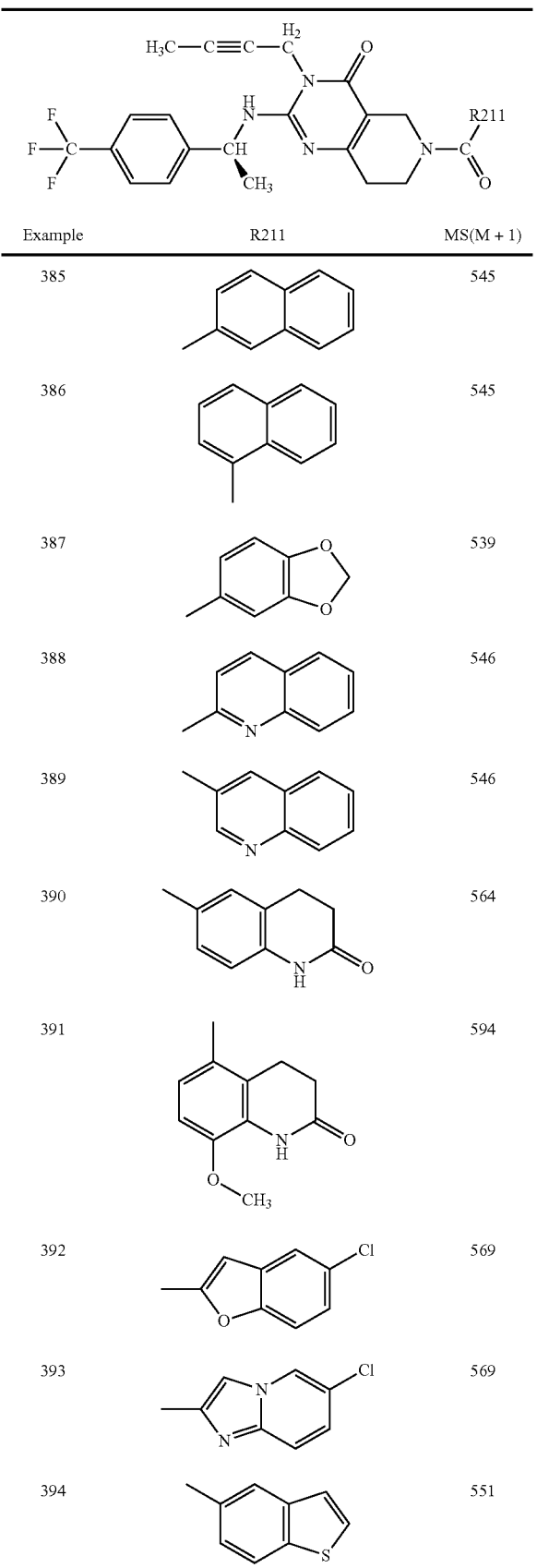

| Example | R211 | MS(M + 1) |
|---|---|---|
| 385 | 2-methylnaphthalene | 545 |
| 386 | 8-methylnaphthalene | 545 |
| 387 | 5-methylbenzo[d][1,3]dioxole | 539 |
| 388 | 2-methylquinoline | 546 |
| 389 | 3-methylquinoline | 546 |
| 390 | 6-methyl-3,4-dihydroquinolin-2(1H)-one | 564 |
| 391 | 8-methoxy-5-methyl-3,4-dihydroquinolin-2(1H)-one | 594 |
| 392 | 5-chloro-2-methylbenzofuran | 569 |
| 393 | 6-chloro-2-methylimidazo[1,2-a]pyridine | 569 |
| 394 | 5-methylbenzo[b]thiophene | 551 |

TABLE 44-continued

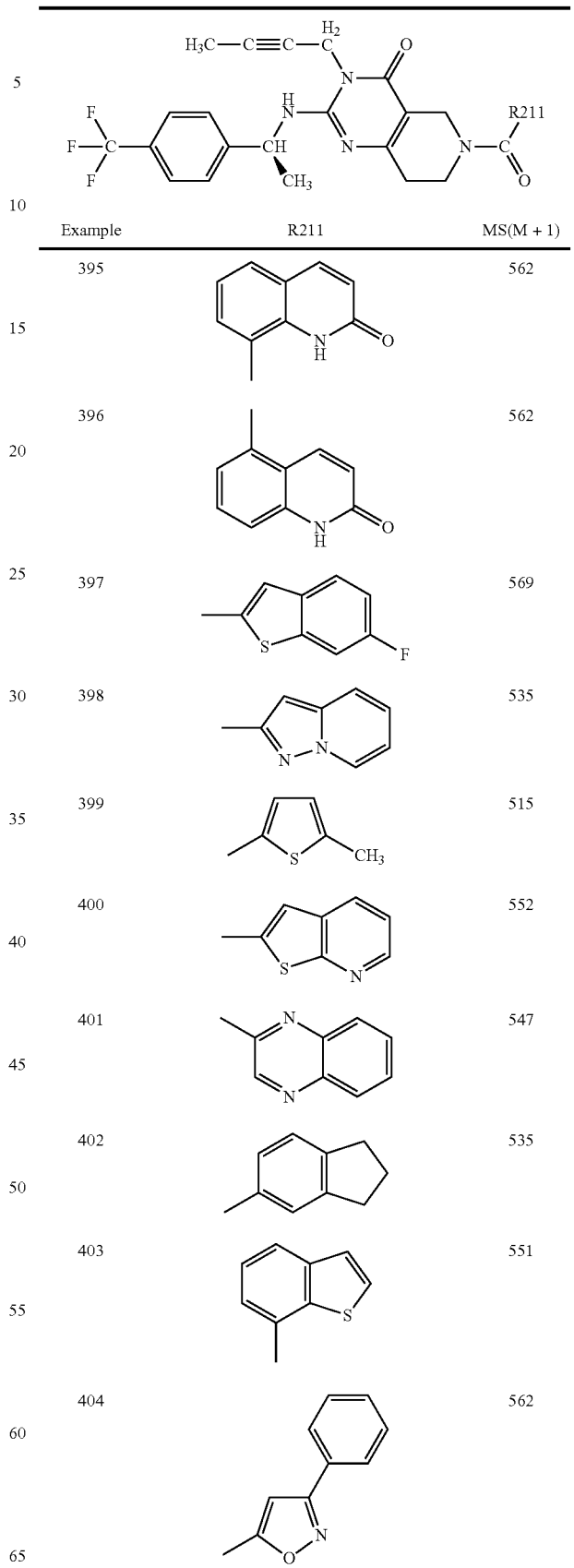

| Example | R211 | MS(M + 1) |
|---|---|---|
| 395 | 8-methylquinolin-2(1H)-one | 562 |
| 396 | 5-methylquinolin-2(1H)-one | 562 |
| 397 | 6-fluoro-2-methylbenzo[b]thiophene | 569 |
| 398 | 2-methylpyrazolo[1,5-a]pyridine | 535 |
| 399 | 2,5-dimethylthiophene | 515 |
| 400 | 2-methylthieno[2,3-b]pyridine | 552 |
| 401 | 3-methylquinoxaline | 547 |
| 402 | 5-methyl-2,3-dihydro-1H-indene | 535 |
| 403 | 7-methylbenzo[b]thiophene | 551 |
| 404 | 5-methyl-3-phenylisoxazole | 562 |

TABLE 44-continued

| Example | R211 | MS(M+1) |
|---------|------|---------|
| 405 | 3-methylpyridazinyl | 497 |
| 406 | 4-methylisoquinolinyl | 546 |
| 407 | 5-methylthien-2-yl-pyridinyl | 578 |
| 408 | 7-methyl-benzo[1,4]oxazepin-3-one | 580 |
| 409 | 5-methyl-1H-1,2,4-triazolyl | 486 |
| 410 | 7-methyl-indolin-2-one | 550 |
| 411 | 5-methyl-1-methyl-indolin-2-one | 564 |
| 412 | 4-methylpyridazinyl | 497 |
| 413 | 3-methyl-1-methyl-indolyl | 548 |
| 414 | 2,5-dimethylpyridinyl | 510 |

TABLE 44-continued

| Example | R211 | MS(M+1) |
|---------|------|---------|
| 415 | 2,6-dimethylpyridinyl | 510 |
| 416 | 4-methyl-3-methoxy-thienyl | 531 |
| 417 | 4-cyanobenzyl | 534 |
| 418 | 1-fluoro-4-methylnaphthyl | 563 |
| 419 | 2-methyl-1H-benzimidazolyl | 535 |
| 420 | 5-methyl-thieno-pyrrolyl | 540 |
| 421 | methyl-dioxino-thienyl | 559 |
| 422 | 7-methyl-1,8-naphthyridinyl | 547 |
| 423 | 5-methyl-indolin-2-one | 550 |
| 424 | 6-methyl-indolin-2-one | 550 |

TABLE 44-continued

Structure: Core scaffold with H₃C—C≡C—CH₂ group on N, 4-(trifluoromethyl)phenyl-CH(CH₃)-NH substituent, and R211-C(=O)- acyl group on the tetrahydropyrido-pyrimidinone core.

| Example | R211 | MS(M + 1) |
|---|---|---|
| 425 | 2-methylpyrimidin-yl | 497 |
| 426 | 6-methyl-4-methyl-2H-benzo[b][1,4]thiazin-3(4H)-one-yl | 596 |
| 427 | 7-methylquinolin-yl | 546 |
| 428 | 2-methylbenzothiazol-yl | 552 |
| 429 | 8-methylquinolin-yl | 546 |
| 430 | 2-methylindolizin-yl | 534 |
| 431 | 5-methyl-1H-imidazol-yl | 485 |
| 432 | 3-methylpyrrolidin-1-yl benzoyl | 592 |
| 433 | 1,3-dimethyl-2-oxo-1,2-dihydropyridin-yl | 526 |
| 434 | 1,5-dimethyl-2-oxo-1,2-dihydropyridin-yl | 526 |

TABLE 45

Structure: Core scaffold with morpholine-N group, 4-(trifluoromethyl)phenyl-CH(CH₃)-NH substituent, and substituted benzoyl (R26, R27, R28, R29, R210) on the tetrahydropyrido-pyrimidinone core.

| Example | R26 | R27 | R28 | R29 | R210 | MS (M + 1) |
|---|---|---|---|---|---|---|
| 435 | —H | —H | —H | —H | —H | 528 |
| 436 | —H | —H | —CH₃ | —H | —H | 542 |
| 437 | —H | —H | —Cl | —H | —H | 562 |
| 438 | —H | —H | —F | —H | —H | 546 |
| 439 | —H | —H | —OCH₃ | —H | —H | 558 |
| 440 | —H | —H | —CF₃ | —H | —H | 596 |
| 441 | —H | —Cl | —H | —H | —H | 562 |
| 442 | —H | —CH₃ | —H | —H | —H | 542 |
| 443 | —H | —H | —CN | —H | —H | 553 |
| 444 | —H | —CH₃ | —CH₃ | —H | —H | 556 |
| 445 | —H | —H | —OCF₃ | —H | —H | 612 |
| 446 | —F | —H | —CN | —H | —H | 571 |
| 447 | —H | —CH₃ | —Cl | —H | —H | 576 |
| 448 | —H | —Cl | —CH₃ | —H | —H | 576 |
| 449 | —H | —H | —OC₂H₅ | —H | —H | 572 |
| 450 | —H | —H | —SCH₃ | —H | —H | 574 |
| 451 | —H | —H | —OCH(CH₃)₂ | —H | —H | 586 |
| 452 | —H | —H | 1-methyl-1H-1,2,4-triazol-yl | —H | —H | 595 |
| 453 | —H | —H | 1-methyl-1H-imidazol-yl | —H | —H | 594 |
| 454 | —H | —H | 4-methyl-4H-1,2,4-triazol-yl | —H | —H | 595 |

TABLE 45-continued

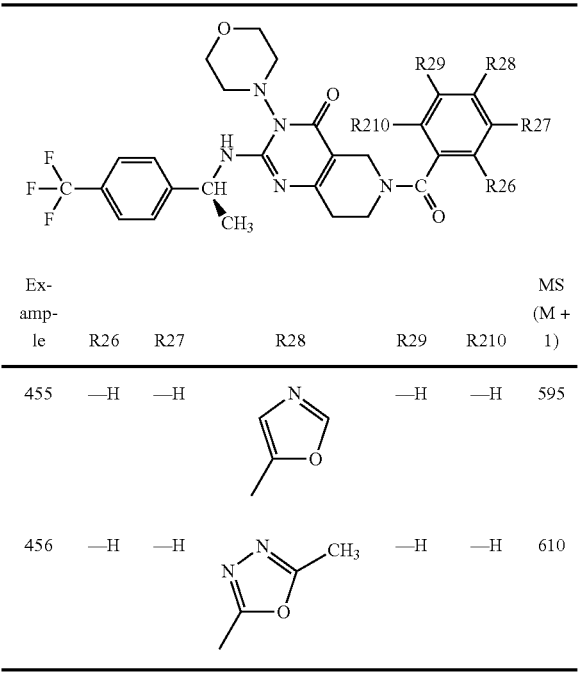

| Example | R26 | R27 | R28 | R29 | R210 | MS (M+1) |
|---|---|---|---|---|---|---|
| 455 | —H | —H | (5-methyloxazole) | —H | —H | 595 |
| 456 | —H | —H | (2,5-dimethyl-1,3,4-oxadiazole) | —H | —H | 610 |

TABLE 46

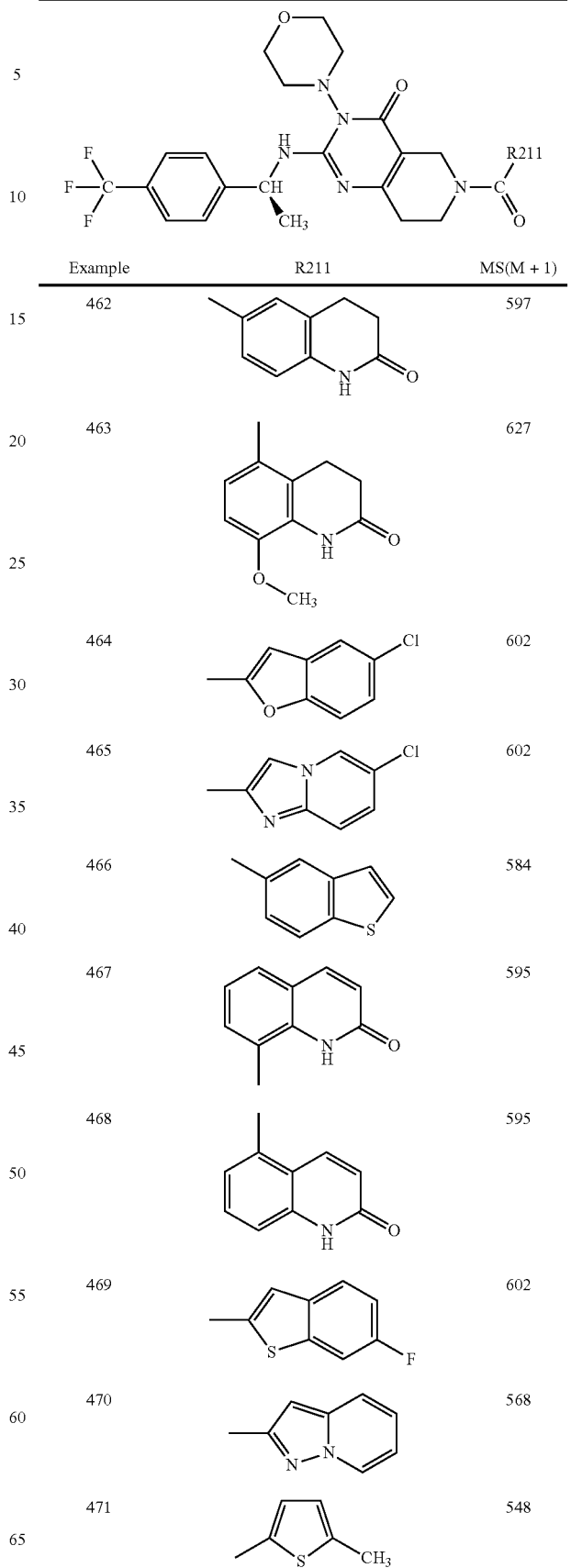

| Example | R211 | MS(M+1) |
|---|---|---|
| 457 | 2-methylnaphthalene | 578 |
| 458 | 1-methylnaphthalene | 578 |
| 459 | 5-methylbenzo[d][1,3]dioxole | 572 |
| 460 | 2-methylquinoline | 579 |
| 461 | 3-methylquinoline | 579 |
| 462 | 6-methyl-3,4-dihydroquinolin-2(1H)-one | 597 |
| 463 | 5-methyl-8-methoxy-3,4-dihydroquinolin-2(1H)-one | 627 |
| 464 | 5-chloro-2-methylbenzofuran | 602 |
| 465 | 6-chloro-2-methylimidazo[1,2-a]pyridine | 602 |
| 466 | 5-methylbenzo[b]thiophene | 584 |
| 467 | 8-methylquinolin-2(1H)-one | 595 |
| 468 | 5-methylquinolin-2(1H)-one | 595 |
| 469 | 6-fluoro-2-methylbenzo[b]thiophene | 602 |
| 470 | 2-methylpyrazolo[1,5-a]pyridine | 568 |
| 471 | 2,5-dimethylthiophene | 548 |

TABLE 46-continued

| Example | R211 | MS(M + 1) |
|---|---|---|
| 472 | 2-methylthieno[2,3-b]pyridine | 585 |
| 473 | 3-methylquinoxaline | 580 |
| 474 | 5-methyl-2,3-dihydro-1H-indene | 568 |
| 475 | 7-methylbenzothiophene | 584 |
| 476 | 5-methyl-3-phenylisoxazole | 595 |
| 477 | 3-methylpyridazine | 530 |
| 478 | 4-methylisoquinoline | 579 |
| 479 | 5-methyl-2-(pyridin-3-yl)thiophene | 611 |
| 480 | 7-methyl-2,3-dihydrobenzo[f][1,4]oxazepin-4(5H)-one | 613 |
| 481 | 5-methyl-4H-1,2,4-triazole | 519 |
| 482 | 7-methylindolin-2-one | 583 |
| 483 | 1,5-dimethylindolin-2-one | 597 |
| 484 | 4-methylpyridazine | 530 |
| 485 | 1,3-dimethyl-1H-indole | 581 |
| 486 | 2,5-dimethylpyridine | 543 |
| 487 | 2,6-dimethylpyridine | 543 |
| 488 | 3-methoxy-4-methylthiophene | 564 |
| 489 | 4-(methyl)benzonitrile | 567 |

TABLE 46-continued

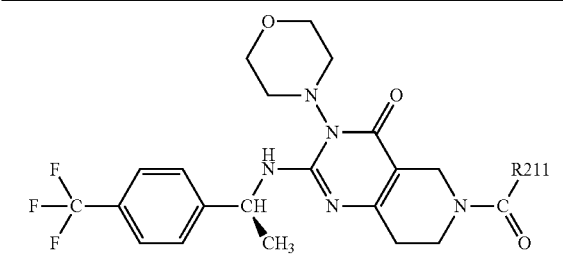

| Example | R211 | MS(M + 1) |
|---|---|---|
| 490 | 5-fluoro-8-methylnaphthalenyl | 596 |
| 491 | 2-methyl-1H-benzimidazolyl | 568 |
| 492 | methyl-thieno-pyrrolyl | 573 |
| 493 | methyl-ethylenedioxythienyl | 592 |
| 494 | methyl-naphthyridinyl | 580 |
| 495 | 5-methyl-2-oxoindolinyl | 583 |
| 496 | 6-methyl-2-oxoindolinyl | 583 |
| 497 | 2-methylpyrimidinyl | 530 |
| 498 | 6-methyl-4-methyl-benzothiazin-3-one | 629 |

TABLE 46-continued

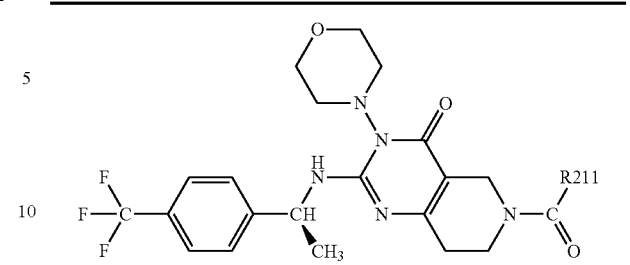

| Example | R211 | MS(M + 1) |
|---|---|---|
| 499 | 7-methylquinolinyl | 579 |
| 500 | 2-methylbenzothiazolyl | 585 |
| 501 | 8-methylquinolinyl | 579 |
| 502 | 2-methylindolizinyl | 567 |
| 503 | 4-methyl-1H-imidazolyl | 518 |
| 504 | 3-methyl-1-benzoylpyrrolidinyl | 625 |
| 505 | 1,3-dimethyl-2-oxopyridinyl | 559 |
| 506 | 1,5-dimethyl-2-oxopyridinyl | 559 |

TABLE 47

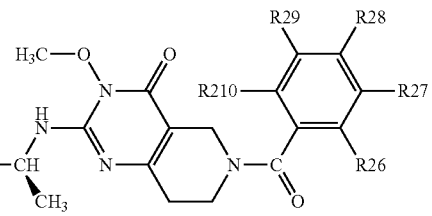

| Example | R26 | R27 | R28 | R29 | R210 | MS(M + 1) |
|---|---|---|---|---|---|---|
| 507 | —H | —H | —H | —H | —H | 473 |
| 508 | —H | —H | —CH₃ | —H | —H | 487 |
| 509 | —H | —H | —F | —H | —H | 491 |
| 510 | —H | —H | —OCH₃ | —H | —H | 503 |
| 511 | —H | —H | —NHCOCH₃ | —H | —H | 530 |
| 512 | —H | —Cl | —Cl | —H | —H | 541 |
| 513 | —F | —H | —CF₃ | —H | —H | 559 |
| 514 | —Cl | —H | —H | —H | —H | 507 |
| 515 | —Cl | —H | —H | —H | —Cl | 541 |
| 516 | —H | —OCH₃ | —H | —H | —H | 503 |
| 517 | —H | —Cl | —H | —H | —H | 507 |
| 518 | —H | —CH₃ | —H | —H | —H | 487 |
| 519 | —H | —CN | —H | —H | —H | 498 |
| 520 | —H | —F | —H | —H | —H | 491 |
| 521 | —H | —N(CH₃)₂ | —H | —H | —H | 516 |
| 522 | —H | —OC₆H₅ | —H | —H | —H | 565 |
| 523 | —H | —Cl | —H | —Cl | —H | 541 |
| 524 | —H | —CH₃ | —H | —CH₃ | —H | 501 |
| 525 | —CH₃ | —CH₃ | —H | —H | —H | 501 |
| 526 | —Cl | —Cl | —H | —H | —H | 541 |
| 527 | —H | —H | —CN | —H | —H | 498 |
| 528 | —H | —H | —N(CH₃)₂ | —H | —H | 516 |
| 529 | —Cl | —H | —Cl | —H | —H | 541 |
| 530 | —CH₃ | —H | —CH₃ | —H | —H | 501 |
| 531 | —F | —H | —F | —H | —H | 509 |
| 532 | —H | —OCH₃ | —OCH₃ | —H | —H | 533 |
| 533 | —H | —CH₃ | —CH₃ | —H | —H | 501 |
| 534 | —H | —F | —F | —H | —H | 509 |
| 535 | —H | —CF₃ | —F | —H | —H | 559 |
| 536 | —F | —H | —F | —H | —F | 527 |
| 537 | —H | —OCH₃ | —OCH₃ | —OCH₃ | —H | 563 |
| 538 | —H | —F | —H | —F | —H | 527 |
| 539 | —H | —CF₃ | —H | —H | —H | 541 |
| 540 | —H | —H | —OC₆H₅ | —H | —H | 565 |
| 541 | —CN | —H | —H | —H | —H | 498 |
| 542 | —F | —H | —H | —H | —F | 509 |
| 543 | —F | —F | —H | —H | —H | 509 |
| 544 | —H | —H | —F | —F | —H | 509 |
| 545 | —Cl | —H | —F | —H | —H | 525 |
| 546 | —F | —F | —F | —H | —H | 527 |
| 547 | —H | —OCF₃ | —H | —H | —H | 557 |
| 548 | —H | —C₆H₅ | —H | —H | —H | 549 |
| 549 | —H | —OH | —NHCOCH₃ | —H | —H | 546 |
| 550 | —F | —H | —OCH₃ | —H | —H | 521 |
| 551 | —F | —H | —H | —Cl | —H | 525 |
| 552 | —CF₃ | —H | —F | —H | —H | 559 |
| 553 | —H | —H | —OC₂H₅ | —H | —H | 517 |
| 554 | —H | —H | —SCH₃ | —H | —H | 519 |
| 555 | —SCH₃ | —H | —H | —H | —H | 519 |
| 556 | —H | —H | —OCH(CH₃)₂ | —H | —H | 531 |
| 557 | —OCH₃ | —CH₃ | —OC₆H₅ | —H | —CH₃ | 623 |
| 558 | —H | —H | —C₆H₅ | —H | —H | 549 |
| 559 | —OCH₃ | —H | —Cl | —H | —H | 537 |
| 560 | —OCH₃ | —H | —H | —Cl | —H | 537 |
| 561 | —H | —Cl | —OCH₃ | —H | —CH₃ | 551 |
| 562 | —H | —H | —SO₂CH₃ | —H | —H | 551 |
| 563 | —H | —F | —CF₃ | —H | —H | 559 |
| 564 | —Cl | —H | —F | —F | —H | 543 |
| 565 | —Cl | —H | —Cl | —F | —H | 559 |
| 566 | —Cl | —H | —OCH₃ | —OCH₃ | —H | 567 |
| 567 | —Cl | —H | —H | —SCH₃ | —H | 553 |
| 568 | —Cl | —H | —H | —F | —H | 525 |
| 569 | —H | —H | —N(C₂H₅)₂ | —H | —H | 544 |
| 570 | —CH₃ | —H | —OCH₃ | —H | —H | 517 |
| 571 | —H | —F | —Cl | —H | —H | 525 |
| 572 | —H | —H | —CH=CH₂ | —H | —H | 499 |
| 573 | —H | —H | —(CH₂)₃CH₃ | —H | —H | 529 |

TABLE 47-continued

| Example | R26 | R27 | R28 | R29 | R210 | MS(M + 1) |
|---|---|---|---|---|---|---|
| 574 | —H | —H | —C(CH₃)₃ | —H | —H | 529 |
| 575 | —H | —OCH₃ | —CH₃ | —H | —H | 517 |
| 576 | —H | —F | —CH₃ | —H | —H | 505 |
| 577 | —H | —CH₃ | —Cl | —H | —H | 521 |
| 578 | —H | —Cl | —CH₃ | —H | —H | 521 |
| 579 | —H | —H | —CH₂OC₆H₅ | —H | —H | 579 |
| 580 | —H | —H | —(CH₂)₂CH₃ | —H | —H | 515 |
| 581 | —H | —H | —OCH₂C₆H₅ | —H | —H | 579 |
| 582 | —CH₃ | —OCH₃ | —H | —H | —H | 517 |
| 583 | —F | —H | —H | —H | —OCH₃ | 521 |
| 584 | —H | —F | —OCH₃ | —H | —H | 521 |
| 585 | —F | —H | —Cl | —H | —H | 525 |
| 586 | —F | —H | —CH₃ | —H | —H | 505 |
| 587 | —H | 4-methylpyridyl | —H | —H | —H | 550 |
| 588 | —H | 3-methylpyridyl | —H | —H | —H | 550 |
| 589 | 3-methylpyridyl | —H | —H | —H | —H | 550 |
| 590 | 4-methylpyridyl | —H | —H | —H | —H | 550 |
| 591 | —H | 2-methylpyridyl | —H | —H | —H | 550 |
| 592 | —H | —CH₂-(1,2,4-triazol-1-yl) | —H | —H | —H | 554 |
| 593 | —H | 1-methyl-1,2,4-triazol-3-yl | —H | —H | —H | 540 |
| 594 | —CH3 | —H | cyclohexyl-O-CH₂ | —H | —H | 585 |
| 595 | —H | 1,3-dimethylpyrazol-5-yl | —H | —H | —H | 553 |

TABLE 47-continued

| Example | R26 | R27 | R28 | R29 | R210 | MS(M + 1) |
|---|---|---|---|---|---|---|
| 596 | —H | 2-pyrimidinyl | —H | —H | —H | 551 |
| 597 | —H | 2-thiazolyl | —H | —H | —H | 556 |
| 598 | —CH3 | —H | methylcycloheptyl | —H | —H | 583 |
| 599 | —H | —H | N-cyclohexyl-N-methyl acetamide | —H | —H | 612 |
| 600 | —H | —H | 1-methyl-2-pyrrolidinone | —H | —H | 556 |
| 601 | —H | —H | 1-methylpyrrolyl | —H | —H | 538 |
| 602 | —H | —H | 1-methylpyrazolyl | —H | —H | 539 |
| 603 | —H | —H | 1-methyl-1,2,4-triazolyl | —H | —H | 540 |
| 604 | —H | —H | 1-methylimidazolyl | —H | —H | 539 |
| 605 | —H | —H | 4-methyl-1,2,4-triazolyl | —H | —H | 540 |

TABLE 47-continued

| Example | R26 | R27 | R28 | R29 | R210 | MS(M + 1) |
|---|---|---|---|---|---|---|
| 606 | —H | —H | 4-thiomorpholinylmethyl | —H | —H | 574 |
| 607 | —H | —H | 4-morpholinylmethyl | —H | —H | 558 |
| 608 | —H | —H | (1,3-dimethyl-5-oxo-4,5-dihydro-1H-pyrazol)methyl | —H | —H | 569 |
| 609 | —H | —H | (1-methyl-1H-tetrazol)methyl | —H | —H | 541 |
| 610 | —H | —H | (pyridin-2-yl)methyl | —H | —H | 550 |
| 611 | —H | —H | (pyridin-3-yl)methyl | —H | —H | 550 |
| 612 | —H | —H | (pyridin-4-yl)methyl | —H | —H | 550 |
| 613 | —H | —H | cyclohexylmethyl | —H | —H | 555 |
| 614 | —H | —H | (1,2-dimethyl-1H-imidazol)methyl | —H | —H | 553 |
| 615 | (1,2-dimethyl-1H-imidazol)methyl | —H | —H | —H | —H | 553 |
| 616 | —H | (1,2-dimethyl-1H-imidazol)methyl | —H | —H | —H | 553 |

TABLE 47-continued

| Example | R26 | R27 | R28 | R29 | R210 | MS(M + 1) |
|---|---|---|---|---|---|---|
| 617 | —H | —H | 2-methylpyrimidin-yl | —H | —H | 551 |
| 618 | 4-methyl-1,4-diazepan-1-yl | —H | —H | —H | —H | 585 |
| 619 | —H | —H | 1-methylpyrrolidin-yl | —H | —H | 542 |
| 620 | —H | 1-methylimidazol-yl | —H | —H | —H | 539 |
| 621 | —H | —H | 5-methyloxazol-yl | —H | —H | 540 |
| 622 | —H | —H | N-methyl cyclobutanecarboxamido | —H | —H | 570 |
| 623 | —H | —H | 2,5-dimethyl-1,3,4-oxadiazol-yl | —H | —H | 555 |
| 624 | —H | —H | (4-chlorophenyl)methoxymethyl | —H | —H | 613 |
| 625 | —H | —H | 2-(4-chlorophenyl)ethoxymethyl | —H | —H | 627 |

TABLE 47-continued
| Example | R26 | R27 | R28 | R29 | R210 | MS(M + 1) |
|---|---|---|---|---|---|---|
| 626 | —H | 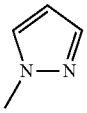 | —H | —H | —H | 538 |
| 627 | 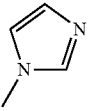 | —H | —H | —H | —H | 539 |
| 628 | 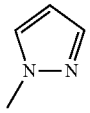 | —H | —H | —H | —H | 539 |
| 629 | —H | 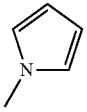 | —H | —H | —H | 539 |
| 630 | 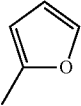 | —H | —H | —H | —H | 538 |
| 631 | —H | —H | 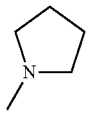 | —H | —H | 539 |
| 632 | —H | 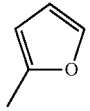 | —H | —H | —H | 540 |
| 633 | —H | 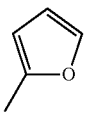 | —H | —H | —H | 539 |
| 634 | 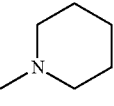 | —H | —H | —H | —H | 539 |
| 635 | —H | —H |  | —H | —H | 556 |

TABLE 47-continued
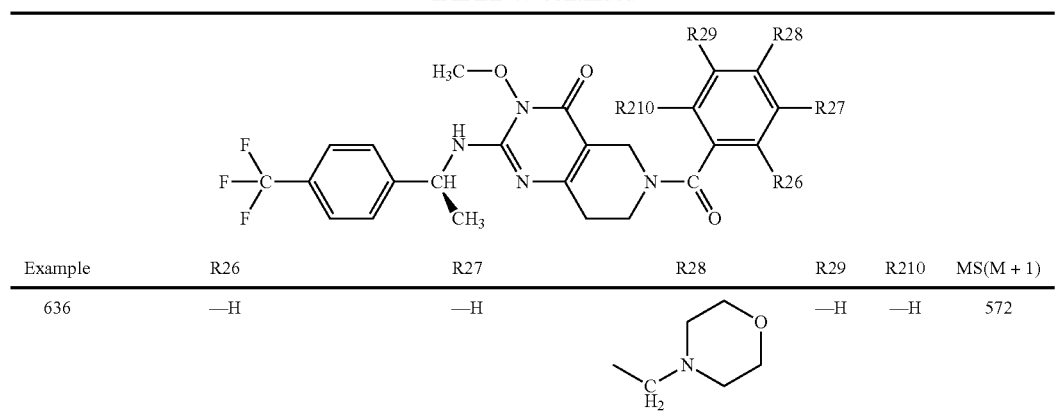
| Example | R26 | R27 | R28 | R29 | R210 | MS(M + 1) |
|---|---|---|---|---|---|---|
| 636 | —H | —H | (4-ethylmorpholine) | —H | —H | 572 |
TABLE 48
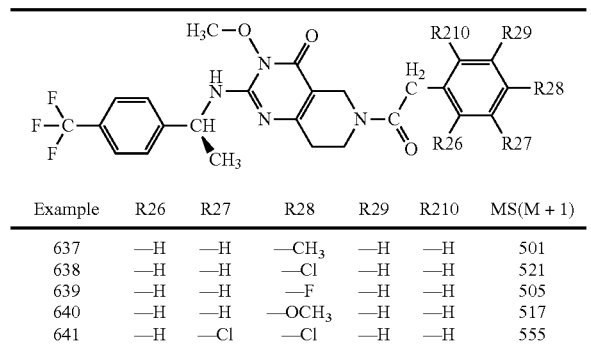
| Example | R26 | R27 | R28 | R29 | R210 | MS(M + 1) |
|---|---|---|---|---|---|---|
| 637 | —H | —H | —CH₃ | —H | —H | 501 |
| 638 | —H | —H | —Cl | —H | —H | 521 |
| 639 | —H | —H | —F | —H | —H | 505 |
| 640 | —H | —H | —OCH₃ | —H | —H | 517 |
| 641 | —H | —Cl | —Cl | —H | —H | 555 |
TABLE 49
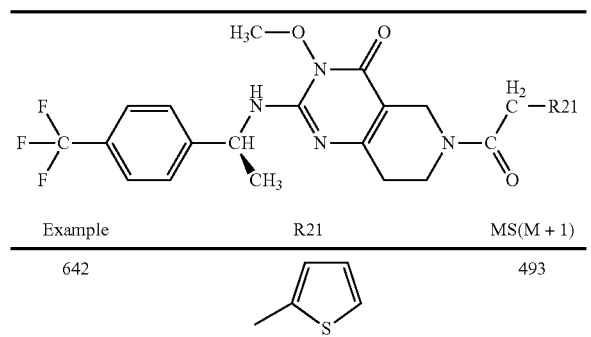
| Example | R21 | MS(M + 1) |
|---|---|---|
| 642 | 2-thienyl | 493 |
| 643 | 3-thienyl | 493 |
| 644 | adamantyl | 545 |
| 645 | 4-pyridyl | 488 |
TABLE 49-continued
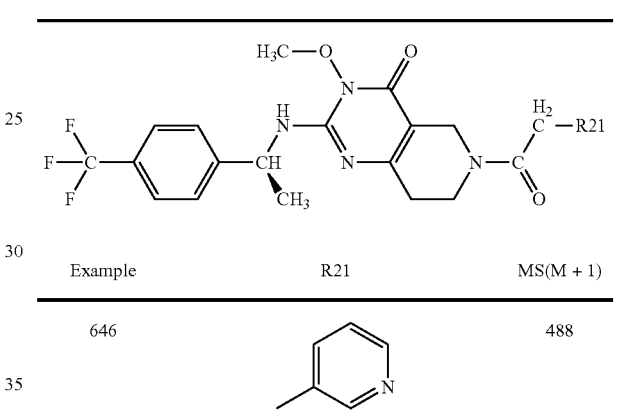
| Example | R21 | MS(M + 1) |
|---|---|---|
| 646 | 3-pyridyl | 488 |
| 647 | 4-chlorophenylthiomethyl | 553 |
TABLE 50
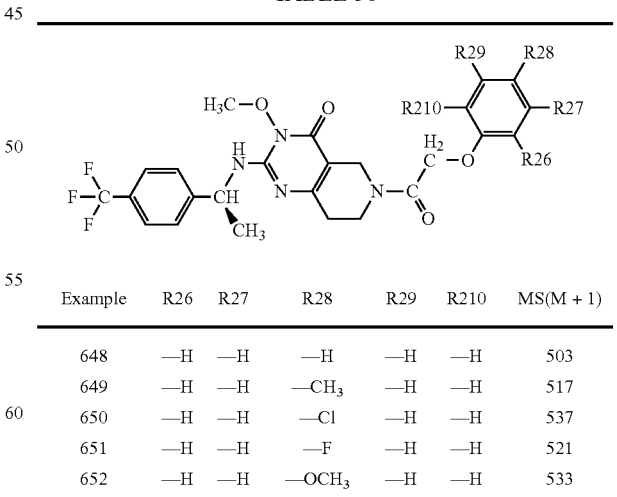
| Example | R26 | R27 | R28 | R29 | R210 | MS(M + 1) |
|---|---|---|---|---|---|---|
| 648 | —H | —H | —H | —H | —H | 503 |
| 649 | —H | —H | —CH₃ | —H | —H | 517 |
| 650 | —H | —H | —Cl | —H | —H | 537 |
| 651 | —H | —H | —F | —H | —H | 521 |
| 652 | —H | —H | —OCH₃ | —H | —H | 533 |
| 653 | —H | —H | —CN | —H | —H | 528 |
| 654 | —H | —F | —H | —H | —H | 521 |

TABLE 51

| Example | R21 | MS(M + 1) |
|---|---|---|
| 655 | methylenedioxyphenyl (benzo[1,3]dioxol-5-yl methyl) | 547 |
| 656 | 2,3-dihydro-benzo[1,4]dioxin-6-ylmethyl | 561 |
| 657 | pyridin-3-ylmethyl | 504 |
| 658 | 2,3-dihydro-1H-inden-5-ylmethyl | 543 |

TABLE 52

| Example | R26 | R27 | R28 | R29 | R210 | MS (M + 1) |
|---|---|---|---|---|---|---|
| 659 | —H | —H | —Cl | —H | —H | 533 |
| 660 | —H | —OC$_2$H$_5$ | —OC$_2$H$_5$ | —H | —H | 587 |
| 661 | —H | —H | —NHCOCH$_3$ | —H | —H | 556 |
| 662 | —H | —H | —SO$_2$CH$_3$ | —H | —H | 577 |
| 663 | —H | —H | pyrrolidin-1-yl | —H | —H | 568 |
| 664 | —H | —H | 1H-pyrrol-1-yl | —H | —H | 564 |
| 665 | —H | —H | 1H-pyrazol-1-yl | —H | —H | 565 |

TABLE 52-continued

| Example | R26 | R27 | R28 | R29 | R210 | MS (M + 1) |
|---|---|---|---|---|---|---|
| 666 | —H | —H | 1H-imidazol-1-yl | —H | —H | 565 |

TABLE 53

| Example | R21 | MS(M + 1) |
|---|---|---|
| 667 | 2-methylbenzofuran-... | 539 |
| 668 | 7-methoxy-2-methylbenzofuran-... | 569 |
| 669 | 2,3-dihydrobenzo[1,4]dioxin-6-yl | 557 |
| 670 | 2,3-dihydrobenzofuran-5-yl | 541 |

TABLE 54
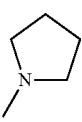
| Example | R27 | R28 | R29 | R210 | MS(M + 1) |
|---|---|---|---|---|---|
| 671 | —H | —H | —H | —H | 474 |
| 672 | —C₆H₅ | —H | —H | —H | 550 |
| 673 | —CH₃ | —H | —H | —H | 488 |
| 674 | —H | —H | —H | —CH₃ | 488 |
| 675 | —H | —H | —H | —F | 492 |
| 676 | —H | —C₆H₅ | —H | —H | 550 |
| 677 | —H | —CH₃ | —H | —H | 488 |
| 678 | —H | —OCH₃ | —H | —H | 504 |
| 679 | —H | —F | —H | —H | 492 |
| 680 | —H | —Cl | —H | —H | 508 |
| 681 | —H | —CN | —H | —H | 499 |
| 682 | 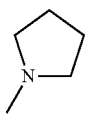 | —H | —H | —H | 543 |
| 683 | —H | 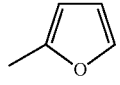 | —H | —H | 543 |
| 684 | —H | 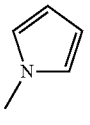 | —H | —H | 540 |
TABLE 55
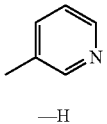
| Example | R27 | R28 | R29 | R210 | MS(M + 1) |
|---|---|---|---|---|---|
| 685 | —H | —H | —H | —H | 474 |
| 686 | —OCH₃ | —H | —H | —H | 504 |
| 687 | —H | —Cl | —H | —H | 508 |
| 688 | —H | —Cl | —Cl | —H | 542 |
| 689 | —C₆H₅ | —H | —H | —H | 550 |
| 690 | —H | —C₆H₅ | —H | —H | 550 |
| 691 | —H | —H | —C₆H₅ | —H | 550 |
| 692 | —H | —H | —H | —CH₃ | 488 |
| 693 | —H | —CH₃ | —H | —H | 488 |
| 694 | —Cl | —Cl | —H | —H | 542 |
| 695 | —H | —CF₃ | —H | —H | 542 |
| 696 | —H | —OH | —Cl | —H | 524 |
| 697 | —H | —H | —CH₃ | —H | 488 |
| 698 | —H | —OH | —H | —H | 490 |
| 699 | —OH | —CH₃ | —H | —H | 504 |
| 700 | —OH | —H | —Cl | —H | 524 |
| 701 | —H | —OCH₃ | —H | —H | 504 |
TABLE 55-continued
| Example | R27 | R28 | R29 | R210 | MS(M + 1) |
|---|---|---|---|---|---|
| 702 | —H |  | —H | —H | 539 |
| 703 | —H | (3-pyridyl) | —H | —H | 551 |
| 704 | (3-pyridyl) | —H | —H | —H | 551 |
| 705 | —H | —H | (2-methylthienyl) | —H | 556 |

TABLE 55-continued
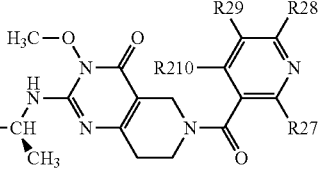
| Example | R27 | R28 | R29 | R210 | MS(M + 1) |
|---|---|---|---|---|---|
| 706 |  | —H | —H | —H | 543 |
TABLE 56
| Example | R27 | R28 | R29 | R210 | MS(M + 1) |
|---|---|---|---|---|---|
| 707 | —H | —H | —H | —H | 474 |
| 708 | —H | —Cl | —H | —H | 508 |
| 709 | —H | —C6H5 | —H | —H | 550 |
| 710 | —F | —H | —H | —H | 492 |
| 711 | —H | —OH | —CH3 | —H | 504 |
| 712 | —CH3 | —H | —H | —H | 488 |
| 713 | —CH3 |  | —H | —H | 606 |
| 714 | —H | 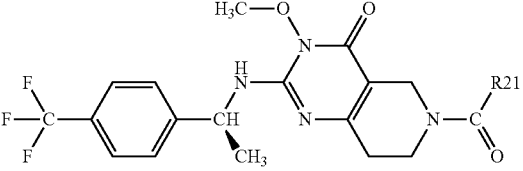 | —H | —H | 559 |
TABLE 57
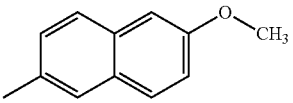
| Example | R21 | MS(M + 1) |
|---|---|---|
| 715 | 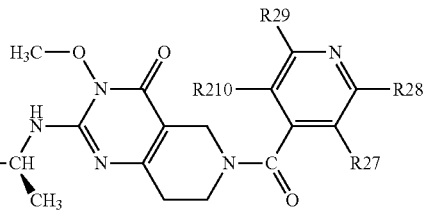 | 523 |
TABLE 57-continued
| Example | R21 | MS(M + 1) |
|---|---|---|
| 716 |  | 553 |
TABLE 57-continued
| Example | R21 | MS(M + 1) |
|---|---|---|
| 717 |  | 537 |

TABLE 57-continued

Structure: 4-(trifluoromethyl)phenyl-CH(CH3)-NH-[3-methoxy-4-oxo-pyrimido-tetrahydropyridine]-N-C(=O)-R21

| Example | R21 | MS(M + 1) |
|---|---|---|
| 718 | 4-fluoro-1-methyl-naphthalene | 541 |
| 719 | 5-methyl-1,2,3,4-tetrahydronaphthalene | 527 |
| 720 | 6-methyl-1,2,3,4-tetrahydronaphthalene | 527 |
| 721 | 2-methyl-indane | 513 |
| 722 | 5-methyl-indane | 513 |

TABLE 58

Structure: 4-(trifluoromethyl)phenyl-CH(CH3)-NH-[3-methoxy-4-oxo-pyrimido-tetrahydropyridine]-N-C(=O)-R21

| Example | R21 | MS(M + 1) |
|---|---|---|
| 723 | 2-methylquinoline | 524 |
| 724 | 3-methylquinoline | 524 |
| 725 | 4-methylquinoline | 524 |
| 726 | 6-methylquinoline | 524 |
| 727 | 7-methylquinoline | 524 |
| 728 | 5-methylquinoline | 524 |
| 729 | 3-methyl-6-methoxyquinoline | 554 |
| 730 | 3-methyl-8-methoxyquinoline | 554 |
| 731 | 8-methylquinoline | 524 |
| 732 | 6-methyl-2-methylquinoline | 538 |
| 733 | 4-methyl-2-methoxyquinoline | 554 |

TABLE 59

| Example | R23 | R24 | R25 | R26 | R27 | MS(M + 1) |
|---|---|---|---|---|---|---|
| 734 | —H | —H | —H | —H | —H | 513 |
| 735 | —H | —H | —Cl | —H | —OCH$_3$ | 577 |
| 736 | —H | —H | —H | —H | —OCH$_3$ | 543 |
| 737 | —CH$_3$ | —H | —H | —H | —H | 527 |
| 738 | —H | —H | —OCH$_3$ | —H | —H | 543 |
| 739 | —H | —H | —Cl | —H | —H | 547 |
| 740 | —CH$_3$ | —H | —H | —OCH$_3$ | —H | 557 |

TABLE 60

| Example | R21 | MS(M + 1) |
|---|---|---|
| 741 | 5-methylbenzofuran-2-yl | 513 |
| 742 | 2-tert-butyl-5-methylbenzofuran-2-yl | 569 |
| 743 | 4-methyl-2-methylbenzofuran-2-yl | 527 |

TABLE 60-continued

| Example | R21 | MS(M + 1) |
|---|---|---|
| 744 | 2,5-dimethylbenzofuran-2-yl | 527 |
| 745 | 3-methylbenzofuran-2-yl | 513 |
| 746 | 2,3-dimethyl-5-methoxybenzofuran-2-yl | 557 |

TABLE 61

| Example | R23 | R24 | R25 | R26 | R27 | MS(M + 1) |
|---|---|---|---|---|---|---|
| 747 | —H | —H | —CH$_3$ | —H | —H | 543 |
| 748 | —Cl | —H | —H | —H | —H | 563 |
| 749 | —CH$_3$ | —H | —H | —H | —H | 543 |
| 750 | —H | —H | —CF$_3$ | —H | —H | 597 |

TABLE 61-continued
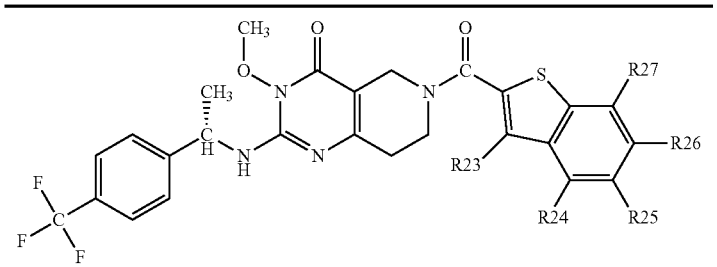
| Example | R23 | R24 | R25 | R26 | R27 | MS(M + 1) |
|---|---|---|---|---|---|---|
| 751 | —H | —F | —H | —H | —H | 547 |
| 752 | —H | —H | —H | —H | —H | 529 |
| 753 | —H | —H | —H | —F | —H | 547 |
| 754 | —H | —H | —H | —OCH₃ | —H | 559 |
| 755 | —H | —H | —H | —Cl | —H | 563 |
TABLE 62
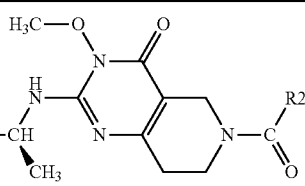
| Example | R21 | MS(M + 1) |
|---|---|---|
| 756 | 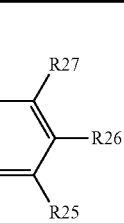 | 529 |
| 757 | (5-methylbenzothiophen-2-yl) | 529 |
| 758 | (5-chloro-3-methylbenzothiophen-2-yl) | 563 |
| 759 | (7-methylbenzothiophen-2-yl) | 529 |
TABLE 63
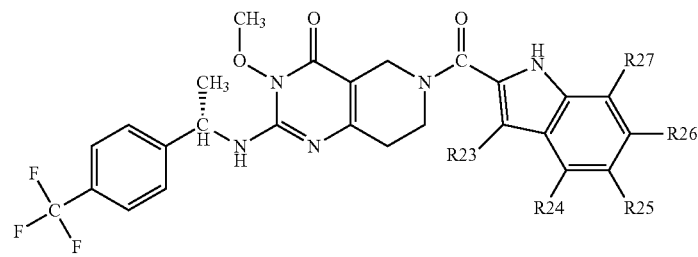
| Example | R23 | R24 | R25 | R26 | R27 | MS(M + 1) |
|---|---|---|---|---|---|---|
| 760 | —H | —H | —H | —H | —H | 512 |
| 761 | —H | —H | —OCH₃ | —H | —H | 542 |
| 762 | —H | —H | —Cl | —H | —H | 546 |
| 763 | —H | —H | —F | —H | —H | 530 |
| 764 | —H | —H | —H | —H | —H | 526 |
| 765 | —H | —H | —CH₃ | —H | —H | 526 |
| 766 | —H | —H | —OCF₃ | —H | —H | 596 |
| 767 | —H | —OCH₃ | —H | —H | —H | 542 |
| 768 | —H | —Cl | —H | —H | —H | 546 |
| 769 | —H | —H | —H | —OCH₃ | —H | 542 |

TABLE 63-continued

| Example | R23 | R24 | R25 | R26 | R27 | MS(M + 1) |
|---|---|---|---|---|---|---|
| 770 | —H | —H | —H | —Cl | —H | 546 |
| 771 | —H | —H | —OCH₃ | —OCH₃ | —H | 572 |
| 772 | —H | —CH₃ | —H | —H | —H | 526 |
| 773 | —H | —H | —H | —CH₃ | —H | 526 |
| 774 | —H | —H | —H | —OCH₃ | —H | 556 |
| 775 | —H | —H | —H | —N(CH₃)₂ | —H | 555 |
| 776 | —H | —H | —Cl | —H | —H | 560 |
| 777 | —H | —H | —F | —H | —H | 544 |
| 778 | —H | —H | —OCH₃ | —H | —H | 556 |
| 779 | —H | —OCH₃ | —H | —H | —H | 556 |

TABLE 64

| Example | R21 | MS(M + 1) |
|---|---|---|
| 780 | 3-methyl-1H-indole | 512 |
| 781 | 1,5-dimethyl-1H-indole | 526 |
| 782 | 1,6-dimethyl-1H-indole | 526 |
| 783 | 1,4-dimethyl-1H-indole | 526 |
| 784 | 4-methyl-1H-indole | 512 |
| 785 | 6-methyl-1H-indole | 512 |
| 786 | 7-methyl-1H-indole | 512 |
| 787 | 1,7-dimethyl-1H-indole | 526 |
| 788 | 1,3-dimethyl-1H-indole | 526 |
| 789 | 5-methoxy-3-methyl-1H-indole | 542 |

TABLE 65

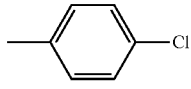

| Example | R23 | R24 | R25 | MS(M + 1) |
|---|---|---|---|---|
| 790 | —H | —H | —H | 463 |
| 791 | —H | —CH₃ | —CH₃ | 491 |
| 792 | —H | —H | —CH₃ | 477 |
| 793 | —H | —H | 4-Cl-C₆H₄ | 573 |
| 794 | —H | —H | CH₂-morpholine | 562 |
| 795 | —H | —H | CH₂-piperidine | 560 |

TABLE 66

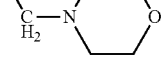

| Example | R23 | R24 | R25 | MS (M + 1) |
|---|---|---|---|---|
| 796 | —H | —H | —H | 463 |
| 797 | —CH₃ | —H | —C₆H₅ | 553 |
| 798 | —CF₃ | —H | —C₆H₅ | 607 |
| 799 | —CH₃ | —H | —H | 477 |
| 800 | —CF₃ | —H | —CH₃ | 545 |
| 801 | —CH₃ | —H | —CH₃ | 491 |
| 802 | —CH₃ | —H | 4-Cl-C₆H₄ | 587 |
| 803 | CH₂-piperidine | —H | —H | 560 |

TABLE 67

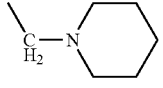

| Example | R23 | R24 | R25 | MS(M + 1) |
|---|---|---|---|---|
| 804 | —H | —H | —H | 479 |
| 805 | —CH₃ | —H | —H | 493 |
| 806 | —Cl | —H | —H | 513 |
| 807 | —H | —H | —Cl | 513 |
| 808 | —H | —H | —C₆H₅ | 555 |
| 809 | —OCH₃ | —H | —H | 509 |
| 810 | —Cl | —Cl | —Cl | 581 |
| 811 | —H | —CH₃ | —H | 493 |
| 812 | —H | —H | —COCH₃ | 521 |
| 813 | —H | —H | —OCH₃ | 509 |
| 814 | —H | —H | 2-pyridyl | 556 |
| 815 | —H | —H | 3-pyridyl | 556 |

TABLE 68

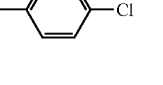

| Example | R23 | R24 | R25 | MS(M + 1) |
|---|---|---|---|---|
| 816 | —H | —H | —H | 479 |
| 817 | —H | —OCH₃ | —H | 509 |
| 818 | —Cl | —H | —Cl | 547 |
| 819 | —H | —H | —Cl | 513 |

TABLE 69

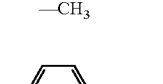

| Example | R21 | MS(M + 1) |
|---|---|---|
| 820 | 3-methyl-2-oxo-1,2-dihydroquinolin-yl | 540 |

TABLE 69-continued

| Example | R21 | MS(M + 1) |
|---|---|---|
| 821 | 6-methyl-quinolin-2(1H)-one | 540 |
| 822 | 8-methyl-quinolin-2(1H)-one | 540 |
| 823 | 5-methyl-quinolin-2(1H)-one | 540 |
| 824 | 7-methyl-quinolin-2(1H)-one | 540 |
| 825 | 3-methyl-7-methoxy-quinolin-2(1H)-one | 570 |
| 826 | 1,3-dimethyl-7-methoxy-quinolin-2(1H)-one | 584 |
| 827 | 4-methyl-quinolin-2(1H)-one | 540 |
| 828 | 1-ethyl-3-methyl-quinolin-2(1H)-one | 568 |

TABLE 69-continued

| Example | R21 | MS(M + 1) |
|---|---|---|
| 829 | 1,3-dimethyl-8-methoxy-quinolin-2(1H)-one | 584 |
| 830 | 3,4-dimethyl-7-methoxy-quinolin-2(1H)-one | 584 |
| 831 | 1,4-dimethyl-quinolin-2(1H)-one | 554 |

| Example | R21 | MS(M + 1) |
|---|---|---|
| 832 | 6-methyl-3,4-dihydroquinolin-2(1H)-one | 542 |
| 833 | 1,6-dimethyl-3,4-dihydroquinolin-2(1H)-one | 556 |
| 834 | 8-methyl-3,4-dihydroquinolin-2(1H)-one | 542 |

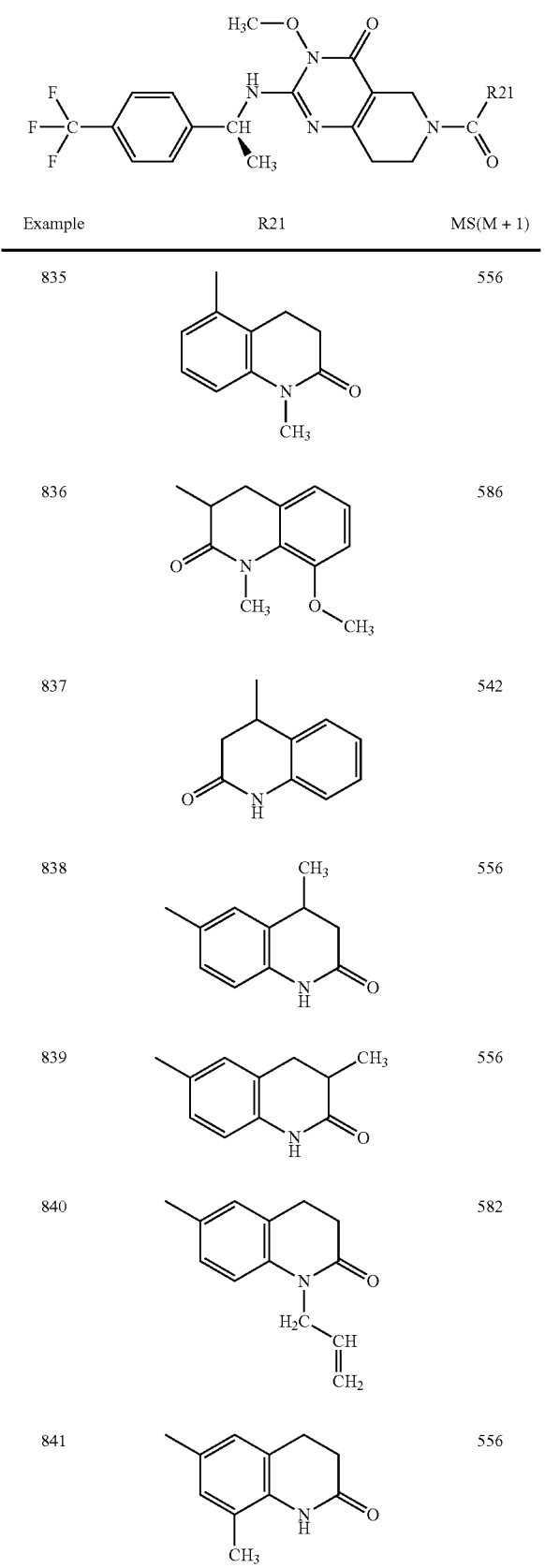
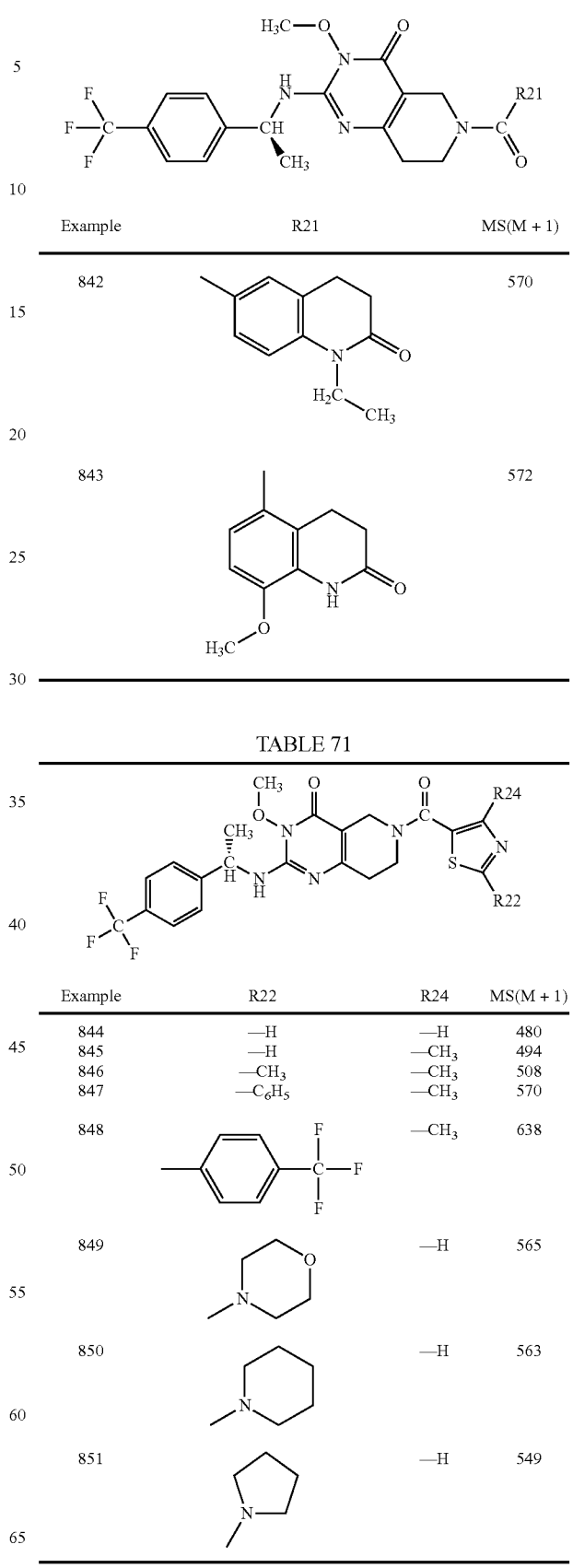

TABLE 72

[Structure: core scaffold with R22 and R24 substituents on thiazole]

| Example | R22 | R24 | MS(M + 1) |
|---|---|---|---|
| 852 | —H | —H | 480 |
| 853 | —C$_6$H$_5$ | —H | 556 |
| 854 | —CH$_3$ | —H | 494 |
| 855 | 3-pyridyl | —H | 557 |
| 856 | 3-chlorophenyl | —H | 590 |
| 857 | 2-thienyl | —H | 562 |
| 858 | —CH$_2$—C$_6$H$_5$ (benzyl) | —H | 570 |

TABLE 73

[Structure: core scaffold with R21 acyl substituent]

| Example | R21 | MS(M + 1) |
|---|---|---|
| 859 | 2,6-dimethylbenzothiazol-yl | 544 |
| 860 | 2-benzothiazolyl | 530 |
| 861 | 6-methylbenzothiazol-2-yl | 530 |

TABLE 73-continued

| Example | R21 | MS(M + 1) |
|---|---|---|
| 862 | 1-methylisoquinolin-yl | 524 |
| 863 | 3-methylisoquinolin-yl | 524 |
| 864 | 4-methylisoquinolin-yl | 524 |
| 865 | 2-methylpyrimidin-yl | 475 |
| 866 | 5-methylpyrimidin-yl | 475 |
| 867 | 5-methyl-2-(2-thienyl)pyrimidin-yl | 557 |
| 868 | 5-methyl-2-phenylpyrimidin-yl | 551 |
| 869 | 5-methyl-2-(pyrrolidin-1-yl)pyrimidin-yl | 544 |

TABLE 74

| Example | R21 | MS(M + 1) |
|---|---|---|
| 870 | 1,5-dimethyl-1H-imidazol-yl | 477 |
| 871 | 1,4-dimethyl-1H-imidazol-yl | 477 |
| 872 | 1,2-dimethyl-1H-imidazol-yl | 477 |
| 873 | 4-methyl-1H-imidazol-yl | 463 |
| 874 | 2-methyl-1H-imidazol-yl | 463 |

TABLE 75

| Example | R22 | R24 | MS(M + 1) |
|---|---|---|---|
| 875 | —CH₃ | —CF₃ | 546 |
| 876 | —CH₃ | —H | 478 |
| 877 | —H | —C₆H₅ | 540 |
| 878 | —CH₃ | —CH₃ | 492 |
| 879 | —C₆H₅ | —CH₃ | 554 |
| 880 | —H | —H | 464 |
| 881 | —H | 4-methoxyphenyl | 570 |

TABLE 76

| Example | R21 | MS(M + 1) |
|---|---|---|
| 882 | 4,5-dimethyloxazol-yl | 478 |
| 883 | 4-methyl-5-methyl-2-phenyloxazol-yl | 554 |
| 884 | 6-methyl-2-phenylbenzoxazol-yl | 590 |
| 885 | 5-methylisoxazol-yl | 464 |
| 886 | 5-methyl-3-phenylisoxazol-yl | 540 |

TABLE 77

| Example | R22 | R24 | MS(M + 1) |
|---|---|---|---|
| 887 | —H | —CH₃ | 478 |
| 888 | —CH₃ | —CH₃ | 492 |
| 889 | —CH₃ | —H | 478 |
| 890 | —C₆H₅ | —CH₃ | 554 |

TABLE 78
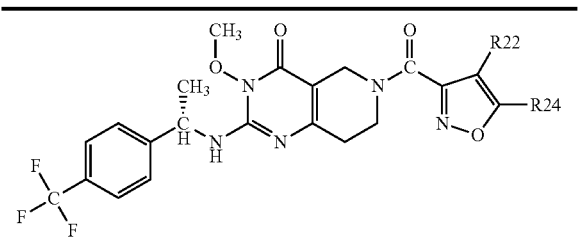
| Example | R22 | R24 | MS(M + 1) |
|---|---|---|---|
| 891 | —H | —CH(CH3)2 | 506 |
| 892 | —H | —CH3 | 478 |
| 893 | —H | —C6H5 | 540 |
TABLE 79
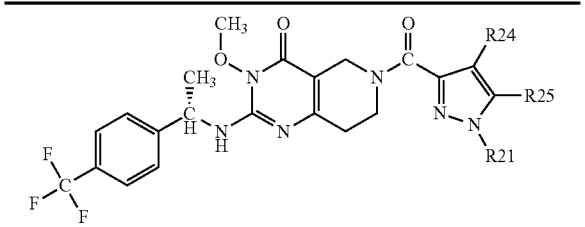
| Example | R21 | R24 | R25 | MS(M + 1) |
|---|---|---|---|---|
| 894 | —CH3 | —H | —C6H5 | 553 |
| 895 | —CH3 | —H | —H | 477 |
| 896 | —H | —H | —H | 463 |
| 897 | —CH3 | —H | —CH3 | 491 |
| 898 | —CH3 | —H | 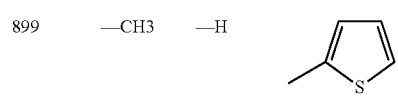 | 543 |
| 899 | —CH3 | —H | 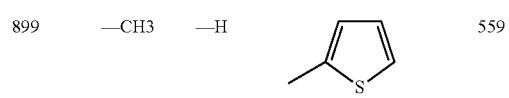 | 559 |
TABLE 80
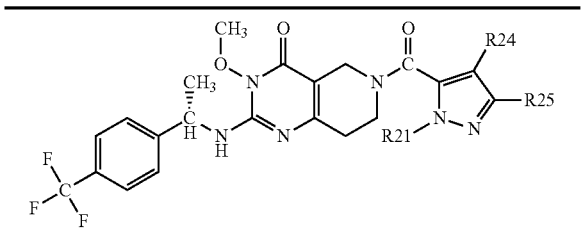
| Example | R21 | R24 | R25 | MS(M + 1) |
|---|---|---|---|---|
| 900 | —CH3 | —H | —C6H5 | 553 |
| 901 | —CH3 | —H | —H | 477 |
| 902 | —C2H5 | —H | —CH3 | 505 |
| 903 | —C6H5 | —H | —H | 539 |
| 904 | —CH3 | —H | —CH3 | 491 |
| 905 | —C(CH3)3 | —H | —CH3 | 533 |
| 906 | —CH3 | —H | —C(CH3)3 | 533 |
| 907 | —CH3 | —H | 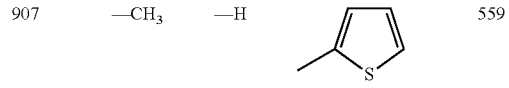 | 559 |
TABLE 80-continued
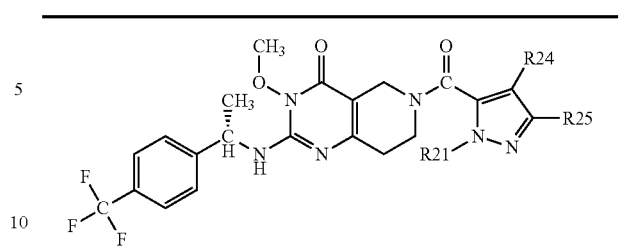
| Example | R21 | R24 | R25 | MS(M + 1) |
|---|---|---|---|---|
| 908 | —CH3 | —H | 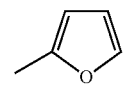 | 543 |
TABLE 81
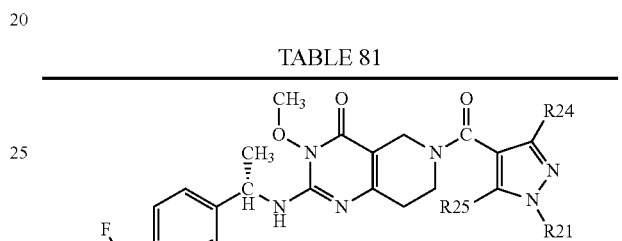
| Example | R21 | R24 | R25 | MS(M + 1) |
|---|---|---|---|---|
| 909 | —CH3 | —H | —H | 477 |
| 910 | —C6H5 | —H | —CH3 | 553 |
| 911 | —CH3 | —H | —C6H5 | 553 |
| 912 | —CH3 | —CF3 | —H | 545 |
TABLE 82
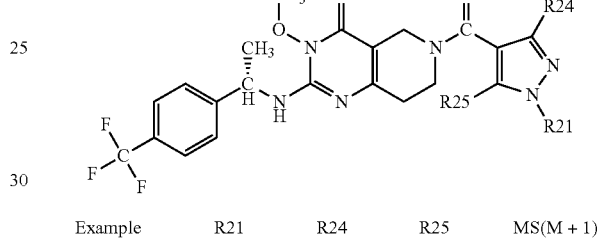
| Example | R21 | MS(M + 1) |
|---|---|---|
| 913 | 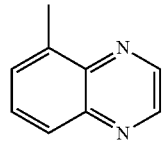 | 525 |
| 914 | 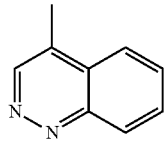 | 525 |
| 915 | 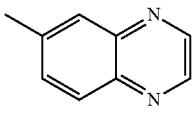 | 525 |

TABLE 82-continued

| Example | R21 | MS(M + 1) |
|---|---|---|
| 916 | 6,7-dimethyl-2,3-dimethylquinoxaline | 553 |
| 917 | 3-methylquinoxaline | 525 |
| 918 | 6-methyl-4-methyl-3,4-dihydro-2H-benzo[b][1,4]oxazine | 544 |
| 919 | 6-methyl-2H-benzo[b][1,4]oxazin-3(4H)-one | 544 |
| 920 | 7-methyl-2H-benzo[b][1,4]oxazin-3(4H)-one | 544 |
| 921 | 7-methyl-4-methyl-2H-benzo[b][1,4]oxazin-3(4H)-one | 558 |
| 922 | 6-methyl-1H-benzo[d][1,3]oxazin-2(4H)-one | 544 |
| 923 | 7-methyl-1H-benzo[d][1,3]oxazin-2(4H)-one | 544 |
| 924 | 5-methyl-1H-benzo[d][1,3]oxazin-2(4H)-one | 544 |

TABLE 82-continued

| Example | R21 | MS(M + 1) |
|---|---|---|
| 925 | 8-methyl-1H-benzo[d][1,3]oxazin-2(4H)-one | 544 |
| 926 | 6-methyl-2H-benzo[b][1,4]thiazin-3(4H)-one | 560 |
| 927 | 6-methyl-4-methyl-2H-benzo[b][1,4]thiazin-3(4H)-one | 574 |
| 928 | 6-methyl-3-ethylquinazoline-2,4(1H,3H)-dione | 585 |
| 929 | 6-methyl-3-methyl-3,4-dihydroquinazolin-2(1H)-one | 557 |
| 930 | 6-methylquinoxaline-2,3(1H,4H)-dione | 557 |
| 931 | 3-methyl-1-methylquinolin-4(1H)-one | 554 |
| 932 | 3-methyl-8-methoxyquinolin-4(1H)-one | 570 |

TABLE 82-continued
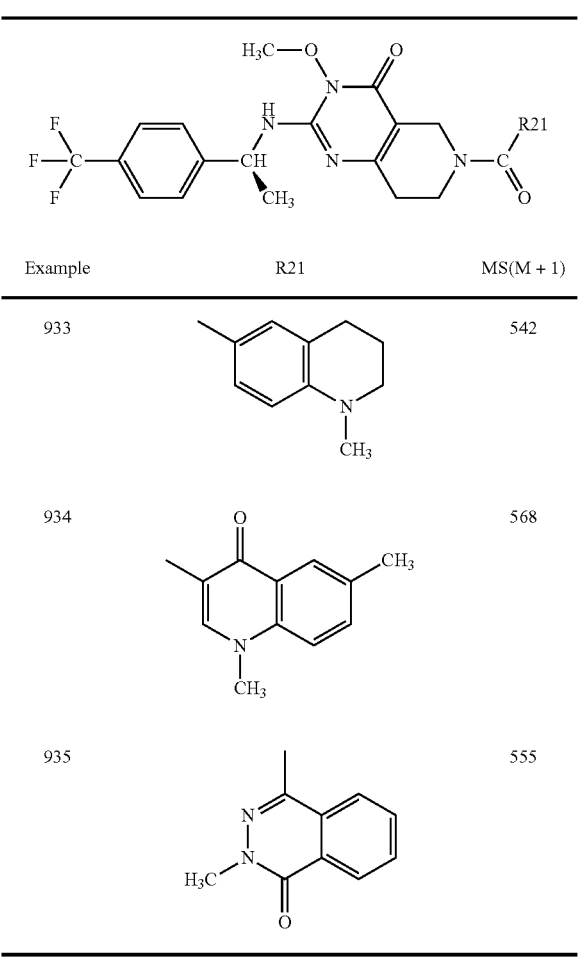
| Example | R21 | MS(M + 1) |
|---|---|---|
| 933 | | 542 |
| 934 | | 568 |
| 935 | | 555 |
TABLE 83
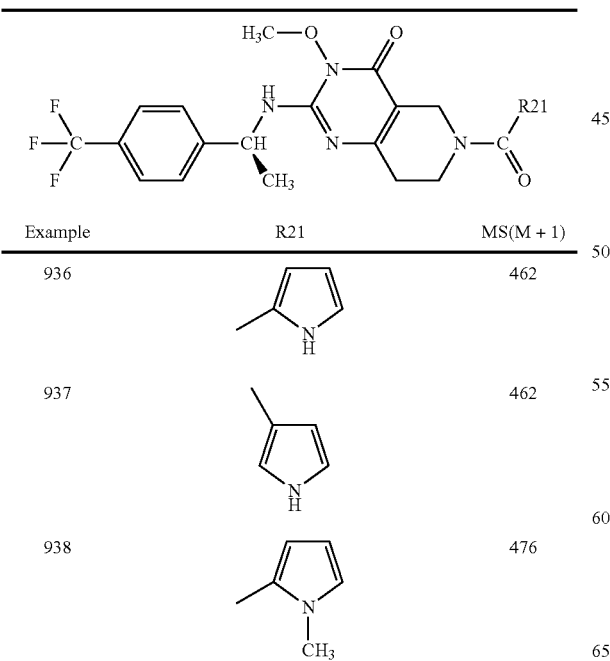
| Example | R21 | MS(M + 1) |
|---|---|---|
| 936 | | 462 |
| 937 | | 462 |
| 938 | | 476 |
TABLE 83-continued
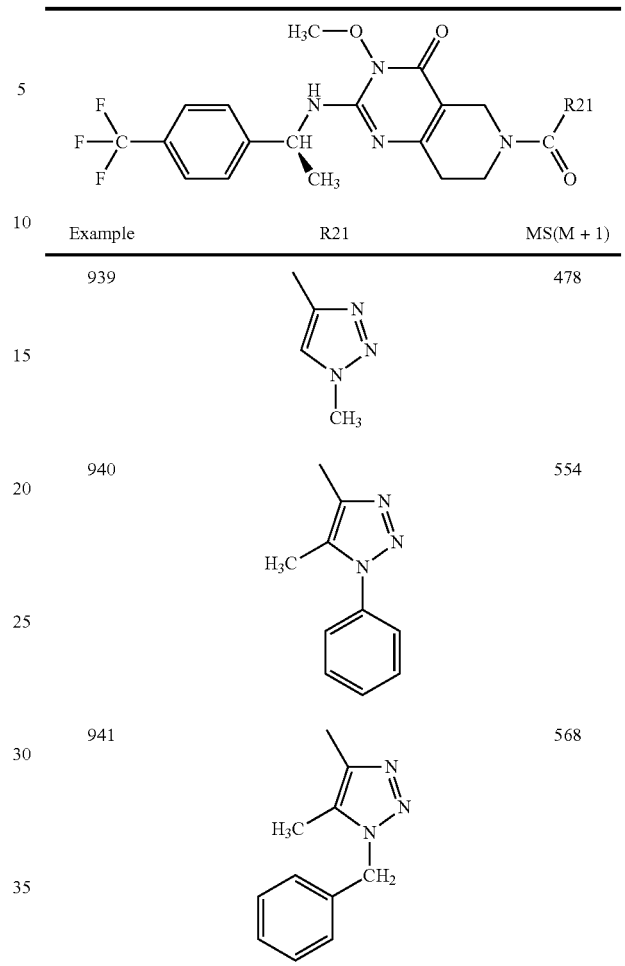
| Example | R21 | MS(M + 1) |
|---|---|---|
| 939 | | 478 |
| 940 | | 554 |
| 941 | | 568 |
| 942 | | 492 |
| 943 | | 464 |
| 944 | | 554 |
| 945 | | 481 |

TABLE 83-continued

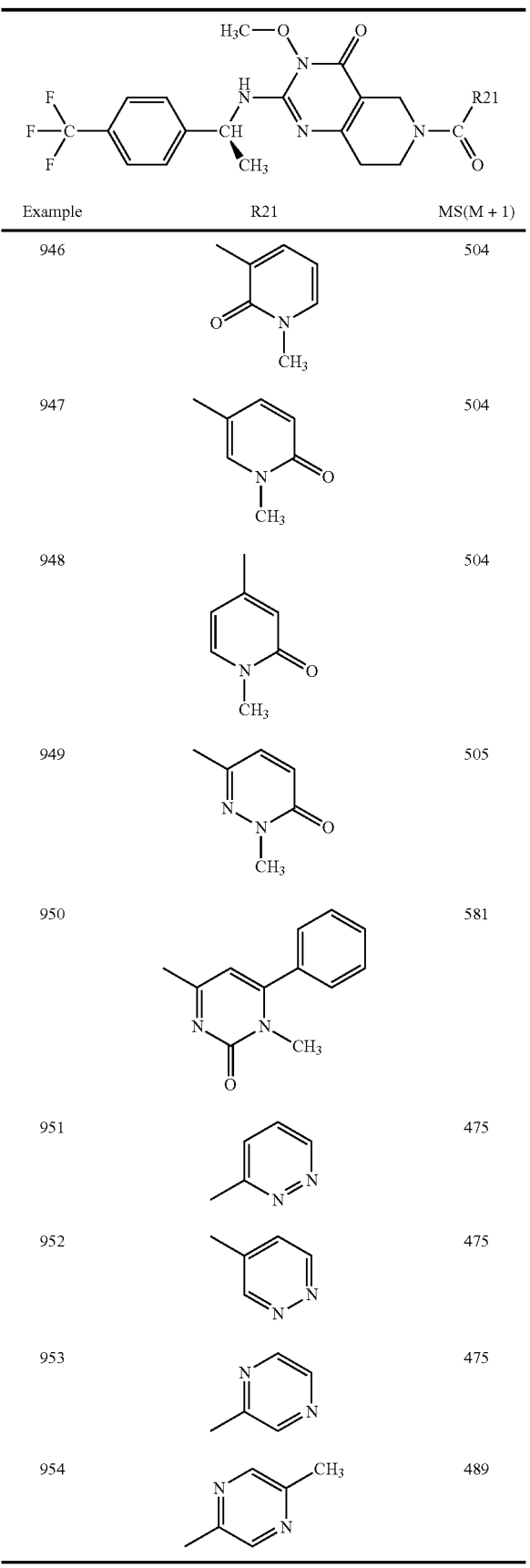

| Example | R21 | MS(M + 1) |
|---|---|---|
| 946 | 3-methyl-1-methyl-pyridin-2-one | 504 |
| 947 | 5-methyl-1-methyl-pyridin-2-one | 504 |
| 948 | 4-methyl-1-methyl-pyridin-2-one | 504 |
| 949 | 6-methyl-2-methyl-pyridazin-3-one | 505 |
| 950 | 4-methyl-6-phenyl-3-methyl-pyrimidin-2-one | 581 |
| 951 | 3-methylpyridazine | 475 |
| 952 | 4-methylpyridazine | 475 |
| 953 | 3-methylpyrazine | 475 |
| 954 | 2,5-dimethylpyrazine | 489 |

TABLE 84

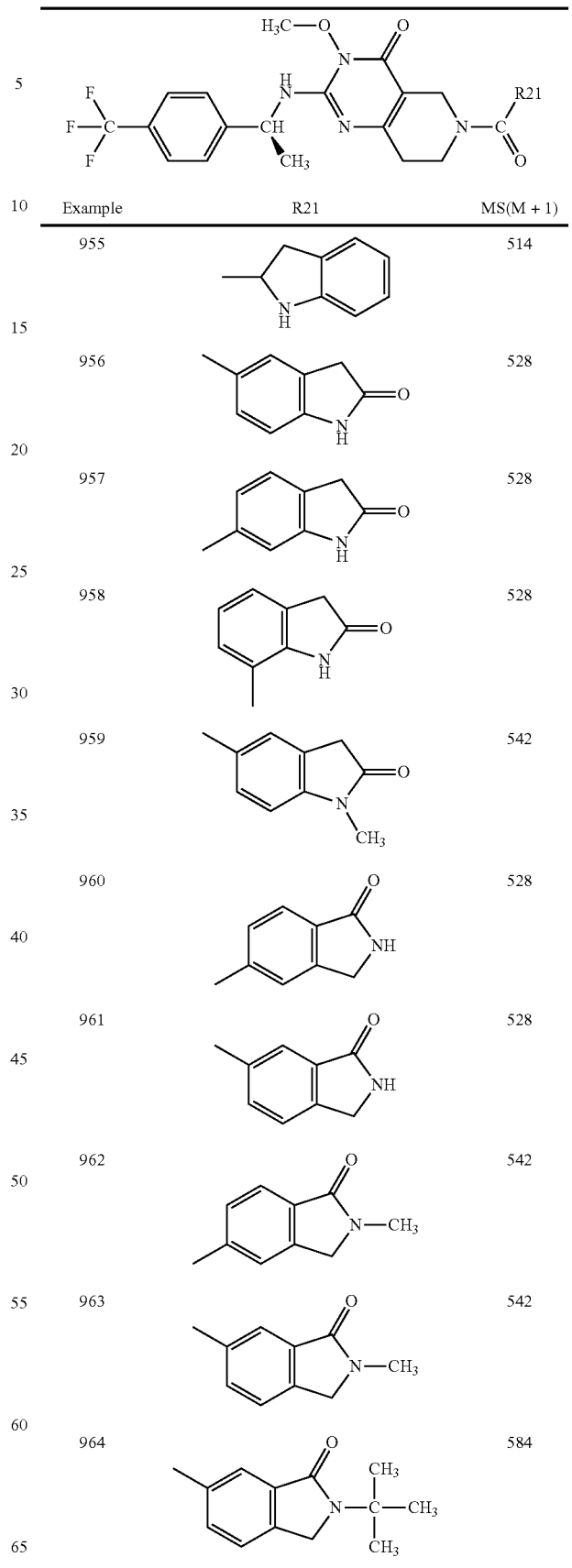

| Example | R21 | MS(M + 1) |
|---|---|---|
| 955 | 2-methylindoline | 514 |
| 956 | 5-methyloxindole | 528 |
| 957 | 6-methyloxindole | 528 |
| 958 | 7-methyloxindole | 528 |
| 959 | 5-methyl-1-methyloxindole | 542 |
| 960 | 5-methylisoindolin-1-one | 528 |
| 961 | 6-methylisoindolin-1-one | 528 |
| 962 | 5-methyl-2-methylisoindolin-1-one | 542 |
| 963 | 6-methyl-2-methylisoindolin-1-one | 542 |
| 964 | 6-methyl-2-tert-butylisoindolin-1-one | 584 |

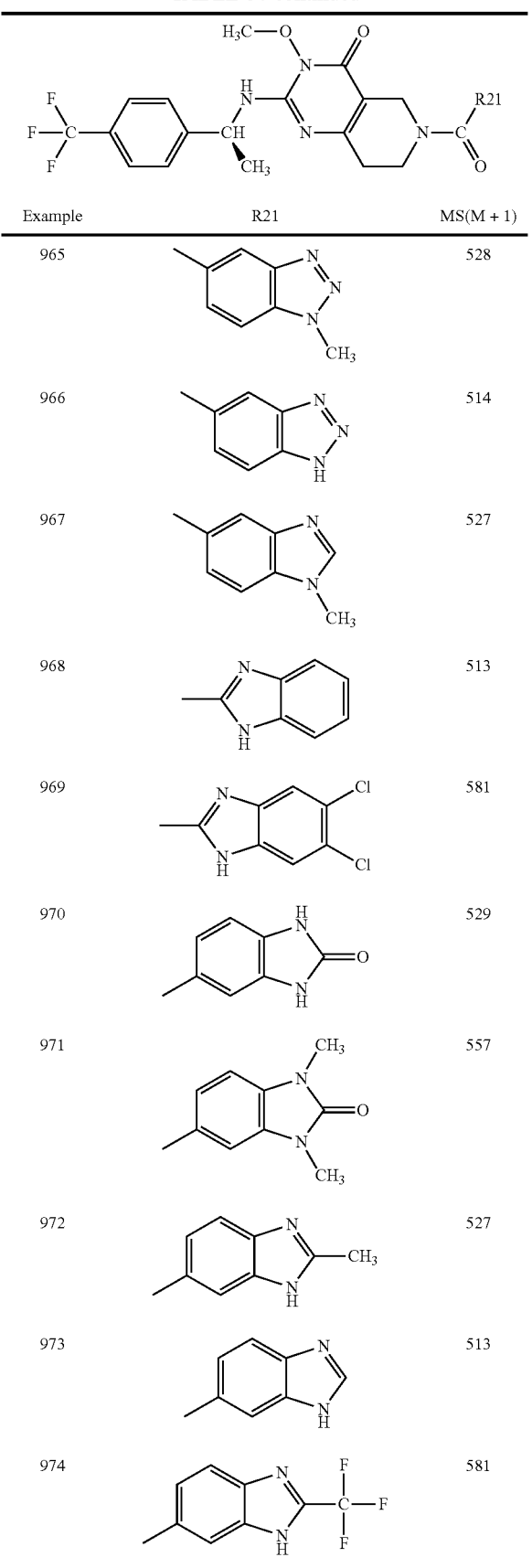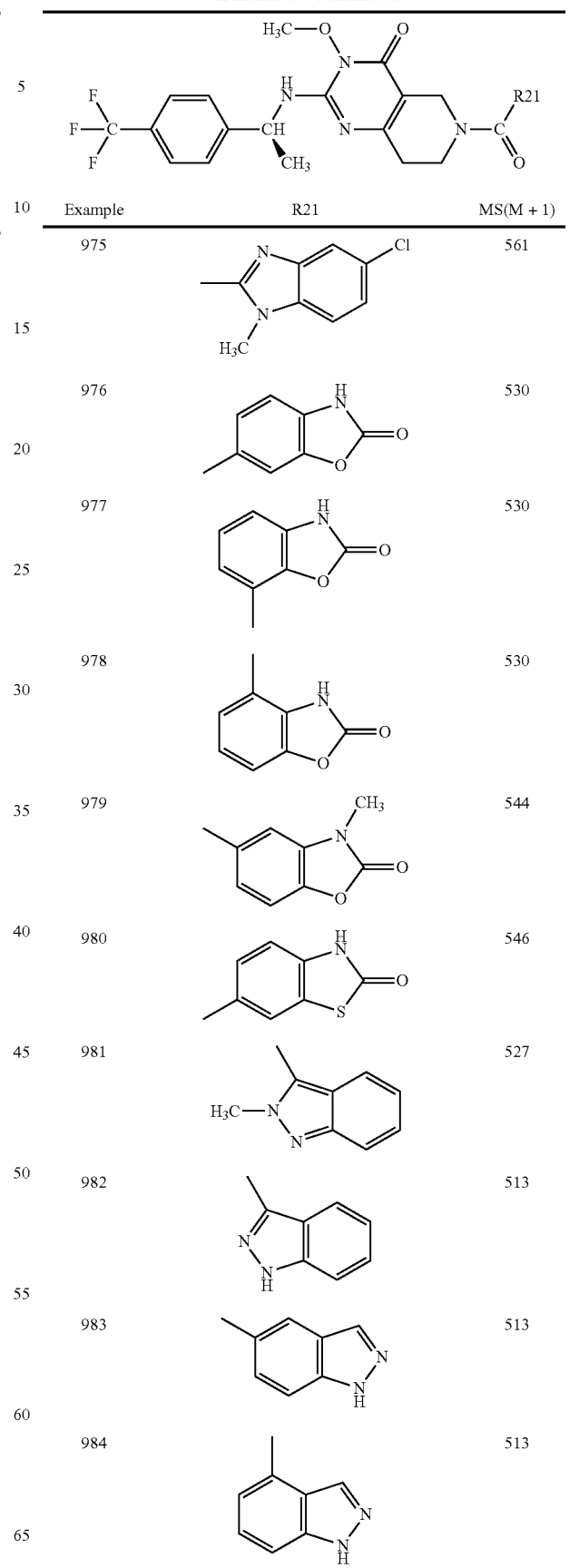

TABLE 84-continued

| Example | R21 | MS(M + 1) |
|---|---|---|
| 985 | (1-methyl-1H-indazol-3-yl) | 527 |

TABLE 85

| Example | R21 | MS(M + 1) |
|---|---|---|
| 986 | (methyl-benzo[1,3]dioxole) | 517 |
| 987 | (methyl-benzo[1,3]dioxole) | 517 |
| 988 | (methyl-2,3-dihydro-benzo[1,4]dioxine) | 531 |
| 989 | (methyl-2,3-dihydro-benzo[1,4]dioxine) | 531 |
| 990 | (methyl-benzodioxepine) | 545 |
| 991 | (methyl-benzodioxepine) | 545 |

TABLE 85-continued

| Example | R21 | MS(M + 1) |
|---|---|---|
| 992 | (methyl-chroman) | 529 |
| 993 | (methyl-chroman) | 529 |
| 994 | (methyl-chroman) | 529 |
| 995 | (methyl-chroman) | 529 |
| 996 | (methyl-2,3-dihydrobenzofuran) | 515 |
| 997 | (dimethyl-methyl-2,3-dihydrobenzofuran) | 543 |
| 998 | (methyl-2,3-dihydrobenzofuran) | 515 |

TABLE 86

| Example | R21 | MS(M + 1) |
|---|---|---|
| 999 | (4-methylpiperidinyl-benzoyl) | 584 |

TABLE 86-continued

| Example | R21 | MS(M + 1) |
|---|---|---|
| 1000 | 4-methyl-1-acetylpiperidine | 522 |
| 1001 | 4-methyl-1-[4-(trifluoromethoxy)phenyl]piperidine | 640 |
| 1002 | 4-methyl-1-(methylsulfonyl)piperidine | 558 |
| 1003 | 5-methyl-2-pyrrolidinone | 480 |
| 1004 | 3-methyl-1-benzoylpyrrolidine | 570 |
| 1005 | 4-methyl-1-phenyl-2-pyrrolidinone | 556 |
| 1006 | 3-methyl-1-phenyl-2-pyrrolidinone | 556 |
| 1007 | 1,4-dimethyl-2-pyrrolidinone | 494 |
| 1008 | 1-benzyl-4-methyl-2-pyrrolidinone | 570 |

TABLE 86-continued

| Example | R21 | MS(M + 1) |
|---|---|---|
| 1009 | 1-phenethyl-4-methyl-2-pyrrolidinone | 584 |

TABLE 87

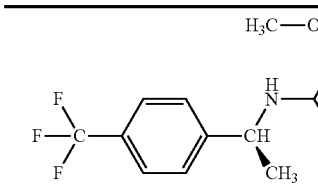

| Example | R21 | MS(M + 1) |
|---|---|---|
| 1010 | 1-methylcyclopropyl | 437 |
| 1011 | 1-methyl-1-phenylcyclopropyl | 513 |
| 1012 | 1-methyl-1-(4-methoxyphenyl)cyclopropyl | 543 |
| 1013 | 1-methyl-1-(4-chlorophenyl)cyclopropyl | 547 |
| 1014 | 1-methyl-1-(4-methylphenyl)cyclopropyl | 527 |
| 1015 | 1,1-dimethylcyclopropyl | 451 |
| 1016 | 1-methyl-1-(trifluoromethyl)cyclopropyl | 505 |

TABLE 87-continued
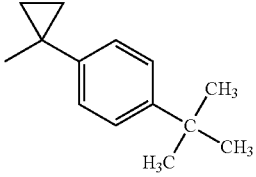
| Example | R21 | MS(M + 1) |
|---|---|---|
| 1017 | 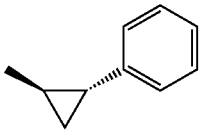 | 569 |
| 1018 | 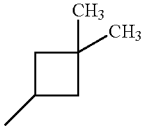 | 513 |
| 1019 | 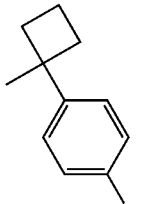 | 479 |
| 1020 |  | 561 |
| 1021 | 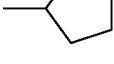 | 451 |
| 1022 | 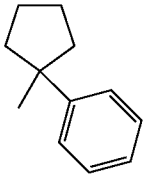 | 465 |
| 1023 | 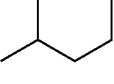 | 541 |
| 1024 | 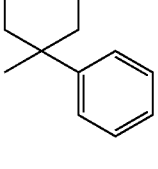 | 479 |
| 1025 | 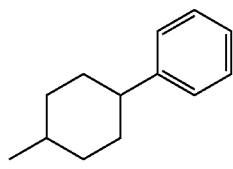 | 555 |
TABLE 87-continued
| Example | R21 | MS(M + 1) |
|---|---|---|
| 1026 | 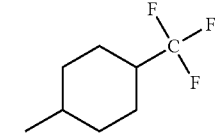 | 555 |
| 1027 | 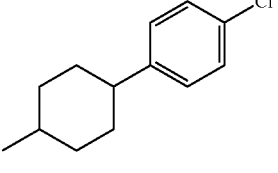 | 493 |
| 1028 | 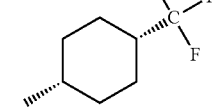 | 547 |
| 1029 | 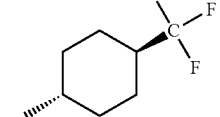 | 589 |
| 1030 | 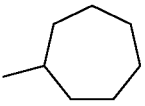 | 547 |
| 1031 |  | 547 |
| 1032 | 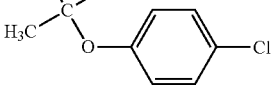 | 493 |
| 1033 | 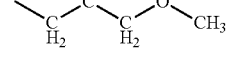 | 439 |
| 1034 | | 565 |
| 1035 | | 469 |

TABLE 87-continued

Structure with R21 group (187):
H3C—O, F3C-phenyl-CH(CH3)-NH, pyrimidinone, N-C(=O)-R21

| Example | R21 | MS(M + 1) |
|---------|-----|-----------|
| 1036 | 1-cyclopentyl-1-phenylmethyl (with CH) | 555 |
| 1037 | cyclohexylidenemethyl | 491 |
| 1038 | 1-methyl-1-(2-thienyl)cyclohexyl | 563 |
| 1039 | 4-methyl-4-phenyltetrahydropyran | 557 |
| 1040 | 4-methyltetrahydropyran | 481 |
| 1041 | 3-methyltetrahydrofuran | 467 |
| 1042 | 2-methyltetrahydrofuran | 467 |

TABLE 88

Structure with R21 group (188):
H3C—O, F3C-phenyl-CH(CH3)-NH, pyrimidinone, N-C(=O)-R21

| Example | R21 | MS(M + 1) |
|---------|-----|-----------|
| 1043 | 4-methyl-5-methylfuro[3,2-b]pyrrole (N-CH3) | 516 |
| 1044 | 2-methylthieno[3,2-b]pyrazine | 531 |
| 1045 | 2-methyl-6-chloroimidazo[1,2-a]pyridine | 547 |
| 1046 | 2,3-dimethylimidazo[1,2-a]pyridine | 527 |
| 1047 | 6-methylimidazo[1,2-a]pyridine | 513 |
| 1048 | 5-methyl-4H-thieno[3,2-b]pyrrole | 518 |
| 1049 | 4,5-dimethylthieno[3,2-b]pyrrole (N-CH3) | 532 |
| 1050 | methyl-thieno-dioxine | 537 |
| 1051 | 2-methyl-1,8-naphthyridine | 525 |
| 1052 | 3-methyl-1-phenyl-cyclopenta[c]pyrazole | 579 |

TABLE 88-continued
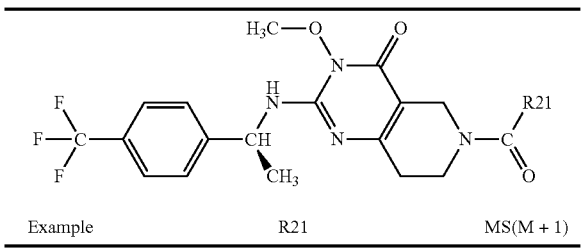
| Example | R21 | MS(M + 1) |
|---|---|---|
| 1053 | 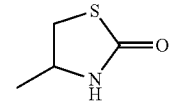 | 512 |
| 1054 | 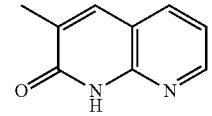 | 498 |
| 1055 | 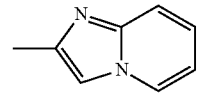 | 541 |
| 1056 | 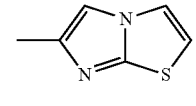 | 513 |
| 1057 | 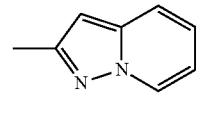 | 519 |
| 1058 | 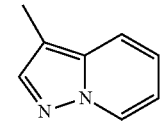 | 513 |
| 1059 | 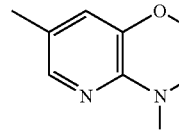 | 513 |
| 1060 | 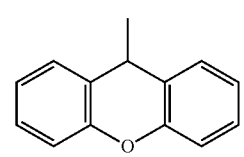 | 545 |
| 1061 | 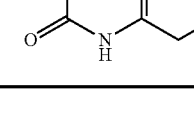 | 577 |
TABLE 88-continued
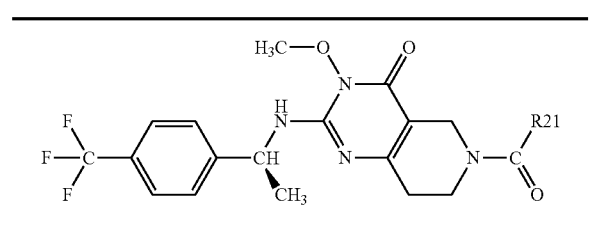
| Example | R21 | MS(M + 1) |
|---|---|---|
| 1062 | 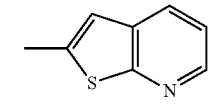 | 530 |
| 1063 | 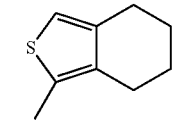 | 533 |
| 1064 | 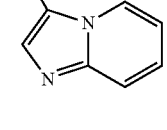 | 513 |
| 1065 | 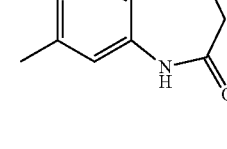 | 558 |
| 1066 | 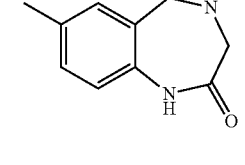 | 585 |
| 1067 | 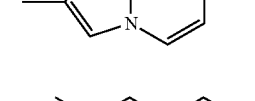 | 527 |
| 1068 | | 544 |

TABLE 89

| Example | R26 | R27 | R28 | R29 | R210 | MS(M + 1) |
|---|---|---|---|---|---|---|
| 1069 | —H | —H | —H | —H | —H | 501 |
| 1070 | —H | —H | —CH₃ | —H | —H | 515 |
| 1071 | —H | —H | —Cl | —H | —H | 535 |
| 1072 | —H | —H | —F | —H | —H | 519 |
| 1073 | —H | —H | —OCH₃ | —H | —H | 531 |
| 1074 | —H | —H | —CF₃ | —H | —H | 569 |
| 1075 | —H | —Cl | —H | —H | —H | 535 |
| 1076 | —H | —CH₃ | —H | —H | —H | 515 |
| 1077 | —H | —H | —CN | —H | —H | 526 |
| 1078 | —H | —H | —OCF₃ | —H | —H | 585 |
| 1079 | —F | —H | —CN | —H | —H | 544 |
| 1080 | —H | —CH₃ | —Cl | —H | —H | 549 |
| 1081 | —H | —Cl | —CH₃ | —H | —H | 549 |
| 1082 | —H | —H | —OC₂H₅ | —H | —H | 545 |
| 1083 | —H | —H | —SCH₃ | —H | —H | 547 |
| 1084 | —H | —H | —OCH(CH₃)₂ | —H | —H | 559 |
| 1085 | —H | —H | 1-methyl-1,2,4-triazol-3-yl | —H | —H | 568 |
| 1086 | —H | —H | 1-methylimidazol-2-yl | —H | —H | 567 |
| 1087 | —H | —H | 4-methyl-1,2,4-triazol-3-yl | —H | —H | 568 |
| 1088 | —H | —H | 5-methyloxazol-2-yl | —H | —H | 568 |
| 1089 | —H | —H | 2,5-dimethyl-1,3,4-oxadiazol-... | —H | —H | 583 |

TABLE 90

| Example | R211 | MS(M+1) |
|---|---|---|
| 1090 | 2-methylnaphthalene | 551 |
| 1091 | 8-methylnaphthalene | 551 |
| 1092 | methyl-benzo[1,3]dioxole | 545 |
| 1093 | 2-methylquinoline | 552 |
| 1094 | 3-methylquinoline | 552 |
| 1095 | 6-methyl-3,4-dihydroquinolin-2(1H)-one | 570 |
| 1096 | 5-methyl-8-methoxy-3,4-dihydroquinolin-2(1H)-one | 600 |
| 1097 | 5-chloro-2-methylbenzofuran | 575 |
| 1098 | 6-chloro-2-methylimidazo[1,2-a]pyridine | 575 |
| 1099 | 5-methylbenzo[b]thiophene | 557 |

TABLE 90-continued

| Example | R211 | MS(M+1) |
|---|---|---|
| 1100 | 8-methylquinolin-2(1H)-one | 568 |
| 1101 | 5-methylquinolin-2(1H)-one | 568 |
| 1102 | 6-fluoro-2-methylbenzo[b]thiophene | 575 |
| 1103 | 2-methylpyrazolo[1,5-a]pyridine | 541 |
| 1104 | 2,5-dimethylthiophene | 521 |
| 1105 | 2-methylthieno[2,3-b]pyridine | 558 |
| 1106 | 3-methylquinoxaline | 553 |
| 1107 | methyl-2,3-dihydro-1H-indene | 541 |
| 1108 | 7-methylbenzo[b]thiophene | 557 |
| 1109 | 5-methyl-3-phenylisoxazole | 568 |

TABLE 90-continued

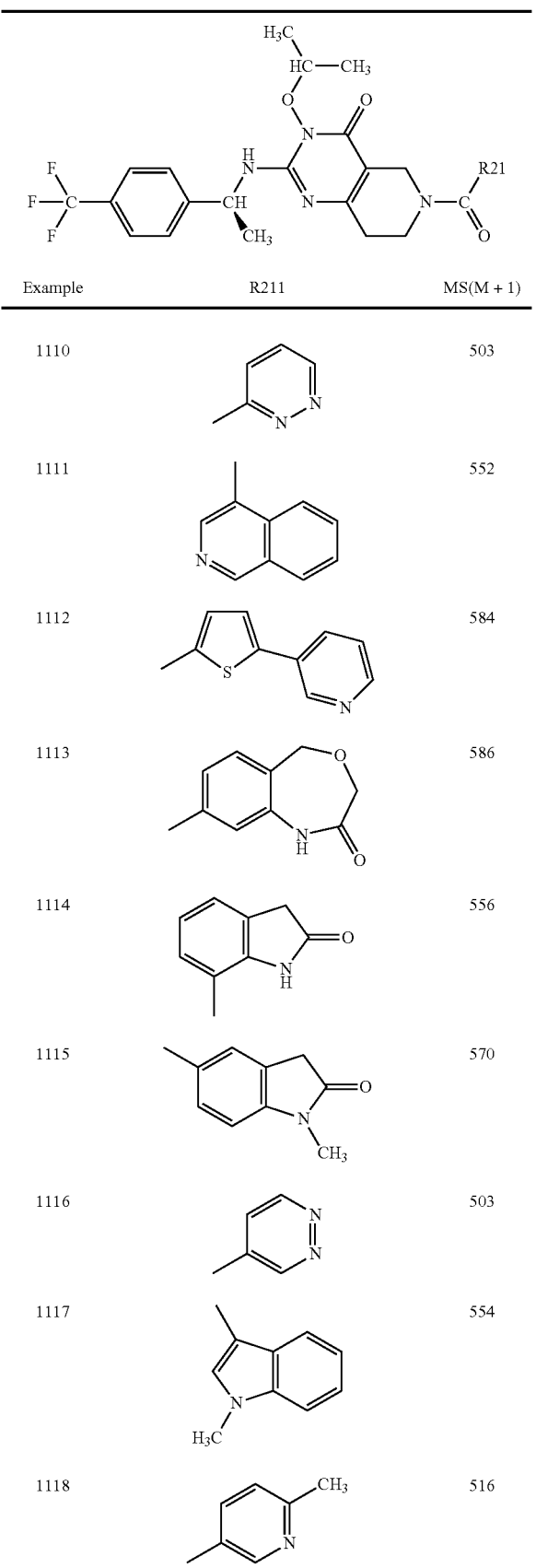

| Example | R211 | MS(M + 1) |
|---|---|---|
| 1110 | (3-methylpyridazine) | 503 |
| 1111 | (4-methylisoquinoline) | 552 |
| 1112 | (5-methyl-2-(pyridin-3-yl)thiophene) | 584 |
| 1113 | (7-methyl-4H-benzo[d][1,3]oxazepin-2(3H)-one) | 586 |
| 1114 | (7-methylindolin-2-one) | 556 |
| 1115 | (1,5-dimethylindolin-2-one) | 570 |
| 1116 | (4-methylpyridazine) | 503 |
| 1117 | (1,3-dimethyl-1H-indole) | 554 |
| 1118 | (2,5-dimethylpyridine) | 516 |

TABLE 90-continued

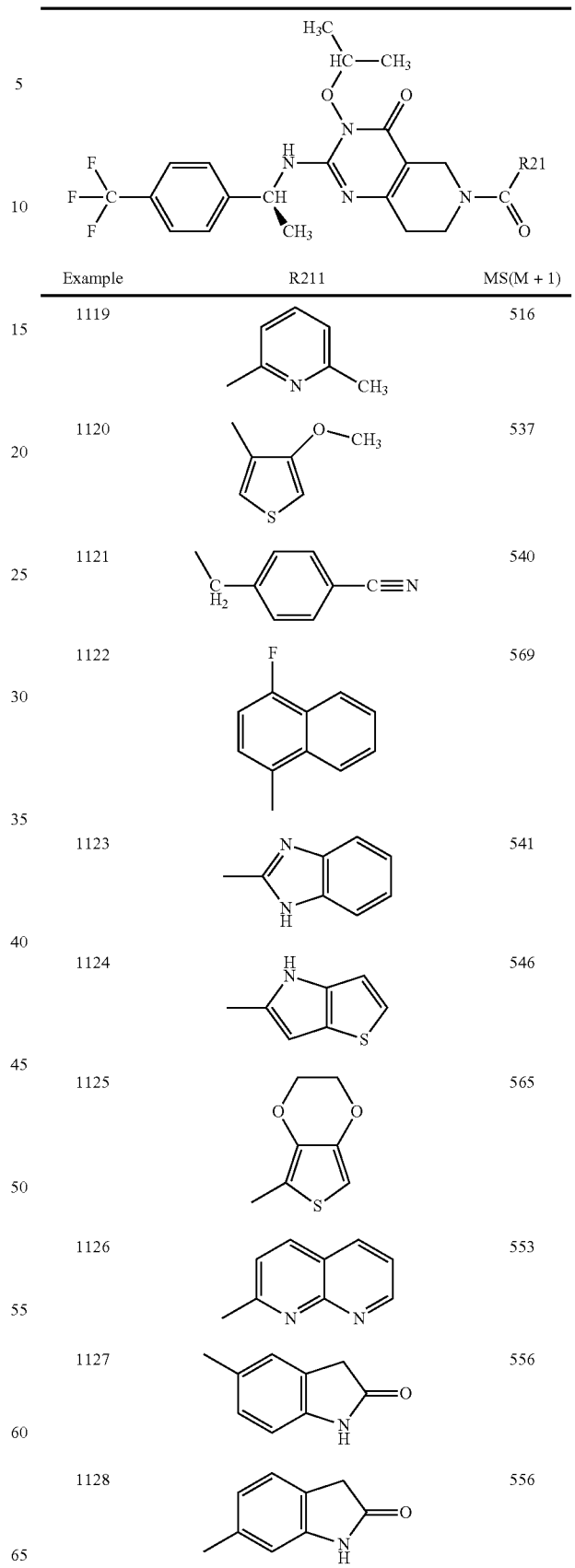

| Example | R211 | MS(M + 1) |
|---|---|---|
| 1119 | (2,6-dimethylpyridine) | 516 |
| 1120 | (3-methoxy-4-methylthiophene) | 537 |
| 1121 | (4-ethylbenzonitrile) | 540 |
| 1122 | (5-fluoro-8-methylnaphthalene) | 569 |
| 1123 | (2-methyl-1H-benzimidazole) | 541 |
| 1124 | (2-methyl-4H-thieno[3,2-b]pyrrole) | 546 |
| 1125 | (methyl-dioxinothiophene) | 565 |
| 1126 | (2-methyl-1,8-naphthyridine) | 553 |
| 1127 | (5-methylindolin-2-one) | 556 |
| 1128 | (6-methylindolin-2-one) | 556 |

TABLE 90-continued
| Example | R211 | MS(M + 1) |
|---|---|---|
| 1129 | 2-pyrimidinyl | 503 |
| 1130 | 6-methyl-4-methyl-2H-benzo[b][1,4]thiazin-3(4H)-one | 602 |
| 1131 | 7-methylquinolin-2-yl | 552 |
| 1132 | 2-methylbenzothiazol-6-yl | 558 |
| 1133 | 5-methylquinolin-2-yl | 552 |
| 1134 | 2-methylindolizinyl | 540 |
| 1135 | 5-methyl-1H-imidazol-2-yl | 491 |
| 1136 | 1-benzoyl-3-methylpyrrolidinyl | 598 |
| 1137 | 1,3-dimethyl-2-oxo-1,2-dihydropyridin-6-yl | 532 |
| 1138 | 1,5-dimethyl-2-oxo-1,2-dihydropyridin-6-yl | 532 |
TABLE 91
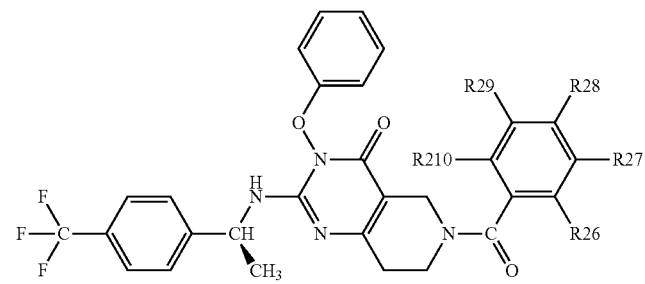
| Example | R26 | R27 | R28 | R29 | R210 | MS(M + 1) |
|---|---|---|---|---|---|---|
| 1139 | —H | —H | —CH₃ | —H | —H | 549 |
| 1140 | —H | —H | —Cl | —H | —H | 569 |
| 1141 | —H | —H | —CN | —H | —H | 560 |
| 1142 | —F | —H | —CN | —H | —H | 578 |

TABLE 91-continued
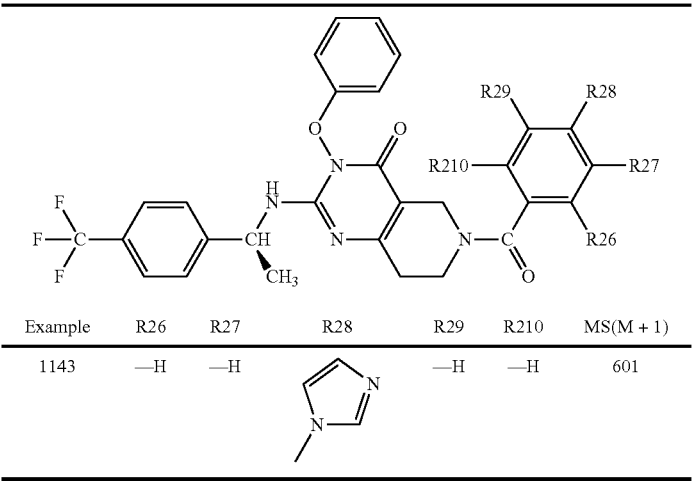
| Example | R26 | R27 | R28 | R29 | R210 | MS(M + 1) |
|---|---|---|---|---|---|---|
| 1143 | —H | —H | (1-methylimidazol-N-yl) | —H | —H | 601 |
TABLE 92
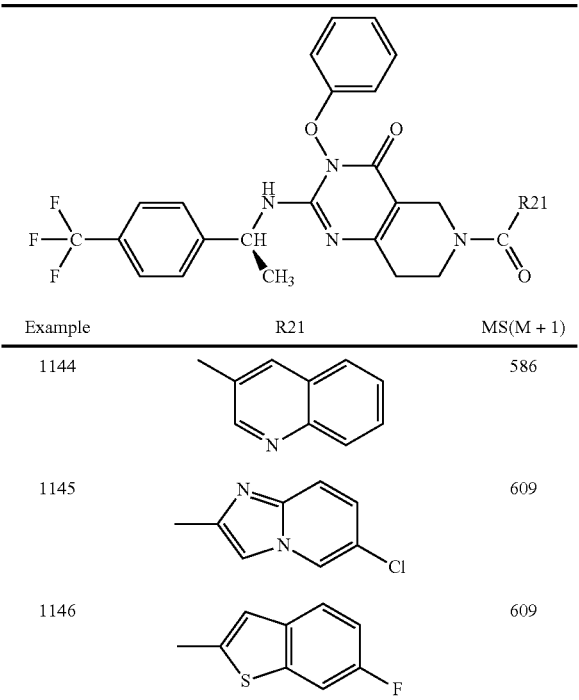
| Example | R21 | MS(M + 1) |
|---|---|---|
| 1144 | 3-methylquinolinyl | 586 |
| 1145 | 2-methyl-6-chloroimidazo[1,2-a]pyridinyl | 609 |
| 1146 | 2-methyl-6-fluorobenzothienyl | 609 |
TABLE 92-continued
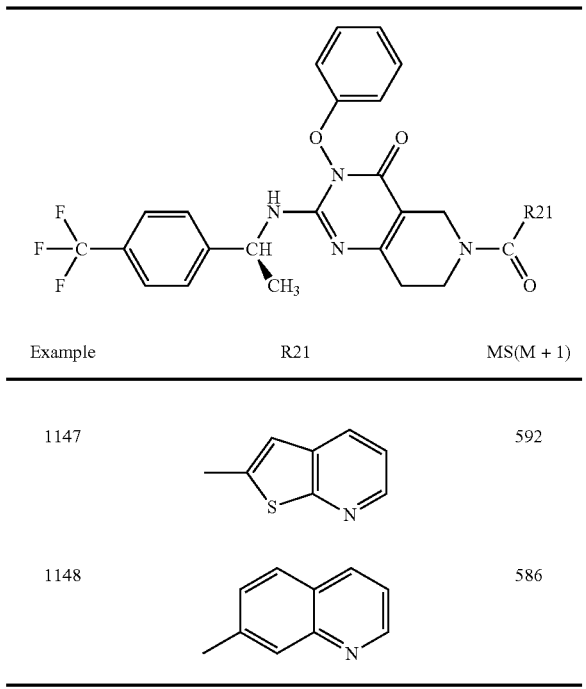
| Example | R21 | MS(M + 1) |
|---|---|---|
| 1147 | 2-methylthieno[2,3-b]pyridinyl | 592 |
| 1148 | 7-methylquinolinyl | 586 |
TABLE 93
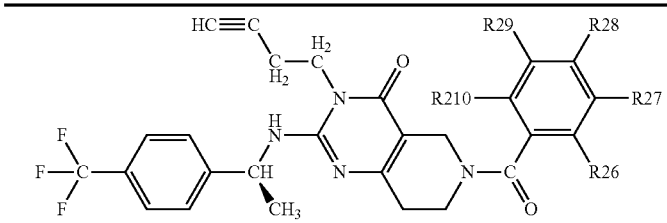
| Example | R26 | R27 | R28 | R29 | R210 | MS(M + 1) |
|---|---|---|---|---|---|---|
| 1149 | —H | —H | —H | —H | —H | 495 |
| 1150 | —H | —H | —CH₃ | —H | —H | 509 |
| 1151 | —H | —H | —Cl | —H | —H | 529 |
| 1152 | —H | —H | —F | —H | —H | 513 |

TABLE 93-continued
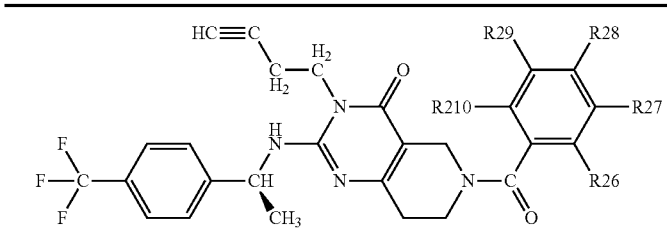
| Example | R26 | R27 | R28 | R29 | R210 | MS(M + 1) |
|---|---|---|---|---|---|---|
| 1153 | —H | —H | —OCH₃ | —H | —H | 525 |
| 1154 | —H | —H | —CF₃ | —H | —H | 563 |
| 1155 | —H | —Cl | —H | —H | —H | 529 |
| 1156 | —H | —CH₃ | —H | —H | —H | 509 |
| 1157 | —H | —H | —CN | —H | —H | 520 |
| 1158 | —H | —CH₃ | —CH₃ | —H | —H | 523 |
| 1159 | —H | —H | —OCF₃ | —H | —H | 579 |
| 1160 | —F | —H | —CN | —H | —H | 538 |
| 1161 | —H | —CH₃ | —Cl | —H | —H | 543 |
| 1162 | —H | —Cl | —CH₃ | —H | —H | 543 |
| 1163 | —H | —H | —OC₂H₅ | —H | —H | 539 |
| 1164 | —H | —H | —SCH₃ | —H | —H | 541 |
| 1165 | —H | —H | —OCH(CH₃)₂ | —H | —H | 553 |
| 1166 | —H | —H | 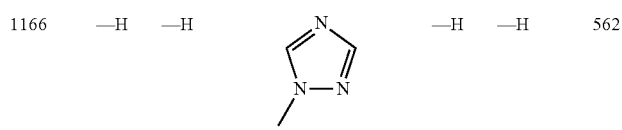 | —H | —H | 562 |
| 1167 | —H | —H | 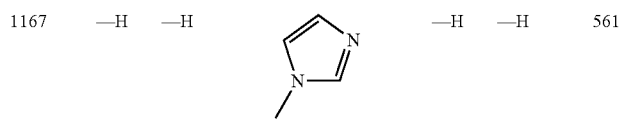 | —H | —H | 561 |
| 1168 | —H | —H | 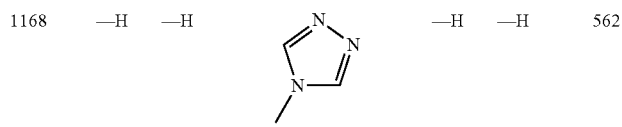 | —H | —H | 562 |
| 1169 | —H | —H | 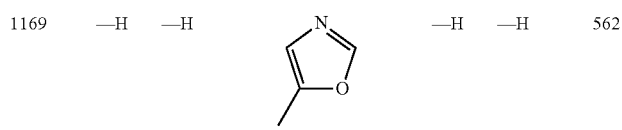 | —H | —H | 562 |
| 1170 | —H | —H | 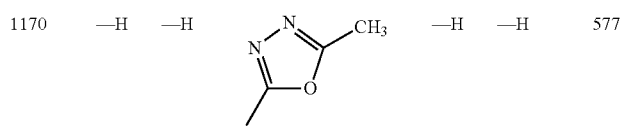 | —H | —H | 577 |

TABLE 94
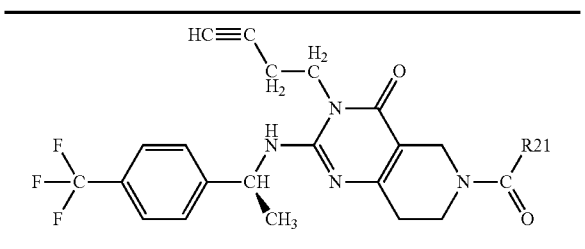
| Example | R211 | MS(M + 1) |
|---|---|---|
| 1171 | 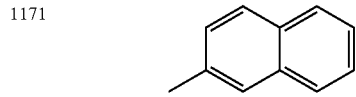 | 545 |
| 1172 | 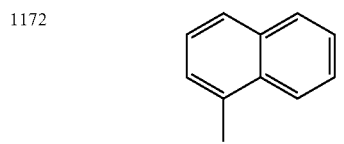 | 545 |
| 1173 | 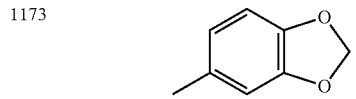 | 539 |
| 1174 | 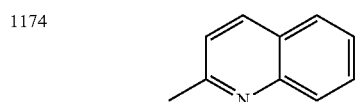 | 546 |
| 1175 | 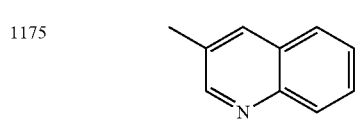 | 546 |
| 1176 | 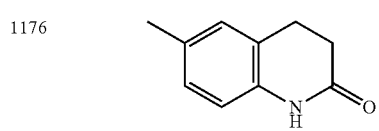 | 564 |
| 1177 | 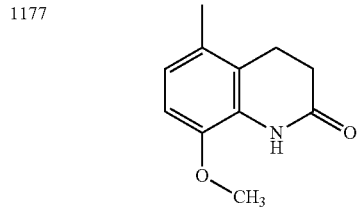 | 594 |
| 1178 | 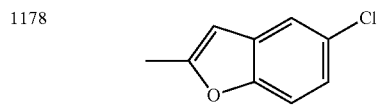 | 569 |
| 1179 | 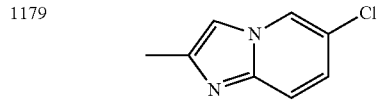 | 569 |
| 1180 | 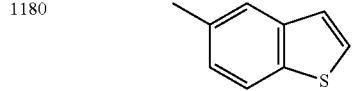 | 551 |
TABLE 94-continued
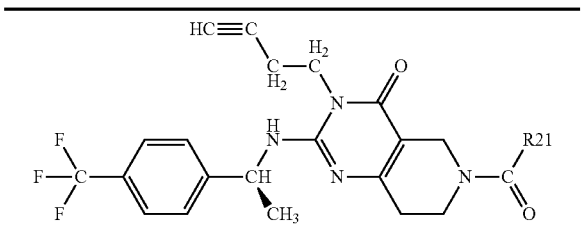
| Example | R211 | MS(M + 1) |
|---|---|---|
| 1181 | 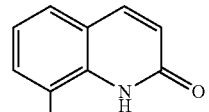 | 562 |
| 1182 | 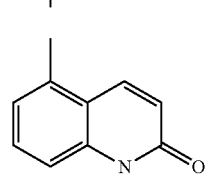 | 562 |
| 1183 | 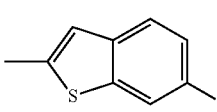 | 569 |
| 1184 | 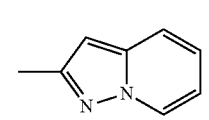 | 535 |
| 1185 | 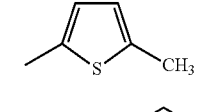 | 515 |
| 1186 | 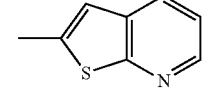 | 552 |
| 1187 | 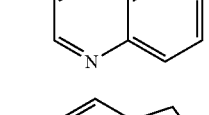 | 547 |
| 1188 | 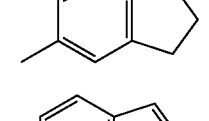 | 535 |
| 1189 | 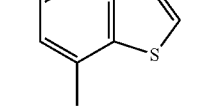 | 551 |
| 1190 | 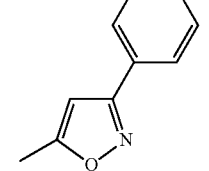 | 562 |

TABLE 94-continued

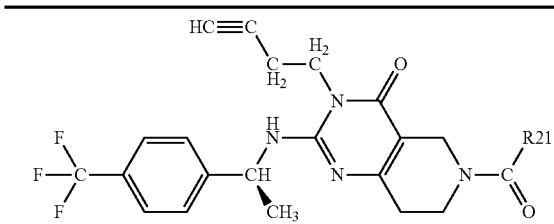

| Example | R211 | MS(M + 1) |
|---|---|---|
| 1191 | 3-methylpyridazinyl | 497 |
| 1192 | 4-methylisoquinolinyl | 546 |
| 1193 | 5-methyl-thiophen-2-yl-pyridin-3-yl | 578 |
| 1194 | 7-methyl-4H-benzo[d][1,4]oxazin-3(2H)-one | 580 |
| 1195 | 7-methylindolin-2-one | 550 |
| 1196 | 1,5-dimethylindolin-2-one | 564 |
| 1197 | 4-methylpyridazinyl | 497 |
| 1198 | 1,3-dimethylindolyl | 548 |
| 1199 | 2,5-dimethylpyridinyl | 510 |
| 1200 | 2,6-dimethylpyridinyl | 510 |

TABLE 94-continued

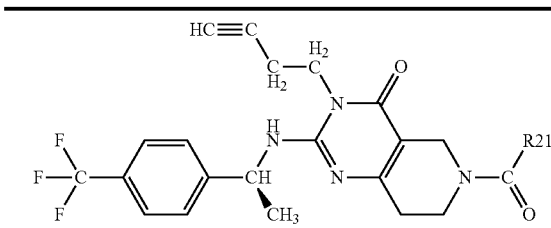

| Example | R211 | MS(M + 1) |
|---|---|---|
| 1201 | 4-methyl-3-methoxythiophenyl | 531 |
| 1202 | 4-cyanobenzyl | 534 |
| 1203 | 5-fluoro-8-methylnaphthyl | 563 |
| 1204 | 2-methylbenzimidazolyl | 535 |
| 1205 | 5-methylthieno[3,2-b]pyrrolyl | 540 |
| 1206 | methyl-ethylenedioxythiophenyl | 559 |
| 1207 | 2-methylpyrido[2,3-d]pyrimidinyl | 547 |
| 1208 | 5-methylindolin-2-one | 550 |
| 1209 | 6-methylindolin-2-one | 550 |
| 1210 | 2-methylpyrimidinyl | 497 |

TABLE 94-continued

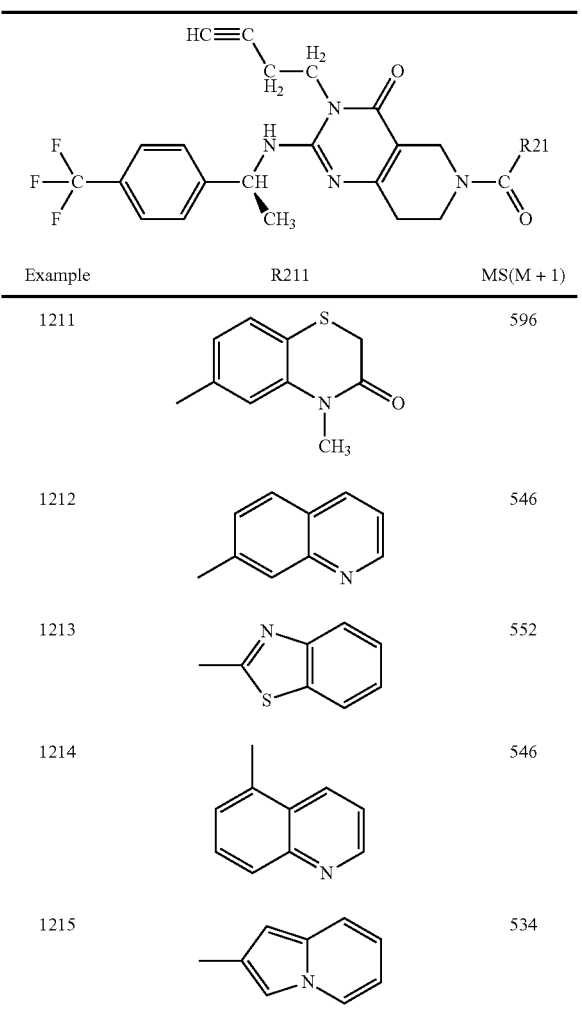

| Example | R211 | MS(M + 1) |
|---|---|---|
| 1211 | 6-methyl-4-methyl-2H-benzo[b][1,4]thiazin-3(4H)-one | 596 |
| 1212 | 7-methylquinoline | 546 |
| 1213 | 2-methylbenzothiazole | 552 |
| 1214 | 8-methylquinoline | 546 |
| 1215 | 2-methylindolizine | 534 |

TABLE 94-continued

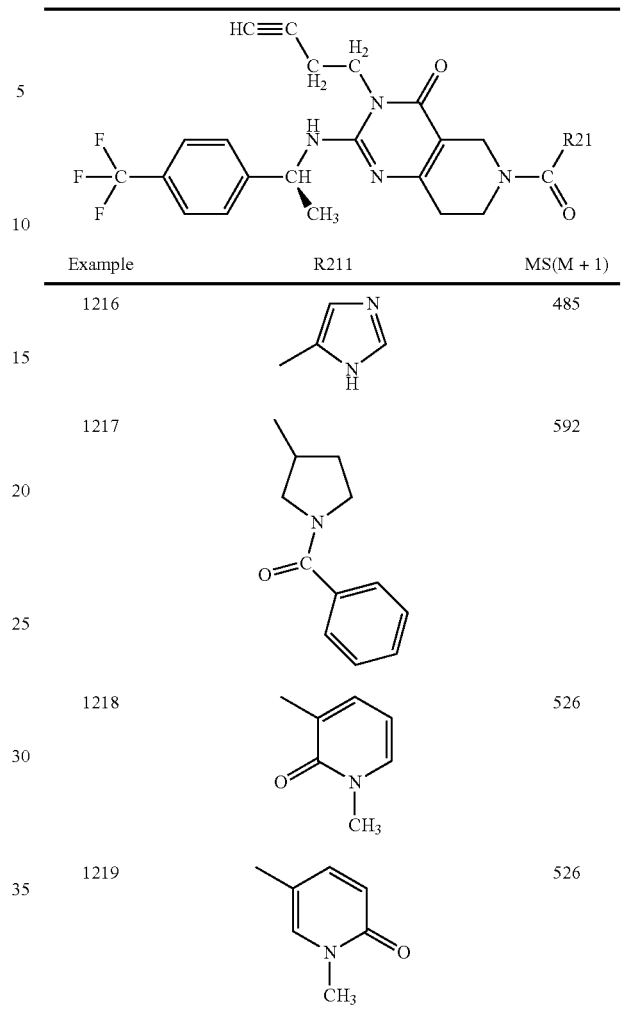

| Example | R211 | MS(M + 1) |
|---|---|---|
| 1216 | 5-methyl-1H-imidazole | 485 |
| 1217 | (3-methylpyrrolidin-1-yl)(phenyl)methanone | 592 |
| 1218 | 1,3-dimethylpyridin-2(1H)-one | 526 |
| 1219 | 1,5-dimethylpyridin-2(1H)-one | 526 |

TABLE 95

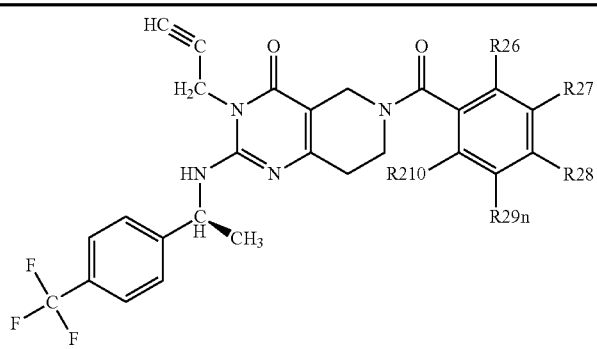

| Example | R26 | R27 | R28 | R29 | R210 | MS (M + 1) |
|---|---|---|---|---|---|---|
| 1220 | —H | —H | —H | —H | —H | 481 |
| 1221 | —H | —H | —CH₃ | —H | —H | 495 |
| 1222 | —H | —H | —OCH₃ | —H | —H | 511 |
| 1223 | —H | —Cl | —Cl | —H | —H | 549 |
| 1224 | —F | —H | —CF₃ | —H | —H | 567 |
| 1225 | —H | —CN | —H | —H | —H | 506 |
| 1226 | —H | —N(CH₃)₂ | —H | —H | —H | 524 |
| 1227 | —H | —CH₃ | —CH₃ | —H | —H | 509 |

TABLE 95-continued
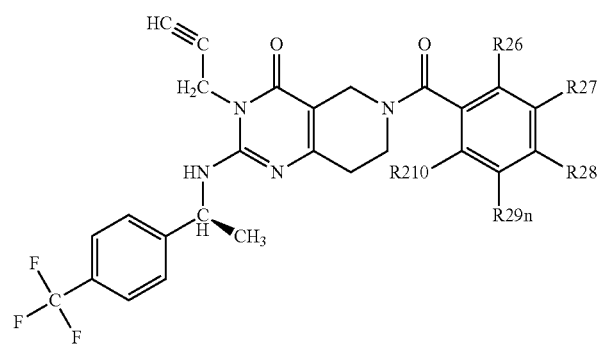
| Example | R26 | R27 | R28 | R29 | R210 | MS (M + 1) |
|---|---|---|---|---|---|---|
| 1228 | —F | —H | —F | —H | —F | 535 |
| 1229 | —F | —H | —H | —H | —F | 517 |
| 1230 | —OCH$_3$ | —H | —Cl | —H | —H | 545 |
| 1231 | —H | —H | —N(C$_2$H$_5$)$_2$ | —H | —H | 552 |
| 1232 | —F | —H | —OCH$_3$ | —H | —H | 529 |
| 1233 | —H | —F | —CH$_3$ | —H | —H | 513 |
| 1234 | —H | —CH$_3$ | —Cl | —H | —H | 529 |
| 1235 | —H | —Cl | —CH$_3$ | —H | —H | 529 |
| 1236 | —H | —H | —OC$_2$H$_5$ | —H | —H | 525 |
| 1237 | —H | —H | —SCH$_3$ | —H | —H | 527 |
| 1238 | —H | —H | N-methylimidazolyl | —H | —H | 547 |
| 1239 | —H | —H | 4-methyl-1,2,4-triazolyl | —H | —H | 548 |
| 1240 | —H | —H | N-methylthiomorpholinyl | —H | —H | 473 |
| 1241 | —H | —H | methylpyridyl | —H | —H | 558 |
| 1242 | —H | methylpyridyl | —H | —H | —H | 558 |
| 1243 | —H | —H | methyloxazolyl | —H | —H | 548 |

TABLE 96

[Structure: core scaffold with HC≡C-CH2-N, H2N, carbonyl, tetrahydropyrimidine-fused piperidine with N-C(=O)-CH2-O-phenyl(R26,R27,R28,R29,R210), and NH-CH(CH3)-C6H4-CF3 substituent]

| Example | R26 | R27 | R28 | R29 | R210 | MS (M + 1) |
|---|---|---|---|---|---|---|
| 1244 | —H | —H | —CH3 | —H | —H | 525 |
| 1245 | —H | —H | —Cl | —H | —H | 545 |
| 1246 | —H | —H | —F | —H | —H | 529 |
| 1247 | —H | —H | —CN | —H | —H | 536 |

TABLE 97

[Structure: core scaffold with HC≡C-CH2-N, carbonyl, tetrahydropyrimidine-fused piperidine with N-C(=O)-R21, and NH-CH(CH3)-C6H4-CF3 substituent]

| Example | R21 | MS (M + 1) |
|---|---|---|
| 1248 | 2-methylchroman | 537 |
| 1249 | (E)-2-(4-chlorophenyl)vinyl | 541 |
| 1250 | 5,6-dichloro-3-methylpyridin-? | 550 |
| 1251 | 2-methyl-1H-indol-? | 520 |
| 1252 | 2-methylquinolin-? | 532 |
| 1253 | 3-methylquinolin-? | 532 |

TABLE 97-continued

| Example | R21 | MS (M + 1) |
|---|---|---|
| 1254 | 3-methylisoquinolin-? | 532 |
| 1255 | 2-methylbenzofuran-? | 521 |
| 1256 | 5-fluoro-2-methyl-1H-indol-? | 538 |
| 1257 | 2-methylbenzothiophen-? | 537 |
| 1258 | 6-methyl-3,4-dihydroquinolin-2(1H)-one | 550 |
| 1259 | 1-ethyl-3-methylquinolin-2(1H)-one | 576 |
| 1260 | 1,6-dimethyl-3,4-dihydroquinolin-2(1H)-one | 564 |
| 1261 | 1-ethyl-6-methyl-3,4-dihydroquinolin-2(1H)-one | 578 |

TABLE 97-continued

| Example | R21 | MS (M + 1) |
|---|---|---|
| 1262 | 4-methoxy-1,2-dimethylindol-1-yl | 550 |
| 1263 | 6-methoxy-1,2-dimethylindol-1-yl | 550 |
| 1264 | 2,3-dimethylbenzofuran-yl | 535 |
| 1265 | 5-methoxy-2-methylbenzofuran-yl | 551 |
| 1266 | 5-chloro-2-methylbenzofuran-yl | 555 |
| 1267 | 6-methylbenzothiazol-yl | 538 |
| 1268 | 5-methyl-2,3-dihydrobenzofuran-yl | 523 |
| 1269 | 6-methylquinoxalin-yl | 533 |
| 1270 | 6-methyl-2,3-dihydrobenzo[1,4]dioxin-yl | 539 |

| Example | R21 | MS (M + 1) |
|---|---|---|
| 1271 | 6-methyl-3-oxo-3,4-dihydro-2H-benzo[1,4]oxazin-yl | 552 |
| 1272 | 6-methyl-3-oxo-3,4-dihydro-2H-benzo[1,4]thiazin-yl | 568 |
| 1273 | 6-methoxy-2-methylnaphthalen-yl | 561 |
| 1274 | 1,6-dimethyl-2-oxo-1,2,3,4-tetrahydroquinolin-yl | 564 |
| 1275 | 4,5-dimethyl-furo[3,2-b]pyrrol-yl | 524 |
| 1276 | 2-methylthieno[2,3-b]pyrazin-yl | 539 |
| 1277 | 6-chloro-2-methylimidazo[1,2-a]pyridin-yl | 555 |
| 1278 | N,N,3-trimethyl-isoxazol-5-amine | 514 |

TABLE 97-continued

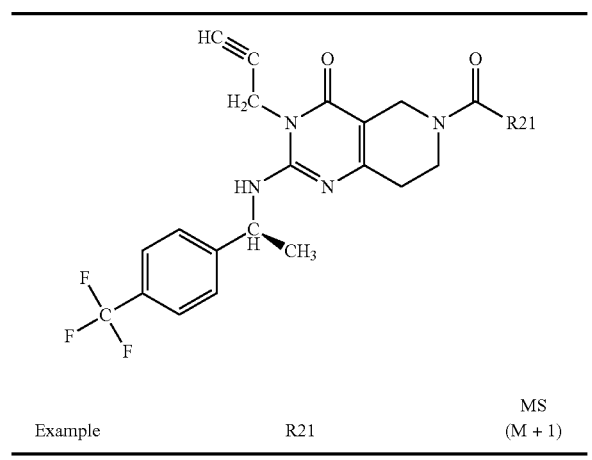

| Example | R21 | MS (M + 1) |
|---|---|---|
| 1279 | (3-methyl-1-methyl-5-(furan-2-yl)-1H-pyrazol-4-yl) | 551 |
| 1280 | (3-methyl-1-methyl-5-(thiophen-2-yl)-1H-pyrazol-4-yl) | 567 |
| 1281 | (5-methylbenzo[b]thiophen-2-yl) | 537 |
| 1282 | (8-methyl-2-oxo-1,2-dihydroquinolin-3-yl) | 548 |
| 1283 | (1,5-dimethyl-2-oxo-1,2,3,4-tetrahydroquinolin-6-yl) | 564 |
| 1284 | (1,5-dimethyl-1H-indol-2-yl) | 534 |
| 1285 | (5-methyl-2-oxo-1,2-dihydroquinolin-3-yl) | 548 |

TABLE 97-continued

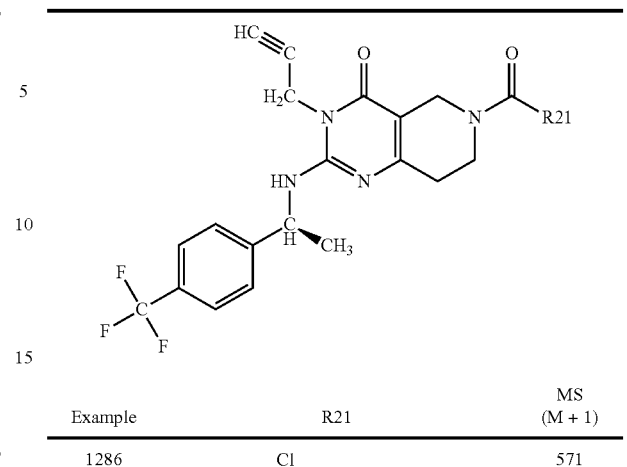

| Example | R21 | MS (M + 1) |
|---|---|---|
| 1286 | (3-chloro-2-methylbenzo[b]thiophen-6-yl) | 571 |
| 1287 | (2,3-dimethylbenzo[b]thiophen-5-yl) | 551 |
| 1288 | (6-fluoro-2-methylbenzo[b]thiophen-3-yl) | 555 |
| 1289 | ((4-chlorophenylthio)methyl) | 561 |
| 1290 | (5-chloro-3-methylbenzo[b]thiophen-2-yl) | 571 |
| 1291 | (1,3-dimethyl-1H-indazol-5-yl) | 535 |
| 1292 | (2-methylpyrazolo[1,5-a]pyridin-3-yl) | 521 |
| 1293 | (2-methylthieno[2,3-b]pyridin-3-yl) | 538 |
| 1294 | (3-methylquinoxalin-2-yl) | 533 |

TABLE 97-continued
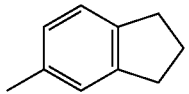
| Example | R21 | MS (M + 1) |
|---|---|---|
| 1295 | 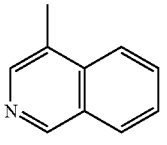 | 521 |
| 1296 | 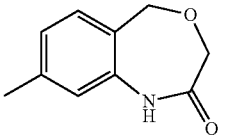 | 532 |
| 1297 | 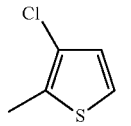 | 566 |
| 1298 | 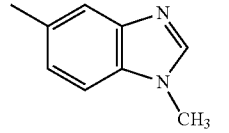 | 521 |
| 1299 | 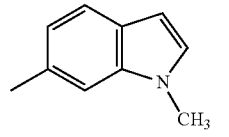 | 535 |
| 1300 | 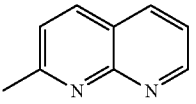 | 534 |
| 1301 | 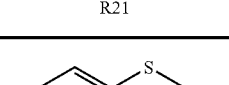 | 533 |
TABLE 97-continued
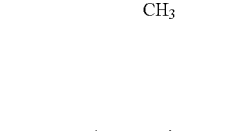
| Example | R21 | MS (M + 1) |
|---|---|---|
| 1302 | 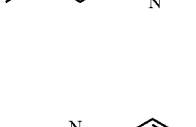 | 582 |
| 1303 | 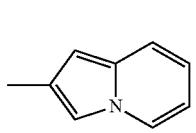 | 532 |
| 1304 | 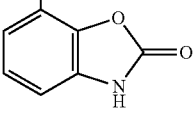 | 538 |
| 1305 | 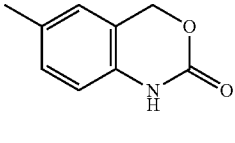 | 520 |
| 1306 | 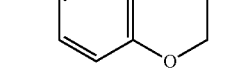 | 538 |
| 1307 | 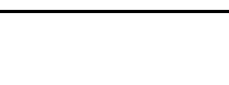 | 552 |
| 1308 |  | 538 |

TABLE 98

| Example | R26 | R27 | R28 | R29 | R210 | MS (M + 1) |
|---|---|---|---|---|---|---|
| 1309 | —H | —H | —H | —H | —H | 486 |
| 1310 | —H | —H | —CH₃ | —H | —H | 500 |
| 1311 | —H | —H | —OCH₃ | —H | —H | 516 |
| 1312 | —H | —Cl | —Cl | —H | —H | 554 |
| 1313 | —F | —H | —CF₃ | —H | —H | 572 |
| 1314 | —H | —CN | —H | —H | —H | 511 |
| 1315 | —H | —CH₃ | —CH₃ | —H | —H | 514 |
| 1316 | —F | —H | —F | —H | —F | 540 |
| 1317 | —OCH₃ | —H | —Cl | —H | —H | 550 |
| 1318 | —H | —H | —CH=CH₂ | —H | —H | 512 |
| 1319 | —F | —H | —OCH₃ | —H | —H | 534 |
| 1320 | —H | —F | —CH₃ | —H | —H | 518 |
| 1321 | —H | —CH₃ | —Cl | —H | —H | 534 |
| 1322 | —H | —Cl | —CH₃ | —H | —H | 534 |
| 1323 | —H | —H | —OC₂H₅ | —H | —H | 530 |
| 1324 | —H | —H | —SCH₃ | —H | —H | 532 |
| 1325 | —H | —H | 4-methyl-1,2,4-triazol-4-yl | —H | —H | 553 |
| 1326 | —H | —H | 1-methyl-tetrazol-1-yl | —H | —H | 554 |
| 1327 | —H | —H | pyridin-3-yl | —H | —H | 563 |
| 1328 | —H | pyridin-4-yl | —H | —H | —H | 563 |

TABLE 99

| Example | R21 | MS (M + 1) |
|---|---|---|
| 1329 | (E)-4-chlorostyryl | 546 |
| 1330 | 2,3-dichloro-5-methylpyridinyl | 555 |

TABLE 99-continued

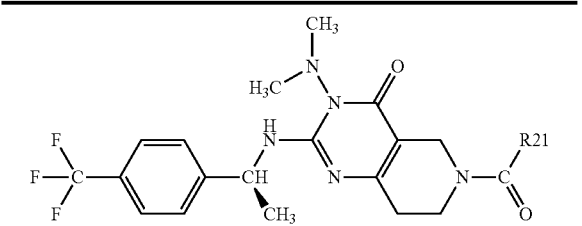

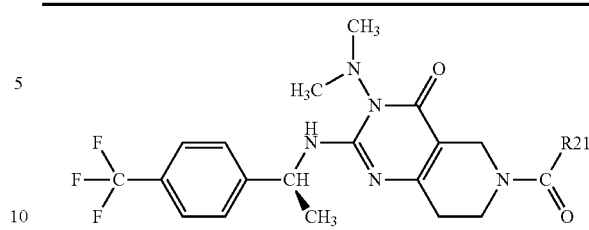

| Example | R21 | MS (M + 1) |
|---|---|---|
| 1331 | 2-methylindole | 525 |
| 1332 | 2-methylquinoline | 537 |
| 1333 | 3-methylquinoline | 537 |
| 1334 | 3-methylisoquinoline | 537 |
| 1335 | 2-methylbenzofuran | 526 |
| 1336 | 5-fluoro-2-methylindole | 543 |
| 1337 | 2-methylbenzothiophene | 542 |
| 1338 | 6-methyl-3,4-dihydroquinolin-2(1H)-one | 555 |
| 1339 | 1-ethyl-3-methylquinolin-2(1H)-one | 581 |
| 1340 | 1-methyl-6-methyl-3,4-dihydroquinolin-2(1H)-one | 569 |
| 1341 | 1-ethyl-6-methyl-3,4-dihydroquinolin-2(1H)-one | 583 |
| 1342 | 4-methoxy-1,2-dimethylindole | 555 |
| 1343 | 6-methoxy-1,2-dimethylindole | 555 |
| 1344 | 5-chloro-2-methylbenzofuran | 560 |
| 1345 | 5-methyl-2,3-dihydrobenzofuran | 528 |
| 1346 | 5-methylbenzofuran | 526 |
| 1347 | 6-methylquinoxaline | 538 |
| 1348 | 6-methyl-2,3-dihydrobenzo[1,4]dioxine | 544 |
| 1349 | 7-methyl-4H-benzo[1,4]oxazin-3-one | 557 |

TABLE 99-continued
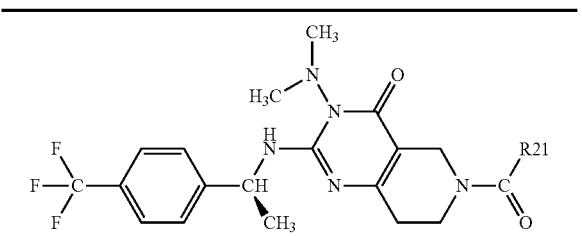
| Example | R21 | MS (M + 1) |
|---|---|---|
| 1350 | 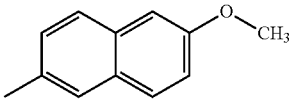 | 573 |
| 1351 | 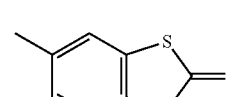 | 566 |
| 1352 | 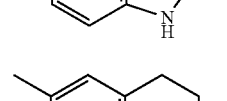 | 559 |
| 1353 | 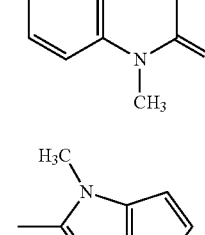 | 569 |
| 1354 | 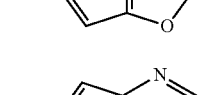 | 529 |
| 1355 | 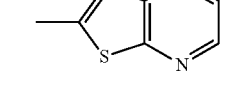 | 544 |
| 1356 | 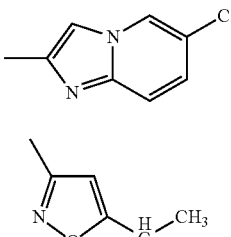 | 560 |
| 1357 | 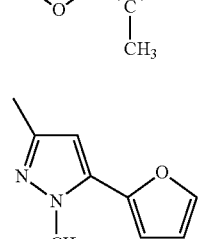 | 519 |
| 1358 | 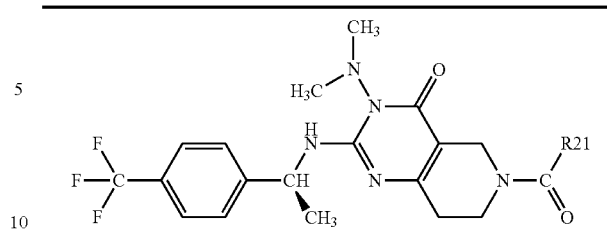 | 556 |
TABLE 99-continued
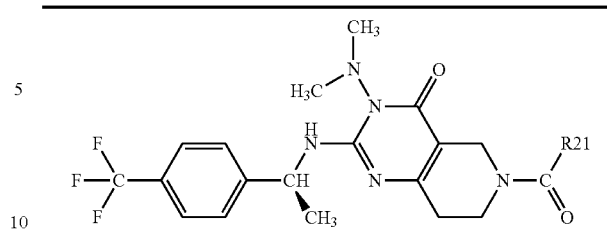
| Example | R21 | MS (M + 1) |
|---|---|---|
| 1359 |  | 572 |
| 1360 | 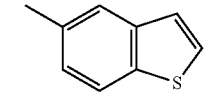 | 542 |
| 1361 | 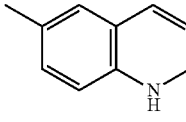 | 553 |
| 1362 | 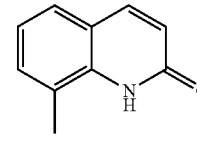 | 553 |
| 1363 | 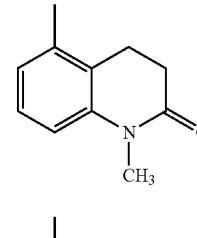 | 569 |
| 1364 | 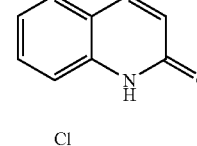 | 553 |
| 1365 | 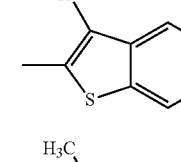 | 576 |
| 1366 | 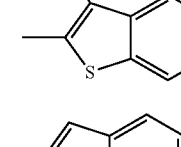 | 556 |
| 1367 |  | 560 |

TABLE 99-continued
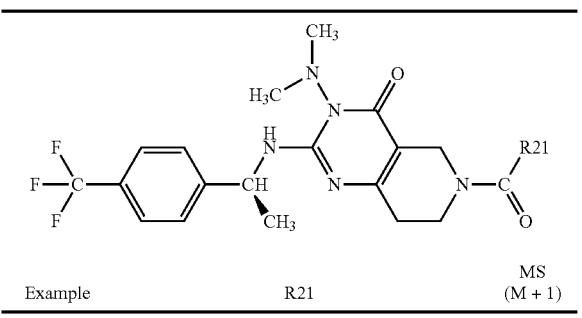
| Example | R21 | MS (M + 1) |
|---|---|---|
| 1368 | 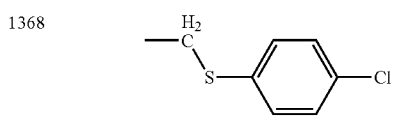 | 566 |
| 1369 | 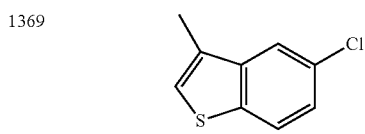 | 576 |
| 1370 | 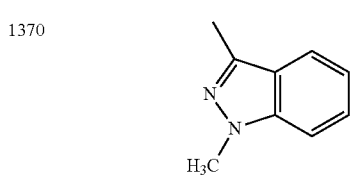 | 540 |
| 1371 | 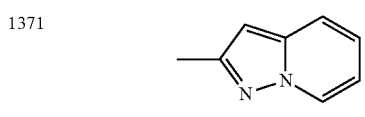 | 526 |
| 1372 | 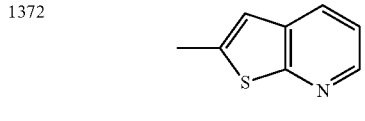 | 543 |
| 1373 | 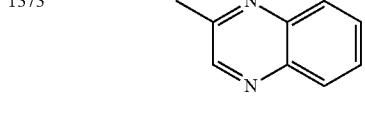 | 538 |
| 1374 | 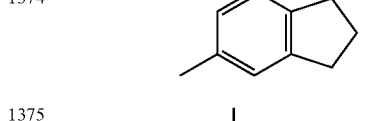 | 527 |
| 1375 | 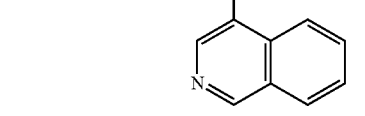 | 537 |
| 1376 | 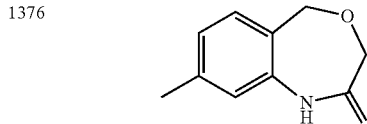 | 571 |
| 1377 | 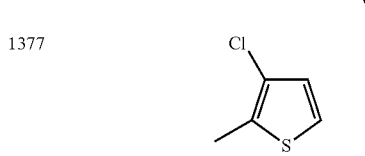 | 526 |
TABLE 99-continued
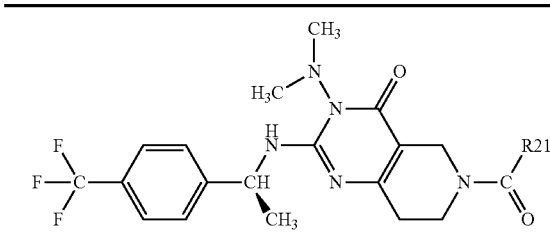
| Example | R21 | MS (M + 1) |
|---|---|---|
| 1378 | 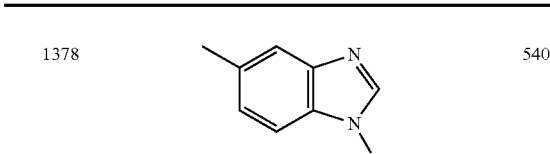 | 540 |
| 1379 | 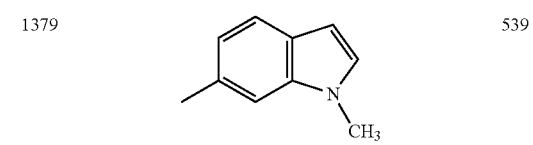 | 539 |
| 1380 | 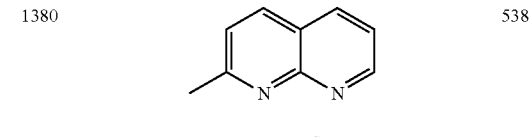 | 538 |
| 1381 | 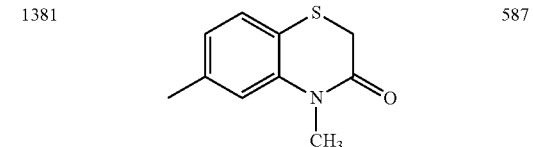 | 587 |
| 1382 | 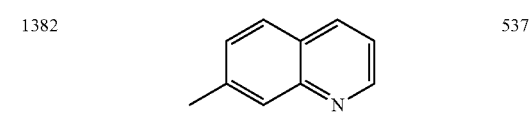 | 537 |
| 1383 | 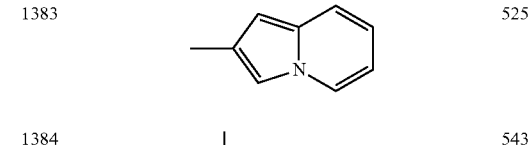 | 525 |
| 1384 | 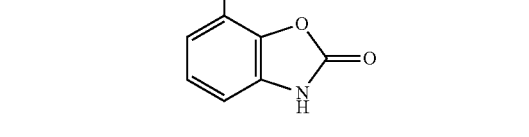 | 543 |
| 1385 | 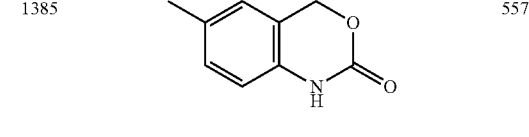 | 557 |
| 1386 | 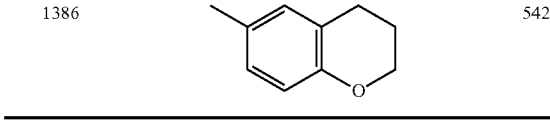 | 542 |

TABLE 100

| Example | R26 | R27 | R28 | R29 | R210 | MS (M + 1) |
|---|---|---|---|---|---|---|
| 1387 | —H | —H | —H | —H | —H | 541 |
| 1388 | —H | —H | —CH₃ | —H | —H | 555 |
| 1389 | —H | —H | —OCH₃ | —H | —H | 571 |
| 1390 | —H | —Cl | —Cl | —H | —H | 609 |
| 1391 | —F | —H | —CF₃ | —H | —H | 627 |
| 1392 | —H | —CN | —H | —H | —H | 566 |
| 1393 | —H | —N(CH₃)₂ | —H | —H | —H | 584 |
| 1394 | —H | —CH₃ | —CH₃ | —H | —H | 569 |
| 1395 | —F | —H | —F | —H | —H | 595 |
| 1396 | —F | —H | —H | —H | —F | 577 |
| 1397 | —OCH₃ | —H | —Cl | —H | —H | 605 |
| 1398 | —H | —H | —N(C₂H₅)₂ | —H | —H | 612 |
| 1399 | —H | —H | —CH=CH₂ | —H | —H | 567 |
| 1400 | —F | —H | —OCH₃ | —H | —H | 589 |
| 1401 | —H | —F | —CH₃ | —H | —H | 573 |
| 1402 | —H | —CH₃ | —Cl | —H | —H | 589 |
| 1403 | —H | —Cl | —CH₃ | —H | —H | 589 |
| 1404 | —H | —H | —OC₂H₅ | —H | —H | 585 |
| 1405 | —H | —H | —SCH₃ | —H | —H | 587 |
| 1406 | —H | —H | N-methylimidazolyl | —H | —H | 607 |
| 1407 | —H | —H | N-methyl-1,2,4-triazolyl | —H | —H | 608 |
| 1408 | —H | —H | N-thiomorpholinyl | —H | —H | 642 |
| 1409 | —H | —H | N-methyltetrazolyl | —H | —H | 609 |
| 1410 | —H | —H | 3-pyridyl | —H | —H | 618 |
| 1411 | —H | —H | 4-pyridyl | —H | —H | 618 |
| 1412 | —H | 4-pyridyl | —H | —H | —H | 618 |

TABLE 100-continued

| Example | R26 | R27 | R28 | R29 | R210 | MS (M + 1) |
|---|---|---|---|---|---|---|
| 1413 | —H | —H | (5-methyl-oxazol-2-yl) | —H | —H | 608 |

TABLE 101

| Example | R26 | R27 | R28 | R29 | R210 | MS (M + 1) |
|---|---|---|---|---|---|---|
| 1414 | —H | —H | —CH₃ | —H | —H | 585 |
| 1415 | —H | —H | —Cl | —H | —H | 605 |
| 1416 | —H | —H | —F | —H | —H | 589 |
| 1417 | —H | —H | —CN | —H | —H | 596 |

TABLE 102

| Example | R21 | MS (M + 1) |
|---|---|---|
| 1418 | 2-methylchroman-2-yl | 597 |

TABLE 102-continued

| Example | R21 | MS (M + 1) |
|---|---|---|
| 1419 | (E)-2-(4-chlorophenyl)vinyl | 601 |

TABLE 102-continued

| Example | R21 | MS (M + 1) |
|---|---|---|
| 1420 | 5-methyl-2,3-dichloropyridin-yl | 610 |
| 1421 | 2-methyl-1H-indol-yl | 580 |
| 1422 | 2-methylquinolin-yl | 592 |
| 1423 | 3-methylquinolin-yl | 592 |
| 1424 | 3-methylisoquinolin-yl | 592 |
| 1425 | 2-methylbenzofuran-yl | 581 |
| 1426 | 5-fluoro-2-methyl-1H-indol-yl | 598 |
| 1427 | 2-methylbenzothiophen-yl | 597 |
| 1428 | 6-methyl-3,4-dihydroquinolin-2(1H)-one-yl | 610 |
| 1429 | 1-ethyl-6-methyl-3,4-dihydroquinolin-2(1H)-one-yl | 638 |
| 1430 | 5-methyl-8-methoxy-3,4-dihydroquinolin-2(1H)-one-yl | 640 |
| 1431 | 4-methoxy-1,2-dimethyl-1H-indol-yl | 610 |
| 1432 | 6-methoxy-1,2-dimethyl-1H-indol-yl | 610 |
| 1433 | 2,3-dimethylbenzofuran-yl | 595 |
| 1434 | 5-methoxy-2-methylbenzofuran-yl | 611 |
| 1435 | 5-chloro-2-methylbenzofuran-yl | 615 |
| 1436 | 6-methylbenzothiazol-yl | 598 |
| 1437 | 5-methyl-2,3-dihydrobenzofuran-yl | 583 |

TABLE 102-continued

Core structure: 3-(4-methylpiperazin-1-yl)-2-{[(1S)-1-(4-(trifluoromethyl)phenyl)ethyl]amino}-6-(R21-carbonyl)-5,6,7,8-tetrahydropyrido[4,3-d]pyrimidin-4(3H)-one

| Example | R21 | MS (M + 1) |
|---|---|---|
| 1438 | 5-methylbenzofuran-2-yl | 581 |
| 1439 | 6-methylquinoxalin-2-yl | 593 |
| 1440 | 6-methyl-2,3-dihydrobenzo[b][1,4]dioxin-2-yl | 599 |
| 1441 | 6-methyl-3-oxo-3,4-dihydro-2H-benzo[b][1,4]oxazin-2-yl | 612 |
| 1442 | 4,5-dimethyl-4H-furo[3,2-b]pyrrol-2-yl | 584 |
| 1443 | 6-methylthieno[3,2-b]pyrazin-2-yl | 599 |
| 1444 | 6-chloro-2-methylimidazo[1,2-a]pyridin-3-yl | 615 |
| 1445 | 5-isopropyl-3-methylisoxazol-4-yl | 574 |
| 1446 | 5-(furan-2-yl)-1,3-dimethyl-1H-pyrazol-4-yl | 611 |
| 1447 | 1,3-dimethyl-5-(thiophen-2-yl)-1H-pyrazol-4-yl | 627 |
| 1448 | 5-methylbenzo[b]thiophen-2-yl | 597 |
| 1449 | 6-methyl-2-oxo-1,2-dihydroquinolin-3-yl | 608 |
| 1450 | 8-methyl-2-oxo-1,2-dihydroquinolin-3-yl | 608 |
| 1451 | 1,5-dimethyl-1H-indol-2-yl | 594 |
| 1452 | 5-methyl-2-oxo-1,2-dihydroquinolin-3-yl | 608 |
| 1453 | 3-chloro-2-methylbenzo[b]thiophen-5-yl | 631 |
| 1454 | 2,3-dimethylbenzo[b]thiophen-5-yl | 611 |

TABLE 102-continued
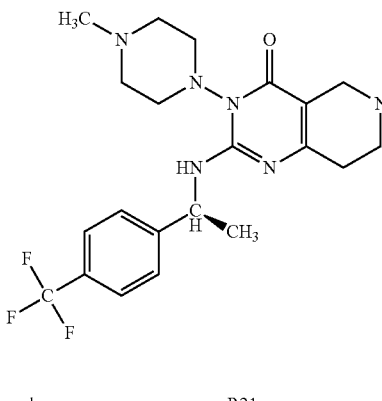
| Example | R21 | MS (M + 1) |
|---|---|---|
| 1455 | 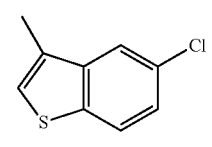 | 615 |
| 1456 | 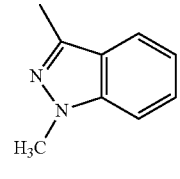 | 631 |
| 1457 | 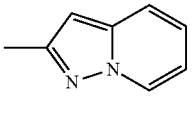 | 595 |
| 1458 | 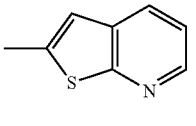 | 581 |
| 1459 | 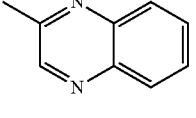 | 598 |
| 1460 | 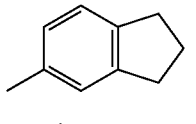 | 593 |
| 1461 | 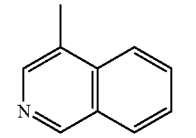 | 581 |
| 1462 | 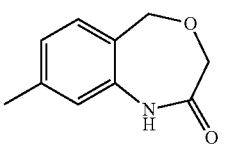 | 592 |
| 1463 | 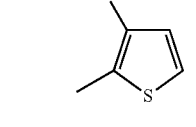 | 626 |
TABLE 102-continued
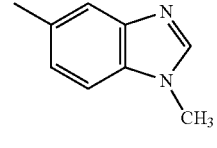
| Example | R21 | MS (M + 1) |
|---|---|---|
| 1464 | 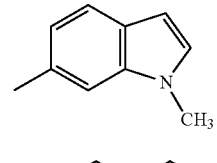 | 581 |
| 1465 | 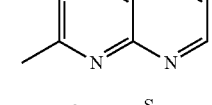 | 595 |
| 1466 | 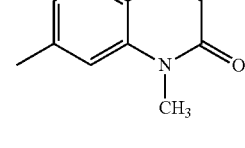 | 594 |
| 1467 | 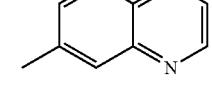 | 593 |
| 1468 | 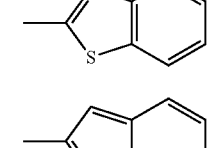 | 642 |
| 1469 | 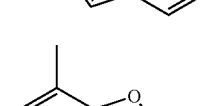 | 592 |
| 1470 | 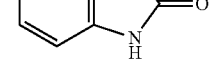 | 598 |
| 1471 | | 580 |
| 1472 | | 598 |

TABLE 102-continued
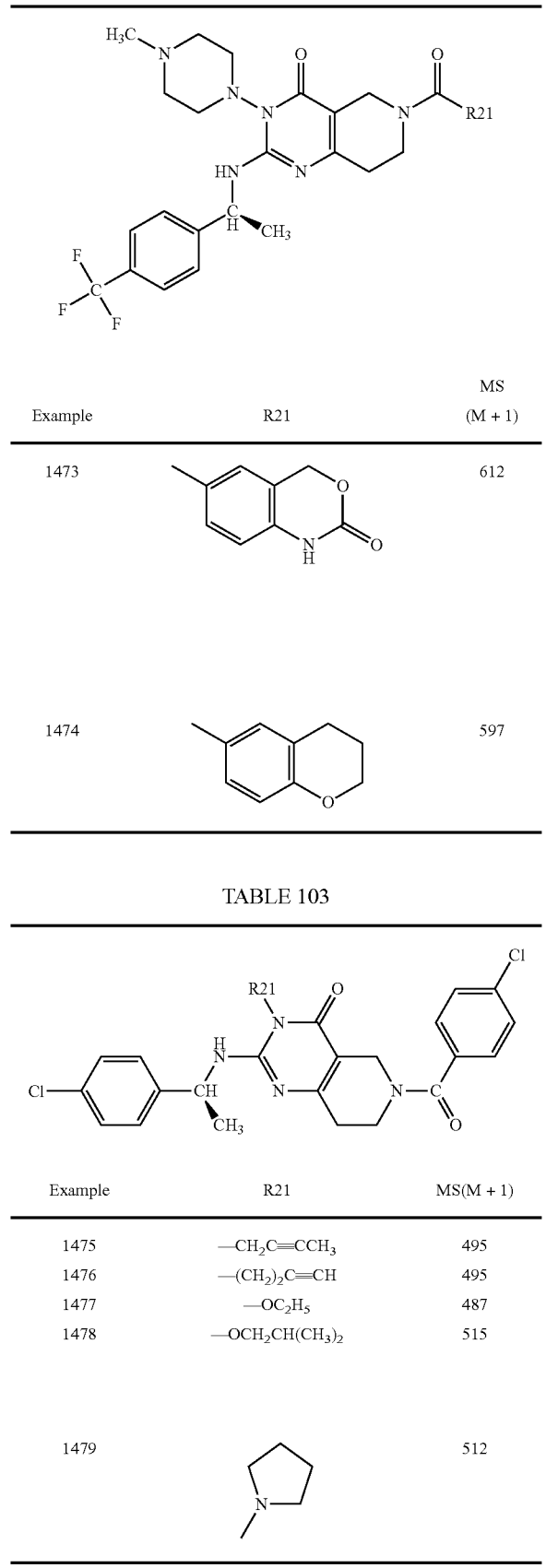
| Example | R21 | MS (M + 1) |
|---|---|---|
| 1473 | (6-methyl-benzoxazin-2-one) | 612 |
| 1474 | (6-methyl-chroman) | 597 |
TABLE 103
| Example | R21 | MS(M + 1) |
|---|---|---|
| 1475 | —CH₂C≡CCH₃ | 495 |
| 1476 | —(CH₂)₂C≡CH | 495 |
| 1477 | —OC₂H₅ | 487 |
| 1478 | —OCH₂CH(CH₃)₂ | 515 |
| 1479 | (1-methylpyrrolidine) | 512 |
TABLE 104
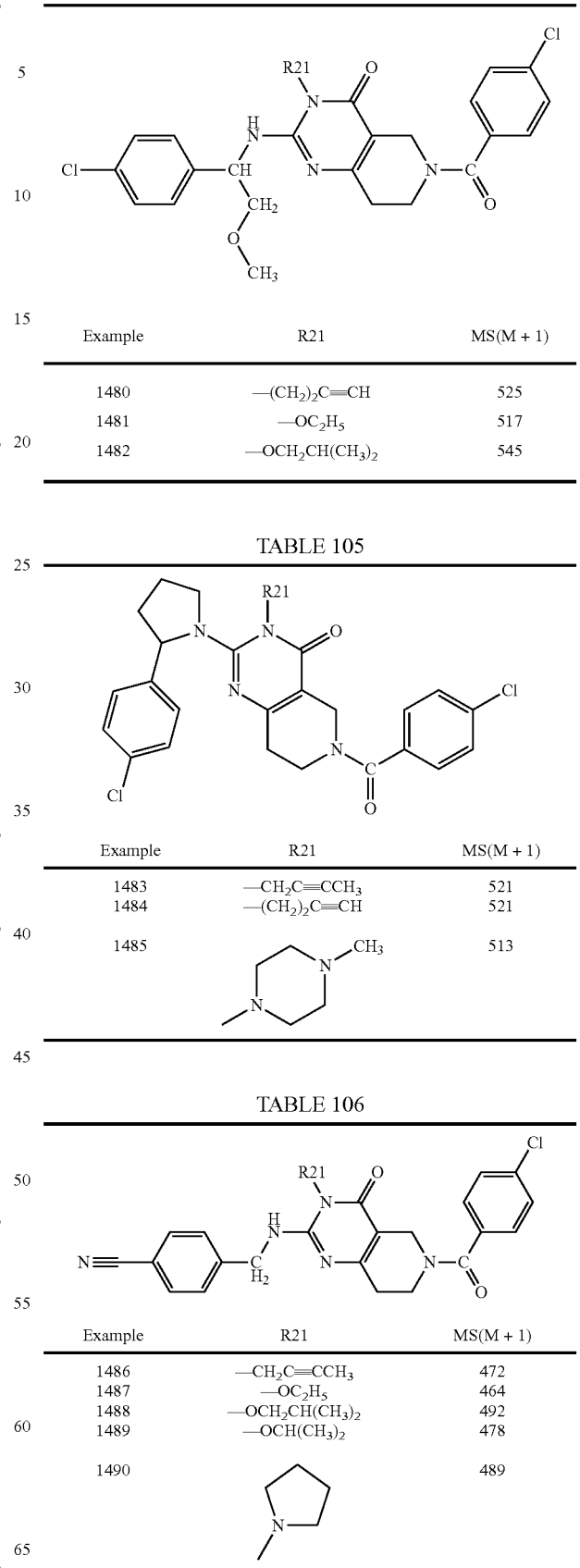
| Example | R21 | MS(M + 1) |
|---|---|---|
| 1480 | —(CH₂)₂C≡CH | 525 |
| 1481 | —OC₂H₅ | 517 |
| 1482 | —OCH₂CH(CH₃)₂ | 545 |
TABLE 105
| Example | R21 | MS(M + 1) |
|---|---|---|
| 1483 | —CH₂C≡CCH₃ | 521 |
| 1484 | —(CH₂)₂C≡CH | 521 |
| 1485 | (4-methylpiperazine) | 513 |
TABLE 106
| Example | R21 | MS(M + 1) |
|---|---|---|
| 1486 | —CH₂C≡CCH₃ | 472 |
| 1487 | —OC₂H₅ | 464 |
| 1488 | —OCH₂CH(CH₃)₂ | 492 |
| 1489 | —OCH(CH₃)₂ | 478 |
| 1490 | (1-methylpyrrolidine) | 489 |

TABLE 107

| Example | R26 | R27 | R28 | R29 | R210 | MS(M+1) |
|---|---|---|---|---|---|---|
| 1491 | —H | —H | —H | —H | —H | 439 |
| 1492 | —H | —H | —CH₃ | —H | —H | 453 |
| 1493 | —H | —H | —OCH₃ | —H | —H | 469 |
| 1494 | —H | —Cl | —Cl | —H | —H | 508 |
| 1495 | —F | —H | —CF₃ | —H | —H | 525 |
| 1496 | —H | —CN | —H | —H | —H | 464 |
| 1497 | —H | —N(CH₃)₂ | —H | —H | —H | 482 |
| 1498 | —H | —CH₃ | —CH₃ | —H | —H | 467 |
| 1499 | —F | —H | —F | —H | —F | 493 |
| 1500 | —F | —H | —H | —H | —F | 475 |
| 1501 | —OCH₃ | —H | —Cl | —H | —H | 503 |
| 1502 | —H | —H | —N(C₂H₅)₂ | —H | —H | 510 |
| 1503 | —H | —H | —CH=CH₂ | —H | —H | 465 |
| 1504 | —F | —H | —OCH₃ | —H | —H | 487 |
| 1505 | —H | —F | —CH₃ | —H | —H | 471 |
| 1506 | —H | —CH₃ | —Cl | —H | —H | 487 |
| 1507 | —H | —Cl | —CH₃ | —H | —H | 487 |
| 1508 | —H | —H | —OC₂H₅ | —H | —H | 483 |
| 1509 | —H | —H | —SCH₃ | —H | —H | 485 |
| 1510 | —H | —H | (1-methylimidazol-2-yl) | —H | —H | 505 |
| 1511 | —H | —H | (4-methyl-1,2,4-triazol-3-yl) | —H | —H | 506 |
| 1512 | —H | —H | (1-methyltetrazol-5-yl) | —H | —H | 507 |
| 1513 | —H | —H | (pyridin-3-yl) | —H | —H | 516 |
| 1514 | —H | —H | (pyridin-4-yl) | —H | —H | 516 |
| 1515 | —H | (pyridin-4-yl) | —H | —H | —H | 516 |
| 1516 | —H | —H | (5-methyloxazol-2-yl) | —H | —H | 506 |

TABLE 108

| Example | R26 | R27 | R28 | R29 | R210 | MS(M+1) |
|---|---|---|---|---|---|---|
| 1517 | —H | —H | —CH₃ | —H | —H | 483 |
| 1518 | —H | —H | —Cl | —H | —H | 503 |
| 1519 | —H | —H | —F | —H | —H | 487 |
| 1520 | —H | —H | —CN | —H | —H | 494 |

TABLE 109

| Example | R21 | MS(M+1) |
|---|---|---|
| 1521 | 2-methylchroman-2-yl | 495 |
| 1522 | (E)-2-(4-chlorophenyl)vinyl | 499 |
| 1523 | 2,3-dichloro-5-methylpyridin-6-yl | 509 |
| 1524 | 2-methyl-1H-indol-3-yl | 478 |
| 1525 | 2-methylquinolin-3-yl | 490 |
| 1526 | 3-methylquinolin-2-yl | 490 |
| 1527 | 3-methylisoquinolin-1-yl | 490 |
| 1528 | 2-methylbenzofuran-3-yl | 479 |

TABLE 109-continued

| Example | R21 | MS(M + 1) |
|---|---|---|
| 1529 | 5-fluoro-2-methyl-1H-indol-3-yl | 496 |
| 1530 | 2-methylbenzo[b]thiophen-3-yl | 495 |
| 1531 | 6-methyl-2-oxo-1,2,3,4-tetrahydroquinolin-7-yl | 508 |
| 1532 | 1-ethyl-3-methyl-2-oxo-1,2-dihydroquinolin-6-yl | 534 |
| 1533 | 6,8-dimethyl-2-oxo-1,2,3,4-tetrahydroquinolin-7-yl | 522 |
| 1534 | 1-ethyl-6-methyl-2-oxo-1,2,3,4-tetrahydroquinolin-7-yl | 536 |
| 1535 | 8-methoxy-5-methyl-2-oxo-1,2,3,4-tetrahydroquinolin-6-yl | 538 |
| 1536 | 4-methoxy-1,2-dimethyl-1H-indol-3-yl | 508 |
| 1537 | 6-methoxy-1,2-dimethyl-1H-indol-3-yl | 508 |
| 1538 | 2,3-dimethylbenzofuran-5-yl | 493 |
| 1539 | 5-methoxy-2-methylbenzofuran-3-yl | 509 |
| 1540 | 5-chloro-2-methylbenzofuran-3-yl | 513 |
| 1541 | 6-methylbenzo[d]thiazol-5-yl | 496 |
| 1542 | 5-methyl-2,3-dihydrobenzofuran-6-yl | 481 |
| 1543 | 5-methylbenzofuran-6-yl | 479 |
| 1544 | 7-methylquinoxalin-6-yl | 491 |
| 1545 | 6-methyl-2,3-dihydrobenzo[b][1,4]dioxin-7-yl | 497 |
| 1546 | 6-methyl-3-oxo-3,4-dihydro-2H-benzo[b][1,4]oxazin-7-yl | 510 |
| 1547 | 6-methyl-3-oxo-3,4-dihydro-2H-benzo[b][1,4]thiazin-7-yl | 526 |

TABLE 109-continued

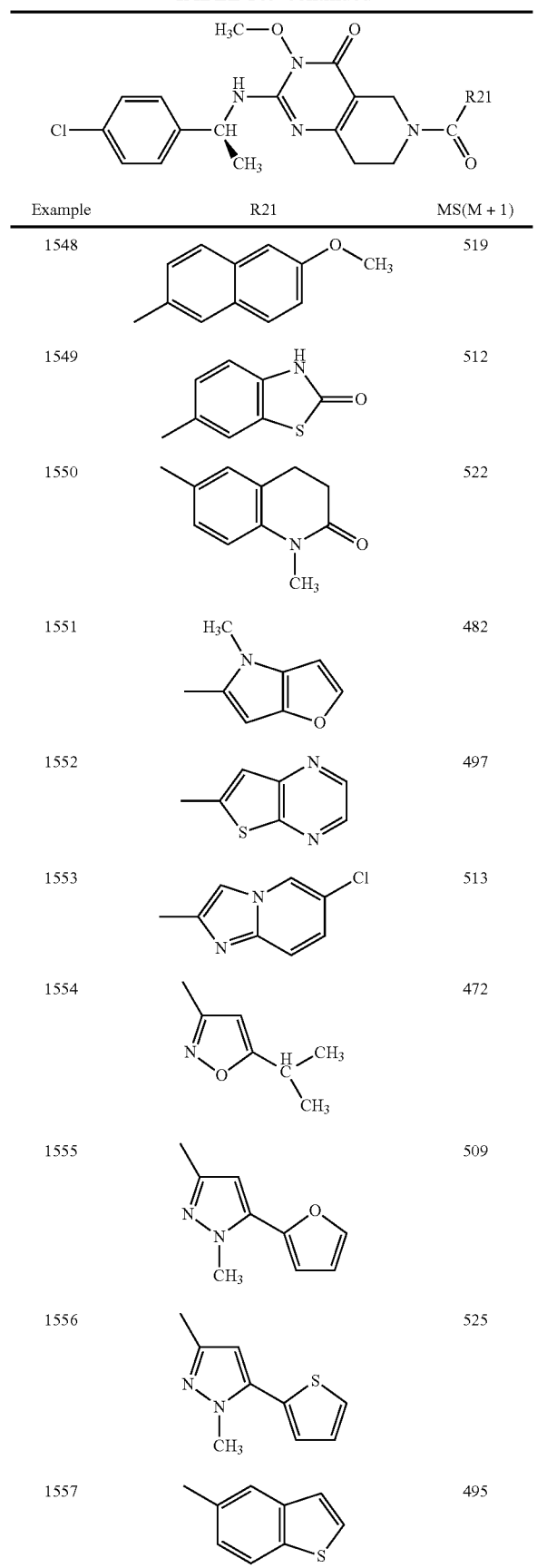

| Example | R21 | MS(M + 1) |
|---|---|---|
| 1548 | 6-methoxy-2-methylnaphthalene | 519 |
| 1549 | 6-methylbenzothiazol-2(3H)-one | 512 |
| 1550 | 1,6-dimethyl-3,4-dihydroquinolin-2(1H)-one | 522 |
| 1551 | 1,5-dimethyl-1H-furo[3,2-b]pyrrole | 482 |
| 1552 | 6-methylthieno[2,3-b]pyrazine | 497 |
| 1553 | 6-chloro-2-methylimidazo[1,2-a]pyridine | 513 |
| 1554 | 5-isopropyl-3-methylisoxazole | 472 |
| 1555 | 5-(furan-2-yl)-1,3-dimethyl-1H-pyrazole | 509 |
| 1556 | 1,3-dimethyl-5-(thiophen-2-yl)-1H-pyrazole | 525 |
| 1557 | 5-methylbenzo[b]thiophene | 495 |

TABLE 109-continued

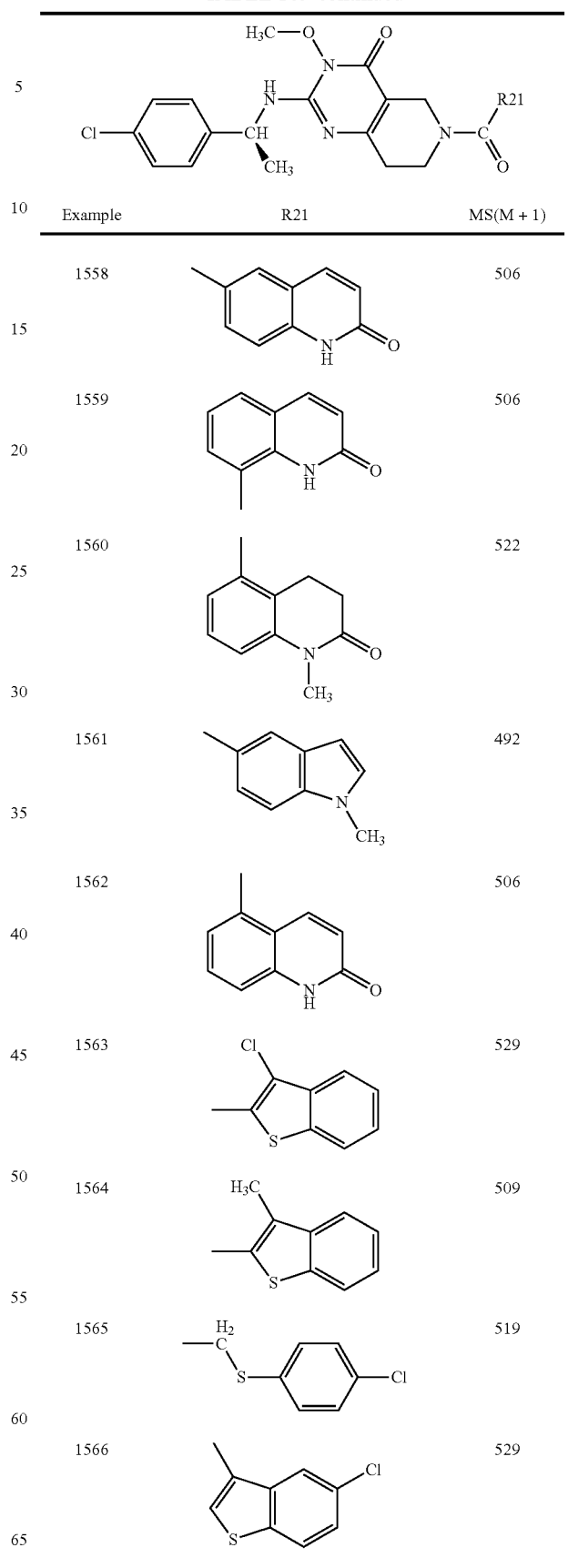

| Example | R21 | MS(M + 1) |
|---|---|---|
| 1558 | 6-methylquinolin-2(1H)-one | 506 |
| 1559 | 8-methylquinolin-2(1H)-one | 506 |
| 1560 | 1,5-dimethyl-3,4-dihydroquinolin-2(1H)-one | 522 |
| 1561 | 1,5-dimethyl-1H-indole | 492 |
| 1562 | 5-methylquinolin-2(1H)-one | 506 |
| 1563 | 3-chloro-2-methylbenzo[b]thiophene | 529 |
| 1564 | 2,3-dimethylbenzo[b]thiophene | 509 |
| 1565 | (4-chlorophenylthio)ethyl | 519 |
| 1566 | 5-chloro-3-methylbenzo[b]thiophene | 529 |

TABLE 109-continued

| Example | R21 | MS(M + 1) |
|---|---|---|
| 1567 | 1-methyl-3-methyl-1H-indazole | 493 |
| 1568 | 2-methylpyrazolo[1,5-a]pyridine | 479 |
| 1569 | 2-methylthieno[2,3-b]pyridine | 496 |
| 1570 | 2-methylquinoxaline | 491 |
| 1571 | 5-methyl-2,3-dihydro-1H-indene | 479 |
| 1572 | 4-methylisoquinoline | 490 |
| 1573 | 7-methyl-4,5-dihydrobenzo[f][1,4]oxazepin-3(2H)-one | 524 |
| 1574 | 3-chloro-2-methylthiophene | 479 |
| 1575 | 1,5-dimethyl-1H-benzimidazole | 493 |
| 1576 | 1,6-dimethyl-1H-indole | 492 |

TABLE 109-continued

| Example | R21 | MS(M + 1) |
|---|---|---|
| 1577 | 2-methyl-1,8-naphthyridine | 491 |
| 1578 | 4,6-dimethyl-2H-benzo[b][1,4]thiazin-3(4H)-one | 540 |
| 1579 | 7-methylquinoline | 490 |
| 1580 | 2-methylbenzo[d]thiazole | 496 |
| 1581 | 2-methylindolizine | 478 |
| 1582 | 7-methylbenzo[d]oxazol-2(3H)-one | 496 |
| 1583 | 6-methyl-4H-benzo[d][1,3]oxazin-2(1H)-one | 510 |
| 1584 | 6-methylchroman | 495 |

TABLE 110

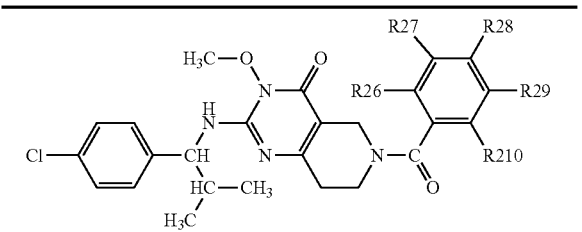

| Example | R26 | R27 | R28 | R29 | R210 | MS (M+1) |
|---|---|---|---|---|---|---|
| 1585 | —H | —H | —H | —H | —H | 467 |
| 1586 | —H | —H | —CH₃ | —H | —H | 481 |
| 1587 | —H | —H | —OCH₃ | —H | —H | 497 |
| 1588 | —H | —H | —Cl | —Cl | —H | 535 |
| 1589 | —H | —H | —CF₃ | —H | —F | 553 |
| 1590 | —H | —H | —H | —CN | —H | 492 |
| 1591 | —H | —H | —H | —N(CH₃)₂ | —H | 510 |
| 1592 | —H | —H | —CH₃ | —CH₃ | —H | 495 |
| 1593 | —F | —H | —F | —H | —F | 521 |
| 1594 | —F | —H | —H | —H | —F | 503 |
| 1595 | —H | —H | —Cl | —H | —OCH₃ | 531 |
| 1596 | —H | —H | —N(C₂H₅)₂ | —H | —H | 538 |
| 1597 | —H | —H | —CH=CH₂ | —H | —H | 493 |
| 1598 | —H | —H | —OCH₃ | —H | —F | 515 |
| 1599 | —H | —H | —CH₃ | —F | —H | 499 |
| 1600 | —H | —H | —Cl | —CH₃ | —H | 515 |
| 1601 | —H | —H | —CH₃ | —Cl | —H | 515 |
| 1602 | —H | —H | —OC₂H₅ | —H | —H | 511 |
| 1603 | —H | —H | —SCH₃ | —H | —H | 513 |
| 1604 | —H | —H | N-methylimidazolyl | —H | —H | 533 |
| 1605 | —H | —H | N-methyltriazolyl | —H | —H | 534 |
| 1606 | —H | —H | N-thiomorpholinyl | —H | —H | 568 |
| 1607 | —H | —H | N-methyltetrazolyl | —H | —H | 535 |
| 1608 | —H | —H | 3-pyridyl | —H | —H | 544 |
| 1609 | —H | —H | 4-pyridyl | —H | —H | 544 |
| 1610 | —H | 4-pyridyl | —H | —H | —H | 544 |
| 1611 | —H | —H | 5-methyloxazolyl | —H | —H | 534 |

TABLE 111

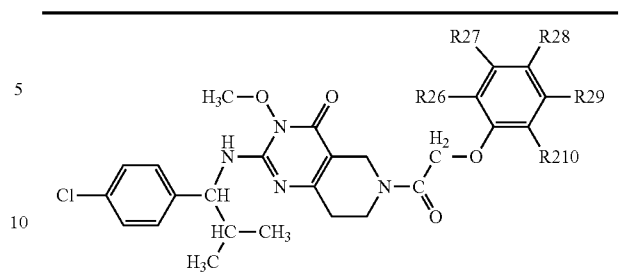

| Example | R26 | R27 | R28 | R29 | R210 | MS(M+1) |
|---|---|---|---|---|---|---|
| 1612 | —H | —H | —CH₃ | —H | —H | 511 |
| 1613 | —H | —H | —Cl | —H | —H | 531 |
| 1614 | —H | —H | —F | —H | —H | 515 |
| 1615 | —H | —H | —CN | —H | —H | 522 |

TABLE 112

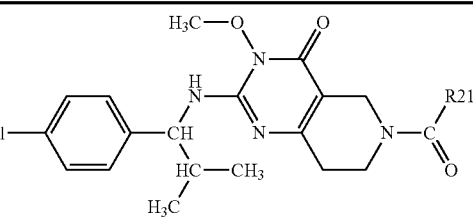

| Example | R21 | MS(M+1) |
|---|---|---|
| 1616 | 2-methylchroman-2-yl | 523 |
| 1617 | 4-chlorostyryl | 527 |
| 1618 | 2,3-dichloro-5-methylpyridyl | 537 |
| 1619 | 2-methylindol-3-yl | 506 |
| 1620 | 2-methylquinolin-3-yl | 518 |
| 1621 | 3-methylquinolin-2-yl | 518 |
| 1622 | 3-methylisoquinolin-1-yl | 518 |

TABLE 112-continued

| Example | R21 | MS(M + 1) |
|---|---|---|
| 1623 | 2-methylbenzofuran | 507 |
| 1624 | 5-fluoro-2-methylindole | 524 |
| 1625 | 2-methylbenzothiophene | 523 |
| 1626 | 6-methyl-3,4-dihydroquinolin-2(1H)-one | 536 |
| 1627 | 1-ethyl-3-methylquinolin-2(1H)-one | 562 |
| 1628 | 1,6-dimethyl-3,4-dihydroquinolin-2(1H)-one | 550 |
| 1629 | 1-ethyl-6-methyl-3,4-dihydroquinolin-2(1H)-one | 564 |
| 1630 | 8-methoxy-5-methyl-3,4-dihydroquinolin-2(1H)-one | 566 |

TABLE 112-continued

| Example | R21 | MS(M + 1) |
|---|---|---|
| 1631 | 4-methoxy-1,2-dimethylindole | 536 |
| 1632 | 6-methoxy-1,2-dimethylindole | 536 |
| 1633 | 2,3-dimethylbenzofuran | 521 |
| 1634 | 5-methoxy-2-methylbenzofuran | 537 |
| 1635 | 5-chloro-2-methylbenzofuran | 541 |
| 1636 | 6-methylbenzothiazole | 524 |
| 1637 | 5-methyl-2,3-dihydrobenzofuran | 509 |
| 1638 | 5-methylbenzofuran | 507 |
| 1639 | 6-methylquinoxaline | 519 |
| 1640 | 6-methyl-2,3-dihydrobenzo[b][1,4]dioxine | 525 |

TABLE 112-continued

[Common structure: 4-chlorophenyl-CH(iPr)-NH-C(=N-)(N(OCH₃))-C(=O)- fused to tetrahydropyridopyrimidinone with N-C(=O)-R21]

| Example | R21 | MS(M + 1) |
|---------|-----|-----------|
| 1641 | 6-methyl-2H-benzo[b][1,4]oxazin-3(4H)-yl | 538 |
| 1642 | 6-methyl-2H-benzo[b][1,4]thiazin-3(4H)-yl | 554 |
| 1643 | 6-methoxy-naphthalen-2-yl (methyl-substituted) | 547 |
| 1644 | 6-methyl-benzothiazol-2(3H)-one | 540 |
| 1645 | 1,6-dimethyl-3,4-dihydroquinolin-2(1H)-one | 550 |
| 1646 | 4,5-dimethyl-4H-furo[3,2-b]pyrrole | 510 |
| 1647 | 6-methyl-thieno[2,3-b]pyrazine | 525 |
| 1648 | 6-chloro-2-methyl-imidazo[1,2-a]pyridine | 541 |
| 1649 | 3-methyl-5-isopropyl-isoxazole | 500 |
| 1650 | 3-methyl-1-methyl-5-(furan-2-yl)-1H-pyrazole | 537 |
| 1651 | 3-methyl-1-methyl-5-(thiophen-2-yl)-1H-pyrazole | 553 |
| 1652 | 5-methyl-benzo[b]thiophene | 523 |
| 1653 | 6-methyl-quinolin-2(1H)-one | 534 |
| 1654 | 8-methyl-quinolin-2(1H)-one | 534 |
| 1655 | 1,5-dimethyl-3,4-dihydroquinolin-2(1H)-one | 550 |
| 1656 | 1,5-dimethyl-1H-indole | 520 |
| 1657 | 5-methyl-quinolin-2(1H)-one | 534 |

TABLE 112-continued

| Example | R21 | MS(M + 1) |
|---|---|---|
| 1658 | 3-chloro-2-methylbenzothiophene | 557 |
| 1659 | 2,3-dimethylbenzothiophene | 537 |
| 1660 | 6-fluoro-2-methylbenzothiophene | 541 |
| 1661 | (4-chlorophenylthio)methyl | 547 |
| 1662 | 5-chloro-3-methylbenzothiophene | 557 |
| 1663 | 1,3-dimethylindazole | 521 |
| 1664 | 2-methylpyrazolo[1,5-a]pyridine | 507 |
| 1665 | 2-methylthieno[2,3-b]pyridine | 524 |
| 1666 | 3-methylquinoxaline | 519 |
| 1667 | 5-methyl-2,3-dihydro-1H-indene | 507 |

TABLE 112-continued

| Example | R21 | MS(M + 1) |
|---|---|---|
| 1668 | 4-methylisoquinoline | 518 |
| 1669 | 7-methyl-1,5-dihydrobenzo[e][1,4]oxazepin-3(2H)-one | 552 |
| 1670 | 3-chloro-2-methylthiophene | 507 |
| 1671 | 1,5-dimethylbenzimidazole | 521 |
| 1672 | 1,6-dimethylindole | 520 |
| 1673 | 7-methyl-1,8-naphthyridine | 519 |
| 1674 | 4,6-dimethyl-2H-benzo[b][1,4]thiazin-3(4H)-one | 568 |
| 1675 | 7-methylquinoline | 518 |
| 1676 | 7-methylindolizine | 506 |

TABLE 112-continued

| Example | R21 | MS(M + 1) |
|---|---|---|
| 1677 | 7-methyl-benzoxazol-2(3H)-one | 524 |
| 1678 | 6-methyl-4H-benzo[d][1,3]oxazin-2(1H)-one | 538 |
| 1679 | 6-methyl-chroman | 523 |

TABLE 113

| Example | R26 | R27 | R28 | R29 | R210 | MS(M + 1) |
|---|---|---|---|---|---|---|
| 1680 | —H | —H | —H | —H | —H | 435 |
| 1681 | —H | —H | —CH₃ | —H | —H | 449 |
| 1682 | —H | —H | —OCH₃ | —H | —H | 465 |
| 1683 | —H | —Cl | —Cl | —H | —H | 503 |
| 1684 | —F | —H | —CF₃ | —H | —H | 521 |
| 1685 | —H | —CN | —H | —H | —H | 460 |
| 1686 | —H | —N(CH₃)₂ | —H | —H | —H | 478 |
| 1687 | —H | —CH₃ | —CH₃ | —H | —H | 463 |
| 1688 | —F | —H | —F | —H | —F | 489 |
| 1689 | —F | —H | —H | —H | —F | 471 |
| 1690 | —OCH₃ | —H | —Cl | —H | —H | 499 |
| 1691 | —H | —H | —N(C₂H₅)₂ | —H | —H | 506 |
| 1692 | —H | —H | —CH=CH₂ | —H | —H | 461 |
| 1693 | —F | —H | —OCH₃ | —H | —H | 483 |
| 1694 | —H | —F | —CH₃ | —H | —H | 467 |
| 1695 | —H | —CH₃ | —Cl | —H | —H | 483 |
| 1696 | —H | —Cl | —CH₃ | —H | —H | 483 |
| 1697 | —H | —H | —OC₂H₅ | —H | —H | 479 |
| 1698 | —H | —H | —SCH₃ | —H | —H | 481 |
| 1699 | —H | —H | 1-methyl-imidazol-3-yl | —H | —H | 501 |
| 1700 | —H | —H | 4-methyl-1,2,4-triazol-3-yl | —H | —H | 502 |
| 1701 | —H | —H | 4-methyl-thiomorpholin-4-yl | —H | —H | 536 |
| 1702 | —H | —H | 1-methyl-tetrazol-5-yl | —H | —H | 503 |
| 1703 | —H | —H | pyridin-3-yl | —H | —H | 512 |
| 1704 | —H | —H | 4-methyl-pyridin-3-yl | —H | —H | 512 |
| 1705 | —H | 4-methyl-pyridin-3-yl | —H | —H | —H | 512 |
| 1706 | —H | —H | 5-methyl-furan-2-yl | —H | —H | 501 |
| 1707 | —H | —H | 5-methyl-oxazol-2-yl | —H | —H | 502 |

TABLE 114

| Example | R26 | R27 | R28 | R29 | R210 | MS(M + 1) |
|---|---|---|---|---|---|---|
| 1708 | —H | —H | —CH₃ | —H | —H | 479 |
| 1709 | —H | —H | —Cl | —H | —H | 499 |
| 1710 | —H | —H | —F | —H | —H | 483 |
| 1711 | —H | —H | —CN | —H | —H | 490 |

TABLE 115

| Example | R21 | MS(M + 1) |
|---|---|---|
| 1712 | 2-methylchroman | 491 |
| 1713 | (E)-1-(4-chlorophenyl)prop-1-ene | 495 |
| 1714 | 2,3-dichloro-5-methylpyridine | 504 |
| 1715 | 2-methyl-1H-indole | 474 |
| 1716 | 2-methylquinoline | 486 |
| 1717 | 3-methylquinoline | 486 |
| 1718 | 3-methylisoquinoline | 486 |
| 1719 | 2-methylbenzofuran | 475 |
| 1720 | 5-fluoro-2-methyl-1H-indole | 492 |
| 1721 | 2-methylbenzothiophene | 491 |
| 1722 | 6-methyl-3,4-dihydroquinolin-2(1H)-one | 504 |

TABLE 115-continued

| Example | R21 | MS(M + 1) |
|---|---|---|
| 1723 | 1-ethyl-3-methylquinolin-2(1H)-one | 530 |
| 1724 | 6,8-dimethyl-3,4-dihydroquinolin-2(1H)-one | 518 |
| 1725 | 1-ethyl-6-methyl-3,4-dihydroquinolin-2(1H)-one | 532 |
| 1726 | 8-methoxy-5-methyl-3,4-dihydroquinolin-2(1H)-one | 534 |
| 1727 | 4-methoxy-1,2-dimethyl-1H-indole | 504 |
| 1728 | 6-methoxy-1,2-dimethyl-1H-indole | 504 |
| 1729 | 2,3-dimethylbenzofuran | 489 |
| 1730 | 5-methoxy-2-methylbenzofuran | 505 |

TABLE 115-continued

| Example | R21 | MS(M + 1) |
|---|---|---|
| 1731 | 5-chloro-2-methylbenzofuran | 509 |
| 1732 | 6-methylbenzothiazole | 492 |
| 1733 | 5-methyl-2,3-dihydrobenzofuran | 477 |
| 1734 | 5-methylbenzofuran | 475 |
| 1735 | 6-methylquinoxaline | 487 |
| 1736 | 6-methyl-2,3-dihydrobenzo[1,4]dioxine | 493 |
| 1737 | 6-methyl-2H-benzo[1,4]oxazin-3(4H)-one | 506 |
| 1738 | 6-methyl-2H-benzo[1,4]thiazin-3(4H)-one | 522 |
| 1739 | 6-methoxy-2-methylnaphthalene | 515 |
| 1740 | 6-methylbenzothiazol-2(3H)-one | 508 |
| 1741 | 1,6-dimethyl-3,4-dihydroquinolin-2(1H)-one | 518 |

| Example | R21 | MS(M + 1) |
|---|---|---|
| 1742 | 4,5-dimethyl-4H-furo[3,2-b]pyrrole | 478 |
| 1743 | 6-methylthieno[3,2-b]pyrazine | 493 |
| 1744 | 6-chloro-2-methylimidazo[1,2-a]pyridine | 509 |
| 1745 | 3-methyl-5-isopropylisoxazole | 468 |
| 1746 | 5-(furan-2-yl)-1,3-dimethyl-1H-pyrazole | 505 |
| 1747 | 1,3-dimethyl-5-(thiophen-2-yl)-1H-pyrazole | 521 |
| 1748 | 5-methylbenzo[b]thiophene | 491 |
| 1749 | 6-methylquinolin-2(1H)-one | 502 |
| 1750 | 1,5-dimethyl-3,4-dihydroquinolin-2(1H)-one | 518 |

TABLE 115-continued

| Example | R21 | MS(M + 1) |
|---|---|---|
| 1751 | 5-methyl-1-methyl-indole | 488 |
| 1752 | 5-methyl-quinolin-2(1H)-one | 502 |
| 1753 | 3-chloro-2-methyl-benzothiophene | 525 |
| 1754 | 2,3-dimethyl-benzothiophene | 505 |
| 1755 | 2-methyl-6-fluoro-benzothiophene | 509 |
| 1756 | 4-chlorophenylthiomethyl | 515 |
| 1757 | 3-methyl-5-chloro-benzothiophene | 525 |
| 1758 | 3-methyl-1-methyl-indazole | 489 |
| 1759 | 2-methyl-pyrazolo[1,5-a]pyridine | 475 |
| 1760 | 2-methyl-thieno[2,3-b]pyridine | 492 |

TABLE 115-continued

| Example | R21 | MS(M + 1) |
|---|---|---|
| 1761 | 2-methyl-quinoxaline | 487 |
| 1762 | 5-methyl-indane | 475 |
| 1763 | 4-methyl-isoquinoline | 486 |
| 1764 | 7-methyl-2,3-dihydro-benzo[f][1,4]oxazepin-3-one | 520 |
| 1765 | 3-chloro-2-methyl-thiophene | 475 |
| 1766 | 5-methyl-1-methyl-benzimidazole | 489 |
| 1767 | 6-methyl-1-methyl-indole | 488 |
| 1768 | 2-methyl-1,8-naphthyridine | 487 |
| 1769 | 6-methyl-4-methyl-2H-benzo[b][1,4]thiazin-3(4H)-one | 536 |
| 1770 | 7-methyl-quinoline | 486 |

TABLE 115-continued

[Structure: methoxy-pyrimidinone core with (R)-1-(4-methoxyphenyl)ethylamino group and N-C(=O)-R21 acyl on tetrahydropyridine]

| Example | R21 | MS(M + 1) |
|---|---|---|
| 1771 | 2-benzothiazolyl | 492 |
| 1772 | 2-indolizinyl | 474 |
| 1773 | 7-methyl-benzoxazol-2(3H)-one-yl | 492 |
| 1774 | 6-methyl-4H-benzo[d][1,3]oxazin-2(1H)-one-yl | 506 |
| 1775 | 6-methylchroman-yl | 491 |

TABLE 116

[Structure: 4-cyanobenzyl-amino pyrimidinone core with N-methoxy, linked via C(=O) to substituted phenyl (R26–R210)]

| Example | R26 | R27 | R28 | R29 | R210 | MS(M + 1) |
|---|---|---|---|---|---|---|
| 1776 | —H | —H | —H | —H | —H | 416 |
| 1777 | —H | —H | —CH₃ | —H | —H | 430 |
| 1778 | —H | —H | —OCH₃ | —H | —H | 446 |
| 1779 | —H | —Cl | —Cl | —H | —H | 484 |
| 1780 | —F | —H | —CF₃ | —H | —H | 502 |
| 1781 | —H | —CN | —H | —H | —H | 441 |
| 1782 | —H | —N(CH₃)₂ | —H | —H | —H | 459 |
| 1783 | —H | —CH₃ | —CH₃ | —H | —H | 444 |
| 1784 | —F | —H | —F | —H | —F | 470 |
| 1785 | —F | —H | —H | —H | —F | 452 |
| 1786 | —OCH₃ | —H | —Cl | —H | —H | 480 |
| 1787 | —H | —H | —N(C₂H₅)₂ | —H | —H | 487 |
| 1788 | —H | —H | —CH=CH₂ | —H | —H | 442 |
| 1789 | —H | —H | —Cl | —H | —H | 450 |
| 1790 | —F | —H | —OCH₃ | —H | —H | 464 |
| 1791 | —H | —F | —CH₃ | —H | —H | 448 |
| 1792 | —H | —H | —Cl | —H | —H | 464 |
| 1793 | —H | —Cl | —CH₃ | —H | —H | 464 |
| 1794 | —H | —H | —OC₂H₅ | —H | —H | 460 |
| 1795 | —H | —H | —SCH₃ | —H | —H | 462 |

TABLE 116-continued

| Example | R26 | R27 | R28 | R29 | R210 | MS(M + 1) |
|---|---|---|---|---|---|---|
| 1796 | —H | —H | 1-methyl-imidazol-yl | —H | —H | 482 |
| 1797 | —H | —H | 4-methyl-1,2,4-triazol-yl | —H | —H | 483 |
| 1798 | —H | —H | 1-methyl-tetrazol-yl | —H | —H | 484 |
| 1799 | —H | —H | 3-pyridyl-methyl | —H | —H | 493 |
| 1800 | —H | —H | 4-pyridyl-methyl | —H | —H | 493 |
| 1801 | —H | 4-pyridyl-methyl | —H | —H | —H | 493 |
| 1802 | —H | —H | 5-methyl-oxazol-yl | —H | —H | 483 |

TABLE 117

[Structure: 4-cyanobenzyl-amino pyrimidinone with N-methoxy, linked via C(=O)-CH₂-O- to substituted phenyl (R26–R210)]

| Example | R26 | R27 | R28 | R29 | R210 | MS(M + 1) |
|---|---|---|---|---|---|---|
| 1803 | —H | —H | —CH₃ | —H | —H | 460 |
| 1804 | —H | —H | —Cl | —H | —H | 480 |
| 1805 | —H | —H | —F | —H | —H | 464 |
| 1806 | —H | —H | —CN | —H | —H | 471 |

TABLE 118

| Example | R21 | MS(M + 1) |
|---|---|---|
| 1807 | 2-methylchroman | 472 |
| 1808 | (E)-4-chlorostyryl | 476 |
| 1809 | 2,3-dichloro-5-methylpyridin-5-yl | 485 |
| 1810 | 2-methyl-1H-indol-3-yl | 455 |
| 1811 | 2-methylquinolin-3-yl | 467 |
| 1812 | 3-methylquinolin-6-yl | 467 |
| 1813 | 3-methylisoquinolin-6-yl | 467 |
| 1814 | 2-methylbenzofuran-3-yl | 456 |
| 1815 | 5-fluoro-2-methyl-1H-indol-3-yl | 473 |
| 1816 | 2-methylbenzo[b]thiophen-3-yl | 472 |
| 1817 | 6-methyl-3,4-dihydroquinolin-2(1H)-one | 485 |

TABLE 118-continued

| Example | R21 | MS(M + 1) |
|---|---|---|
| 1818 | 1-ethyl-3-methylquinolin-2(1H)-one | 511 |
| 1819 | 6,8-dimethyl-3,4-dihydroquinolin-2(1H)-one | 499 |
| 1820 | 1-ethyl-6-methyl-3,4-dihydroquinolin-2(1H)-one | 513 |
| 1821 | 8-methoxy-5-methyl-3,4-dihydroquinolin-2(1H)-one | 515 |
| 1822 | 4-methoxy-2-methyl-1H-indol-3-yl | 485 |
| 1823 | 6-methoxy-2-methyl-1H-indol-3-yl | 485 |
| 1824 | 2,3-dimethylbenzofuran-3-yl | 470 |
| 1825 | 5-methoxy-2-methylbenzofuran-3-yl | 486 |

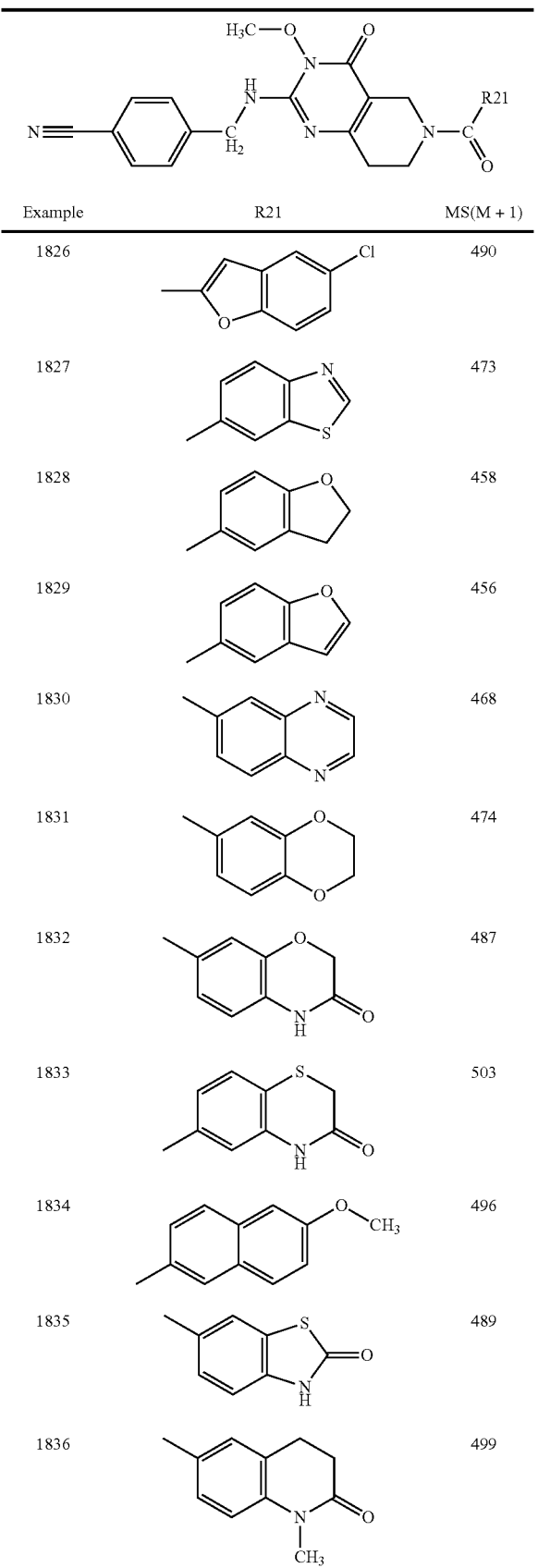
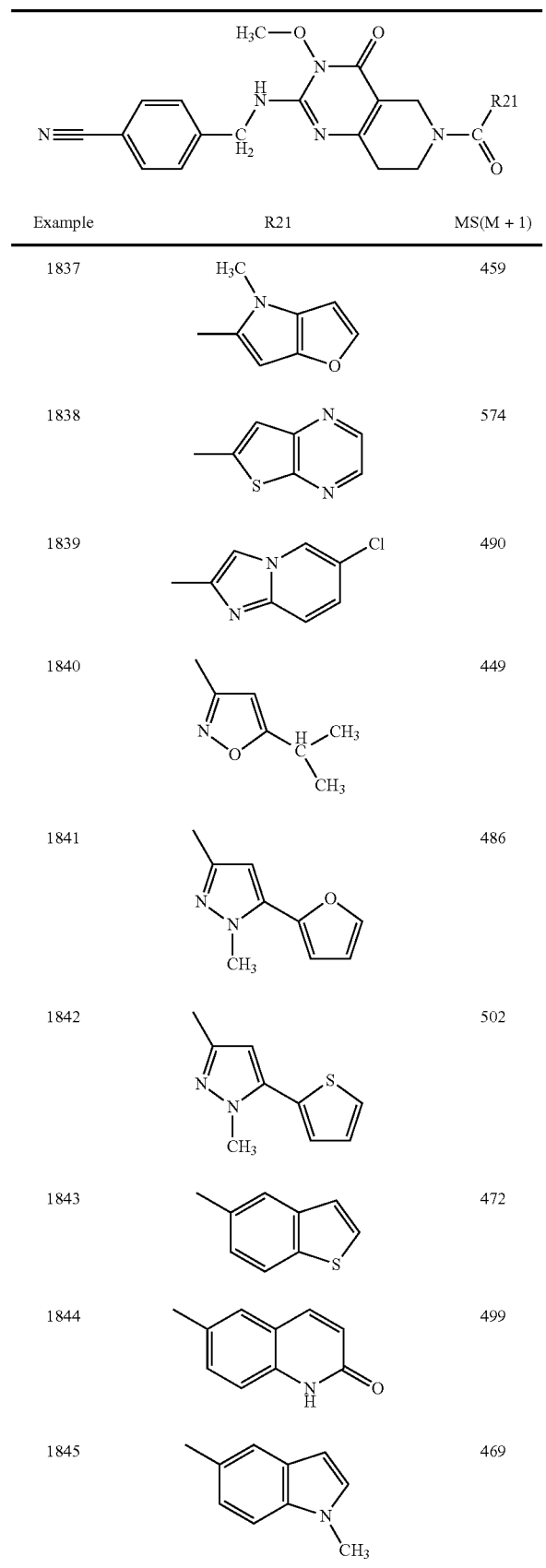

TABLE 118-continued

| Example | R21 | MS(M + 1) |
|---|---|---|
| 1846 | 5-methyl-quinolin-2(1H)-one | 483 |
| 1847 | 3-chloro-2-methyl-benzothiophene | 506 |
| 1848 | 2,3-dimethyl-benzothiophene | 486 |
| 1849 | 6-fluoro-2-methyl-benzothiophene | 490 |
| 1850 | (4-chlorophenylthio)methyl | 496 |
| 1851 | 5-chloro-3-methyl-benzothiophene | 506 |
| 1852 | 1,3-dimethyl-1H-indazole | 470 |
| 1853 | 2-methyl-pyrazolo[1,5-a]pyridine | 456 |
| 1854 | 2-methyl-thieno[2,3-b]pyridine | 473 |
| 1855 | 3-methyl-quinoxaline | 468 |

TABLE 118-continued

| Example | R21 | MS(M + 1) |
|---|---|---|
| 1856 | 5-methyl-indane | 456 |
| 1857 | 4-methyl-isoquinoline | 467 |
| 1858 | 7-methyl-2,3-dihydro-benzo[f][1,4]oxazepin-4(5H)-one | 501 |
| 1859 | 3-chloro-2-methyl-thiophene | 456 |
| 1860 | 1,5-dimethyl-1H-benzimidazole | 470 |
| 1861 | 1,6-dimethyl-1H-indole | 469 |
| 1862 | 7-methyl-pyrido[2,3-b]pyrazine | 468 |
| 1863 | 4,6-dimethyl-2H-benzo[b][1,4]thiazin-3(4H)-one | 517 |
| 1864 | 7-methyl-quinoline | 467 |
| 1865 | 2-methyl-benzothiazole | 473 |

TABLE 118-continued

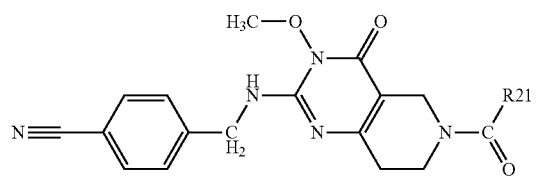

| Example | R21 | MS(M + 1) |
|---|---|---|
| 1866 | (2-methylindolizine) | 455 |
| 1867 | (7-methylbenzoxazol-2(3H)-one) | 473 |
| 1868 | (6-methyl-4H-benzo[d][1,3]oxazin-2(3H)-one) | 487 |
| 1869 | (6-methylchroman) | 472 |

TABLE 119

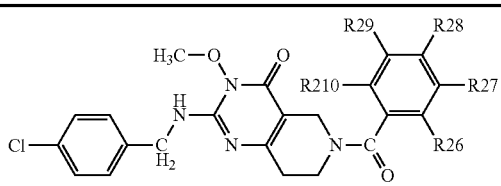

| Example | R26 | R27 | R28 | R29 | R210 | MS(M + 1) |
|---|---|---|---|---|---|---|
| 1870 | —H | —H | —H | —H | —H | 425 |
| 1871 | —H | —H | —CH$_3$ | —H | —H | 439 |
| 1872 | —H | —H | —OCH$_3$ | —H | —H | 455 |
| 1873 | —H | —Cl | —Cl | —H | —H | 494 |
| 1874 | —F | —H | —CF$_3$ | —H | —H | 511 |
| 1875 | —H | —CN | —H | —H | —H | 450 |
| 1876 | —H | —N(CH$_3$)$_2$ | —H | —H | —H | 468 |
| 1877 | —H | —CH$_3$ | —CH$_3$ | —H | —H | 453 |
| 1878 | —F | —H | —F | —H | —F | 479 |
| 1879 | —F | —H | —H | —H | —F | 461 |
| 1880 | —OCH$_3$ | —H | —Cl | —H | —H | 489 |
| 1881 | —H | —H | —N(C$_2$H$_5$)$_2$ | —H | —H | 496 |
| 1882 | —H | —H | —CH=CH$_2$ | —H | —H | 451 |
| 1883 | —F | —H | —OCH$_3$ | —H | —H | 473 |
| 1884 | —H | —F | —CH$_3$ | —H | —H | 457 |
| 1885 | —H | —CH$_3$ | —Cl | —H | —H | 473 |
| 1886 | —H | —Cl | —CH$_3$ | —H | —H | 473 |
| 1887 | —H | —H | —OC$_2$H$_5$ | —H | —H | 469 |
| 1888 | —H | —H | —SCH$_3$ | —H | —H | 471 |

TABLE 119-continued

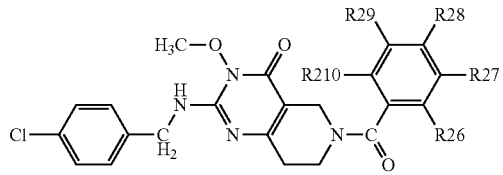

| Example | R26 | R27 | R28 | R29 | R210 | MS(M + 1) |
|---|---|---|---|---|---|---|
| 1889 | —H | —H | (1-methyl-1H-imidazol-2-yl) | —H | —H | 491 |
| 1890 | —H | —H | (4-methyl-4H-1,2,4-triazol-3-yl) | —H | —H | 492 |
| 1891 | —H | —H | (3-methylpyridin-2-yl) | —H | —H | 502 |
| 1892 | —H | —H | (4-methylpyridin-3-yl) | —H | —H | 502 |
| 1893 | —H | (4-methylpyridin-3-yl) | —H | —H | —H | 502 |
| 1894 | —H | —H | (2-methylfuran) | —H | —H | 491 |
| 1895 | —H | —H | (5-methyloxazole) | —H | —H | 492 |

TABLE 120

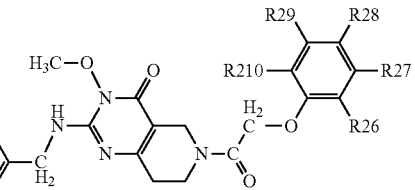

| Example | R26 | R27 | R28 | R29 | R210 | MS(M + 1) |
|---|---|---|---|---|---|---|
| 1896 | —H | —H | —CH$_3$ | —H | —H | 469 |
| 1897 | —H | —H | —Cl | —H | —H | 489 |
| 1898 | —H | —H | —F | —H | —H | 473 |
| 1899 | —H | —H | —CN | —H | —H | 480 |

TABLE 121
| Example | R21 | MS(M + 1) |
|---|---|---|
| 1900 | 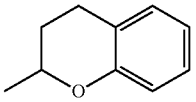 | 481 |
| 1901 | 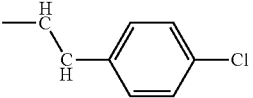 | 485 |
| 1902 | 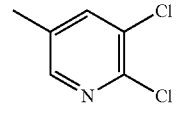 | 495 |
| 1903 | 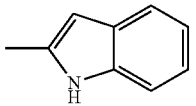 | 464 |
| 1904 | 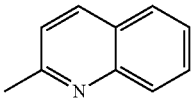 | 476 |
| 1905 | 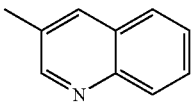 | 476 |
| 1906 | 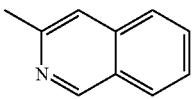 | 476 |
| 1907 | 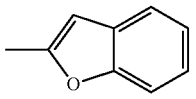 | 465 |
| 1908 | 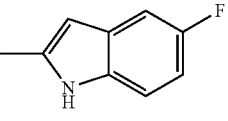 | 482 |
| 1909 | 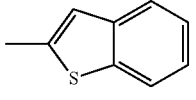 | 481 |
| 1910 | 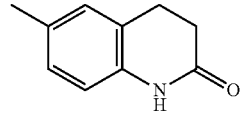 | 494 |
TABLE 121-continued
| Example | R21 | MS(M + 1) |
|---|---|---|
| 1911 | 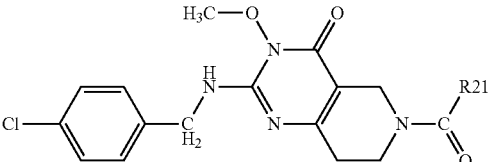 | 520 |
| 1912 | 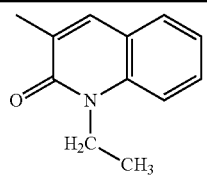 | 508 |
| 1913 | 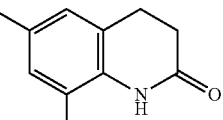 | 522 |
| 1914 | 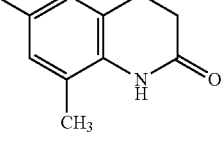 | 524 |
| 1915 | 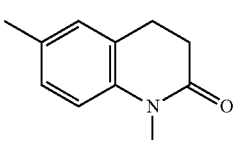 | 494 |
| 1916 | 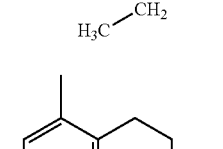 | 494 |
| 1917 | 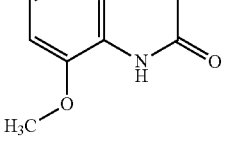 | 479 |
| 1918 | 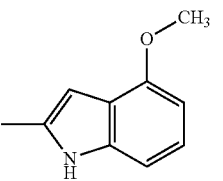 | 495 |

TABLE 121-continued

[Structure: 4-chlorobenzyl-NH-C(=N)-N(OCH₃)-C(=O) fused to tetrahydropyrido ring N-C(=O)-R21]

| Example | R21 | MS(M + 1) |
|---------|-----|-----------|
| 1919 | 5-chloro-2-methylbenzofuran | 499 |
| 1920 | 6-methylbenzothiazole | 482 |
| 1921 | 1-(4-methylphenyl)tetrazole | 493 |
| 1922 | 5-methyl-2,3-dihydrobenzofuran | 467 |
| 1923 | 5-methylbenzofuran | 465 |
| 1924 | 6-methylquinoxaline | 477 |
| 1925 | 6-methyl-2,3-dihydrobenzo[1,4]dioxine | 483 |
| 1926 | 7-methyl-2H-benzo[1,4]oxazin-3(4H)-one | 496 |
| 1927 | 6-methyl-2H-benzo[1,4]thiazin-3(4H)-one | 512 |
| 1928 | 6-methoxy-2-methylnaphthalene | 505 |
| 1929 | 6-methyl-2,3-dihydrobenzothiazol-2-one | 498 |
| 1930 | 1,6-dimethyl-3,4-dihydroquinolin-2(1H)-one | 508 |
| 1931 | 4,5-dimethyl-4H-furo[3,2-b]pyrrole | 468 |
| 1932 | 6-methylthieno[2,3-b]pyrazine | 483 |
| 1933 | 6-chloro-2-methyl-2,3-dihydroimidazo[1,2-a]pyridine | 499 |
| 1934 | 3-methyl-5-ethylisoxazole | 458 |
| 1935 | 1,3-dimethyl-5-(2-furyl)pyrazole | 495 |
| 1936 | 1,3-dimethyl-5-(2-thienyl)pyrazole | 511 |
| 1937 | 5-methylbenzothiophene | 481 |
| 1938 | 6-methylquinolin-2(1H)-one | 492 |

TABLE 121-continued

| Example | R21 | MS(M+1) |
|---|---|---|
| 1939 | 5-methyl-1-methyl-3,4-dihydroquinolin-2(1H)-one | 508 |
| 1940 | 5-methyl-1-methyl-indole | 478 |
| 1941 | 5-methyl-quinolin-2(1H)-one | 492 |
| 1942 | 3-chloro-2-methyl-benzothiophene | 515 |
| 1943 | 2,3-dimethyl-benzothiophene | 495 |
| 1944 | 2-methyl-6-fluoro-benzothiophene | 499 |
| 1945 | -CH2-S-C6H4-Cl | 505 |
| 1946 | 3-methyl-5-chloro-benzothiophene | 515 |
| 1947 | 3-methyl-1-methyl-indazole | 479 |

TABLE 121-continued

| Example | R21 | MS(M+1) |
|---|---|---|
| 1948 | 2-methyl-pyrazolo[1,5-a]pyridine | 465 |
| 1949 | 2-methyl-thieno[2,3-b]pyridine | 482 |
| 1950 | 2-methyl-quinoxaline | 477 |
| 1951 | 5-methyl-indane | 465 |
| 1952 | 4-methyl-isoquinoline | 476 |
| 1953 | 7-methyl-benzo[f][1,4]oxazepin-3(4H)-one | 510 |
| 1954 | 3-chloro-2-methyl-thiophene | 465 |
| 1955 | 5-methyl-1-methyl-benzimidazole | 479 |
| 1956 | 6-methyl-1-methyl-indole | 478 |
| 1957 | 2-methyl-1,8-naphthyridine | 477 |

TABLE 121-continued

Structure: 4-chlorobenzyl-NH-C(=N-)-N(OCH₃)-C(=O)- fused pyrimidine with tetrahydropyridine N-C(=O)-R21

| Example | R21 | MS(M + 1) |
|---|---|---|
| 1958 | 4-methyl-2H-benzo[b][1,4]thiazin-3(4H)-on-6-yl (N-CH₃) | 526 |
| 1959 | benzothiazol-2-yl | 482 |
| 1960 | indolizin-2-yl | 464 |
| 1961 | 7-methyl-benzoxazol-2(3H)-on-yl | 482 |
| 1962 | 6-methyl-2H-benzo[d][1,3]oxazin-2-on-yl | 496 |
| 1963 | 6-methyl-chroman-yl | 481 |

TABLE 122

Structure: 4-(trifluoromethyl)benzyl-NH-C(=N-)-N(OCH₃)-C(=O)- fused pyrimidine with tetrahydropyridine N-C(=O)-phenyl(R26-R210)

| Example | R26 | R27 | R28 | R29 | R210 | MS(M + 1) |
|---|---|---|---|---|---|---|
| 1964 | —H | —H | —H | —H | —H | 459 |
| 1965 | —H | —H | —CH₃ | —H | —H | 473 |
| 1966 | —H | —H | —OCH₃ | —H | —H | 489 |
| 1967 | —H | —Cl | —Cl | —H | —H | 527 |
| 1968 | —F | —H | —CF₃ | —H | —H | 545 |
| 1969 | —H | —CN | —H | —H | —H | 484 |
| 1970 | —H | —N(CH₃)₂ | —H | —H | —H | 502 |
| 1971 | —H | —CH₃ | —CH₃ | —H | —H | 487 |
| 1972 | —F | —H | —F | —H | —F | 513 |
| 1973 | —F | —H | —H | —H | —F | 495 |
| 1974 | —OCH₃ | —H | —Cl | —H | —H | 523 |
| 1975 | —H | —H | —N(C₂H₅)₂ | —H | —H | 530 |
| 1976 | —H | —H | —CH=CH₂ | —H | —H | 485 |

TABLE 122-continued

| Example | R26 | R27 | R28 | R29 | R210 | MS(M + 1) |
|---|---|---|---|---|---|---|
| 1977 | —F | —H | —OCH₃ | —H | —H | 507 |
| 1978 | —H | —F | —CH₃ | —H | —H | 491 |
| 1979 | —H | —CH₃ | —Cl | —H | —H | 507 |
| 1980 | —H | —Cl | —CH₃ | —H | —H | 507 |
| 1981 | —H | —H | —OC₂H₅ | —H | —H | 503 |
| 1982 | —H | —H | —SCH₃ | —H | —H | 505 |
| 1983 | —H | —H | 1-methyl-imidazol-yl | —H | —H | 525 |
| 1984 | —H | —H | 4-methyl-1,2,4-triazol-yl | —H | —H | 526 |
| 1985 | —H | —H | 4-methyl-thiomorpholin-yl | —H | —H | 560 |
| 1986 | —H | —H | 1-methyl-tetrazol-yl | —H | —H | 527 |
| 1987 | —H | —H | 3-methyl-pyridin-yl | —H | —H | 536 |
| 1988 | —H | —H | 4-methyl-pyridin-yl | —H | —H | 536 |
| 1989 | —H | 4-methyl-pyridin-yl | —H | —H | —H | 536 |
| 1990 | —H | —H | 2-methyl-furan-yl | —H | —H | 525 |
| 1991 | —H | —H | 5-methyl-oxazol-yl | —H | —H | 526 |

TABLE 123

| Example | R26 | R27 | R28 | R29 | R210 | MS (M + 1) |
|---|---|---|---|---|---|---|
| 1992 | —H | —H | —CH₃ | —H | —H | 503 |
| 1993 | —H | —H | —Cl | —H | —H | 523 |
| 1994 | —H | —H | —F | —H | —H | 507 |
| 1995 | —H | —H | —CN | —H | —H | 514 |

TABLE 124

| Example | R21 | MS (M + 1) |
|---|---|---|
| 1996 | 2-methylchroman | 515 |
| 1997 | 1-(4-chlorophenyl)ethyl | 519 |
| 1998 | 2,3-dichloro-5-methylpyridine | 528 |
| 1999 | 2-methyl-1H-indole | 498 |
| 2000 | 2-methyl-1,8-naphthyridine | 510 |
| 2001 | 3-methylquinoline | 510 |
| 2002 | 3-methylisoquinoline | 510 |
| 2003 | 2-methylbenzofuran | 499 |

TABLE 124-continued

| Example | R21 | MS (M + 1) |
|---|---|---|
| 2004 | 5-fluoro-2-methyl-1H-indole | 516 |
| 2005 | 2-methylbenzothiophene | 515 |
| 2006 | 6-methyl-3,4-dihydroquinolin-2(1H)-one | 528 |
| 2007 | 1-ethyl-3-methylquinolin-2(1H)-one | 554 |
| 2008 | 6,8-dimethyl-3,4-dihydroquinolin-2(1H)-one | 542 |
| 2009 | 1-ethyl-6-methyl-3,4-dihydroquinolin-2(1H)-one | 556 |
| 2010 | 8-methoxy-5-methyl-3,4-dihydroquinolin-2(1H)-one | 558 |
| 2011 | 4-methoxy-2-methyl-1H-indole | 528 |

TABLE 124-continued
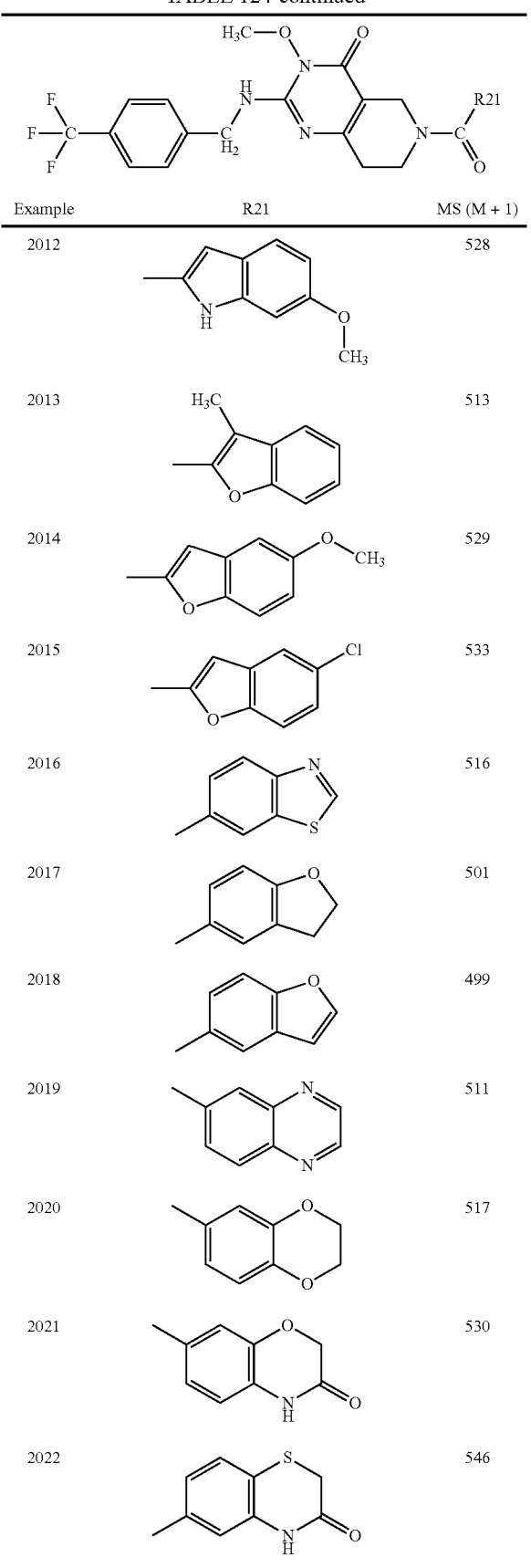
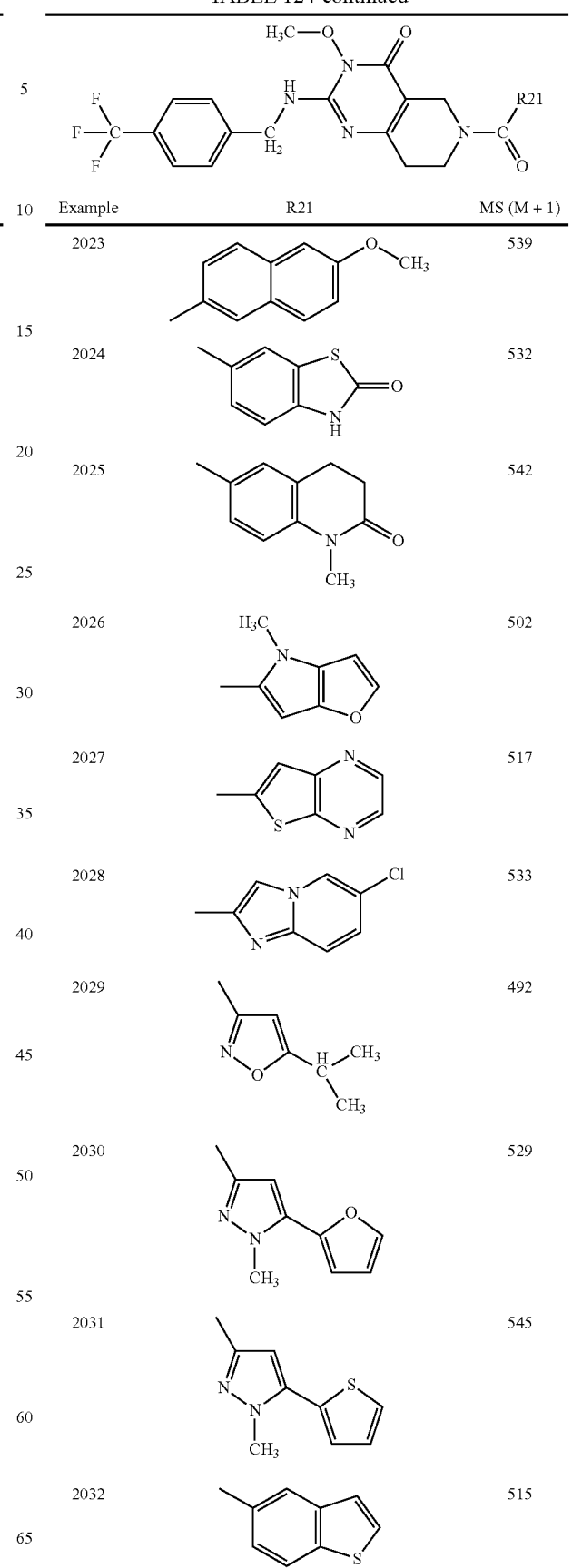
| Example | MS (M+1) |
|---|---|
| 2012 | 528 |
| 2013 | 513 |
| 2014 | 529 |
| 2015 | 533 |
| 2016 | 516 |
| 2017 | 501 |
| 2018 | 499 |
| 2019 | 511 |
| 2020 | 517 |
| 2021 | 530 |
| 2022 | 546 |
| 2023 | 539 |
| 2024 | 532 |
| 2025 | 542 |
| 2026 | 502 |
| 2027 | 517 |
| 2028 | 533 |
| 2029 | 492 |
| 2030 | 529 |
| 2031 | 545 |
| 2032 | 515 |

TABLE 124-continued

| Example | R21 | MS (M + 1) |
|---|---|---|
| 2033 | 6-methyl-quinolin-2(1H)-one | 526 |
| 2034 | 1,5-dimethyl-3,4-dihydroquinolin-2(1H)-one | 542 |
| 2035 | 1,5-dimethyl-1H-indole | 512 |
| 2036 | 5-methylquinolin-2(1H)-one | 526 |
| 2037 | 3-chloro-2-methylbenzo[b]thiophene | 549 |
| 2038 | 2,3-dimethylbenzo[b]thiophene | 529 |
| 2039 | 6-fluoro-2-methylbenzo[b]thiophene | 533 |
| 2040 | (4-chlorophenylthio)methyl | 539 |
| 2041 | 5-chloro-3-methylbenzo[b]thiophene | 549 |
| 2042 | 1,3-dimethyl-1H-indazole | 513 |
| 2043 | 2-methylpyrazolo[1,5-a]pyridine | 499 |
| 2044 | 2-methylthieno[2,3-b]pyridine | 516 |
| 2045 | 3-methylquinoxaline | 511 |
| 2046 | 5-methyl-2,3-dihydro-1H-indene | 499 |
| 2047 | 4-methylisoquinoline | 510 |
| 2048 | 7-methyl-4,5-dihydrobenzo[f][1,4]oxazepin-3(2H)-one | 544 |
| 2049 | 3-chloro-2-methylthiophene | 499 |
| 2050 | 1,5-dimethyl-1H-benzo[d]imidazole | 513 |
| 2051 | 1,6-dimethyl-1H-indole | 512 |

TABLE 124-continued

[Structure: H3C-O, F3C-phenyl-CH2-NH-pyrimidinone-N-C(=O)-R21]

| Example | R21 | MS (M + 1) |
|---|---|---|
| 2052 | 2-methyl-1,8-naphthyridine | 511 |
| 2053 | 6-methyl-4-methyl-2H-benzo[b][1,4]thiazin-3(4H)-one | 560 |
| 2054 | 7-methylquinoline | 510 |
| 2055 | 2-methylbenzothiazole | 516 |
| 2056 | 2-methylindolizine | 498 |
| 2057 | 7-methylbenzoxazol-2(3H)-one | 516 |
| 2058 | 6-methyl-2H-benzo[d][1,3]oxazin-2(1H)-one | 530 |
| 2059 | 6-methylchroman | 515 |

TABLE 125

[Structure: H3C-O, Cl-phenyl-CH(cyclopropyl)-NH-pyrimidinone-N-C(=O)-phenyl with R26, R27, R28, R29, R210]

| Example | R26 | R27 | R28 | R29 | R210 | MS (M + 1) |
|---|---|---|---|---|---|---|
| 2060 | —H | —H | —H | —H | —H | 465 |
| 2061 | —H | —H | —CH3 | —H | —H | 479 |
| 2062 | —H | —H | —Cl | —H | —H | 499 |
| 2063 | —H | —H | —OCH3 | —H | —H | 495 |
| 2064 | —H | —Cl | —Cl | —H | —H | 535 |
| 2065 | —F | —H | —CF3 | —H | —H | 551 |
| 2066 | —H | —CN | —H | —H | —H | 490 |
| 2067 | —H | —N(CH3)2 | —H | —H | —H | 508 |
| 2068 | —H | —CH3 | —CH3 | —H | —H | 493 |
| 2069 | —F | —H | —F | —H | —F | 519 |
| 2070 | —F | —H | —H | —H | —F | 501 |
| 2071 | —OCH3 | —H | —Cl | —H | —H | 529 |
| 2072 | —H | —H | —N(C2H5)2 | —H | —H | 536 |
| 2073 | —H | —H | —CH=CH2 | —H | —H | 491 |
| 2074 | —F | —H | —OCH3 | —H | —H | 513 |
| 2075 | —H | —F | —CH3 | —H | —H | 497 |
| 2076 | —H | —CH3 | —Cl | —H | —H | 523 |
| 2077 | —H | —Cl | —CH3 | —H | —H | 513 |
| 2078 | —H | —H | —OC2H5 | —H | —H | 509 |
| 2079 | —H | —H | —SCH3 | —H | —H | 511 |
| 2080 | —H | —F | —OCH3 | —H | —H | 513 |
| 2081 | —F | —H | —Cl | —H | —H | 517 |
| 2082 | —F | —H | —CH3 | —H | —H | 497 |
| 2083 | —H | —CN | —H | —F | —H | 508 |
| 2084 | —H | —F | —CN | —H | —H | 508 |
| 2085 | —H | —CN | —F | —H | —H | 508 |
| 2086 | —H | —H | N-methylimidazole | —H | —H | 531 |
| 2087 | —H | —H | N-methyl-1,2,4-triazole | —H | —H | 532 |
| 2088 | —H | —H | N-methylthiomorpholine | —H | —H | 566 |
| 2089 | —H | —H | N-methyltetrazole | —H | —H | 533 |
| 2090 | —H | —H | 3-methylpyridine | —H | —H | 542 |
| 2091 | —H | —H | 4-methylpyridine | —H | —H | 542 |
| 2092 | —H | 4-methylpyridine | —H | —H | —H | 542 |

TABLE 125-continued

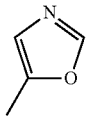

| Example | R26 | R27 | R28 | R29 | R210 | MS (M + 1) |
|---|---|---|---|---|---|---|
| 2093 | —H | —H | (5-methyloxazole) | —H | —H | 532 |

TABLE 126

| Example | R26 | R27 | R28 | R29 | R210 | MS (M + 1) |
|---|---|---|---|---|---|---|
| 2094 | —H | —H | —CH₃ | —H | —H | 509 |
| 2095 | —H | —H | —Cl | —H | —H | 529 |
| 2096 | —H | —H | —F | —H | —H | 513 |
| 2097 | —H | —H | —CN | —H | —H | 520 |

TABLE 127

| Example | R21 | MS (M + 1) |
|---|---|---|
| 2098 | 2-methylchroman | 521 |
| 2099 | 4-chlorostyryl | 525 |
| 2100 | 2,3-dichloro-5-methylpyridine | 535 |

TABLE 127-continued

| Example | R21 | MS (M + 1) |
|---|---|---|
| 2101 | 2-methylindole | 504 |
| 2102 | 2-methylquinoline | 516 |
| 2103 | 3-methylquinoline | 516 |
| 2104 | 3-methylisoquinoline | 516 |
| 2105 | 2-methylbenzofuran | 505 |
| 2106 | 5-fluoro-2-methylindole | 522 |
| 2107 | 2-methylbenzothiophene | 521 |
| 2108 | 6-methyl-3,4-dihydroquinolin-2(1H)-one | 534 |
| 2109 | 1-ethyl-3-methylquinolin-2(1H)-one | 560 |
| 2110 | 6,8-dimethyl-3,4-dihydroquinolin-2(1H)-one | 548 |

TABLE 127-continued

| Example | R21 | MS (M + 1) |
|---|---|---|
| 2111 | 1-ethyl-6-methyl-3,4-dihydroquinolin-2(1H)-one | 562 |
| 2112 | 8-methoxy-5-methyl-3,4-dihydroquinolin-2(1H)-one | 564 |
| 2113 | 4-methoxy-2-methyl-1H-indole | 534 |
| 2114 | 6-methoxy-2-methyl-1H-indole | 534 |
| 2115 | 2,3-dimethylbenzofuran | 519 |
| 2116 | 5-methoxy-2-methylbenzofuran | 535 |
| 2117 | 5-chloro-2-methylbenzofuran | 539 |
| 2118 | 6-methylbenzo[d]thiazole | 522 |
| 2119 | 5-methyl-2,3-dihydrobenzofuran | 507 |
| 2120 | 5-methylbenzofuran | 505 |
| 2121 | 6-methylquinoxaline | 517 |
| 2122 | 6-methyl-2,3-dihydrobenzo[b][1,4]dioxine | 523 |
| 2123 | 6-methyl-2H-benzo[b][1,4]oxazin-3(4H)-one | 536 |
| 2124 | 6-methyl-2H-benzo[b][1,4]thiazin-3(4H)-one | 552 |
| 2125 | 2-methoxy-6-methylnaphthalene | 545 |
| 2126 | 6-methylbenzo[d]thiazol-2(3H)-one | 538 |
| 2127 | 1,6-dimethyl-3,4-dihydroquinolin-2(1H)-one | 548 |
| 2128 | 4,5-dimethyl-4H-furo[3,2-b]pyrrole | 508 |
| 2129 | 6-methylthieno[2,3-b]pyrazine | 523 |

TABLE 127-continued

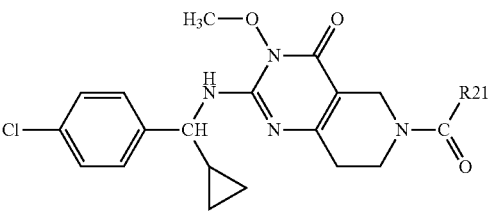

| Example | R21 | MS (M + 1) |
|---|---|---|
| 2130 | 2-methyl-6-chloroimidazo[1,2-a]pyrimidine | 539 |
| 2131 | 3-methyl-5-isopropylisoxazole | 498 |
| 2132 | 1,3-dimethyl-5-(furan-2-yl)pyrazole | 535 |
| 2133 | 1,3-dimethyl-5-(thien-2-yl)pyrazole | 551 |
| 2134 | 5-methylbenzothiophene | 521 |
| 2135 | 1,5-dimethyl-3,4-dihydroquinolin-2(1H)-one | 548 |
| 2136 | 1,5-dimethylindole | 518 |
| 2137 | 5-methylquinolin-2(1H)-one | 532 |
| 2138 | 3-chloro-2-methylbenzothiophene | 555 |
| 2139 | 2,3-dimethylbenzothiophene | 535 |
| 2140 | 2-methyl-6-fluorobenzothiophene | 539 |
| 2141 | (4-chlorophenylthio)methyl | 545 |
| 2142 | 3-methyl-5-chlorobenzothiophene | 555 |
| 2143 | 1,3-dimethylindazole | 519 |
| 2144 | 2-methylpyrazolo[1,5-a]pyridine | 505 |
| 2145 | 2-methylthieno[2,3-b]pyridine | 522 |
| 2146 | 3-methylquinoxaline | 517 |
| 2147 | 5-methyl-2,3-dihydro-1H-indene | 505 |

TABLE 127-continued

| Example | R21 | MS (M + 1) |
|---|---|---|
| 2148 | 4-methylisoquinoline | 516 |
| 2149 | 7-methyl-4,5-dihydrobenzo[f][1,4]oxazepin-3(2H)-one | 550 |
| 2150 | 3-chloro-2-methylthiophene | 505 |
| 2151 | 1,5-dimethylbenzimidazole | 519 |
| 2152 | 1,6-dimethylindole | 518 |
| 2153 | 2-methyl-1,8-naphthyridine | 517 |
| 2154 | 4,6-dimethyl-2H-benzo[b][1,4]thiazin-3(4H)-one | 566 |
| 2155 | 7-methylquinoline | 516 |
| 2156 | 2-methylbenzothiazole | 522 |
| 2157 | 2-methylindolizine | 504 |
| 2158 | 7-methylbenzoxazol-2(3H)-one | 522 |
| 2159 | 6-methyl-4H-benzo[d][1,3]oxazin-2(1H)-one | 536 |
| 2160 | 6-methylchroman | 521 |
| 2161 | 6-methylisoindolin-1-one | 520 |
| 2162 | 3,5-dimethylbenzoxazol-2(3H)-one | 536 |
| 2163 | 2,5-dimethylpyridine | 480 |
| 2164 | 5-methoxy-2-methylpyridine | 496 |
| 2165 | 6-methyl-1,2,3,4-tetrahydronaphthalene | 519 |
| 2166 | 6-methylnicotinonitrile | 491 |
| 2167 | 2-methoxy-5-methylthiophene | 501 |

TABLE 127-continued
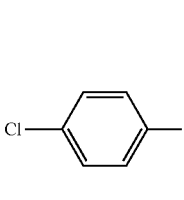
| Example | R21 | MS (M + 1) |
|---|---|---|
| 2168 | 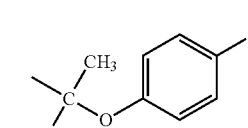 | 548 |
| 2169 | 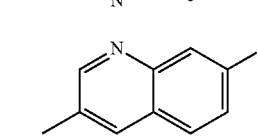 | 550 |
| 2170 | 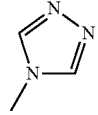 | 550 |
TABLE 128
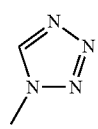
| Example | R26 | R27 | R28 | R29 | R210 | MS (M + 1) |
|---|---|---|---|---|---|---|
| 2171 | —H | —H | —H | —H | —H | 465 |
| 2172 | —H | —H | —CH₃ | —H | —H | 479 |
| 2173 | —H | —H | —OCH₃ | —H | —H | 495 |
| 2174 | —H | —Cl | —Cl | —H | —H | 534 |
| 2175 | —F | —H | —CF₃ | —H | —H | 551 |
| 2176 | —H | —CN | —H | —H | —H | 490 |
| 2177 | —H | —N(CH₃)₂ | —H | —H | —H | 508 |
| 2178 | —H | —CH₃ | —CH₃ | —H | —H | 493 |
| 2179 | —F | —H | —F | —H | —F | 519 |
| 2180 | —F | —H | —H | —H | —F | 501 |
| 2181 | —OCH₃ | —H | —Cl | —H | —H | 529 |
| 2182 | —H | —H | —N(C₂H₅)₂ | —H | —H | 536 |
| 2183 | —H | —H | —CH=CH₂ | —H | —H | 491 |
| 2184 | —F | —H | —OCH₃ | —H | —H | 513 |
| 2185 | —H | —F | —CH₃ | —H | —H | 497 |
| 2186 | —H | —CH₃ | —Cl | —H | —H | 513 |
| 2187 | —H | —Cl | —CH₃ | —H | —H | 513 |
| 2188 | —H | —H | —OC₂H₅ | —H | —H | 509 |
| 2189 | —H | —H | —SCH₃ | —H | —H | 511 |
| 2190 | —H | —H | 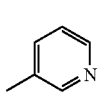 | —H | —H | 531 |
TABLE 128-continued
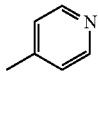
| Example | R26 | R27 | R28 | R29 | R210 | MS (M + 1) |
|---|---|---|---|---|---|---|
| 2191 | —H | —H | 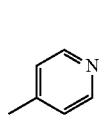 | —H | —H | 532 |
| 2192 | —H | —H | 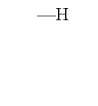 | —H | —H | 533 |
| 2193 | —H | —H | 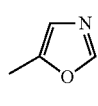 | —H | —H | 542 |
| 2194 | —H | —H | 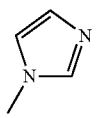 | —H | —H | 542 |
| 2195 | —H | —H | | —H | —H | 542 |
| 2196 | —H | —H | | —H | —H | 532 |
TABLE 129
| Example | R26 | R27 | R28 | R29 | R210 | MS (M + 1) |
|---|---|---|---|---|---|---|
| 2197 | —H | —H | —CH₃ | —H | —H | 509 |
| 2198 | —H | —H | —Cl | —H | —H | 529 |
| 2199 | —H | —H | —F | —H | —H | 513 |
| 2200 | —H | —H | —CN | —H | —H | 520 |

TABLE 130

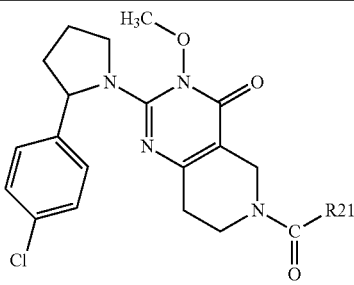

| Example | R21 | MS (M + 1) |
|---|---|---|
| 2201 | 2-methylchroman | 521 |
| 2202 | 4-chlorostyryl | 525 |
| 2203 | 2,3-dichloro-5-methylpyridin-yl | 535 |
| 2204 | 2-methyl-1H-indol-yl | 504 |
| 2205 | 2-methylquinolin-yl | 516 |
| 2206 | 3-methylquinolin-yl | 516 |
| 2207 | 3-methylisoquinolin-yl | 516 |
| 2208 | 2-methylbenzofuran-yl | 505 |
| 2209 | 5-fluoro-2-methyl-1H-indol-yl | 522 |
| 2210 | 2-methylbenzo[b]thiophen-yl | 521 |
| 2211 | 6-methyl-3,4-dihydroquinolin-2(1H)-one | 534 |

TABLE 130-continued

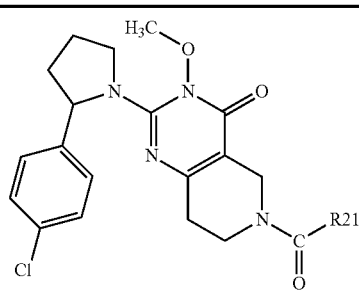

| Example | R21 | MS (M + 1) |
|---|---|---|
| 2212 | 1-ethyl-3-methylquinolin-2(1H)-one | 560 |
| 2213 | 6,8-dimethyl-3,4-dihydroquinolin-2(1H)-one | 548 |
| 2214 | 1-ethyl-6-methyl-3,4-dihydroquinolin-2(1H)-one | 562 |
| 2215 | 8-methoxy-5-methyl-3,4-dihydroquinolin-2(1H)-one | 564 |
| 2216 | 4-methoxy-2-methyl-1H-indol-yl | 534 |
| 2217 | 6-methoxy-2-methyl-1H-indol-yl | 534 |
| 2218 | 2,3-dimethylbenzofuran-yl | 519 |

TABLE 130-continued

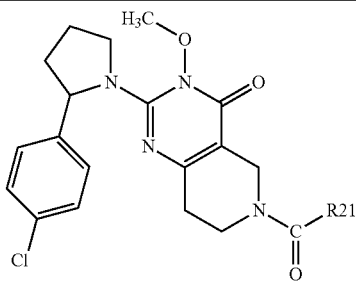

| Example | R21 | MS (M + 1) |
|---|---|---|
| 2219 | 2-methyl-5-methoxybenzofuran | 535 |
| 2220 | 2-methyl-5-chlorobenzofuran | 539 |
| 2221 | 6-methylbenzothiazole | 522 |
| 2222 | 5-methyl-2,3-dihydrobenzofuran | 507 |
| 2223 | 5-methylbenzofuran | 505 |
| 2224 | 6-methylquinoxaline | 517 |
| 2225 | 6-methyl-2,3-dihydrobenzo[1,4]dioxine | 523 |
| 2226 | 7-methyl-3-oxo-3,4-dihydro-2H-benzo[1,4]oxazine | 536 |
| 2227 | 6-methyl-3-oxo-3,4-dihydro-2H-benzo[1,4]thiazine | 552 |
| 2228 | 6-methoxy-2-methylnaphthalene | 545 |
| 2229 | 6-methyl-2-oxo-2,3-dihydrobenzothiazole | 538 |

TABLE 130-continued

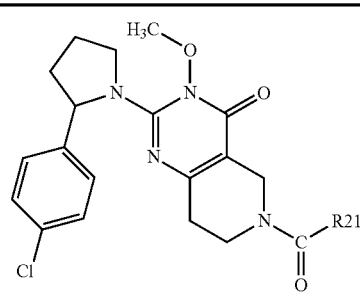

| Example | R21 | MS (M + 1) |
|---|---|---|
| 2230 | 6-methyl-1-methyl-3,4-dihydroquinolin-2(1H)-one | 548 |
| 2231 | 1,5-dimethyl-4H-furo[3,2-b]pyrrole | 508 |
| 2232 | 6-methylthieno[2,3-b]pyrazine | 523 |
| 2233 | 6-chloro-2-methylimidazo[1,2-a]pyridine | 539 |
| 2234 | 3-methyl-5-isopropylisoxazole | 498 |
| 2235 | 1,3-dimethyl-5-(2-furyl)pyrazole | 535 |
| 2236 | 1,3-dimethyl-5-(2-thienyl)pyrazole | 551 |
| 2237 | 5-methylbenzothiophene | 521 |

TABLE 130-continued
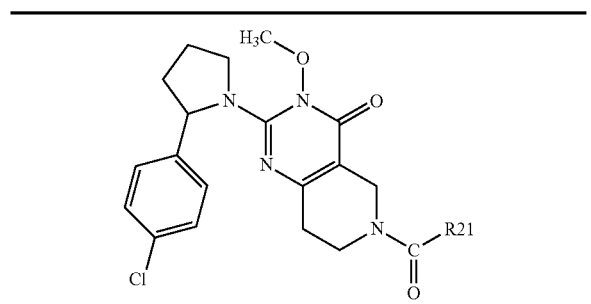
| Example | R21 | MS (M + 1) |
|---------|-----|------------|
| 2238 | | 532 |
| 2239 | | 548 |
| 2240 | | 518 |
| 2241 | | 532 |
| 2242 | | 555 |
| 2243 | | 535 |
| 2244 | | 539 |
| 2245 | | 545 |
TABLE 130-continued
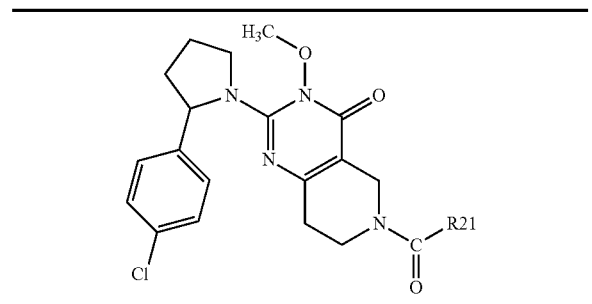
| Example | R21 | MS (M + 1) |
|---------|-----|------------|
| 2246 | | 555 |
| 2247 | | 519 |
| 2248 | | 505 |
| 2249 | | 522 |
| 2250 | | 517 |
| 2251 | | 505 |
| 2252 | | 516 |
| 2253 | | 550 |
| 2254 | | 505 |

TABLE 130-continued
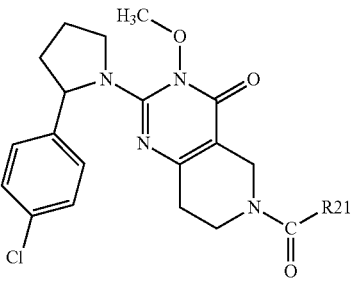
| Example | R21 | MS (M + 1) |
|---|---|---|
| 2255 | 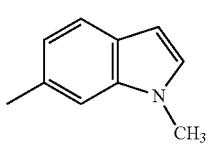 | 519 |
| 2256 | 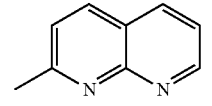 | 518 |
| 2257 | 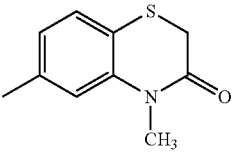 | 517 |
| 2258 | 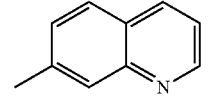 | 566 |
| 2259 | 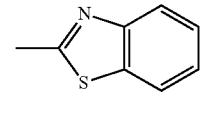 | 516 |
| 2260 | 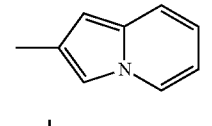 | 522 |
| 2261 | 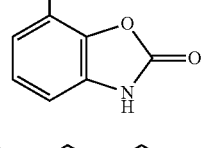 | 504 |
| 2262 | 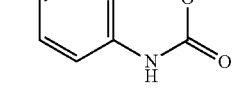 | 522 |
| 2263 | 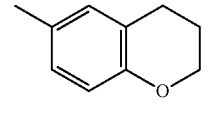 | 536 |
| 2264 | 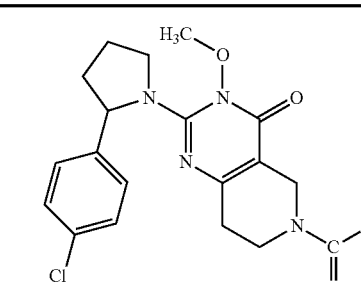 | 521 |
TABLE 131
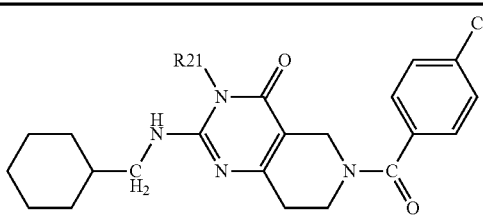
| Example | R21 | MS (M + 1) |
|---|---|---|
| 2265 | —CH$_2$C≡CCH$_3$ | 453 |
| 2266 | —(CH$_2$)$_2$C≡CH | 453 |
| 2267 | —OC$_2$H$_5$ | 445 |
| 2268 | —OCH$_2$CH(CH$_3$)$_2$ | 473 |
| 2269 | —OCH(CH$_3$)$_2$ | 459 |
| 2270 | —CH$_2$C≡CH | 439 |
| 2271 | —N(CH$_3$)$_2$ | 444 |
| 2272 | 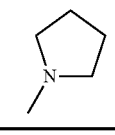 | 470 |
TABLE 132
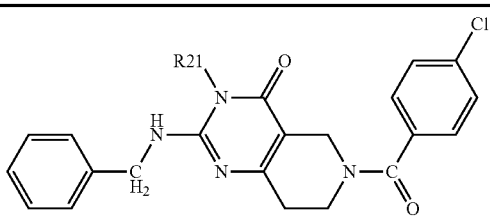
| Example | R21 | MS (M + 1) |
|---|---|---|
| 2273 | —CH$_2$C≡CCH$_3$ | 447 |
| 2274 | —(CH$_2$)$_2$C≡CH | 447 |
| 2275 | —OCH(CH$_3$)$_2$ | 453 |
| 2276 | —CH$_2$C≡CH | 433 |
| 2277 | —N(CH$_3$)$_2$ | 438 |
| 2278 |  | 464 |

TABLE 133
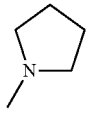
| Example | R21 | MS (M + 1) |
|---|---|---|
| 2279 | —CH₂C≡CCH₃ | 479 |
| 2280 | —(CH₂)₂C≡CH | 479 |
| 2281 | —OC₂H₅ | 471 |
| 2282 | —OCH₂CH(CH₃)₂ | 499 |
| 2283 | —OCH(CH₃)₂ | 485 |
| 2284 | 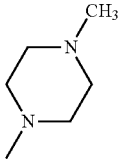 | 496 |
| 2285 | 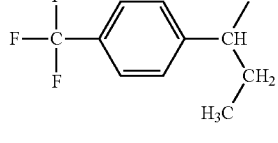 | 525 |
TABLE 134
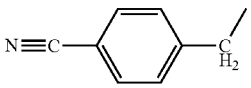
| Example | R21 | MS (M + 1) |
|---|---|---|
| 2286 | 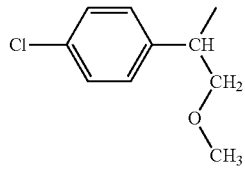 | 529 |
| 2287 | 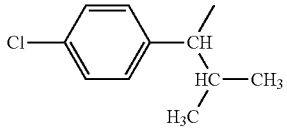 | 458 |
| 2288 | 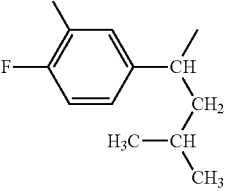 | 511 |
TABLE 134-continued
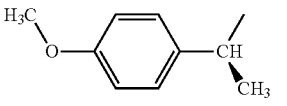
| Example | R21 | MS (M + 1) |
|---|---|---|
| 2289 | 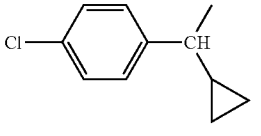 | 509 |
| 2290 | 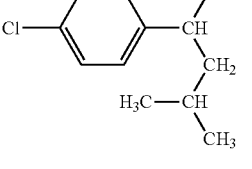 | 541 |
| 2291 | 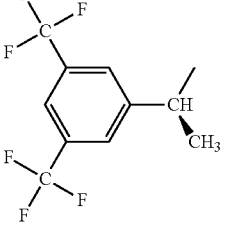 | 477 |
| 2292 | | 507 |
| 2293 | | 523 |
| 2294 | | 583 |

TABLE 135

Structure: core with H3C-N(CH3)- and NH-R21 substituents on pyrimidinone fused to tetrahydropyridine bearing 4-chlorobenzoyl group.

| Example | R21 | MS (M + 1) |
|---|---|---|
| 2295 | 1-(4-trifluoromethylphenyl)propyl (CH(CH3)CH2- with 4-CF3-phenyl) | 534 |
| 2296 | 4-cyanobenzyl | 463 |
| 2297 | 1-(4-chlorophenyl)-2-methoxyethyl | 516 |
| 2298 | 1-(4-chlorophenyl)-2-methylpropyl (isopropyl branch) | 514 |
| 2299 | 1-(3-chloro-4-fluorophenyl)-3-methylbutyl | 546 |
| 2300 | 1-(4-methoxyphenyl)ethyl | 482 |
| 2301 | 1-(4-chlorophenyl)-4,4,4-trifluorobutyl | 568 |
| 2302 | 1-(4-chlorophenyl)-1-cyclopropylmethyl | 512 |

TABLE 135-continued

| Example | R21 | MS (M + 1) |
|---|---|---|
| 2303 | 1-(4-chlorophenyl)-3-methylbutyl | 528 |
| 2304 | 1-[3,5-bis(trifluoromethyl)phenyl]ethyl | 588 |

TABLE 136

Structure: core with H3C-O-N, NH-CH(CH3)-(4-chlorophenyl), and benzoyl group bearing R26, R27, R28, R29, R210 substituents.

| Example | R26 | R27 | R28 | R29 | R210 | MS (M + 1) |
|---|---|---|---|---|---|---|
| 2305 | —H | —CN | —H | —F | —H | 482 |
| 2306 | —H | —F | —CN | —H | —H | 482 |
| 2307 | —H | —CN | —F | —H | —H | 482 |
| 2308 | —F | —H | —H | —H | —Cl | 491 |

TABLE 137

Structure: core with H3C-O-N, NH-CH(CH3)-(4-chlorophenyl), and acyl group C(O)-R21.

| Example | R21 | MS (M + 1) |
|---|---|---|
| 2309 | (pyridin-3-yloxy)methyl | 470 |

TABLE 137-continued

| Example | R21 | MS (M + 1) |
|---|---|---|
| 2310 | 4-cyanophenyl O-C(CH3)2-CH3 | 522 |
| 2311 | 5-chloro-1-methyl-indol-2-yl | 526 |
| 2312 | 6-methyl-5,6,7,8-tetrahydronaphthalen-2-yl | 493 |
| 2313 | (2,3-dihydro-1H-inden-5-yloxy)methyl CH2 with ethyl | 509 |
| 2314 | 5-chloro-1,2-dimethyl-benzimidazol-2-yl | 526 |
| 2315 | 6-methyl-5-cyano-pyridin-3-yl | 464 |
| 2316 | 5-methyl-2-methoxy-thiophen-... | 475 |
| 2317 | 6-chloro-3-methylquinolin-... | 524 |
| 2318 | 7-chloro-3-methylquinolin-... | 524 |
| 2319 | 3-chloro-4-cyanophenoxy-ethyl | 528 |
| 2320 | 6-chloro-2-methylquinolin-... | 524 |

TABLE 138

| Example | R26 | R27 | R28 | R29 | R210 | MS (M + 1) |
|---|---|---|---|---|---|---|
| 2321 | —H | —CN | —H | —F | —H | 495 |
| 2322 | —H | —F | —CN | —H | —H | 495 |
| 2323 | —H | —CN | —F | —H | —H | 495 |
| 2324 | —F | —H | —H | —H | —Cl | 504 |

TABLE 139

| Example | R21 | MS (M + 1) |
|---|---|---|
| 2325 | pyridin-3-yloxymethyl | 483 |
| 2326 | 6-methyl-5,6,7,8-tetrahydronaphthalen-2-yl | 506 |
| 2327 | (2,3-dihydro-1H-inden-5-yloxy)methyl | 522 |
| 2328 | 6-methyl-5-cyano-pyridin-3-yl | 478 |
| 2329 | 5-methyl-2-methoxy-thiophen- | 488 |
| 2330 | 4-cyanophenyl-O-C(CH3)2-CH3 | 535 |
| 2331 | 6-chloro-3-methylquinolin- | 537 |
| 2332 | 7-chloro-3-methylquinolin- | 537 |

TABLE 139-continued

Structure: 4-chlorophenyl-CH(CH3)-NH connected to pyrimidinone core with N(CH3)2 and N-C(=O)-R21

| Example | R21 | MS (M + 1) |
|---------|-----|------------|
| 2333 | -CH2-O-C6H3(Cl)-CN (3-chloro-4-(ethoxy)benzonitrile type) | 541 |
| 2334 | 2-methyl-6-chloroquinolin-yl | 537 |
| 2335 | 1-methyl-2-methyl-5-chloroindol-yl | 539 |
| 2336 | 1-methyl-2-methyl-5-chlorobenzimidazol-yl | 540 |

TABLE 140

Structure: 4-(trifluoromethyl)phenyl-CH(CH3)-NH connected to pyrimidinone core with N(CH3)2 and N-C(=O)-phenyl(R26,R27,R28,R29,R210)

| Example | R26 | R27 | R28 | R29 | R210 | MS (M + 1) |
|---------|-----|-----|-----|-----|------|------------|
| 2337 | —H | —CN | —H | —F | —H | 529 |
| 2338 | —H | —F | —CN | —H | —H | 529 |
| 2339 | —H | —CN | —F | —H | —H | 529 |
| 2340 | —F | —H | —H | —H | —Cl | 538 |

TABLE 141

Structure: 4-(trifluoromethyl)phenyl-CH(CH3)-NH connected to pyrimidinone core with N(CH3)2 and N-C(=O)-R21

| Example | R21 | MS (M + 1) |
|---------|-----|------------|
| 2341 | CH2-O-(pyridin-3-yl) | 517 |
| 2342 | 6-methyl-tetrahydronaphthalen-2-yl | 540 |
| 2343 | CH2-O-(indan-5-yl) | 556 |
| 2344 | 6-methyl-pyridin-3-yl-CN | 512 |
| 2345 | 5-methyl-2-methoxy-thiophen-yl | 522 |
| 2346 | (CH3)2C(O-)-C6H4-CN | 569 |
| 2347 | 3-methyl-6-chloroquinolin-yl | 571 |
| 2348 | 3-methyl-7-chloroquinolin-yl | 571 |
| 2349 | 2-methyl-6-chloroquinolin-yl | 571 |
| 2350 | 1-methyl-2-methyl-5-chloroindol-yl | 573 |
| 2351 | 1-methyl-2-methyl-5-chlorobenzimidazol-yl | 574 |

TABLE 141-continued
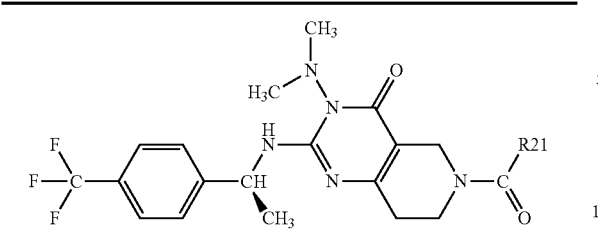
| Example | R21 | MS (M + 1) |
|---|---|---|
| 2352 | 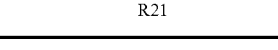 | 575 |
TABLE 142
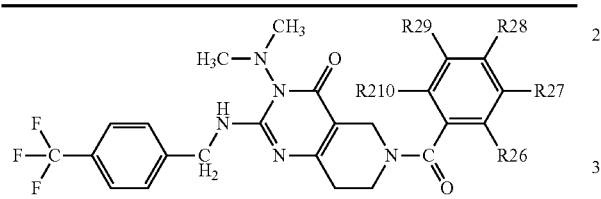
| Example | R26 | R27 | R28 | R29 | R210 | MS (M + 1) |
|---|---|---|---|---|---|---|
| 2353 | —H | —CN | —H | —F | —H | 515 |
| 2354 | —H | —F | —CN | —H | —H | 515 |
| 2355 | —H | —CN | —F | —H | —H | 515 |
| 2356 | —F | —H | —H | —H | —Cl | 542 |
TABLE 143
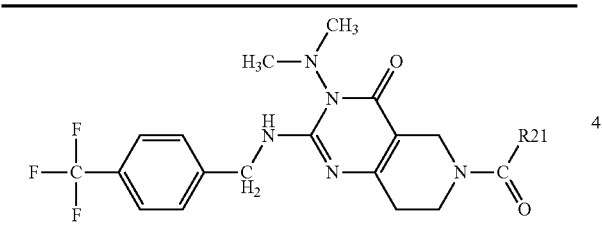
| Example | R21 | MS (M + 1) |
|---|---|---|
| 2357 | 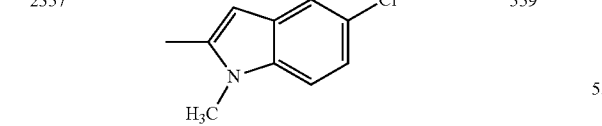 | 559 |
| 2358 | 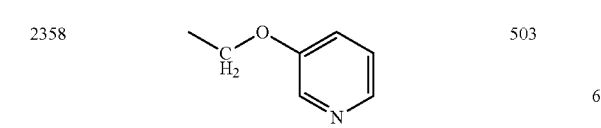 | 503 |
| 2359 | 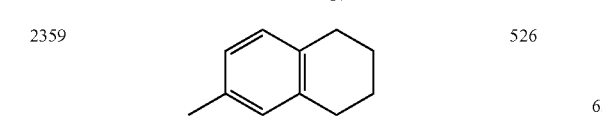 | 526 |
TABLE 143-continued
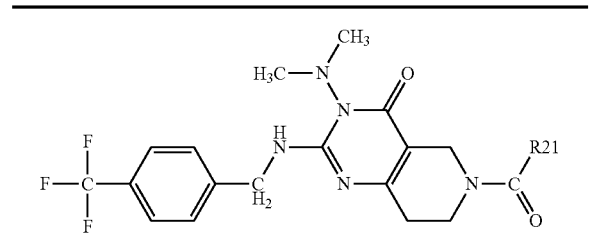
| Example | R21 | MS (M + 1) |
|---|---|---|
| 2360 | 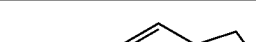 | 542 |
| 2361 |  | 498 |
| 2362 | 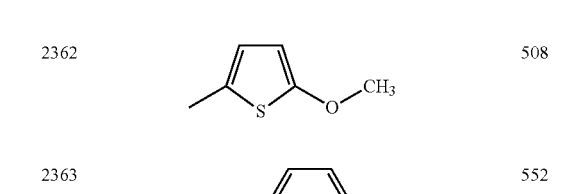 | 508 |
| 2363 | 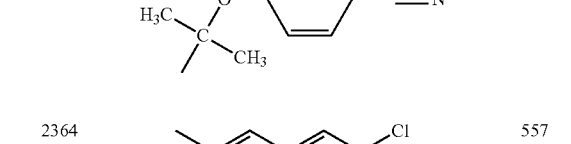 | 552 |
| 2364 | 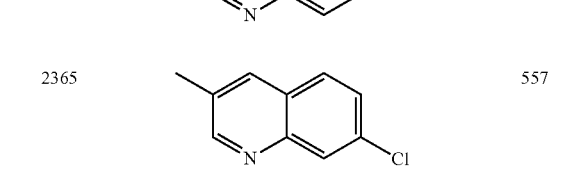 | 557 |
| 2365 | 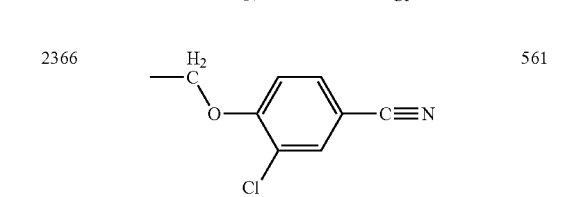 | 557 |
| 2366 | 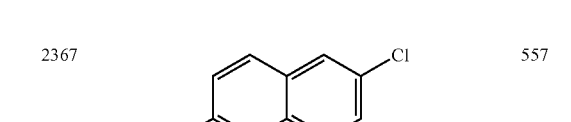 | 561 |
| 2367 | 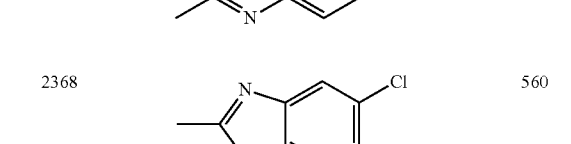 | 557 |
| 2368 |  | 560 |

TABLE 144

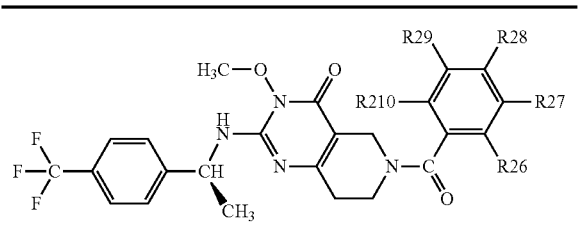

| Example | R26 | R27 | R28 | R29 | R210 | MS (M + 1) |
|---|---|---|---|---|---|---|
| 2369 | —F | —H | —H | —H | —Cl | 525 |
| 2370 | —H | —CN | —H | —F | —H | 515 |
| 2371 | —H | —F | —CN | —H | —H | 515 |
| 2372 | —H | —CN | —F | —H | —H | 515 |

TABLE 145

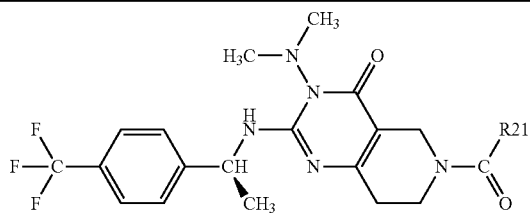

| Example | R21 | MS (M + 1) |
|---|---|---|
| 2373 | 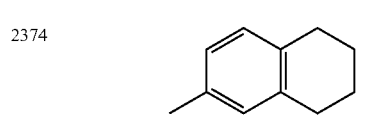 | 504 |
| 2374 | 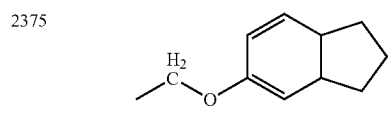 | 527 |
| 2375 | 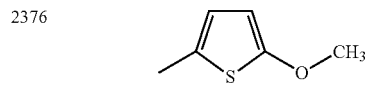 | 543 |
| 2376 | 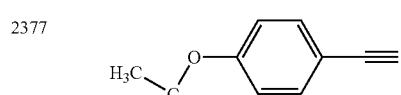 | 509 |
| 2377 | 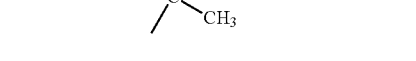 | 556 |
| 2378 | 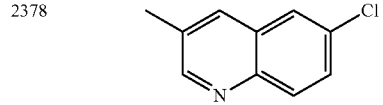 | 558 |
| 2379 | 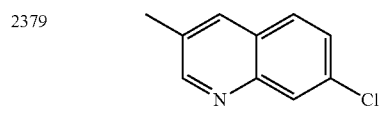 | 558 |

TABLE 145-continued

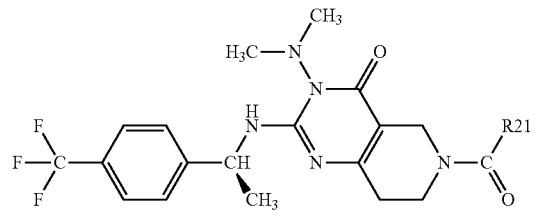

| Example | R21 | MS (M + 1) |
|---|---|---|
| 2380 | 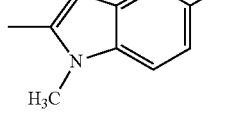 | 559 |
| 2381 | 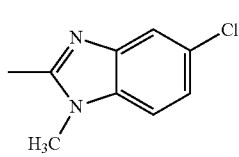 | 560 |
| 2382 | 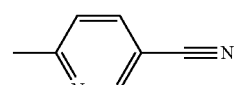 | 498 |
| 2383 | 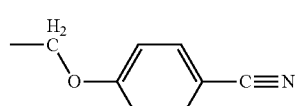 | 561 |
| 2384 | 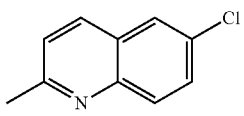 | 557 |

Example 2385

Synthesis of 6-(4-chlorobenzoyl)-3-methoxy-2-[(S)-1-(4-trifluoromethylphenyl)ethylamino]-5,6,7,8-tetrahydro-3H-pyrido[4,3-d]pyrimidin-4-one

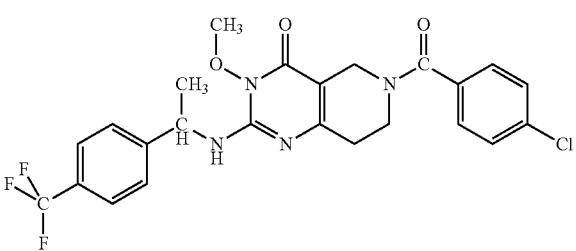 [SMILES: COn1c(NC(C)c2ccc(C(F)(F)F)cc2)nc2c(c1=O)CN(C(=O)c1ccc(Cl)cc1)CC2]

Using an appropriate starting material and following the procedure of Example 11, the object compound was synthesized.

White Powder (Ether-Ethyl Acetate)

Melting Point 208-209° C.

Example 2386

Synthesis of 4-{3-methoxy-4-oxo-2-[(S)-1-(4-trifluoromethylphenyl)ethylamino]-3,5,7,8-tetrahydro-4H-pyrido[4,3-d]pyrimidine-6-carbonyl}benzonitrile

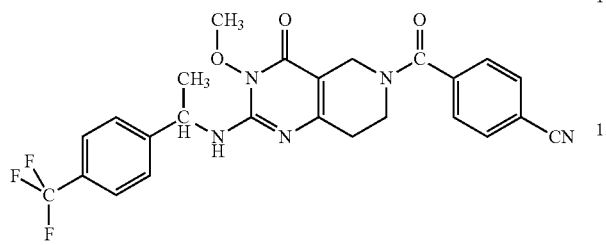

Using an appropriate starting material and following the procedure of Example 2, the object compound was synthesized.

White Powder $^1$H-NMR (CDCl$_3$) δ ppm: 1.61 (d, J=7.0 Hz, 3H), 2.31-2.79 (m, 2H), 3.40-4.06 (m, 5H), 4.15-4.68 (m, 2H), 5.12-5.30 (m, 1H), 5.70 (d, J=7.4 Hz, 1H), 7.47 (d, J=8.1 Hz, 2H), 7.53 (d, J=8.1 Hz, 2H), 7.62 (d, J=8.1 Hz, 2H), 7.71 (d, J=8.1 Hz, 2H).

Example 2387

Synthesis of 4-{4-oxo-3-pyrrolidin-1-yl-2-[(S)-1-(4-trifluoromethylphenyl)ethylamino]-3,5,7,8-tetrahydro-4H-pyrido[4,3-d]pyrimidine-6-carbonyl}benzonitrile hydrochloride

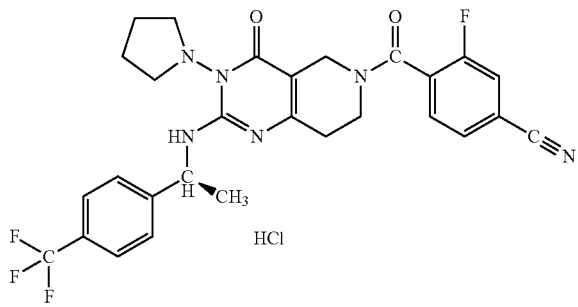 [SMILES: C[C@H](Nc1nc2c(c(=O)n1N1CCCC1)CN(C(=O)c1ccc(C#N)cc1F)CC2)c1ccc(C(F)(F)F)cc1 ; Cl]

Using an appropriate starting material and following the procedure of Example 1, the object compound was synthesized.

White Solid (Salt)

Melting Point 173.7° C.

Example 2388

Synthesis of 3-fluoro-4-{4-oxo-3-pyrrolidin-1-yl-2-[(S)-1-(4-trifluoromethylphenyl)ethylamino]-3,5,7,8-tetrahydro-4H-pyrido[4,3-d]pyrimidine-6-carbonyl}benzonitrile hydrochloride

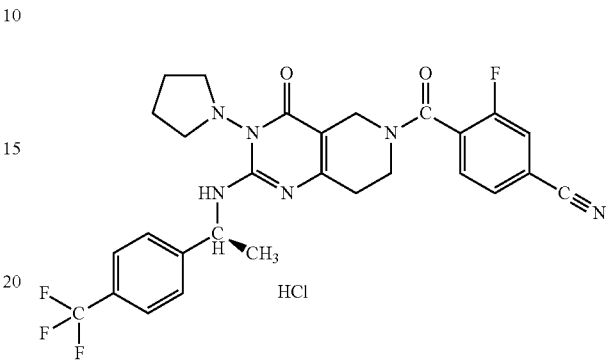

Using an appropriate starting material and following the procedure of Example 1, the object compound was synthesized.

Solid

Melting Point 124.3° C.

Example 2389

Synthesis of 6-[2-(4-chlorophenoxy)acetyl]-3-methoxy-2-[(S)-1-(4-trifluoromethylphenyl)ethylamino]-5,6,7,8-tetrahydro-3H-pyrido[4,3-d]pyrimidin-4-one

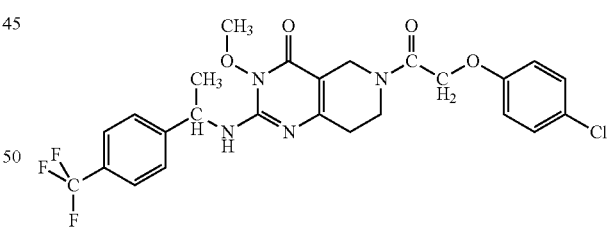

Using an appropriate starting material and following the procedure of Example 1, the object compound was synthesized.

Colorless Amorphous $^1$H-NMR (CDCl$_3$) δ ppm: 1.61 (d, J=6.8 Hz, 3H), 2.35-2.66 (m, 2H), 3.57-3.93 (m, 2H), 4.08 (s, 3H), 4.25-4.53 (m, 2H), 4.73 (s, 2H), 5.16-5.32 (m, 1H), 5.60-5.82 (m, 1H), 6.88 (d, J=8.9 Hz, 2H), 7.22 (d, J=8.9 Hz, 2H), 7.47 (d, J=8.2 Hz, 2H), 7.62 (d, J=8.2 Hz, 2H).

Example 2390

Synthesis of 6-[2-(4-chlorophenylsulfanyl)acetyl]-3-methoxy-2-[(S)-1-(4-trifluoromethylphenyl)ethylamino]-5,6,7,8-tetrahydro-3H-pyrido[4,3-d]pyrimidin-4-one

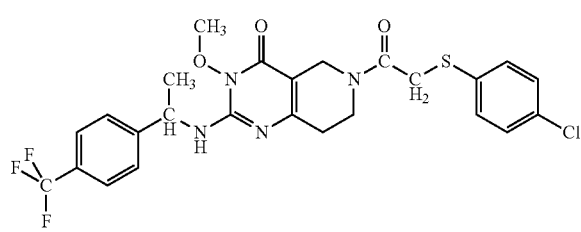 [SMILES: COn1c(NC(C)c2ccc(C(F)(F)F)cc2)nc2c(c1=O)CN(C(=O)CSc1ccc(Cl)cc1)CC2]

Using an appropriate starting material and following the procedure of Example 1, the object compound was synthesized.

Colorless Amorphous $^1$H-NMR (CDCl$_3$) δ ppm: 1.53-1.70 (m, 3H), 2.31-2.69 (m, 2H), 3.50-3.87 (m, 4H), 4.00-4.11 (m, 3H), 4.14-4.53 (m, 2H), 5.17-5.28 (m, 1H), 5.58-5.75 (m, 1H), 7.04-7.21 (m, 2H), 7.31-7.40 (m, 2H), 7.47 (d, J=7.9 Hz, 2H), 7.62 (d, J=8.3 Hz, 2H).

Example 2391

Synthesis of 6-[3-(4-chlorophenyl)propionyl]-3-methoxy-2-[(S)-1-(4-trifluoromethylphenyl)ethylamino]-5,6,7,8-tetrahydro-3H-pyrido[4,3-d]pyrimidin-4-one

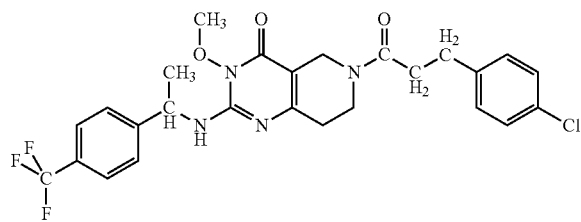 [SMILES: COn1c(NC(C)c2ccc(C(F)(F)F)cc2)nc2c(c1=O)CN(C(=O)CCc1ccc(Cl)cc1)CC2]

Using an appropriate starting material and following the procedure of Example 1, the object compound was synthesized.

Colorless Amorphous $^1$H-NMR (CDCl$_3$) δ ppm: 1.60 (d, J=6.9 Hz, 3H), 2.30-2.55 (m, 2H), 2.60-2.81 (m, 2H), 2.86-3.02 (m, 2H), 3.47-3.70 (m, 1H), 3.77-3.94 (m, 1H), 4.07 (s, 3H), 4.11-4.52 (m, 2H), 5.15-5.32 (m, 1H), 5.68 (d, J=7.5 Hz, 1H), 7.10-7.22 (m, 4H), 7.48 (d, J=8.0 Hz, 2H), 7.62 (d, J=8.0 Hz, 2H).

Example 2392

Synthesis of 6-[(E)-3-(4-chlorophenyl)acryloyl]-3-methoxy-2-[(S)-1-(4-trifluoromethylphenyl)ethylamino]-5,6,7,8-tetrahydro-3H-pyrido[4,3-d]pyrimidin-4-one

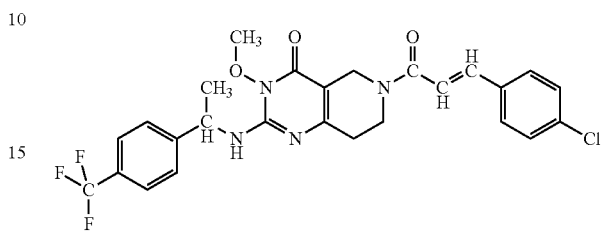

Using an appropriate starting material and following the procedure of Example 1, the object compound was synthesized.

Colorless Amorphous $^1$H-NMR (CDCl$_3$) δ ppm: 1.61 (d, J=7.0 Hz, 3H), 2.44-2.69 (m, 2H), 3.68-4.02 (m, 2H), 4.09 (s, 3H), 4.40-4.62 (m, 2H), 5.20-5.34 (m, 1H), 5.72 (d, J=7.6 Hz, 1H), 6.95 (d, J=15.6 Hz, 1H), 7.34 (d, J=6.6 Hz, 2H), 7.38-7.46 (m, 4H), 7.60-7.67 (m, 3H).

Example 2393

Synthesis of 6-(4-chlorobenzoyl)-3-ethoxy-2-[(S)-1-(4-trifluoromethylphenyl)ethylamino]-5,6,7,8-tetrahydro-3H-pyrido[4,3-d]pyrimidin-4-one hydrochloride

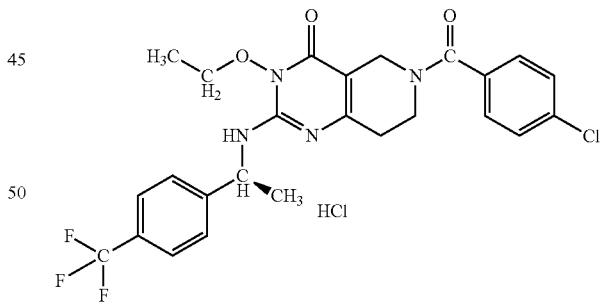

Using an appropriate starting material and following the procedure of Example 2, the object compound was synthesized.

White Solid $^1$H-NMR (DMSO-d$_6$) δ ppm: 7.97 (d, J=7.92 Hz, 1H), 7.70 (d, J=8.32 Hz, 2H), 7.63 ((d, J=8.32 Hz, 2H), 7.52 (d, J=8.4 Hz, 2H), 7.46 (J=8.4 Hz, 2H), 5.30 (m, 1H), 4.29-4.08 (m, 4H), 3.74 (br, 1H), 3.00 (br, 1H), 2.51-2.48 (m, 2H), 1.54 (d, J=7.12 Hz, 3H), 1.32 (br, 3H). H of HCl sat was not observed.

Example 2394

Synthesis of 3-methoxy-6-(4-methylbenzoyl)-2-[(S)-1-(4-trifluoromethylphenyl)ethylamino]-5,6,7,8-tetrahydro-3H-pyrido[4,3-d]pyrimidin-4-one

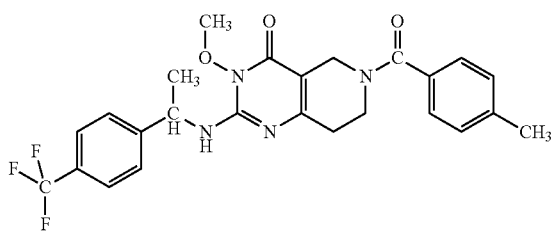 [SMILES: COn1c(NC(C)c2ccc(C(F)(F)F)cc2)nc2c(c1=O)CN(C(=O)c1ccc(C)cc1)CC2]

Using an appropriate starting material and following the procedure of Example 2, the object compound was synthesized.
White Powder
¹H-NMR (CDCl₃) δ ppm: 1.61 (d, J=6.9 Hz, 3H), 2.37 (s, 3H), 2.43-2.75 (m, 2H), 3.51-4.17 (m, 5H), 4.18-4.71 (m, 2H), 5.16-5.37 (m, 1H), 5.70 (d, J=7.5 Hz, 1H), 7.19 (d, J=8.0 Hz, 2H), 7.33 (d, J=8.0 Hz, 2H), 7.47 (d, J=8.0 Hz, 2H), 7.61 (d, J=8.0 Hz, 2H).

Example 2395

Synthesis of 3-methoxy-6-(4-trifluoromethoxybenzoyl)-2-[(S)-1-(4-trifluoromethylphenyl)ethylamino]-5,6,7,8-tetrahydro-3H-pyrido[4,3-d]pyrimidin-4-one

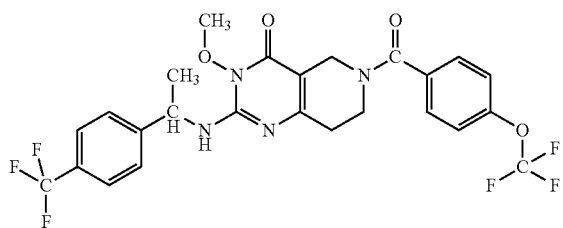 [SMILES: COn1c(NC(C)c2ccc(C(F)(F)F)cc2)nc2c(c1=O)CN(C(=O)c1ccc(OC(F)(F)F)cc1)CC2]

Using an appropriate starting material and following the procedure of Example 2, the object compound was synthesized.
White Powder
¹H-NMR (CDCl₃) δ ppm: 1.61 (d, J=7.0 Hz, 3H), 2.34-2.77 (m, 2H), 3.52-4.14 (m, 5H), 4.18-4.70 (m, 2H), 5.16-5.36 (m, 1H), 5.71 (d, J=7.9 Hz, 1H), 7.24 (d, J=8.1 Hz, 2H), 7.38-7.56 (m, 4H), 7.62 (d, J=8.1 Hz, 2H).

Example 2396

Synthesis of 6-(4-chloro-3-methylbenzoyl)-3-methoxy-2-[(S)-1-(4-trifluoromethylphenyl)ethylamino]-5,6,7,8-tetrahydro-3H-pyrido[4,3-d]pyrimidin-4-one

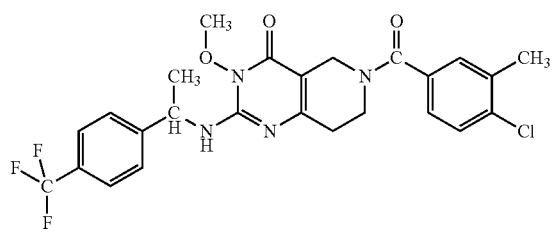 [SMILES: COn1c(NC(C)c2ccc(C(F)(F)F)cc2)nc2c(c1=O)CN(C(=O)c1ccc(Cl)c(C)c1)CC2]

Using an appropriate starting material and following the procedure of Example 1, the object compound was synthesized.
White Powder
¹H-NMR (CDCl₃) δ ppm: 1.61 (d, J=7.0 Hz, 3H), 2.38 (s, 3H), 2.43-2.73 (m, 2H), 3.34-4.15 (m, 5H), 4.17-4.70 (m, 2H), 5.17-5.35 (m, 1H), 5.68 (d, J=7.6 Hz, 1H), 7.19 (dd, J=1.8 Hz, 8.2 Hz, 1H), 7.28-7.40 (m, 2H), 7.47 (d, J=8.2 Hz, 2H), 7.62 (d, J=8.2 Hz, 2H).

Example 2397

Synthesis of 6-(4-chloro-2-methylbenzoyl)-3-methoxy-2-[(S)-1-(4-trifluoromethylphenyl)ethylamino]-5,6,7,8-tetrahydro-3H-pyrido[4,3-d]pyrimidin-4-one

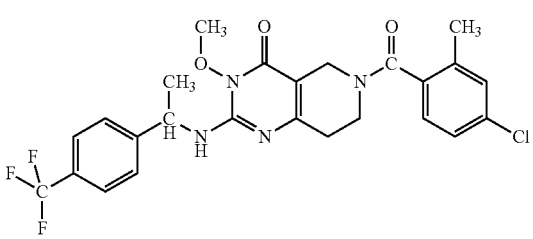 [SMILES: COn1c(NC(C)c2ccc(C(F)(F)F)cc2)nc2c(c1=O)CN(C(=O)c1ccc(Cl)cc1C)CC2]

Using an appropriate starting material and following the procedure of Example 1, the object compound was synthesized.
White Powder
¹H-NMR (CDCl₃) δ ppm: 1.61 (d, J=7.0 Hz, 3H), 2.22-2.28 (m, 3H), 2.32-2.73 (m, 2H), 3.25-4.90 (m, 7H), 5.15-5.36 (m, 1H), 5.69 (d, J=7.5 Hz, 1H), 7.06-7.11 (m, 1H), 7.15-7.29 (m, 2H), 7.44-7.49 (m, 2H), 7.61-7.64 (d, J=8.3 Hz, 2H).

Example 2398

Synthesis of 3-ethoxy-6-(thieno[2,3-b]pyridine-2-carbonyl)-2-[(S)-1-(4-trifluoromethylphenyl)ethylamino]-5,6,7,8-tetrahydro-3H-pyrido[4,3-d]pyrimidin-4-one dihydrochloride

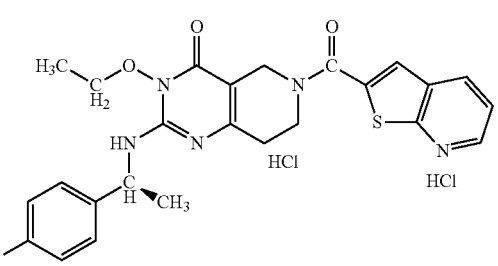

Using an appropriate starting material and following the procedure of Example 1, the object compound was synthesized.
White Solid
Melting Point 155-156.5° C.

Example 2399

Synthesis of 4-{3-ethoxy-4-oxo-2-[(S)-1-(4-trifluoromethylphenyl)ethylamino]-3,5,7,8-tetrahydro-4H-pyrido[4,3-d]pyrimidine-6-carbonyl}-3-fluorobenzonitrile hydrochloride

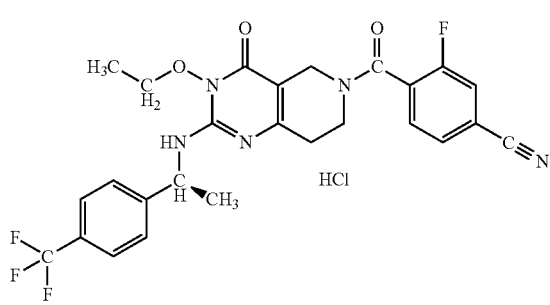 [SMILES: CCOn1c(N[C@@H](C)c2ccc(C(F)(F)F)cc2)nc2c(c1=O)CN(C(=O)c1ccc(C#N)cc1F)CC2 ; Cl]

Using an appropriate starting material and following the procedure of Example 1, the object compound was synthesized.

White Solid

Melting Point 121-122.1° C.

Example 2400

Synthesis of 3-ethoxy-6-(4-oxazol-5-ylbenzoyl)-2-[(S)-1-(4-trifluoromethylphenyl)ethylamino]-5,6,7,8-tetrahydro-3H-pyrido[4,3-d]pyrimidin-4-one hydrochloride

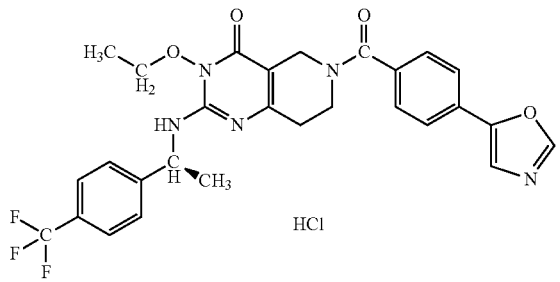 [SMILES: CCOn1c(N[C@@H](C)c2ccc(C(F)(F)F)cc2)nc2c(c1=O)CN(C(=O)c1ccc(-c3cnco3)cc1)CC2 ; Cl]

Using an appropriate starting material and following the procedure of Example 1, the object compound was synthesized.

White Solid free form: $^1$H-NMR (CDCl$_3$) δ ppm: 7.95 (s, 1H), 7.69 (d, J=8.22 Hz, 2H), 7.62 (d, J=8.18 Hz, 2H), 7.51 (d, J=8.22 Hz, 2H), 7.46 (d, J=8.18 Hz, 2H), 7.41 (s, 1H), 5.66 (brd, J=7.52 Hz, 1H), 5.27 (m, 1H), 4.70-4.20 (br, 3H), 4.00-3.80 (br, 2H), 3.58 (br, 1H), 2.60 (br, 2H), 1.61 (d, J=6.96 Hz, 3H), 1.39 (br, 3H).

Example 2401

Synthesis of 4-{3-ethoxy-4-oxo-2-[(S)-1-(4-trifluoromethylphenyl)ethylamino]-3,5,7,8-tetrahydro-4H-pyrido[4,3-d]pyrimidine-6-carbonyl}benzonitrile hydrochloride

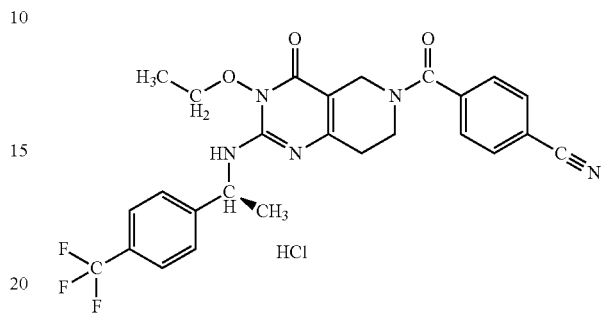

Using an appropriate starting material and following the procedure of Example 1, the object compound was synthesized.

White Amorphous free form: $^1$H-NMR (CDCl$_3$) δ ppm: 7.71 (brd, J=8.02 Hz, 2H), 7.59 (d, J=8.3 Hz, 2H), 7.53 (d, J=8.3 Hz, 2H), 7.46 (d, J=8.02 Hz, 2H), 5.68 (brd, J=7.24 Hz, 1H), 5.25 (br, 1H), 4.59-4.10 (br, 3H), 4.00-3.80 (br, 2H), 3.49 (br, 2H), 2.63-2.48 (br, 2H), 1.61 (d, J=7.00 Hz, 3H), 1.40 (br, 3H).

Example 2402

Synthesis of 3-(2-butynyl)-6-(4-imidazol-1-ylbenzoyl)-2-[(S)-1-(4-trifluoromethylphenyl)ethylamino]-5,6,7,8-tetrahydro-3H-pyrido[4,3-d]pyrimidin-4-one dihydrochloride

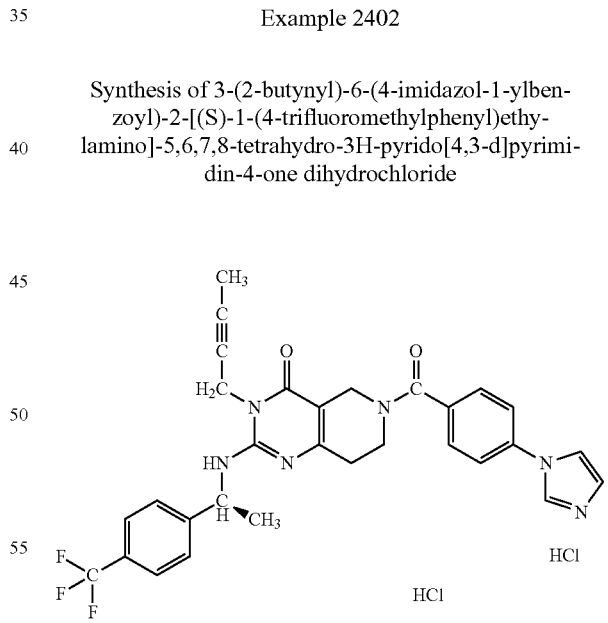

Using an appropriate starting material and following the procedure of Example 1, the object compound was synthesized.

White Amorphous free form: $^1$H-NMR (CDCl$_3$) δ ppm: 7.88 (s, 1H), 7.62-7.56 (m, 4H), 7.52 (m, 4H), 7.30-7.23 (m, 2H, overlapping CHCl3), 5.50 (d, J=6.68 Hz, 1H), 5.36 (m, 1H), 4.88-4.83 (br, 1H), 4.69-4.65 (br, 1H), 4.32 (br, 1H), 4.00 (br, 1H), 3.85 (br, 1H), 3.60 (br, 1H), 2.65-2.50 (br, 2H), 1.79 (brs, 3H), 1.61 (d, J=6.92 Hz, 3H).

Example 2403

Synthesis of 6-(5-chlorobenzofuran-2-carbonyl)-3-methoxy-2-[(S)-1-(4-trifluoromethylphenyl)ethylamino]-5,6,7,8-tetrahydro-3H-pyrido[4,3-d]pyrimidin-4-one

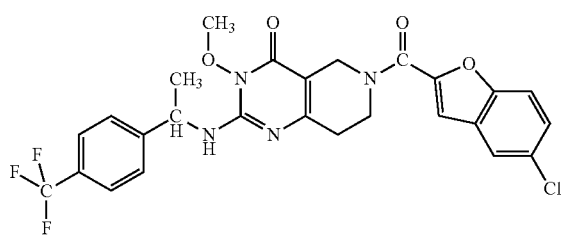 [SMILES: COn1c(NC(C)c2ccc(C(F)(F)F)cc2)nc2c(c1=O)CN(C(=O)c1cc3cc(Cl)ccc3o1)CC2]

Using an appropriate starting material and following the procedure of Example 1, the object compound was synthesized.

Beige Amorphous

¹H-NMR (DMSO-d₆) δ ppm: 1.54 (d, J=7.1 Hz, 3H), 2.32-2.61 (m, 2H), 3.70-4.04 (m, 5H), 4.15-4.62 (m, 2H), 5.24-5.38 (m, 1H), 7.42 (s, 1H), 7.47 (dd, J=2.2, 8.8 Hz, 1H), 7.63 (d, J=8.3 Hz, 2H), 7.69 (d, J=8.3 Hz, 2H), 7.73 (d, J=8.8 Hz, 1H), 7.84 (brs, 1H), 8.20 (d, J=8.2 Hz, 1H).

Example 2404

Synthesis of 3-methoxy-6-(5-methyl-thiophene-2-carbonyl)-2-[(S)-1-(4-trifluoromethylphenyl)ethylamino]-5,6,7,8-tetrahydro-3H-pyrido[4,3-d]pyrimidin-4-one

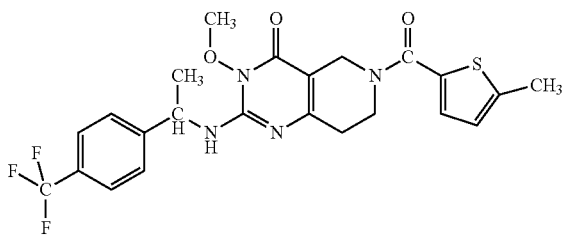 [SMILES: COn1c(NC(C)c2ccc(C(F)(F)F)cc2)nc2c(c1=O)CN(C(=O)c1ccc(C)s1)CC2]

Using an appropriate starting material and following the procedure of Example 1, the object compound was synthesized.

Beige Amorphous

¹H-NMR (CDCl₃) δ ppm: 1.61 (d, J=7.0 Hz, 3H), 2.49 (s, 3H), 2.51-2.72 (m, 2H), 3.71-3.85 (m, 1H), 3.85-3.94 (m, 1H), 4.05 (s, 3H), 4.47-4.71 (m, 2H), 5.15-5.36 (m, 1H), 5.69 (d, J=7.4 Hz, 1H), 6.71 (d, J=3.6 Hz, 1H), 7.21 (d, J=3.6 Hz, 1H), 7.47 (d, J=8.3 Hz, 2H), 7.62 (d, J=8.3 Hz, 2H).

Example 2405

Synthesis of 6-(5-chlorothiophene-2-carbonyl)-3-methoxy-2-[(S)-1-(4-trifluoromethylphenyl)ethylamino]-5,6,7,8-tetrahydro-3H-pyrido[4,3-d]pyrimidin-4-one

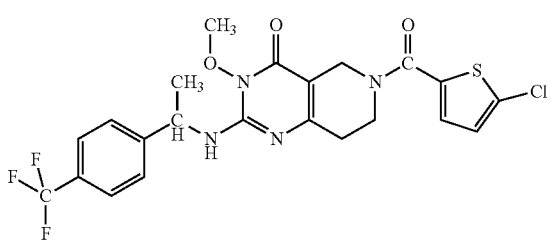 [SMILES: COn1c(NC(C)c2ccc(C(F)(F)F)cc2)nc2c(c1=O)CN(C(=O)c1ccc(Cl)s1)CC2]

Using an appropriate starting material and following the procedure of Example 1, the object compound was synthesized.

Beige Amorphous

¹H-NMR (CDCl₃) δ ppm: 1.61 (d, J=7.0 Hz, 3H), 2.45-2.71 (m, 2H), 3.72-3.85 (m, 1H), 3.86-3.97 (m, 1H), 4.06 (s, 3H), 4.46-4.69 (m, 2H), 5.18-5.35 (m, 1H), 5.71 (d, J=7.7 Hz, 1H), 6.88 (d, J=3.9 Hz, 1H), 7.18 (d, J=3.9 Hz, 1H), 7.47 (d, J=8.1 Hz, 2H), 7.61 (d, J=8.1 Hz, 2H).

Example 2406

Synthesis of 4-{3-(2-butynyl)-4-oxo-2-[(S)-1-(4-trifluoromethylphenyl)ethylamino]-3,5,7,8-tetrahydro-4H-pyrido[4,3-d]pyrimidine-6-carbonyl}-3-fluorobenzonitrile hydrochloride

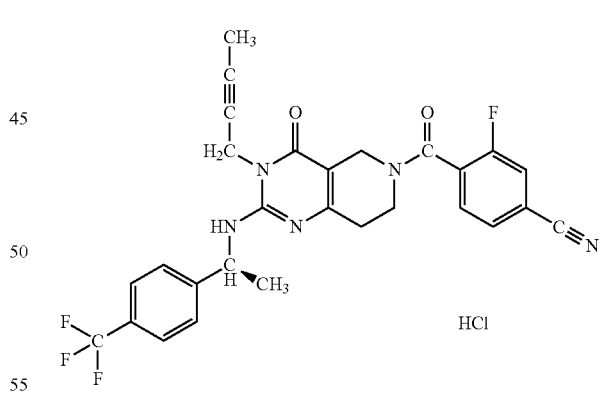

Using an appropriate starting material and following the procedure of Example 1, the object compound was synthesized.

White Amorphous free form: ¹H-NMR (CDCl₃) δ ppm: 7.62-7.59 (m, 2H), 7.54-7.40 (m, 5H), 5.52 (d, J=6.92 Hz, 1H), 5.40-5.30 (m, 1H), 4.97-4.57 (m, 3H), 4.17-4.10 (m, 1H), 4.00-3.70 (br, 1H), 3.43 (br, 1H), 2.70-2.46 (m, 2H), 1.81-1.79 (m, 3H), 1.61 (d, J=6.92 Hz, 3H). Two isomers were observed due to the amide rotamers.

Example 2407

Synthesis of 4-{3-(2-butynyl)-4-oxo-2-[(S)-1-(4-trifluoromethylphenyl)ethylamino]-3,5,7,8-tetrahydro-4H-pyrido[4,3-d]pyrimidine-6-carbonyl}benzonitrile hydrochloride

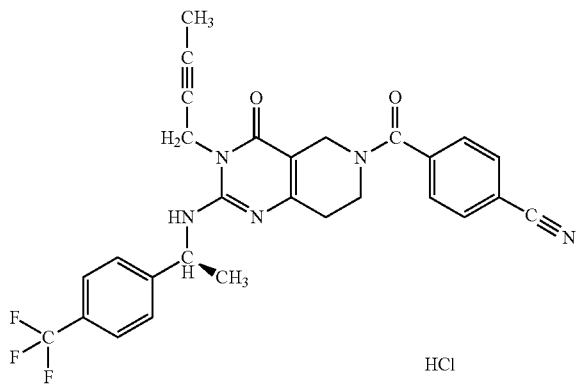 [SMILES: CC#CCn1c(N[C@@H](C)c2ccc(C(F)(F)F)cc2)nc2c(c1=O)CN(C(=O)c1ccc(C#N)cc1)CC2 ; Cl]

Using an appropriate starting material and following the procedure of Example 1, the object compound was synthesized.

White Solid free form: $^1$H-NMR (CDCl$_3$) δ ppm: 7.70 (brd, J=7.64 Hz, 2H), 7.61 (d, J=8.2 Hz, 2H), 7.53-7.48 (m, 4H), 5.51 (d, J=6.8 Hz, 1H), 5.36 (m, 1H), 5.00-4.50 (br, 2H), 4.21 (br, 1H), 4.00 (br, 1H), 3.90-3.80 (br, 1H), 3.60-3.40 (br, 1H), 2.80-2.40 (br, 2H), 1.79 (brs, 3H), 1.61 (d, J=6.96 Hz, 3H). Salt form: $^1$H NMR was observed as broad peaks.

Example 2408

Synthesis of 3-(2-butynyl)-6-(4-methylbenzoyl)-2-[(S)-1-(4-trifluoromethylphenyl)ethylamino]-5,6,7,8-tetrahydro-3H-pyrido[4,3-d]pyrimidin-4-one hydrochloride

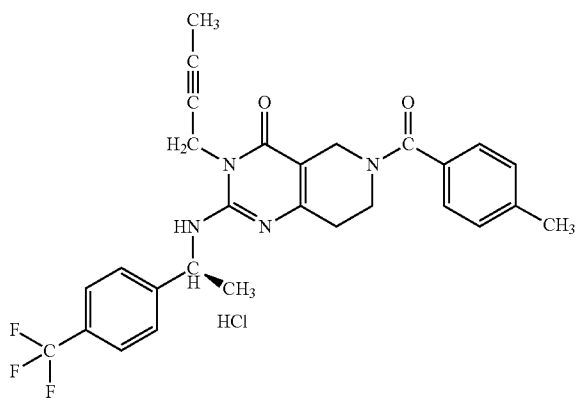 [SMILES: CC#CCn1c(N[C@@H](C)c2ccc(C(F)(F)F)cc2)nc2c(c1=O)CN(C(=O)c1ccc(C)cc1)CC2 ; Cl]

Using an appropriate starting material and following the procedure of Example 1, the object compound was synthesized.

White Solid free form: $^1$H-NMR (CDCl$_3$) δ ppm: 7.60 (d, J=8.16 Hz, 2H), 7.49 (d, J=8.16 Hz, 2H), 7.32 (d, J=7.64 Hz, 2H), 7.18 (d, J=7.64 Hz, 2H), 5.47 (d, J=6.28 Hz, 1H), 5.36 (m, 1H), 4.88-4.82 (br, 1H), 4.67 (br, 1H), 4.32 (br, 1H), 3.98 (br, 1H), 3.81 (br, 1H), 3.56 (br, 1H), 2.65-2.46 (br, 2H), 2.36 (brs, 3H), 1.78 (s, 3H), 1.60 (d, J=6.92 Hz, 3H).

Example 2409

Synthesis of 3-(2-butynyl)-6-(4-chlorobenzoyl)-2-[(S)-1-(4-trifluoromethylphenyl)ethylamino]-5,6,7,8-tetrahydro-3H-pyrido[4,3-d]pyrimidin-4-one hydrochloride

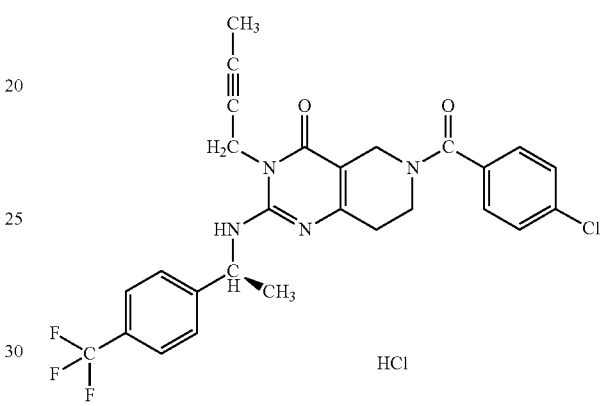

Using an appropriate starting material and following the procedure of Example 1, the object compound was synthesized.

White Solid free form: $^1$H-NMR (CDCl$_3$) δ ppm: 7.61 (d, J=8.20 Hz, 2H), 7.49 (d, J=8.20 Hz, 2H), 7.37 (s, 4H), 5.49 (d, J=6.84 Hz, 1H), 5.35 (m, 1H), 4.89-4.83 (br, 1H), 4.72-4.65 (br, 1H), 4.27 (br, 1H), 3.96 (br, 1H), 3.82 (br, 1H), 3.54 (br, 1H), 2.70-2.40 (br, 2H), 1.79 (s, 3H), 1.60 (d, J=6.96 Hz, 3H).

Example 2410

Synthesis of 3-(2-butynyl)-6-(4-oxazol-5-ylbenzoyl)-2-[(S)-1-(4-trifluoromethylphenyl)ethylamino]-5,6,7,8-tetrahydro-3H-pyrido[4,3-d]pyrimidin-4-one hydrochloride

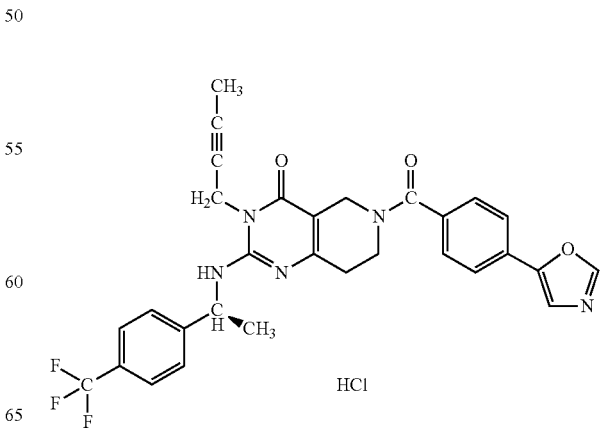

Using an appropriate starting material and following the procedure of Example 1, the object compound was synthesized.
White Solid free form: $^1$H-NMR (CDCl$_3$) δ ppm: 7.94 (s, 1H), 7.69 (d, J=8.16 Hz, 2H), 7.61 (d, J=8.16 Hz, 2H), 7.52-7.48 (m, 4H), 7.41 (s, 1H), 5.49 (d, J=6.68 Hz, 1H), 5.36 (m, 1H), 4.94-4.83 (br, 1H), 4.66 (br, 1H), 4.31 (br, 1H), 4.00 (br, 1H), 3.84 (br, 1H), 3.58 (br, 1H), 2.58 (br, 2H), 1.79 (br, 3H), 1.61 (d, J=6.92 Hz, 3H).

Example 2411

Synthesis of 3-(2-butynyl)-6-(pyrazolo[1,5-a]pyridine-2-carbonyl)-2-[(S)-1-(4-trifluoromethylphenyl)ethylamino]-5,6,7,8-tetrahydro-3H-pyrido[4,3-d]pyrimidin-4-one hydrochloride

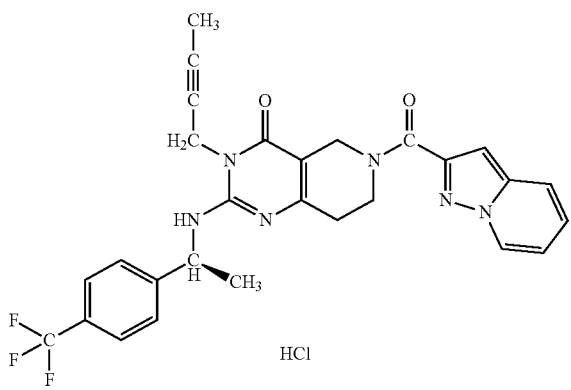 [SMILES: CC#CCn1c(N[C@@H](C)c2ccc(C(F)(F)F)cc2)nc2c(c1=O)CN(C(=O)c1cc3ccccn3n1)CC2 ; Cl]

Using an appropriate starting material and following the procedure of Example 1, the object compound was synthesized.
White Solid $^1$H-NMR (CDCl$_3$) δ ppm: 8.43 (d, J=7.04 Hz, 1H), 7.71-7.52 (m, 5H), 7.29-7.15 (m, 1H), 7.00-6.84 (m, 2H), 6.50 (br, 1H), 6.00-5.80 (br, 1H), 4.97-4.58 (m, 4H), 4.27-3.98 (m, 2H), 3.37 (br, 1H), 3.20-2.70 (m, 1H), 2.00-1.50 (br, 6H). Two isomers were observed due to the amide rotamers. H of HCl sat was not observed.

Example 2412

Synthesis of 3-(2-butynyl)-6-(2-oxo-1,2,3,4-tetrahydro-quinoline-6-carbonyl)-2-[(S)-1-(4-trifluoromethylphenyl)ethylamino]-5,6,7,8-tetrahydro-3H-pyrido[4,3-d]pyrimidin-4-one hydrochloride

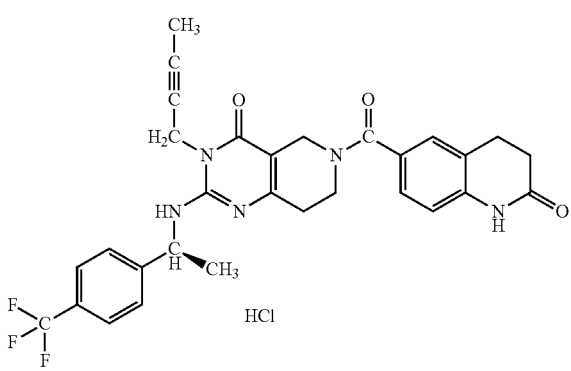 [SMILES: CC#CCn1c(N[C@@H](C)c2ccc(C(F)(F)F)cc2)nc2c(c1=O)CN(C(=O)c1ccc3c(c1)CCC(=O)N3)CC2 ; Cl]

Using an appropriate starting material and following the procedure of Example 1, the object compound was synthesized.
Yellow Solid Free form: $^1$H-NMR (CDCl$_3$) δ ppm: 7.61 (d, J=8.15 Hz, 3H), 7.49 (d, J=8.15 Hz, 2H), 7.31-7.25 (m, 2H), 6.72 (d, J=8.04 Hz, 1H), 5.48 (d, J=6.80 Hz, 1H), 5.36 (m, 1H), 4.86 (brd, J=17.14 Hz, 1H), 4.68 (brd, J=17.14 Hz, 1H), 4.35 (br, 2H), 4.00-3.70 (br, 2H), 2.98 (t, J=7.50 Hz, 2H), 2.65 (t, J=7.50 Hz, 2H), 2.65-2.49 (br, 2H), 1.79 (brs, 3H), 1.60 (d, J=6.92 Hz, 3H).

Example 2413

Synthesis of 6-(4-chloro-3-methoxybenzoyl)-3-methoxy-2-[(S)-1-(4-trifluoromethylphenyl)ethylamino]-5,6,7,8-tetrahydro-3H-pyrido[4,3-d]pyrimidin-4-one

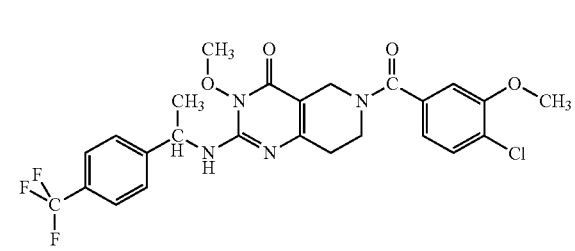 [SMILES: COc1cc(C(=O)N2CCc3nc(NC(C)c4ccc(C(F)(F)F)cc4)n(OC)c(=O)c3C2)ccc1Cl]

Using an appropriate starting material and following the procedure of Example 1, the object compound was synthesized.
White Powder $^1$H-NMR (CDCl$_3$) δ ppm: 1.61 (d, J=7.1 Hz, 3H), 2.31-2.83 (m, 2H), 3.43-3.97 (m, 5H), 4.04 (s, 3H), 4.19-4.75 (m, 2H), 5.18-5.34 (m, 1H), 5.71 (d, J=7.8 Hz, 1H), 6.95 (d, J=8.0 Hz, 1H), 7.03 (s, 1H), 7.38 (d, J=8.0 Hz, 1H), 7.47 (d, J=8.2 Hz, 2H), 7.62 (d, J=8.2 Hz, 2H).

Example 2414

Synthesis of 6-(4-chloro-2-methoxybenzoyl)-3-methoxy-2-[(S)-1-(4-trifluoromethylphenyl)ethylamino]-5,6,7,8-tetrahydro-3H-pyrido[4,3-d]pyrimidin-4-one

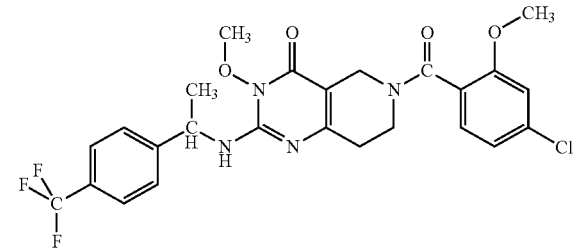 [SMILES: COc1cc(Cl)ccc1C(=O)N1CCc2nc(NC(C)c3ccc(C(F)(F)F)cc3)n(OC)c(=O)c2C1]

Using an appropriate starting material and following the procedure of Example 1, the object compound was synthesized.
White Powder $^1$H-NMR (CDCl$_3$) δ ppm: 1.61 (d, J=7.1 Hz, 3H), 2.18-2.80 (m, 2H), 3.27-3.91 (m, 5H), 4.00-4.78 (m, 5H), 5.10-

5.37 (m, 1H), 5.58-5.81 (m, 1H), 6.79-7.04 (m, 2H), 7.07-7.23 (m, 1H), 7.37-7.55 (m, 2H), 7.56-7.74 (m, 2H).

Example 2415

Synthesis of 3-methoxy-6-(thieno[2,3-b]pyridine-2-carbonyl)-2-[(S)-1-(4-trifluoromethylphenyl)ethylamino]-5,6,7,8-tetrahydro-3H-pyrido[4,3-d]pyrimidin-4-one

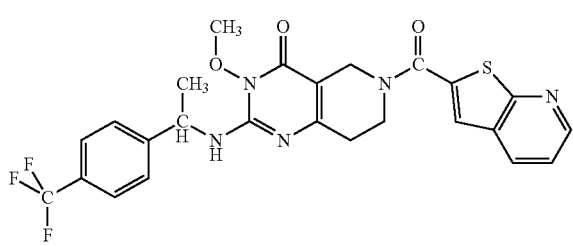 [SMILES: COn1c(NC(C)c2ccc(C(F)(F)F)cc2)nc2c(c1=O)CN(C(=O)c1cc3cccnc3s1)CC2]

Using an appropriate starting material and following the procedure of Example 1, the object compound was synthesized.

Beige Powder $^1$H-NMR (CDCl$_3$) δ ppm: 1.62 (d, J=7.0 Hz, 3H), 2.52-2.75 (m, 2H), 3.76-4.12 (m, 5H), 4.49-4.74 (m, 2H), 5.14-5.38 (m, 1H), 5.71 (d, J=7.8 Hz, 1H), 7.35 (dd, J=4.6, 8.1 Hz, 1H), 7.42-7.55 (m, 3H), 7.62 (d, J=8.2 Hz, 2H), 8.10 (dd, J=1.6, 8.1 Hz, 1H), 8.62 (dd, J=1.6, 4.6 Hz, 1H).

Example 2416

Synthesis of 3-fluoro-4-{3-isobutoxy-4-oxo-2-[(S)-1-(4-trifluoromethylphenyl)ethylamino]-3,5,7,8-tetrahydro-4H-pyrido[4,3-d]pyrimidine-6-carbonyl}benzonitrile

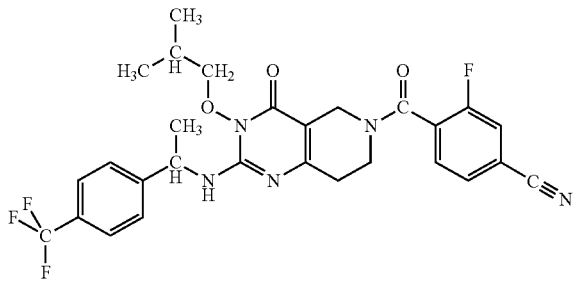 [SMILES: CC(C)COn1c(NC(C)c2ccc(C(F)(F)F)cc2)nc2c(c1=O)CN(C(=O)c1ccc(C#N)cc1F)CC2]

Using an appropriate starting material and following the procedure of Example 1, the object compound was synthesized.

Colorless Amorphous $^1$H-NMR (CDCl$_3$) δ ppm: 1.06-1.15 (m, 6H), 1.60 (d, J=6.9 Hz, 3H), 1.95-2.27 (m, 1H), 2.31-2.80 (m, 2H), 3.40-4.77 (m, 6H), 5.09-5.33 (m, 1H), 5.59-5.78 (m, 1H), 7.35-7.57 (m, 5H), 7.62 (d, J=8.2 Hz, 2H).

Example 2417

Synthesis of 3-(2-butynyl)-6-(quinoline-7-carbonyl)-2-[(S)-1-(4-trifluoromethylphenyl)ethylamino]-5,6,7,8-tetrahydro-3H-pyrido[4,3-d]pyrimidin-4-one dihydrochloride

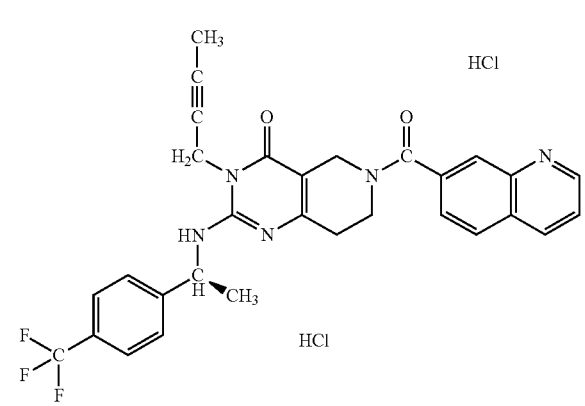 [SMILES: CC#CCn1c(N[C@@H](C)c2ccc(C(F)(F)F)cc2)nc2c(c1=O)CN(C(=O)c1ccc3cccnc3c1)CC2 ; Cl ; Cl]

Using an appropriate starting material and following the procedure of Example 1, the object compound was synthesized.

Yellow Solid free form: $^1$H-NMR (CDCl$_3$) δ ppm: 8.96 (br, 1H), 8.17 (brd, J=6.24 Hz, 1H), 8.13 (s, 1H), 7.87 (br, 1H), 7.61 (d, J=8.14 Hz, 3H), 7.50 (d, J=8.14 Hz, 2H), 7.46 (m, 1H), 5.48 (br, 1H), 5.37 (br, 1H), 5.00-4.80 (br, 1H), 4.63 (br, 1H), 4.33 (br, 1H), 4.04 (br, 1H), 3.91 (br, 1H), 3.61 (br, 1H), 2.58 (br, 2H), 1.78 (br, 3H), 1.61 (d, J=6.92 Hz, 3H).

Example 2418

Synthesis of 3-methoxy-6-(quinoline-3-carbonyl)-2-[(S)-1-(4-trifluoromethylphenyl)ethylamino]-5,6,7,8-tetrahydro-3H-pyrido[4,3-d]pyrimidin-4-one

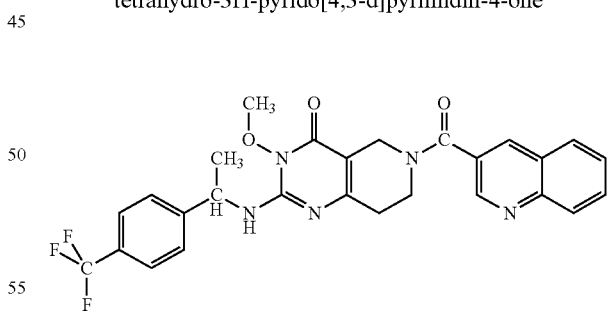

Using an appropriate starting material and following the procedure of Example 1, the object compound was synthesized.

Beige Powder $^1$H-NMR (CDCl$_3$) δ ppm: 1.59 (d, J=7.0 Hz, 3H), 2.37-2.91 (m, 2H), 3.45-4.22 (m, 5H), 4.26-4.82 (m, 2H), 5.18-5.37 (m, 1H), 5.72 (d, J=7.6 Hz, 1H), 7.47 (d, J=8.1 Hz, 2H), 7.55-7.70 (m, 3H), 7.73-7.83 (m, 1H), 7.90 (d, J=7.9 Hz, 1H), 8.13 (d, J=8.6 Hz, 1H), 8.26 (s, 1H), 8.98 (d, J=2.0 Hz, 1H).

Example 2419

Synthesis of 6-(2,6-dimethoxypyridine-3-carbonyl)-3-methoxy-2-[(S)-1-(4-trifluoromethylphenyl)ethylamino]-5,6,7,8-tetrahydro-3H-pyrido[4,3-d]pyrimidin-4-one

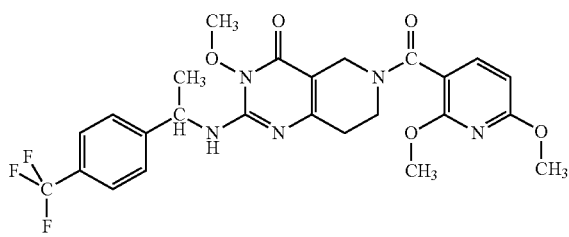 [SMILES: COc1ccc(C(=O)N2CCc3nc(NC(C)c4ccc(C(F)(F)F)cc4)n(OC)c(=O)c3C2)c(OC)n1]

Using an appropriate starting material and following the procedure of Example 1, the object compound was synthesized.
White Powder
$^1$H-NMR (CDCl$_3$) δ ppm: 1.61 (d, J=7.0 Hz, 3H), 2.27-2.83 (m, 2H), 3.24-4.11 (m, 1H), 4.12-4.79 (m, 2H), 5.09-5.37 (m, 1H), 5.68 (d, J=7.4 Hz, 1H), 6.22-6.44 (m, 1H), 7.40-7.69 (m, 5H).

Example 2420

Synthesis of 6-(4-chlorobenzoyl)-2-[1-(4-chlorophenyl)propylamino]-3-methoxy-5,6,7,8-tetrahydro-3H-pyrido[4,3-d]pyrimidin-4-one

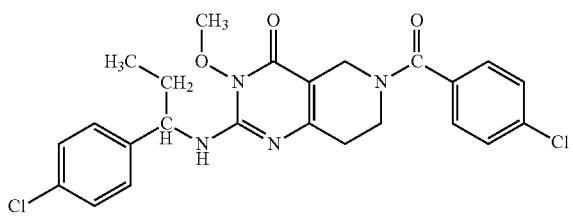 [SMILES: CCC(Nc1nc2c(c(=O)n1OC)CN(C(=O)c1ccc(Cl)cc1)CC2)c1ccc(Cl)cc1]

Using an appropriate starting material and following the procedure of Example 2, the object compound was synthesized.
Colorless Amorphous
$^1$H-NMR (CDCl$_3$) δ ppm: 0.95 (t, J=7.4 Hz, 3H), 1.79-2.00 (m, 2H), 2.35-2.70 (m, 2H), 3.48-4.16 (m, 5H), 4.16-4.63 (m, 2H), 4.82-5.01 (m, 1H), 5.65 (d, J=8.3 Hz, 1H), 7.18-7.41 (m, 8H).

Example 2421

Synthesis of 6-(4-chlorobenzoyl)-2-[1-(4-chlorophenyl)propylamino]-3-methoxy-5,6,7,8-tetrahydro-3H-pyrido[4,3-d]pyrimidin-4-one hydrochloride

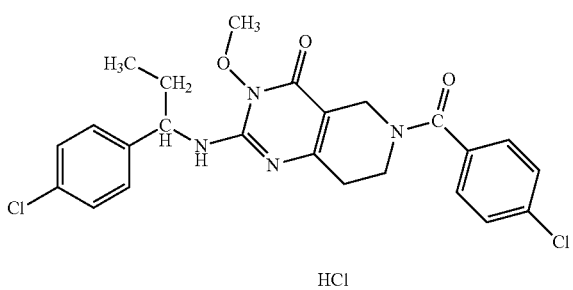 [SMILES: CCC(Nc1nc2c(c(=O)n1OC)CN(C(=O)c1ccc(Cl)cc1)CC2)c1ccc(Cl)cc1 ; Cl]

White Solid
Melting Point 118.1-123.7° C.

Example 2422

Synthesis of 6-(4-chlorobenzoyl)-2-[(R)-1-(4-chlorophenyl)propylamino]-3-methoxy-5,6,7,8-tetrahydro-31'-pyrido[4,3-d]pyrimidin-4-one

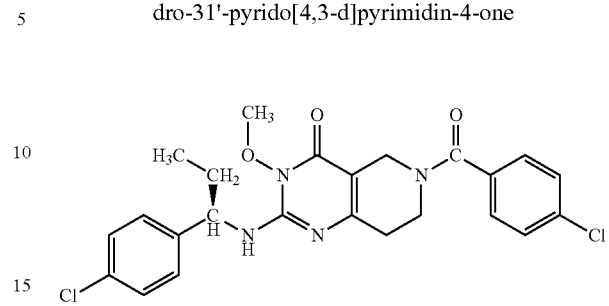

Using an appropriate starting material and following the procedure of Example 2, the object compound was synthesized.
Colorless Solid
$^1$H-NMR (CDCl$_3$) δ ppm: 0.95 (t, J=7.4 Hz, 3H), 1.79-2.00 (m, 2H), 2.32-2.71 (m, 2H), 3.50-4.17 (m, 5H), 4.17-4.66 (m, 2H), 4.81-5.01 (m, 1H), 5.65 (d, J=8.3 Hz, 1H), 7.18-7.41 (m, 8H).

Example 2423

Synthesis of 6-(4-chlorobenzoyl)-2-[(R)-1-(4-chlorophenyl)propylamino]-3-methoxy-5,6,7,8-tetrahydro-3H-pyrido[4,3-d]pyrimidin-4-one hydrochloride

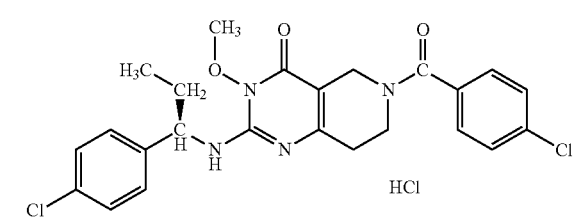 [SMILES: CC[C@@H](Nc1nc2c(c(=O)n1OC)CN(C(=O)c1ccc(Cl)cc1)CC2)c1ccc(Cl)cc1 ; Cl]

White Solid
Melting Point 127-129.5° C.

Example 2424

Synthesis of 6-(4-chlorobenzoyl)-3-(2-propynyl)-2-[1-(4-trifluoromethylphenyl)ethylamino]-5,6,7,8-tetrahydro-3H-pyrido[4,3-d]pyrimidin-4-one

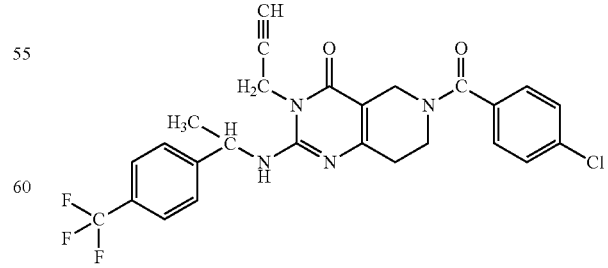

Using an appropriate starting material and following the procedure of Example 2, the object compound was synthesized.

Colorless Amorphous

¹H-NMR (CDCl₃) δ ppm: 1.60 (d, J=6.6 Hz, 3H), 2.39-2.72 (m, 3H), 3.40-4.10 (m, 2H), 4.17-4.67 (m, 2H), 4.70-4.95 (m, 2H), 5.25-5.41 (m, 2H), 7.30-7.40 (m, 4H), 7.48 (d, J=8.1 Hz, 2H), 7.60 (d, J=8.1 Hz, 2H).

Example 2425

Synthesis of 6-(4-chlorobenzoyl)-3-dimethylamino-2-[1-(4-trifluoromethylphenyl)ethylamino]-5,6,7,8-tetrahydro-3H-pyrido[4,3-d]pyrimidin-4-one

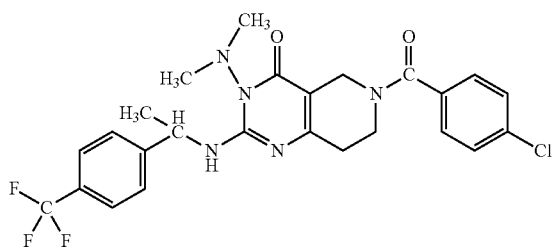 [SMILES: CC(Nc1nc2c(c(=O)n1N(C)C)CN(C(=O)c1ccc(Cl)cc1)CC2)c1ccc(C(F)(F)F)cc1]

Using an appropriate starting material and following the procedure of Example 2, the object compound was synthesized.

Colorless Amorphous

¹H-NMR (CDCl₃) δ ppm: 1.57 (d, J=7.0 Hz, 3H), 2.30-2.68 (m, 2H), 2.81-3.14 (m, 6H), 3.37-4.05 (m, 2H), 4.09-4.57 (m, 2H), 5.11-5.28 (m, 1H), 6.89 (d, J=7.9 Hz, 1H), 7.32-7.41 (m, 4H), 7.44 (d, J=8.1 Hz, 2H), 7.60 (d, J=8.1 Hz, 2H).

Example 2426

Synthesis of 6-(4-chlorobenzoyl)-2-[1-(4-chlorophenyl)ethylamino]-3-dimethylamino-5,6,7,8-tetrahydro-3H-pyrido[4,3-d]pyrimidin-4-one

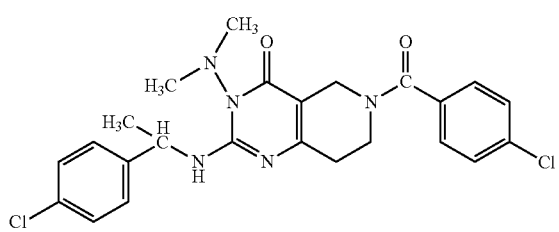 [SMILES: CC(Nc1nc2c(c(=O)n1N(C)C)CN(C(=O)c1ccc(Cl)cc1)CC2)c1ccc(Cl)cc1]

Using an appropriate starting material and following the procedure of Example 2, the object compound was synthesized.

Colorless Amorphous

¹H-NMR (CDCl₃) δ ppm: 1.54 (d, J=7.0 Hz, 3H), 2.37-2.70 (m, 2H), 2.82-3.12 (m, 6H), 3.39-4.02 (m, 2H), 4.10-4.66 (m, 2H), 5.06-5.18 (m, 1H), 6.83 (d, J=8.2 Hz, 1H), 7.20-7.33 (m, 4H), 7.36-7.44 (m, 4H).

Example 2427

Synthesis of 6-(4-chlorobenzoyl)-3-methoxy-2-[1-(4-trifluoromethylphenyl)ethylamino]-5,6,7,8-tetrahydro-3H-pyrido[4,3-d]pyrimidin-4-one

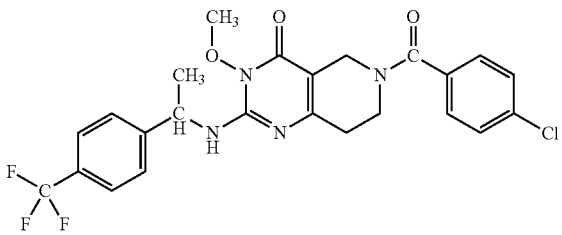 [SMILES: COn1c(NC(C)c2ccc(C(F)(F)F)cc2)nc2c(c1=O)CN(C(=O)c1ccc(Cl)cc1)CC2]

Using an appropriate starting material and following the procedure of Example 2, the object compound was synthesized.

Colorless Amorphous

¹H-NMR (CDCl₃) δ ppm: 1.60 (d, J=7.0 Hz, 3H), 2.32-2.75 (m, 2H), 3.30-4.15 (m, 5H), 4.17-4.70 (m, 2H), 5.12-5.32 (m, 1H), 5.72 (d, J=7.5 Hz, 1H), 7.28-7.40 (m, 4H), 7.47 (d, J=8.2 Hz, 2H), 7.62 (d, J=8.2 Hz, 2H).

Example 2428

Synthesis of 3-fluoro-4-{3-methoxy-4-oxo-2-[1-(4-trifluoromethylphenyl)ethylamino]-3,5,7,8-tetrahydro-4H-pyrido[4,3-d]pyrimidine-6-carbonyl}benzonitrile

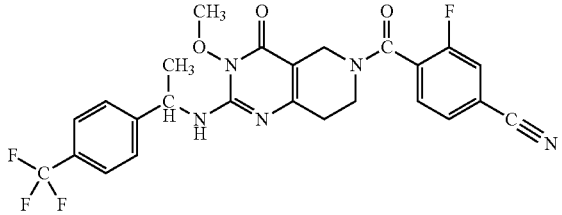 [SMILES: COn1c(NC(C)c2ccc(C(F)(F)F)cc2)nc2c(c1=O)CN(C(=O)c1ccc(C#N)cc1F)CC2]

Using an appropriate starting material and following the procedure of Example 1, the object compound was synthesized.

Colorless Amorphous

¹H-NMR (CDCl₃) δ ppm: 1.61 (d, J=7.0 Hz, 3H), 2.36-2.77 (m, 2H), 3.32-4.71 (m, 7H), 5.16-5.35 (m, 1H), 5.60-5.79 (m, 1H), 7.35-7.58 (m, 5H), 7.62 (d, J=8.3 Hz, 2H).

Example 2429

Synthesis of 3-(2-butynyl)-6-(1-methyl-2-oxo-1,2-dihydropyridine-3-carbonyl)-2-[(S)-1-(4-trifluoromethylphenyl)ethylamino]-5,6,7,8-tetrahydro-3H-pyrido[4,3-d]pyrimidin-4-one hydrochloride

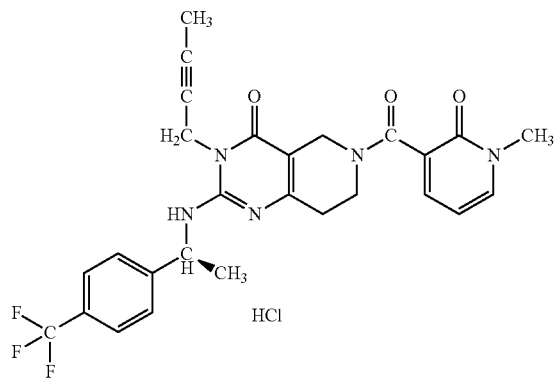 [SMILES: CC#CCn1c(N[C@@H](C)c2ccc(C(F)(F)F)cc2)nc2c(c1=O)CN(C(=O)c1cccn(C)c1=O)CC2 ; Cl]

Using an appropriate starting material and following the procedure of Example 1, the object compound was synthesized.

White Solid $^1$H-NMR (DMSO-d$_6$) δ ppm: 7.81 (m, 1H), 7.69 (d, J=8.28 Hz, 2H), 7.64 (d, J=8.28 Hz, 2H), 7.49-7.44 (m, 2H), 6.27 (t, J=6.8 Hz, 1H), 5.37 (m, 1H), 4.99-4.69 (m, 2H), 4.24 (brd, J=4.72 Hz, 1H), 3.94 (brs, 1H), 3.76 (br, 1H), 3.46 (s, 3H), 3.34 (brt, J=5.72 Hz, 1H), 2.50-2.28 (brm, 2H), 1.81 (d, J=9.12 Hz, 3H), 1.53 (d, J=7.04 Hz, 3H).

Example 2430

Synthesis of 6-[2-(4-chlorophenoxy)acetyl]-2-[(S)-1-(4-chlorophenyl)ethylamino]-3-methoxy-5,6,7,8-tetrahydro-3H-pyrido[4,3-d]pyrimidin-4-one

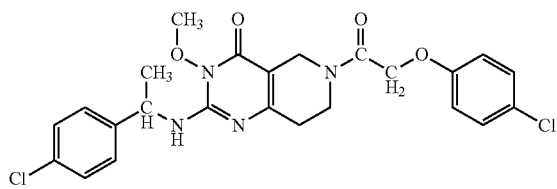 [SMILES: COn1c(NC(C)c2ccc(Cl)cc2)nc2c(c1=O)CN(C(=O)COc1ccc(Cl)cc1)CC2]

Using an appropriate starting material and following the procedure of Example 1, the object compound was synthesized.

White Powder $^1$H-NMR (CDCl$_3$) δ ppm: 1.49-1.61 (m, 3H), 2.37-2.64 (m, 2H), 3.57-3.93 (m, 2H), 3.97-4.12 (m, 3H), 4.25-4.56 (m, 2H), 4.63-4.81 (m, 2H), 5.07-5.27 (m, 1H), 5.55-5.74 (m, 1H), 6.78-6.96 (m, 2H), 7.10-7.42 (m, 6H).

Example 2431

Synthesis of 6-[2-(4-chlorophenoxy)acetyl]-2-[(S)-1-(4-chlorophenyl)ethylamino]-3-dimethylamino-5,6,7,8-tetrahydro-3H-pyrido[4,3-d]pyrimidin-4-one

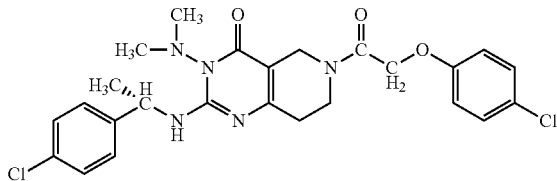

Using an appropriate starting material and following the procedure of Example 1, the object compound was synthesized.

Pale Pink Powder

Melting Point 141.6-144.0° C.

Example 2432

Synthesis of 4-{3-morpholin-4-yl-4-oxo-2-[(S)-1-(4-trifluoromethylphenyl)ethylamino]-3,5,7,8-tetrahydro-4H-pyrido[4,3-d]pyrimidine-6-carbonyl}benzonitrile hydrochloride

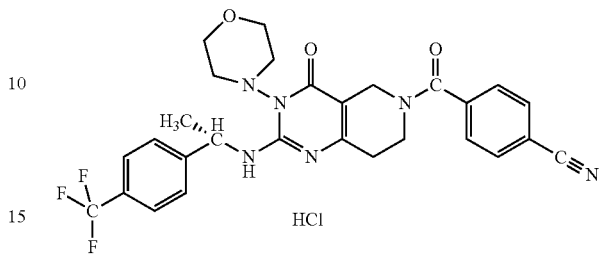

Using an appropriate starting material and following the procedure of Example 11, the object compound was synthesized.

Pale Yellow Powder (Ethanol-Ether)
Melting Point 126-129° C.

Example 2433

Synthesis of 4-{3-(3-butynyl)-4-oxo-2-[(S)-1-(4-trifluoromethylphenyl)ethylamino]-3,5,7,8-tetrahydro-4H-pyrido[4,3-d]pyrimidine-6-carbonyl}benzonitrile

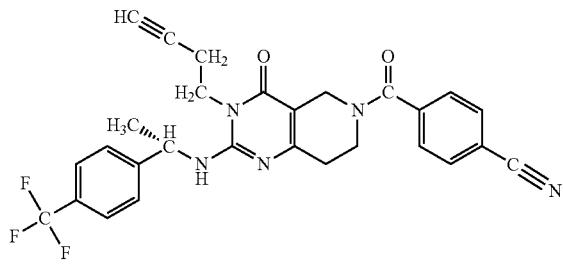

Using an appropriate starting material and following the procedure of Example 2, the object compound was synthesized.

Yellow Amorphous $^1$H-NMR (CDCl$_3$) δ ppm: 1.58 (d, J=6.9 Hz, 3H), 1.99 (s, 1H), 2.26-2.82 (m, 4H), 3.32-4.68 (m, 6H), 5.18-5.38 (m, 1H), 5.55 (d, J=6.1 Hz, 1H), 7.37-7.80 (m, 8H).

Example 2434

Synthesis of 3-(3-butynyl)-6-(4-imidazol-1-ylbenzoyl)-2-[(S)-1-(4-trifluoromethylphenyl)ethylamino]-5,6,7,8-tetrahydro-3H-pyrido[4,3-d]pyrimidin-4-one

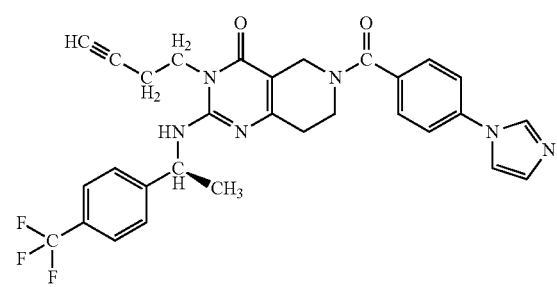 [SMILES: C#CCCn1c(N[C@@H](C)c2ccc(C(F)(F)F)cc2)nc2c(c1=O)CN(C(=O)c1ccc(-n3ccnc3)cc1)CC2]

Using an appropriate starting material and following the procedure of Example 1, the object compound was synthesized.
Colorless Amorphous
¹H-NMR (CDCl₃) δ ppm: 1.58 (d, J=7.0 Hz, 3H), 1.99 (s, 1H), 2.29-2.83 (m, 4H), 3.39-4.19 (m, 4H), 4.19-4.69 (m, 2H), 5.19-5.40 (m, 1H), 5.57 (d, J=5.9 Hz, 1H), 7.10-7.35 (m, 2H), 7.35-7.67 (m, 8H), 7.89 (s, 1H).

Example 2435

Synthesis of 4-{3-(3-butynyl)-4-oxo-2-[(S)-1-(4-trifluoromethylphenyl)ethylamino]-3,5,7,8-tetrahydro-4H-pyrido[4,3-d]pyrimidine-6-carbonyl}-3-fluorobenzonitrile

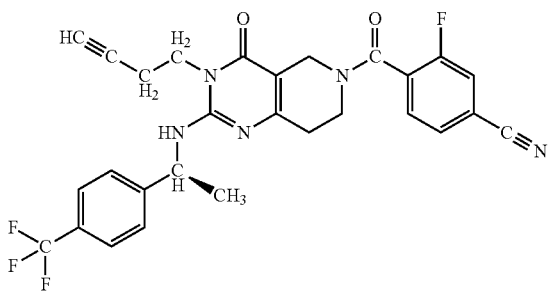 [SMILES: C#CCCn1c(N[C@@H](C)c2ccc(C(F)(F)F)cc2)nc2c(c1=O)CN(C(=O)c1ccc(C#N)cc1F)CC2]

Using an appropriate starting material and following the procedure of Example 1, the object compound was synthesized.
White Solid
¹H-NMR (CDCl₃) δ ppm: 7.62-7.41 (m, 7H), 5.53 (d, J=6.12 Hz, 1H), 5.29 (m, 1H), 4.70-4.40 (br, 1H), 4.21-3.87 (m, 4H), 3.45 (br, 1H), 2.76-2.48 (m, 4H), 1.98 (m, 1H), 1.58 (d, J=6.96 Hz, 1H).

Example 2436

Synthesis of 6-[2-(4-chlorophenoxy)acetyl]-3-(2-propynyl)-2-[(S)-1-(4-trifluoromethylphenyl)ethylamino]-5,6,7,8-tetrahydro-3H-pyrido[4,3-d]pyrimidin-4-one

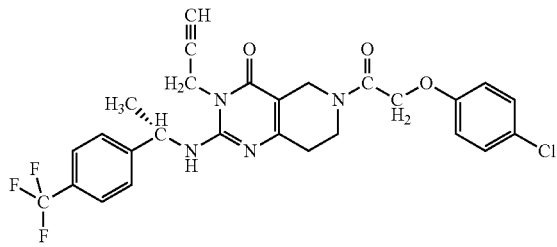

Using an appropriate starting material and following the procedure of Example 1, the object compound was synthesized.
Beige Powder
Melting Point 202.6-204.2° C.

Example 2437

Synthesis of 6-[2-(4-chlorophenoxy)acetyl]-2-[(S)-1-(4-chlorophenyl)ethylamino]-3-(2-propynyl)-5,6,7,8-tetrahydro-3H-pyrido[4,3-d]pyrimidin-4-one

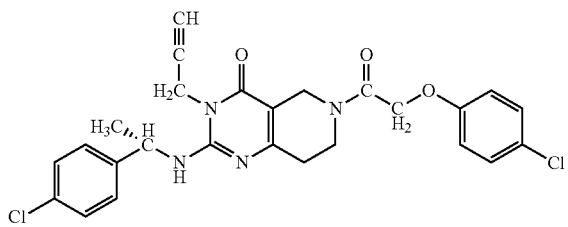

Using an appropriate starting material and following the procedure of Example 1, the object compound was synthesized.
White Powder
Melting Point 185.2-186.8° C.

Example 2438

Synthesis of 3-(3-butynyl)-6-(4-oxazol-5-ylbenzoyl)-2-[(S)-1-(4-trifluoromethylphenyl)ethylamino]-5,6,7,8-tetrahydro-3H-pyrido[4,3-d]pyrimidin-4-one

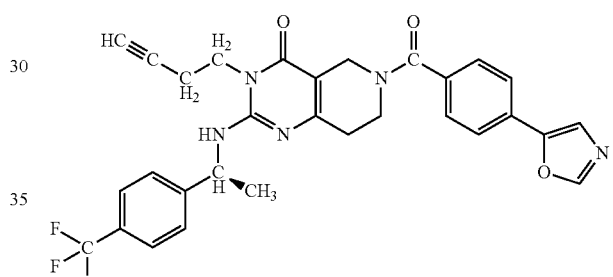

Using an appropriate starting material and following the procedure of Example 1, the object compound was synthesized.
White Solid
¹H-NMR (CDCl₃) δ ppm: 7.94 (s, 1H), 7.69 (brd, J=7.76 Hz, 2H), 7.60 (d, J=8.24 Hz, 2H), 7.52 (d, J=8.24 Hz, 2H), 7.50 (d, J=7.76 Hz, 2H), 7.41 (s, 1H), 5.51 (d, J=5.92 Hz, 1H), 5.29 (br, 1H), 4.57-4.48 (br, 2H), 4.31-3.58 (br, 4H), 2.82-2.46 (br, 4H), 1.98 (br, 1H), 1.58 (d, J=7.64 Hz, 3H).

Example 2439

Synthesis of 3-(3-butynyl)-6-(4-chlorobenzoyl)-2-[(S)-1-(4-trifluoromethylphenyl)ethylamino]-5,6,7,8-tetrahydro-3H-pyrido[4,3-d]pyrimidin-4-one

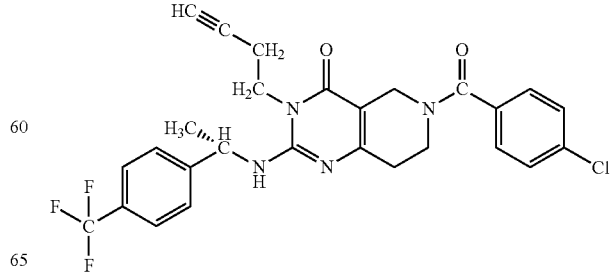

Using an appropriate starting material and following the procedure of Example 2, the object compound was synthesized.

White Solid

¹H-NMR (CDCl₃) δ ppm: 1.58 (d, J=6.9 Hz, 3H), 1.98 (s, 1H), 2.25-2.80 (m, 4H), 3.35-4.66 (m, 6H), 5.16-5.38 (m, 1H), 5.54 (d, J=6.0 Hz, 1H), 7.27-7.66 (m, 8H).

Example 2440

Synthesis of 6-(4-chlorobenzoyl)-2-[(S)-1-(4-chlorophenyl)propylamino]-3-methoxy-5,6,7,8-tetrahydro-3H-pyrido[4,3-d]pyrimidin-4-one

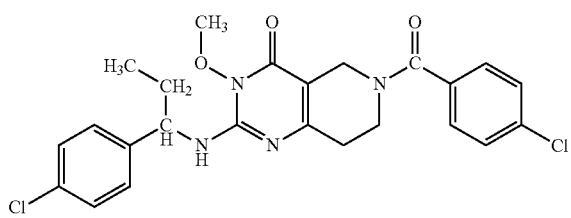 [SMILES: CCC(Nc1nc2c(c(=O)n1OC)CN(C(=O)c1ccc(Cl)cc1)CC2)c1ccc(Cl)cc1]

Using an appropriate starting material and following the procedure of Example 2, the object compound was synthesized.

White Solid

¹H-NMR (CDCl₃) δ ppm: 0.95 (t, J=7.3 Hz, 3H), 1.74-1.97 (m, 2H), 2.57 (brs, 2H), 3.31-4.12 (m, 5H), 4.12-4.67 (m, 2H), 4.81-4.99 (m, 1H), 5.67 (d, J=7.6 Hz, 1H), 7.15-7.51 (m, 8H).

Example 2441

Synthesis of 6-(4-chlorobenzoyl)-2-[1-(4-chlorophenyl)-2-methylpropylamino]-3-methoxy-5,6,7,8-tetrahydro-3H-pyrido[4,3-d]pyrimidin-4-one

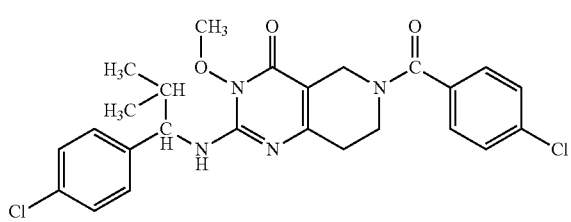 [SMILES: COn1c(NC(c2ccc(Cl)cc2)C(C)C)nc2c(c1=O)CN(C(=O)c1ccc(Cl)cc1)CC2]

Using an appropriate starting material and following the procedure of Example 2, the object compound was synthesized.

Yellow Amorphous

¹H-NMR (CDCl₃) δ ppm: 0.87 (d, J=6.7 Hz, 3H), 1.03 (d, J=6.7 Hz, 3H), 1.97-2.19 (m, 1H), 2.55 (brs, 2H), 3.30-4.64 (m, 7H), 4.77 (dd, J=8.3, 8.3 Hz, 1H), 5.78 (d, J=8.5 Hz, 1H), 7.13-7.44 (m, 8H).

Example 2442

Synthesis of 6-[2-(4-chlorophenoxy)acetyl]-3-dimethylamino-2-[(S)-1-(4-trifluoromethylphenyl)ethylamino]-5,6,7,8-tetrahydro-3H-pyrido[4,3-d]pyrimidin-4-one hydrochloride

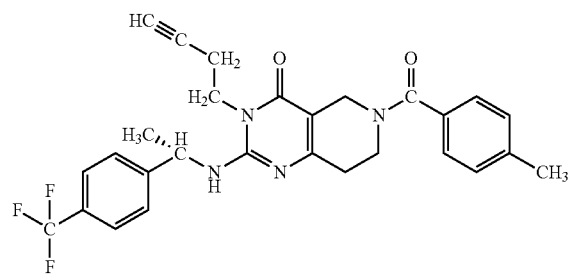

Using an appropriate starting material and following the procedure of Example 1, the object compound was synthesized.

White Powder

¹H-NMR (DMSO-d₆) δ ppm: 1.53 (d, J=7.0 Hz, 3H), 2.13-2.47 (m, 2H), 2.84-3.03 (m, 6H), 3.30-3.70 (m, 2H), 4.01-4.28 (m, 2H), 4.89 (s, 2H), 5.12-5.36 (m, 1H), 6.93 (d, J=8.7 Hz, 2H), 7.19-7.38 (m, 2H), 7.61 (d, J=8.2 Hz, 2H), 7.69 (d, J=8.2 Hz, 2H), 8.16 (d, J=8.7 Hz, 1H).

Example 2443

Synthesis of 3-(3-butynyl)-6-(4-methylbenzoyl)-2-[(S)-1-(4-trifluoromethylphenyl)ethylamino]-5,6,7,8-tetrahydro-3H-pyrido[4,3-d]pyrimidin-4-one Using an appropriate starting material and following the procedure of Example 2, the object compound was synthesized.

White Amorphous

¹H-NMR (CDCl₃) δ ppm: 1.57 (d, J=6.9 Hz, 3H), 1.97 (s, 1H), 2.36 (s, 3H), 2.42-2.80 (m, 4H), 3.31-4.69 (m, 6H), 5.15-5.35 (m, 1H), 5.54 (d, J=6.1 Hz, 1H), 7.19 (d, J=7.9 Hz, 2H), 7.33 (d, J=7.9 Hz, 2H), 7.49 (d, J=8.3 Hz, 2H), 7.59 (d, J=8.3 Hz, 2H).

Example 2444

Synthesis of 6-(benzo[1,3]dioxole-5-carbonyl)-3-(2-butynyl)-2-[(S)-1-(4-trifluoromethylphenyl)ethylamino]-5,6,7,8-tetrahydro-3H-pyrido[4,3-d]pyrimidin-4-one

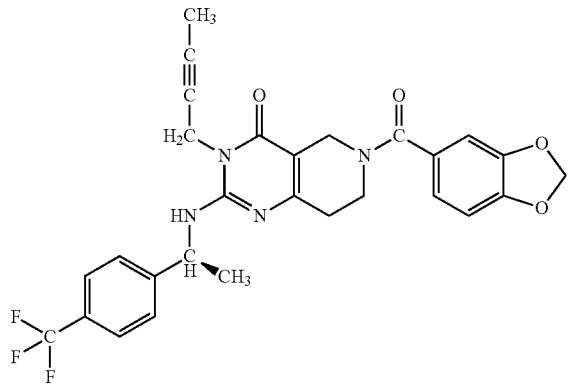 [SMILES: CC#CCn1c(N[C@@H](C)c2ccc(C(F)(F)F)cc2)nc2c(c1=O)CN(C(=O)c1ccc3c(c1)OCO3)CC2]

Using an appropriate starting material and following the procedure of Example 2, the object compound was synthesized.
White Amorphous
$^1$H-NMR (CDCl$_3$) δ ppm: 1.60 (d, J=6.9 Hz, 3H), 1.79 (s, 3H), 2.34-2.74 (m, 2H), 3.49-4.03 (m, 2H), 4.37 (brs, 2H), 4.52-4.73 (m, 1H), 4.97-4.95 (m, 1H), 5.24-5.42 (m, 1H), 5.50 (d, J=6.8 Hz, 1H), 6.00 (s, 2H), 6.80 (d, J=7.9 Hz, 1H), 6.86-7.03 (m, 2H), 7.49 (d, J=8.2 Hz, 2H), 7.60 (d, J=8.2 Hz, 2H).

Example 2445

Synthesis of 3-(2-butynyl)-6-(4-fluorobenzoyl)-2-[(S)-1-(4-trifluoromethylphenyl)ethylamino]-5,6,7,8-tetrahydro-3H-pyrido[4,3-d]pyrimidin-4-one

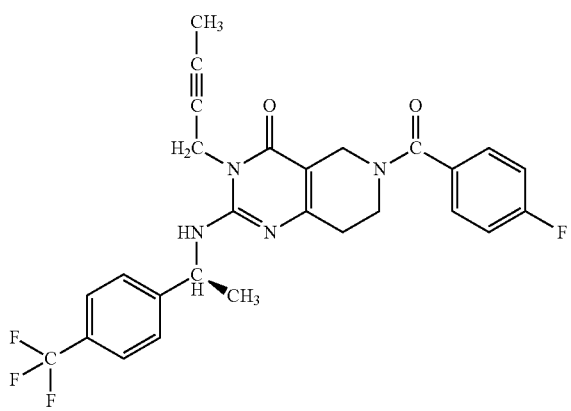 [SMILES: CC#CCn1c(N[C@@H](C)c2ccc(C(F)(F)F)cc2)nc2c(c1=O)CN(C(=O)c1ccc(F)cc1)CC2]

Using an appropriate starting material and following the procedure of Example 2, the object compound was synthesized.
White Amorphous
$^1$H-NMR (CDCl$_3$) δ ppm: 1.60 (d, J=7.0 Hz, 3H), 1.79 (s, 3H), 2.33-2.72 (m, 2H), 3.33-4.04 (m, 2H), 4.17-5.00 (m, 4H), 5.25-5.44 (m, 1H), 5.50 (d, J=6.8 Hz, 1H), 7.00-7.16 (m, 2H), 7.38-7.55 (m, 4H), 7.61 (d, J=8.2 Hz, 2H).

Example 2446

Synthesis of 3-(2-butynyl)-6-(quinoline-3-carbonyl)-2-[(S)-1-(4-trifluoromethylphenyl)ethylamino]-5,6,7,8-tetrahydro-3H-pyrido[4,3-d]pyrimidin-4-one

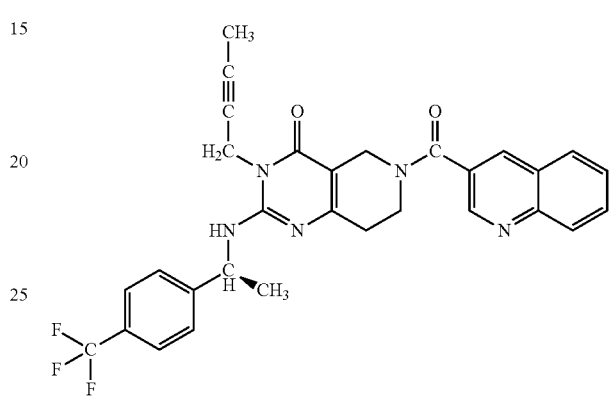

Using an appropriate starting material and following the procedure of Example 1, the object compound was synthesized.
White Solid
$^1$H-NMR (CDCl$_3$) δ ppm: 1.61 (d, J=7.0 Hz, 3H), 1.78 (s, 3H), 2.35-2.79 (m, 2H), 3.40-4.20 (m, 2H), 4.20-5.01 (m, 4H), 5.24-5.41 (m, 1H), 5.51 (d, J=6.8 Hz, 1H), 7.49 (d, J=8.1 Hz, 2H), 7.53-7.68 (m, 3H), 7.68-7.90 (m, 2H), 8.13 (d, J=8.3 Hz, 1H), 8.26 (s, 1H), 8.97 (d, J=2.1 Hz, 1H).

Example 2447

Synthesis of 3-(2-butynyl)-6-(3,4-dimethylbenzoyl)-2-[(S)-1-(4-trifluoromethylphenyl)ethylamino]-5,6,7,8-tetrahydro-3H-pyrido[4,3-d]pyrimidin-4-one

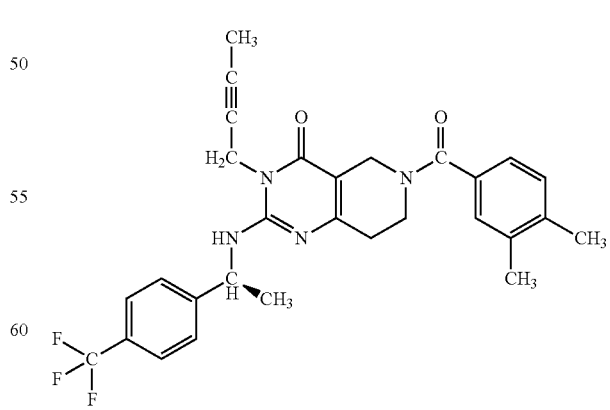

Using an appropriate starting material and following the procedure of Example 1, the object compound was synthesized.

White Solid $^1$H-NMR (CDCl$_3$) δ ppm: 7.60 (d, J=8.24 Hz, 2H), 7.49 (d, J=8.24 Hz, 2H), 7.20 (s, 1H), 7.13 (s, 2H), 5.46 (d, J=6.6 Hz, 1H), 5.36 (m, 1H), 5.00-4.50 (br, 2H), 4.36-4.26 (br, 1H), 3.96 (br, 1H), 3.85-3.50 (br, 2H), 2.70-2.40 (br, 2H), 2.26 (s, 6H), 1.78 (s, 3H), 1.60 (d, J=6.92 Hz, 3H).

Example 2448

Synthesis of 3-(2-butynyl)-6-(4-methoxybenzoyl)-2-[(S)-1-(4-trifluoromethylphenyl)ethylamino]-5,6,7,8-tetrahydro-3H-pyrido[4,3-d]pyrimidin-4-one

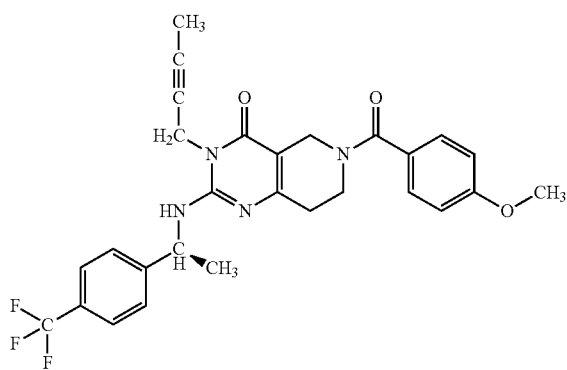 [SMILES: CC#CCn1c(N[C@@H](C)c2ccc(C(F)(F)F)cc2)nc2c(c1=O)CN(C(=O)c1ccc(OC)cc1)CC2]

Using an appropriate starting material and following the procedure of Example 2, the object compound was synthesized.

White Amorphous $^1$H-NMR (CDCl$_3$) δ ppm: 1.60 (d, J=6.9 Hz, 3H), 1.79 (s, 3H), 2.37-2.73 (m, 2H), 3.53-4.00 (m, 5H), 4.39 (brs, 2H), 4.54-4.94 (m, 2H), 5.25-5.42 (m, 1H), 5.49 (d, J=6.8 Hz, 1H), 6.89 (d, J=8.7 Hz, 2H), 7.41 (d, J=8.7 Hz, 2H), 7.49 (d, J=8.2 Hz, 2H), 7.60 (d, J=8.2 Hz, 2H).

Example 2449

Synthesis of 3-(2-butynyl)-6-(quinoline-2-carbonyl)-2-[(S)-1-(4-trifluoromethylphenyl)ethylamino]-5,6,7,8-tetrahydro-3H-pyrido[4,3-d]pyrimidin-4-one

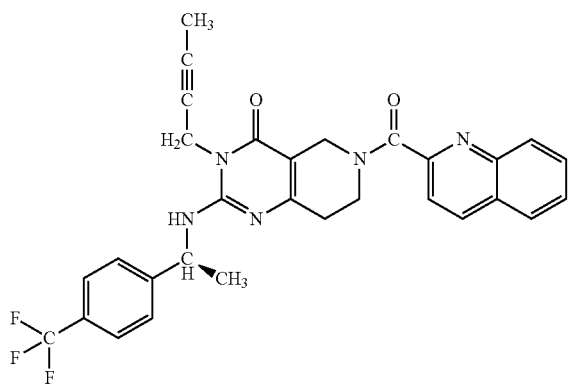 [SMILES: CC#CCn1c(N[C@@H](C)c2ccc(C(F)(F)F)cc2)nc2c(c1=O)CN(C(=O)c1ccc3ccccc3n1)CC2]

Using an appropriate starting material and following the procedure of Example 1, the object compound was synthesized.

Yellow Amorphous $^1$H-NMR (CDCl$_3$) δ ppm: 1.50-1.70 (m, 3H), 1.70-1.88 (m, 3H), 2.50-2.84 (m, 2H), 3.68-4.18 (m, 2H), 4.39-5.03 (m, 4H), 5.26-5.57 (m, 2H), 7.40-7.92 (m, 8H), 8.00-8.18 (m, 1H), 8.18-8.32 (m, 1H).

Example 2450

Synthesis of 6-(4-chlorobenzoyl)-2-[1-(4-chlorophenyl)-4,4,4-trifluorobutylamino]-3-methoxy-5,6,7,8-tetrahydro-3H-pyrido[4,3-d]pyrimidin-4-one

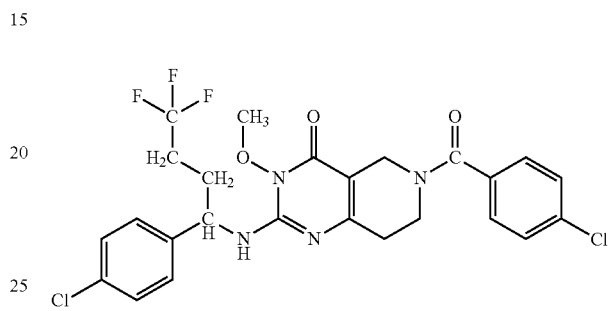

Using an appropriate starting material and following the procedure of Example 2, the object compound was synthesized.

White Solid $^1$H-NMR (CDCl$_3$) δ ppm: 1.92-2.29 (m, 4H), 2.60 (brs, 2H), 3.37-4.10 (m, 2H), 4.01 (s, 3H), 4.18-4.66 (m, 2H), 5.02-5.20 (m, 1H), 5.63 (d, J=8.7 Hz, 1H), 7.18-7.33 (m, 4H), 7.33-7.46 (m, 4H).

Example 2451

Synthesis of 6-(4-ethoxybenzoyl)-3-methoxy-2-[(S)-1-(4-trifluoromethylphenyl)ethylamino]-5,6,7,8-tetrahydro-3H-pyrido[4,3-d]pyrimidin-4-one

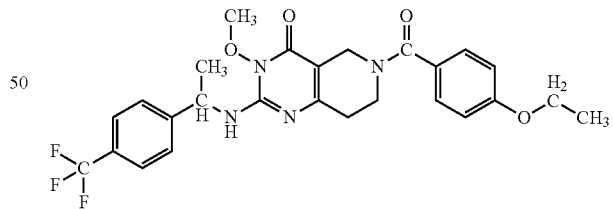

Using an appropriate starting material and following the procedure of Example 1, the object compound was synthesized.

Colorless Amorphous $^1$H-NMR (CDCl$_3$) δ ppm: 1.42 (t, J=7.0 Hz, 3H), 1.60 (d, J=7.0 Hz, 3H), 2.34-2.72 (m, 2H), 3.52-3.93 (m, 2H), 3.93-4.20 (m, 5H), 4.41 (brs, 2H), 5.17-5.38 (m, 1H), 5.79 (d, J=7.2 Hz, 1H), 6.88 (d, J=8.7 Hz, 2H), 7.41 (d, J=8.7 Hz, 2H), 7.47 (d, J=8.2 Hz, 2H), 7.61 (d, J=8.2 Hz, 2H).

Example 2452

Synthesis of 6-(3,4-dimethylbenzoyl)-3-methoxy-2-[(S)-1-(4-trifluoromethylphenyl)ethylamino]-5,6,7,8-tetrahydro-3H-pyrido[4,3-d]pyrimidin-4-one

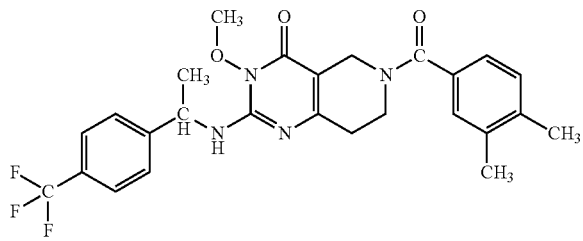 [SMILES: COn1c(NC(C)c2ccc(C(F)(F)F)cc2)nc2c(c1=O)CN(C(=O)c1ccc(C)c(C)c1)CC2]

Using an appropriate starting material and following the procedure of Example 1, the object compound was synthesized.
Colorless Amorphous
¹H-NMR (CDCl₃) δ ppm: 1.61 (d, J=7.0 Hz, 3H), 2.26 (s, 3H), 2.27 (s, 3H), 2.37-2.75 (m, 2H), 3.33-4.14 (m, 2H), 4.03 (s, 3H), 4.14-4.69 (m, 2H), 5.18-5.35 (m, 1H), 5.75 (d, J=7.5 Hz, 1H), 7.05-7.18 (m, 2H), 7.21 (s, 1H), 7.47 (d, J=8.2 Hz, 2H), 7.61 (d, J=8.2 Hz, 2H).

Example 2453

Synthesis of 4-{1-[6-(4-chlorobenzoyl)-3-methoxy-4-oxo-3,4,5,6,7,8-hexahydropyrido[4,3-d]pyrimidin-2-ylamino]-ethyl}benzonitrile

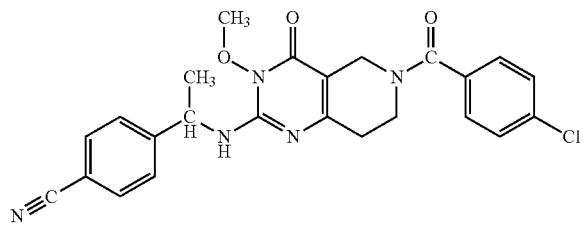 [SMILES: COn1c(NC(C)c2ccc(C#N)cc2)nc2c(c1=O)CN(C(=O)c1ccc(Cl)cc1)CC2]

Using an appropriate starting material and following the procedure of Example 2, the object compound was synthesized.
White Solid
¹H-NMR (CDCl₃) δ ppm: 1.60 (d, J=7.0 Hz, 3H), 2.52 (brs, 2H), 3.31-4.14 (m, 5H), 4.14-4.75 (m, 2H), 5.11-5.32 (m, 1H), 5.75 (d, J=7.2 Hz, 1H), 7.38 (s, 4H), 7.46 (d, J=8.3 Hz, 2H), 7.65 (d, J=8.3 Hz, 2H).

Example 2454

Synthesis of 6-(5-chloro-furan-2-carbonyl)-3-methoxy-2-[(S)-1-(4-trifluoromethylphenyl)ethylamino]-5,6,7,8-tetrahydro-3H-pyrido[4,3-d]pyrimidin-4-one

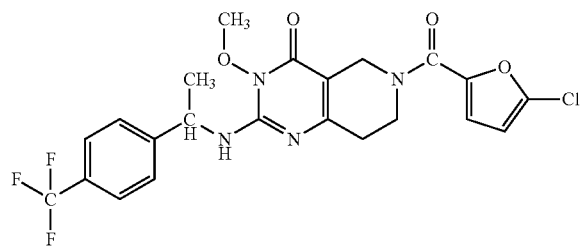 [SMILES: COn1c(NC(C)c2ccc(C(F)(F)F)cc2)nc2c(c1=O)CN(C(=O)c1ccc(Cl)o1)CC2]

Using an appropriate starting material and following the procedure of Example 1, the object compound was synthesized.
Pale Yellow Amorphous
¹H-NMR (CDCl₃) δ ppm: 1.61 (d, J=7.0 Hz, 3H), 2.43-2.75 (m, 2H), 3.70-4.03 (m, 2H), 4.07 (s, 3H), 4.44-4.74 (m, 2H), 5.18-5.34 (m, 1H), 5.72 (d, J=7.6 Hz, 1H), 6.28 (d, J=3.5 Hz, 1H), 7.00 (d, J=3.5 Hz, 1H), 7.47 (d, J=8.2 Hz, 2H), 7.62 (d, J=8.2 Hz, 2H).

Example 2455

Synthesis of 4-{1-[6-(2,6-difluorobenzoyl)-3-methoxy-4-oxo-3,4,5,6,7,8-hexahydropyrido[4,3-d]pyrimidin-2-ylamino]ethyl}benzonitrile

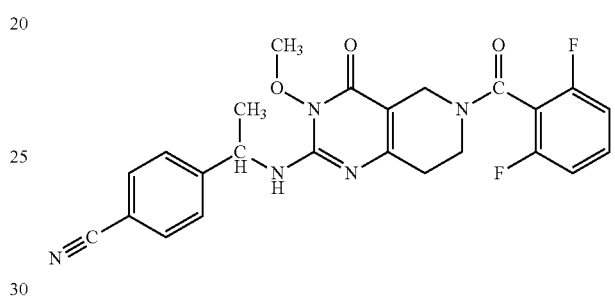

Using an appropriate starting material and following the procedure of Example 1, the object compound was synthesized.
Colorless Amorphous
¹H-NMR (CDCl₃) δ ppm: 1.61 (d, J=7.0 Hz, 3H), 2.28-2.70 (m, 2H), 3.37-3.56 (m, 1H), 3.72-3.93 (m, 1H), 3.93-4.21 (m, 4H), 4.50-4.74 (m, 1H), 5.13-5.36 (m, 1H), 5.78 (d, J=7.1 Hz, 1H), 6.83-7.04 (m, 2H), 7.29-7.51 (m, 3H), 7.57-7.71 (m, 2H).

Example 2456

Synthesis of 3-methoxy-2-[(S)-1-(4-trifluoromethylphenyl)ethylamino]-6-(4-vinylbenzoyl)-5,6,7,8-tetrahydro-3H-pyrido[4,3-d]pyrimidin-4-one

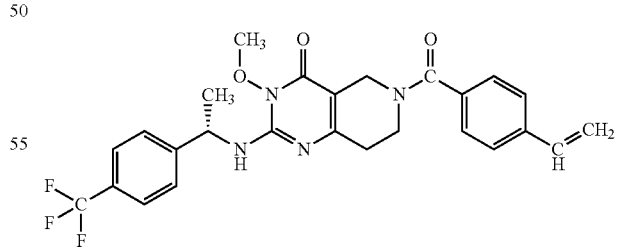

Using an appropriate starting material and following the procedure of Example 1, the object compound was synthesized.
Colorless Amorphous
¹H-NMR (CDCl₃) δ ppm: 1.61 (d, J=7.0 Hz, 3H), 2.57 (brs, 2H), 3.30-4.68 (m, 7H), 5.12-5.38 (m, 2H), 5.72 (d, J=7.4 Hz, 1H), 5.75 (dd, J=17.6, 0.5 Hz, 1H), 6.72 (dd, J=17.6, 10.9 Hz, 1H), 7.29-7.52 (m, 6H), 7.62 (d, J=8.2 Hz, 2H).

Example 2457

Synthesis of 6-(3-fluoro-4-methylbenzoyl)-3-methoxy-2-[(S)-1-(4-trifluoromethylphenyl)ethylamino]-5,6,7,8-tetrahydro-3H-pyrido[4,3-d]pyrimidin-4-one

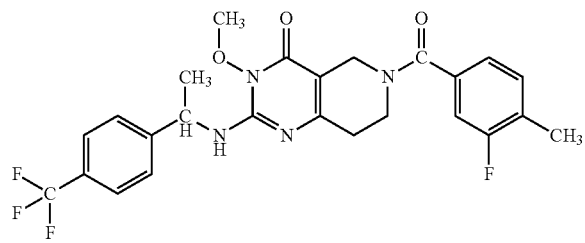 [SMILES: COn1c(NC(C)c2ccc(C(F)(F)F)cc2)nc2c(c1=O)CN(C(=O)c1ccc(C)c(F)c1)CC2]

Using an appropriate starting material and following the procedure of Example 1, the object compound was synthesized.

Colorless Amorphous

¹H-NMR (CDCl₃) δ ppm: 1.58-1.70 (m, 3H), 2.30 (s, 3H), 2.56 (brs, 2H), 3.35-4.16 (m, 5H), 4.16-4.68 (m, 2H), 5.12-5.38 (m, 1H), 5.72 (d, J=7.5 Hz, 1H), 6.98-7.30 (m, 3H), 7.47 (d, J=8.1 Hz, 2H), 7.62 (d, J=8.1 Hz, 2H).

Example 2458

Synthesis of 6-(1H-benzoimidazole-2-carbonyl)-3-(3-butynyl)-2-[(S)-1-(4-trifluoromethylphenyl)ethylamino]-5,6,7,8-tetrahydro-3H-pyrido[4,3-d]pyrimidin-4-one

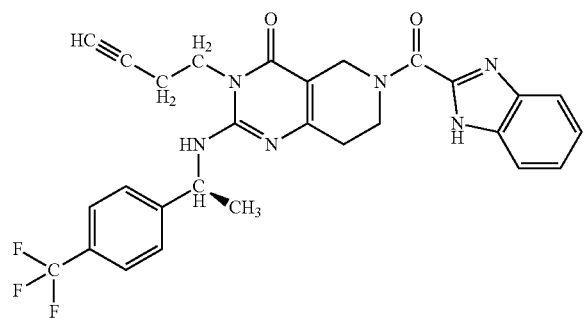 [SMILES: C#CCCn1c(N[C@@H](C)c2ccc(C(F)(F)F)cc2)nc2c(c1=O)CN(C(=O)c1nc3ccccc3[nH]1)CC2]

Using an appropriate starting material and following the procedure of Example 1, the object compound was synthesized.

Colorless Amorphous

¹H-NMR (CDCl₃) δ ppm: 1.47-1.63 (m, 3H), 1.99 (t, J=2.6 Hz, 1H), 2.41-2.88 (m, 4H), 3.80-4.27 (m, 3H), 4.51-4.73 (m, 1H), 4.73-4.98 (m, 1H), 5.18-5.65 (m, 3H), 7.19-7.42 (m, 2H), 7.42-7.67 (m, 5H), 7.75-7.90 (m, 2H), 10.74-11.21 (m, 1H).

Example 2459

Synthesis of 6-(2,3-dihydrobenzo[1,4]dioxine-6-carbonyl)-3-methoxy-2-[(S)-1-(4-trifluoromethylphenyl)ethylamino]-5,6,7,8-tetrahydro-3H-pyrido[4,3-d]pyrimidin-4-one

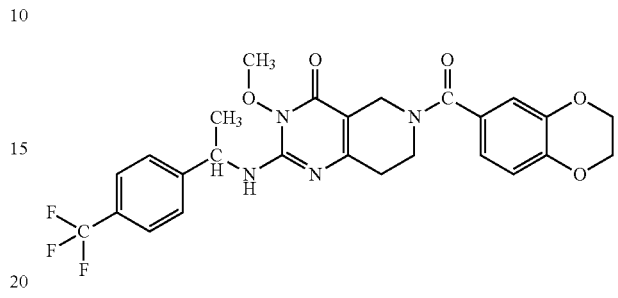

Using an appropriate starting material and following the procedure of Example 1, the object compound was synthesized.

Colorless Amorphous

¹H-NMR (CDCl₃) δ ppm: 1.61 (d, J=7.0 Hz, 3H), 2.33-2.69 (m, 2H), 3.32-4.08 (m, 5H), 4.17-4.62 (m, 6H), 5.13-5.34 (m, 1H), 5.72 (dd, J=7.3, 7.3 Hz, 1H), 6.78-7.03 (m, 3H), 7.47 (d, J=8.3 Hz, 2H), 7.62 (d, J=8.3 Hz, 2H).

Example 2460

Synthesis of 3-methoxy-6-(5-methoxybenzofuran-2-carbonyl)-2-[(S)-1-(4-trifluoromethylphenyl)ethylamino]-5,6,7,8-tetrahydro-3H-pyrido[4,3-d]pyrimidin-4-one

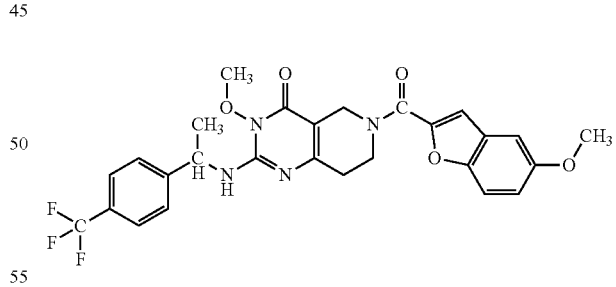

Using an appropriate starting material and following the procedure of Example 1, the object compound was synthesized.

Colorless Amorphous

¹H-NMR (CDCl₃) δ ppm: 1.62 (d, J=7.0 Hz, 3H), 2.42-2.77 (m, 2H), 3.71-4.11 (m, 8H), 4.70 (brs, 2H), 5.16-5.35 (m, 1H), 5.74 (d, J=7.6 Hz, 1H), 6.94-7.09 (m, 2H), 7.28 (s, 1H), 7.42-7.54 (m, 3H), 7.62 (d, J=8.2 Hz, 2H).

Example 2461

Synthesis of 3-methoxy-6-(1-methyl-2-oxo-1,2,3,4-tetrahydro-quinoline-6-carbonyl)-2-[(S)-1-(4-trifluoromethylphenyl)ethylamino]-5,6,7,8-tetrahydro-3H-pyrido[4,3-d]pyrimidin-4-one

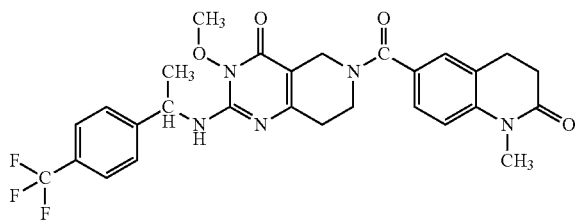 [SMILES: COn1c(NC(C)c2ccc(C(F)(F)F)cc2)nc2c(c1=O)CN(C(=O)c1ccc3c(c1)CCC(=O)N3C)CC2]

Using an appropriate starting material and following the procedure of Example 1, the object compound was synthesized.
Colorless Amorphous
$^1$H-NMR (CDCl$_3$) δ ppm: 1.61 (d, J=7.0 Hz, 3H), 2.31-2.72 (m, 4H), 2.79-3.04 (m, 2H), 3.34 (s, 3H), 3.45-4.18 (m, 5H), 4.18-4.70 (m, 2H), 5.15-5.37 (m, 1H), 5.74 (d, J=7.6 Hz, 1H), 6.91-7.11 (m, 2H), 7.18 (d, J=7.9 Hz, 1H), 7.47 (d, J=8.2 Hz, 2H), 7.62 (d, J=8.2 Hz, 2H).

Example 2462

Synthesis of 6-(4-chlorobenzoyl)-2-(4-chlorobenzylamino)-3-methoxy-5,6,7,8-tetrahydro-3H-pyrido[4,3-d]pyrimidin-4-one hydrochloride

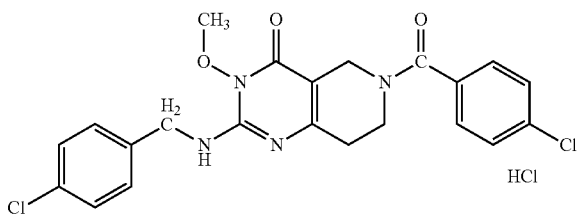 [SMILES: COn1c(NCc2ccc(Cl)cc2)nc2c(c1=O)CN(C(=O)c1ccc(Cl)cc1)CC2 ; Cl]

Using an appropriate starting material and following the procedure of Example 2, the object compound was synthesized.
White Powder (Ethanol-Ether)
Melting Point 113-117° C.

Example 2463

Synthesis of 3-fluoro-4-{3-morpholin-4-yl-4-oxo-2-[(S)-1-(4-trifluoromethylphenyl)ethylamino]-3,5,7,8-tetrahydro-4H-pyrido[4,3-d]pyrimidine-6-carbonyl}benzonitrile hydrochloride

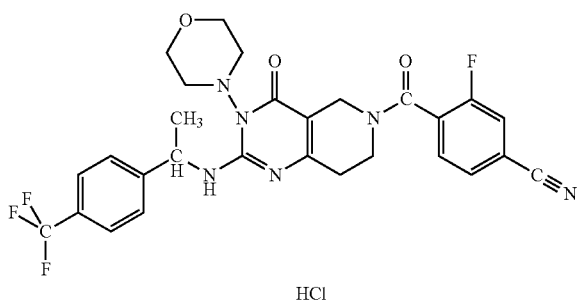 [SMILES: CC(Nc1nc2c(c(=O)n1N1CCOCC1)CN(C(=O)c1ccc(C#N)cc1F)CC2)c1ccc(C(F)(F)F)cc1 ; Cl]

Using an appropriate starting material and following the procedure of Example 11, the object compound was synthesized.
White Powder (Ether-Ethyl Acetate)
Melting Point 132-135° C.

Example 2464

Synthesis of 3-methoxy-6-(1-methyl-5-thiophen-2-yl-1H-pyrazole-3-carbonyl)-2-[(S)-1-(4-trifluoromethylphenyl)ethylamino]-5,6,7,8-tetrahydro-3H-pyrido[4,3-d]pyrimidin-4-one

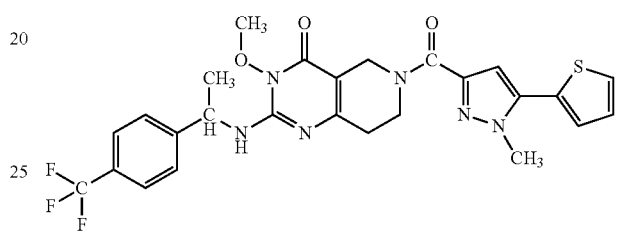

Using an appropriate starting material and following the procedure of Example 1, the object compound was synthesized.
Colorless Amorphous
$^1$H-NMR (CDCl$_3$) δ ppm: 1.61 (d, J=6.9 Hz, 3H), 2.41-2.75 (m, 2H), 3.68-4.25 (m, 8H), 4.42-4.93 (m, 2H), 5.13-5.34 (m, 1H), 5.70 (d, J=7.5 Hz, 1H), 6.66-6.88 (m, 1H), 7.03-7.23 (m, 2H), 7.34-7.52 (m, 3H), 7.61 (d, J=8.2 Hz, 2H).

Example 2465

Synthesis of 3-methoxy-6-(4-methyl-4H-furo[3,2-b]pyrrole-5-carbonyl)-2-[(S)-1-(4-trifluoromethylphenyl)ethylamino]-5,6,7,8-tetrahydro-3H-pyrido[4,3-d]pyrimidin-4-one

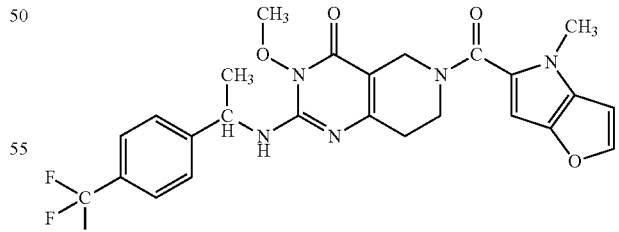

Using an appropriate starting material and following the procedure of Example 1, the object compound was synthesized.
Pale Yellow Amorphous
$^1$H-NMR (CDCl$_3$) δ ppm: 1.61 (d, J=7.0 Hz, 3H), 2.44-2.70 (m, 2H), 3.71-3.99 (m, 5H), 4.05 (s, 3H), 4.43-4.73 (m, 2H), 5.17-5.34 (m, 1H), 5.73 (d, J=7.7 Hz, 1H), 6.34 (s, 1H), 6.40-6.48 (m, 1H), 7.43 (d, J=2.2 Hz, 1H), 7.48 (d, J=8.3 Hz, 2H), 7.62 (d, J=8.3 Hz, 2H).

Example 2466

Synthesis of 3-(3-butynyl)-6-(4-fluorobenzoyl)-2-[(S)-1-(4-trifluoromethylphenyl)ethylamino]-5,6,7,8-tetrahydro-3H-pyrido[4,3-d]pyrimidin-4-one

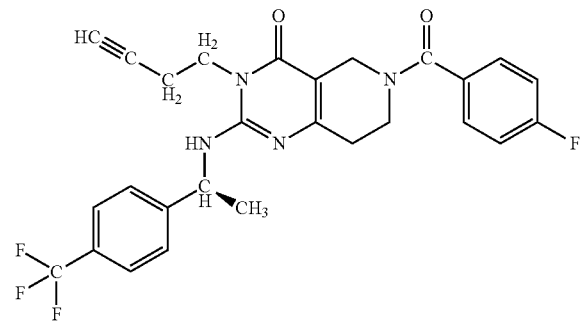 [SMILES: C#CCCn1c(N[C@@H](C)c2ccc(C(F)(F)F)cc2)nc2c(c1=O)CN(C(=O)c1ccc(F)cc1)CC2]

Using an appropriate starting material and following the procedure of Example 2, the object compound was synthesized.
Colorless Amorphous
$^1$H-NMR (CDCl$_3$) δ ppm: 1.58 (d, J=6.9 Hz, 3H), 1.98 (t, J=2.6 Hz, 1H), 2.30-2.79 (m, 4H), 3.34-4.70 (m, 6H), 5.16-5.37 (m, 1H), 5.53 (d, J=5.9 Hz, 1H), 7.07 (d, J=8.6 Hz, 1H), 7.10 (d, J=8.6 Hz, 1H), 7.34-7.54 (m, 4H), 7.60 (d, J=8.2 Hz, 2H).

Example 2467

Synthesis of 6-(4-chlorobenzoyl)-3-methoxy-2-[(S)-1-(4-methoxyphenyl)ethylamino]-5,6,7,8-tetrahydro-3H-pyrido[4,3-d]pyrimidin-4-one hydrochloride

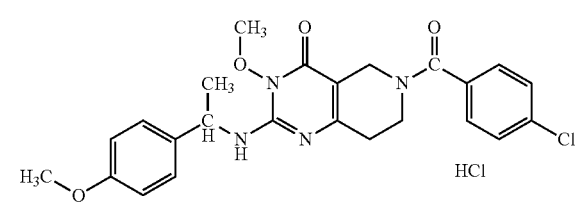 [SMILES: COc1ccc(C(C)Nc2nc3c(c(=O)n2OC)CN(C(=O)c2ccc(Cl)cc2)CC3)cc1 ; Cl]

Using an appropriate starting material and following the procedure of Example 4, the object compound was synthesized.
White Powder (Ethanol-Ether)
Melting Point 105-108° C.

Example 2468

Synthesis of 4-(2-{3-methoxy-4-oxo-2-[(S)-1-(4-trifluoromethylphenyl)ethylamino]-3,5,7,8-tetrahydro-4H-pyrido[4,3-d]pyrimidin-6-yl}-2-oxo-ethoxy)benzonitrile

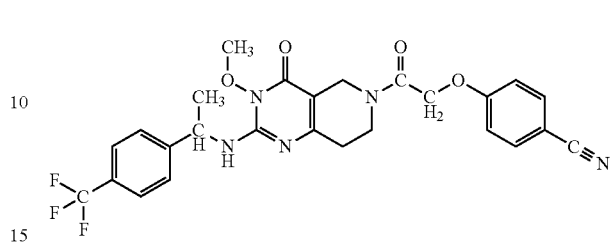

Using an appropriate starting material and following the procedure of Example 1, the object compound was synthesized.
Colorless Amorphous
$^1$H-NMR (CDCl$_3$) δ ppm: 1.48-1.73 (m, 3H), 2.34-2.63 (m, 2H), 3.50-3.93 (m, 2H), 4.09 (s, 3H), 4.19-4.57 (m, 2H), 4.82 (s, 2H), 5.09-5.35 (m, 1H), 5.60-5.81 (m, 1H), 6.91-7.11 (m, 2H), 7.47 (d, J=7.9 Hz, 2H), 7.52-7.72 (m, 4H).

Example 2469

Synthesis of 4-[2-((S)-1-cyclohexylethylamino)-3-methoxy-4-oxo-3,5,7,8-tetrahydro-4H-pyrido[4,3-d]pyrimidine-6-carbonyl]-3-fluorobenzonitrile

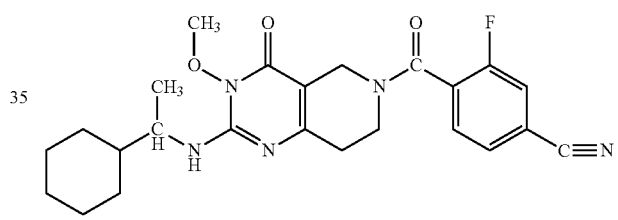

Using an appropriate starting material and following the procedure of Example 1, the object compound was synthesized.
Colorless Amorphous
$^1$H-NMR (CDCl$_3$) δ ppm: 0.85-1.52 (m, 9H), 1.63-1.87 (m, 5H), 2.43-2.73 (m, 2H), 3.37-4.85 (m, 8H), 5.29 (d, J=9.0 Hz, 1H), 7.36-7.48 (m, 1H), 7.48-7.61 (m, 2H).

Example 2470

Synthesis of 6-(4-chlorobenzoyl)-2-((S)-1-cyclohexyl-ethylamino)-3-methoxy-5,6,7,8-tetrahydro-3H-pyrido[4,3-d]pyrimidin-4-one

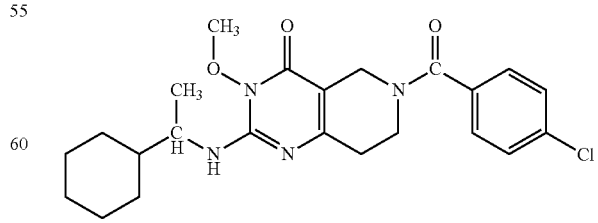

Using an appropriate starting material and following the procedure of Example 2, the object compound was synthesized.

Colorless Amorphous

¹H-NMR (CDCl₃) δ ppm: 0.85-1.52 (m, 9H), 1.53-1.92 (m, 5H), 2.35-2.79 (m, 2H), 3.38-4.14 (m, 6H), 4.16-4.73 (m, 2H), 5.28 (d, J=8.9 Hz, 1H), 7.29-7.51 (m, 4H).

<

Example 2471

Synthesis of 6-(4-chlorobenzoyl)-3-methoxy-2-[(R)-2-(4-trifluoromethylphenyl)pyrrolidin-1-yl]-5,6,7,8-tetrahydro-3H-pyrido[4,3-d]pyrimidin-4-one

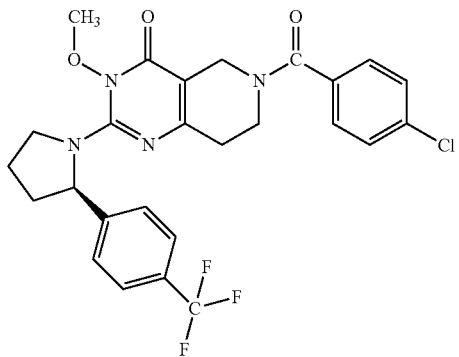 [SMILES: COn1c(N2CCC[C@@H]2c2ccc(C(F)(F)F)cc2)nc2c(c1=O)CN(C(=O)c1ccc(Cl)cc1)CC2]

Using an appropriate starting material and following the procedure of Example 2, the object compound was synthesized.

Colorless Amorphous

¹H-NMR (CDCl₃) δ ppm: 1.77-2.23 (m, 3H), 2.23-2.75 (m, 3H), 3.39-4.07 (m, 7H), 4.12-4.67 (m, 2H), 5.26 (t, J=7.1 Hz, 1H), 7.30-7.46 (m, 6H), 7.56 (d, J=8.2 Hz, 2H).

Example 2472

Synthesis of 4-[2-((R)-1-cyclohexyl-ethylamino)-3-methoxy-4-oxo-3,5,7,8-tetrahydro-4H-pyrido[4,3-d]pyrimidine-6-carbonyl]-3-fluorobenzonitrile

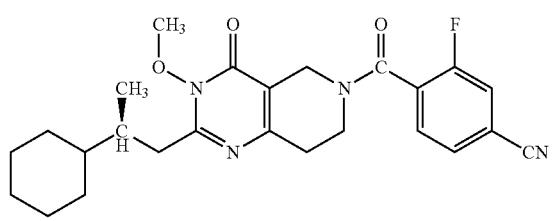 [SMILES: COn1c(C[C@H](C)C2CCCCC2)nc2c(c1=O)CN(C(=O)c1ccc(C#N)cc1F)CC2]

Using an appropriate starting material and following the procedure of Example 1, the object compound was synthesized.

Colorless Amorphous

¹H-NMR (CDCl₃) δ ppm: 0.85-1.52 (m, 9H), 1.63-1.87 (m, 5H), 2.43-2.73 (m, 2H), 3.37-4.85 (m, 8H), 5.29 (d, J=9.0 Hz, 1H), 7.36-7.48 (m, 1H), 7.48-7.61 (m, 2H).

Example 2473

Synthesis of 6-(4-chlorobenzoyl)-2-(R)-1-cyclohexyl-ethylamino)-3-methoxy-5,6,7,8-tetrahydro-3H-pyrido[4,3-d]pyrimidin-4-one

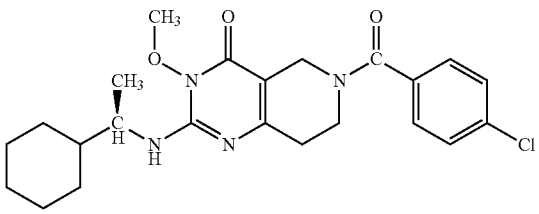 [SMILES: COn1c(N[C@H](C)C2CCCCC2)nc2c(c1=O)CN(C(=O)c1ccc(Cl)cc1)CC2]

Using an appropriate starting material and following the procedure of Example 2, the object compound was synthesized.

Colorless Amorphous

¹H-NMR (CDCl₃) δ ppm: 0.85-1.52 (m, 9H), 1.53-1.92 (m, 5H), 2.35-2.79 (m, 2H), 3.38-4.14 (m, 6H), 4.16-4.73 (m, 2H), 5.28 (d, J=8.9 Hz, 1H), 7.29-7.51 (m, 4H).

Example 2474

Synthesis of 6-(benzo[b]thiophene-2-carbonyl)-3-methoxy-2-[(S)-1-(4-trifluoromethylphenyl)ethylamino]-5,6,7,8-tetrahydro-3H-pyrido[4,3-d]pyrimidin-4-one

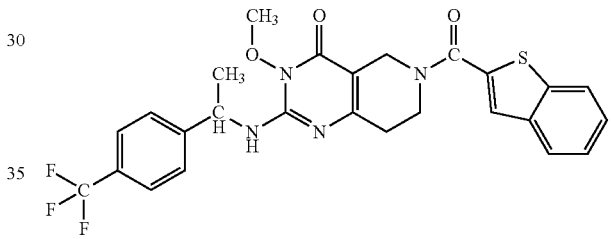

Using an appropriate starting material and following the procedure of Example 1, the object compound was synthesized.

White Solid

¹H-NMR (CDCl₃) δ ppm: 1.61 (d, J=7.0 Hz, 3H), 2.47-2.74 (m, 2H), 3.75-4.03 (m, 2H), 4.05 (s, 3H), 4.47-4.74 (m, 2H), 5.16-5.35 (m, 1H), 5.76 (d, J=7.7 Hz, 1H), 7.30-7.50 (m, 4H), 7.50-7.66 (m, 3H), 7.73-7.90 (m, 2H).

Example 2475

Synthesis of 6-(4-chlorobenzoyl)-3-methoxy-2-[2-(4-trifluoromethylphenyl)pyrrolidin-1-yl]-5,6,7,8-tetrahydro-3H-pyrido[4,3-d]pyrimidin-4-one

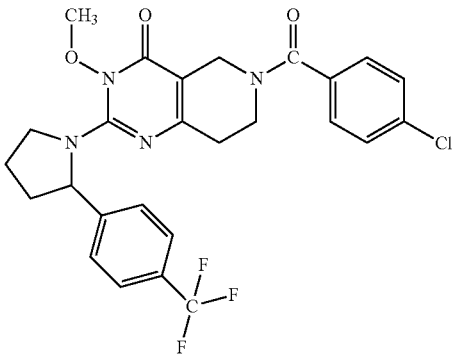 [SMILES: COn1c(N2CCCC2c2ccc(C(F)(F)F)cc2)nc2c(c1=O)CN(C(=O)c1ccc(Cl)cc1)CC2]

Using an appropriate starting material and following the procedure of Example 2, the object compound was synthesized.

Colorless Amorphous $^1$H-NMR (CDCl$_3$) δ ppm: 1.77-2.23 (m, 3H), 2.23-2.75 (m, 3H), 3.39-4.07 (m, 7H), 4.12-4.67 (m, 2H), 5.26 (t, J=7.1 Hz, 1H), 7.30-7.46 (m, 6H), 7.56 (d, J=8.2 Hz, 2H).

Example 2476

Synthesis of 3-{4-oxo-3-(2-propynyl)-2-[(S)-1-(4-trifluoromethylphenyl)ethylamino]-3,5,7,8-tetrahydro-4H-pyrido[4,3-d]pyrimidine-6-carbonyl}benzonitrile

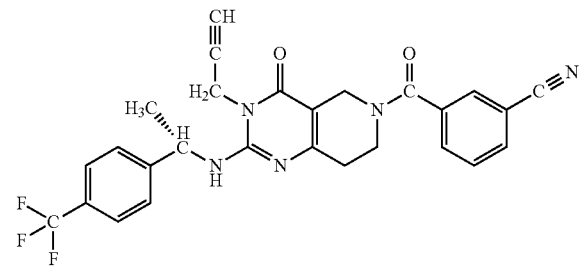

Using an appropriate starting material and following the procedure of Example 1, the object compound was synthesized.

Colorless Amorphous $^1$H-NMR (CDCl$_3$) δ ppm: 1.61 (d, J=6.6 Hz, 3H), 2.26-2.80 (m, 3H), 3.31-4.63 (m, 4H), 4.83 (brs, 2H), 5.18-5.43 (m, 2H), 7.34-7.80 (m, 8H).

Example 2477

Synthesis of 6-(4-chlorobenzoyl)-3-methoxy-2-(4-trifluoromethylbenzylamino)-5,6,7,8-tetrahydro-3H-pyrido[4,3-d]pyrimidin-4-one hydrochloride

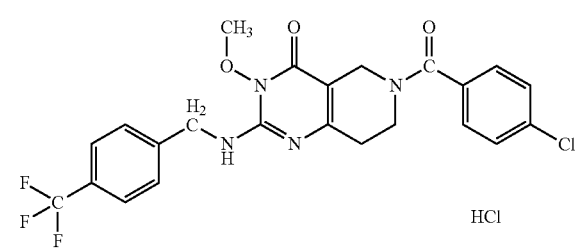 [SMILES: COn1c(NCc2ccc(C(F)(F)F)cc2)nc2c(c1=O)CN(C(=O)c1ccc(Cl)cc1)CC2 ; Cl]

Using an appropriate starting material and following the procedure of Example 2, the object compound was synthesized.

White Powder (Ethanol-Ether)

Melting Point 109-112° C.

Example 2478

Synthesis of 6-(2,6-difluorobenzoyl)-3-(2-propynyl)-2-[(S)-1-(4-trifluoromethylphenyl)ethylamino]-5,6,7,8-tetrahydro-3H-pyrido[4,3-d]pyrimidin-4-one

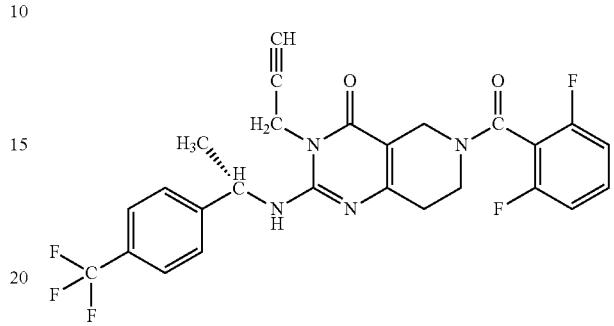

Using an appropriate starting material and following the procedure of Example 1, the object compound was synthesized.

Colorless Amorphous $^1$H-NMR (CDCl$_3$) δ ppm: 1.50-1.70 (m, 3H), 2.33-2.77 (m, 3H), 3.39-3.59 (m, 1H), 3.72-3.91 (m, 1H), 4.01-4.27 (m, 2H), 4.43-4.95 (m, 2H), 5.19-5.45 (m, 2H), 6.79-7.01 (m, 2H), 7.27-7.45 (m, 1H), 7.45-7.56 (m, 2H), 7.56-7.78 (m, 2H).

Example 2479

Synthesis of 2-[(S)-1-(4-chlorophenyl)-2-methylpropylamino]-6-(2,3-dihydrobenzo[1,4]dioxine-6-carbonyl)-3-methoxy-5,6,7,8-tetrahydro-3H-pyrido[4,3-d]pyrimidin-4-one

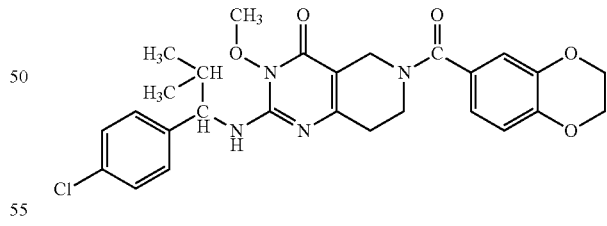

Using an appropriate starting material and following the procedure of Example 1, the object compound was synthesized.

Colorless Amorphous $^1$H-NMR (CDCl$_3$) δ ppm: 0.87 (d, J=6.7 Hz, 3H), 1.03 (d, J=6.7 Hz, 3H), 1.99-2.20 (m, 1H), 2.33-2.72 (m, 2H), 3.46-3.95 (m, 2H), 4.04 (s, 3H), 4.15-4.58 (m, 5H), 4.77 (dd, J=8.3, 8.3 Hz, 1H), 5.73 (d, J=8.6 Hz, 1H), 6.89-7.03 (m, 4H), 7.10-7.38 (m, 4H).

Example 2480

Synthesis of 4-(2-{2-[(S)-1-(4-chlorophenyl)-2-methylpropylamino]-3-methoxy-4-oxo-3,5,7,8-tetrahydro-4H-pyrido[4,3-d]pyrimidin-6-yl}-2-oxo-ethoxy)benzonitrile

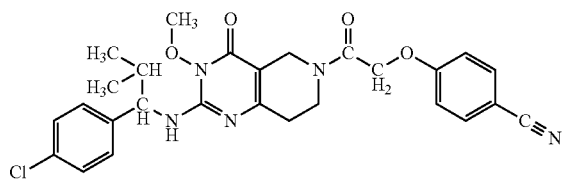 [SMILES: COn1c(NC(c2ccc(Cl)cc2)C(C)C)nc2c(c1=O)CN(C(=O)COc1ccc(C#N)cc1)CC2]

Using an appropriate starting material and following the procedure of Example 1, the object compound was synthesized.

Colorless Amorphous $^1$H-NMR (CDCl$_3$) δ ppm: 0.87 (d, J=6.7 Hz, 3H), 1.02 (d, J=6.7 Hz, 3H), 1.98-2.20 (m, 1H), 2.31-2.63 (m, 2H), 3.47-3.92 (m, 2H), 4.08 (s, 3H), 4.18-4.54 (m, 2H), 4.62-4.86 (m, 3H), 5.62-5.86 (m, 1H), 6.88-7.08 (m, 2H), 7.10-7.38 (m, 4H), 7.48-7.65 (m, 2H).

Example 2481

Synthesis of 2-[(S)-1-(4-chlorophenyl)-2-methylpropylamino]-6-(4-imidazol-1-ylbenzoyl)-3-methoxy-5,6,7,8-tetrahydro-3H-pyrido[4,3-d]pyrimidin-4-one

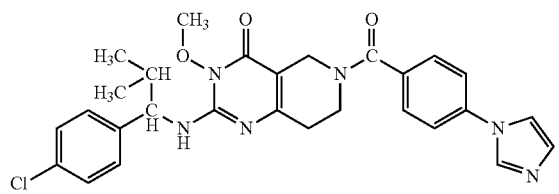 [SMILES: COn1c(NC(c2ccc(Cl)cc2)C(C)C)nc2c(c1=O)CN(C(=O)c1ccc(-n3ccnc3)cc1)CC2]

Using an appropriate starting material and following the procedure of Example 1, the object compound was synthesized.

Colorless Amorphous $^1$H-NMR (CDCl$_3$) δ ppm: 0.87 (d, J=6.7 Hz, 3H), 1.04 (d, J=6.7 Hz, 3H), 1.96-2.20 (m, 1H), 2.31-2.73 (m, 2H), 3.30-4.17 (m, 5H), 4.17-4.66 (m, 2H), 4.78 (dd, J=8.4, 8.4 Hz, 1H), 5.80 (d, J=8.6 Hz, 1H), 7.07-7.38 (m, 6H), 7.43 (d, J=8.4 Hz, 2H), 7.57 (d, J=8.4 Hz, 2H), 7.89 (s, 1H).

Example 2482

Synthesis of 3-fluoro-4-{3-methoxy-4-oxo-2-[(S)-1-(4-trifluoromethylphenyl)propylamino]-3,5,7,8-tetrahydro-4H-pyrido[4,3-d]pyrimidine-6-carbonyl}benzonitrile

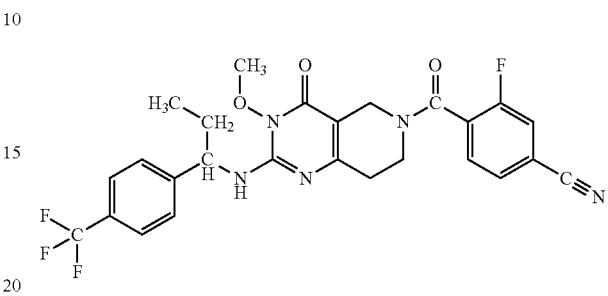

Using an appropriate starting material and following the procedure of Example 1, the object compound was synthesized.

Colorless Amorphous $^1$H-NMR (CDCl$_3$) δ ppm: 0.97 (t, J=7.3 Hz, 3H), 1.88-1.99 (m, 2H), 2.26-2.73 (m, 2H), 3.24-3.52 (m, 1H), 3.62-4.20 (m, 5H), 4.39-4.74 (m, 1H), 4.88-5.08 (m, 1H), 5.60-5.80 (m, 1H), 7.34-7.56 (m, 5H), 7.56-7.79 (m, 2H).

Example 2483

Synthesis of 2-[(S)-1-(4-chlorophenyl)-2-methylpropylamino]-3-methoxy-6-(pyrazolo[1,5-a]pyridine-2-carbonyl)-5,6,7,8-tetrahydro-3H-pyrido[4,3-d]pyrimidin-4-one

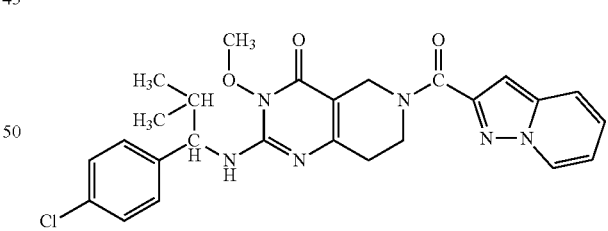

Using an appropriate starting material and following the procedure of Example 1, the object compound was synthesized.

Colorless Amorphous $^1$H-NMR (CDCl$_3$) δ ppm: 0.87 (d, J=6.7 Hz, 3H), 1.03 (d, J=6.7 Hz, 3H), 1.98-2.20 (m, 1H), 2.44-2.76 (m, 2H), 3.70-4.20 (m, 5H), 4.45-4.88 (m, 3H), 5.63-5.84 (m, 1H), 6.71-6.92 (m, 2H), 7.03-7.37 (m, 5H), 7.54 (d, J=8.7 Hz, 1H), 8.43 (d, J=6.7 Hz, 1H).

Example 2484

Synthesis of 3-dimethylamino-6-(2,4,6-trifluorobenzoyl)-2-[(S)-1-(4-trifluoromethylphenyl)ethylamino]-5,6,7,8-tetrahydro-3H-pyrido[4,3-d]pyrimidin-4-one hydrochloride

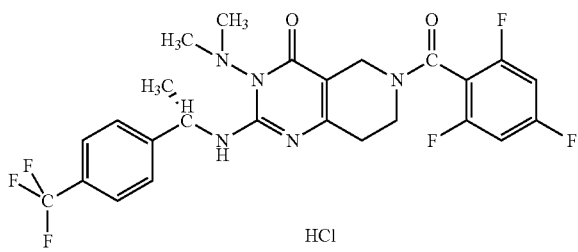

Using an appropriate starting material and following the procedure of Example 11, the object compound was synthesized.
White Powder (Ethanol-Ether)
Melting Point 104-106° C.

Example 2485

Synthesis of 3-dimethylamino-6-(4-methylbenzoyl)-2-[(S)-1-(4-trifluoromethylphenyl)ethylamino]-5,6,7,8-tetrahydro-3H-pyrido[4,3-d]pyrimidin-4-one hydrochloride

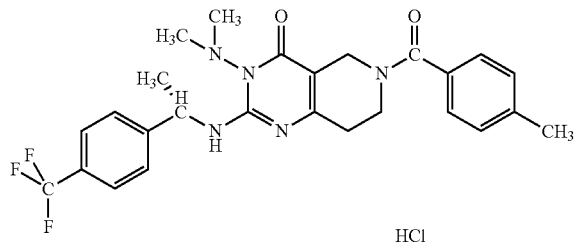

Using an appropriate starting material and following the procedure of Example 11, the object compound was synthesized.
White Powder (Ethanol-Ether)
Melting Point 106-109° C.

Example 2486

Synthesis of 4-{3-(2-butynyl)-2-[(S)-1-(4-chlorophenyl)-2-methylpropylamino]-4-oxo-3,5,7,8-tetrahydro-4H-pyrido[4,3-d]pyrimidine-6-carbonyl}-3-fluorobenzonitrile

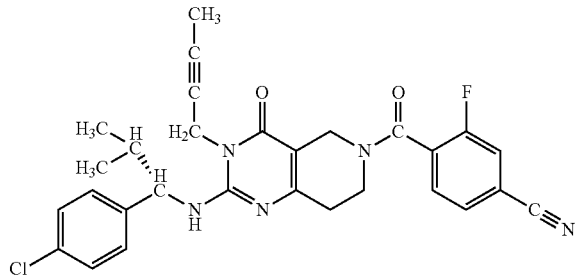

Using an appropriate starting material and following the procedure of Example 1, the object compound was synthesized.
Colorless Amorphous
$^1$H-NMR (CDCl$_3$) δ ppm: 0.91 (d, J=6.7 Hz, 3H), 1.03 (d, J=6.7 Hz, 3H), 1.70-1.90 (m, 3H), 1.90-2.21 (m, 1H), 2.21-2.77 (m, 2H), 3.20-4.28 (m, 3H), 4.38-4.97 (m, 4H), 5.66 (d, J=7.4 Hz, 1H), 7.12-7.35 (m, 4H), 7.35-7.58 (m, 3H).

Example 2487

Synthesis of 2-[(S)-1-(4-chlorophenyl)-2-methylpropylamino]-3-methoxy-6-(1-methyl-2-oxo-1,2,3,4-tetrahydro-quinoline-6-carbonyl)-5,6,7,8-tetrahydro-3H-pyrido[4,3-d]pyrimidin-4-one

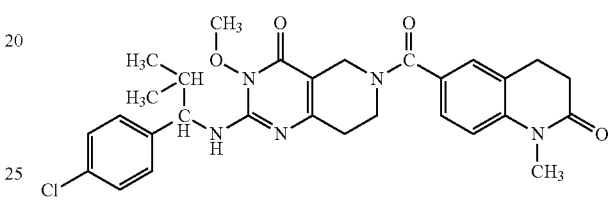

Using an appropriate starting material and following the procedure of Example 1, the object compound was synthesized.
Colorless Amorphous
$^1$H-NMR (CDCl$_3$) δ ppm: 0.87 (d, J=6.7 Hz, 3H), 1.04 (d, J=6.7 Hz, 3H), 2.00-2.18 (m, 1H), 2.39-2.73 (m, 4H), 2.80-3.00 (m, 2H), 3.37 (s, 3H), 3.50-4.20 (m, 5H), 4.20-4.63 (m, 2H), 4.77 (dd, J=8.4, 8.4 Hz, 1H), 5.75 (d, J=8.4 Hz, 1H), 6.97 (d, J=8.3 Hz, 1H), 7.21 (d, J=8.5 Hz, 2H), 7.24-7.41 (m, 4H).

Example 2488

Synthesis of 3-(2-butynyl)-6-(4-chlorobenzoyl)-2-[(S)-1-(4-chlorophenyl)-2-methylpropylamino]-5,6,7,8-tetrahydro-3H-pyrido[4,3-d]pyrimidin-4-one

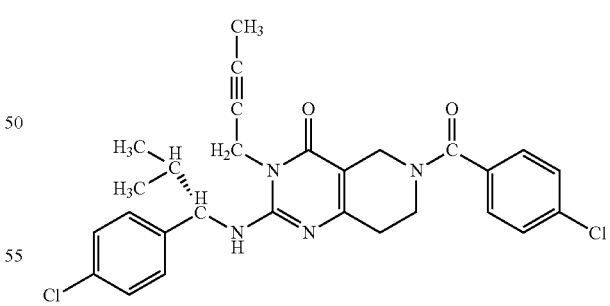

Using an appropriate starting material and following the procedure of Example 2, the object compound was synthesized.
Colorless Amorphous
$^1$H-NMR (CDCl$_3$) δ ppm: 0.91 (d, J=6.7 Hz, 3H), 1.03 (d, J=6.7 Hz, 3H), 1.83 (s, 3H), 2.00-2.20 (m, 1H), 2.28-2.78 (m, 2H), 3.27-4.61 (m, 4H), 4.79 (brs, 2H), 4.92 (dd, J=7.3, 7.3 Hz, 1H), 5.63 (d, J=7.2 Hz, 1H), 7.10-7.30 (m, 4H), 7.37 (s, 4H).

Example 2489

Synthesis of 2-[(S)-1-(4-chlorophenyl)-2-methylpropylamino]-6-(isoquinoline-3-carbonyl)-3-methoxy-5,6,7,8-tetrahydro-3H-pyrido[4,3-d]pyrimidin-4-one

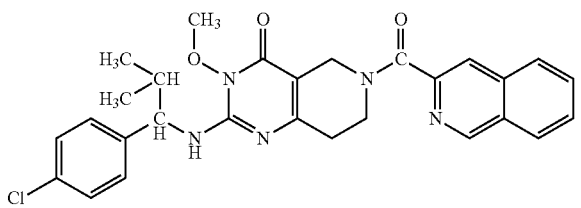 [SMILES: COn1c(NC(c2ccc(Cl)cc2)C(C)C)nc2c(c1=O)CN(C(=O)c1cc3ccccc3cn1)CC2]

Using an appropriate starting material and following the procedure of Example 1, the object compound was synthesized.
Pale Yellow Amorphous
¹H-NMR (CDCl₃) δ ppm: 0.89 (d, J=6.7 Hz, 3H), 1.05 (d, J=6.7 Hz, 3H), 1.97-2.22 (m, 1H), 2.47-2.80 (m, 2H), 3.56-4.20 (m, 5H), 4.30-4.70 (m, 2H), 4.80 (dd, J=8.3, 8.3 Hz, 1H), 5.58-5.84 (m, 1H), 7.10-7.39 (m, 4H), 7.58-7.80 (m, 2H), 7.80-8.18 (m, 3H), 9.25 (s, 1H).

Example 2490

Synthesis of 4-[2-(4-ethoxybenzylamino)-3-methoxy-4-oxo-3,5,7,8-tetrahydro-4H-pyrido[4,3-d]pyrimidine-6-carbonyl]-3-fluorobenzonitrile

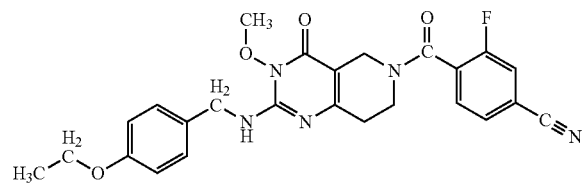 [SMILES: CCOc1ccc(CNc2nc3c(c(=O)n2OC)CN(C(=O)c2ccc(C#N)cc2F)CC3)cc1]

Using an appropriate starting material and following the procedure of Example 1, the object compound was synthesized.
Colorless Amorphous
¹H-NMR (CDCl₃) δ ppm: 1.42 (t, J=7.0 Hz, 3H), 2.45-2.76 (m, 2H), 3.35-3.56 (m, 1H), 3.84-4.21 (m, 7H), 4.38-4.72 (m, 3H), 5.58-5.78 (m, 1H), 6.76-6.96 (m, 2H), 7.12-7.32 (m, 2H), 7.34-7.61 (m, 3H).

Example 2491

Synthesis of 6-(4-chlorobenzoyl)-2-(4-ethoxybenzylamino)-3-methoxy-5,6,7,8-tetrahydro-3H-pyrido[4,3-d]pyrimidin-4-one

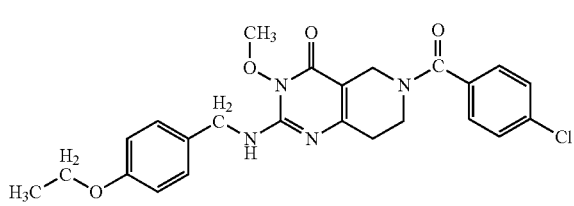 [SMILES: CCOc1ccc(CNc2nc3c(c(=O)n2OC)CN(C(=O)c2ccc(Cl)cc2)CC3)cc1]

Using an appropriate starting material and following the procedure of Example 2, the object compound was synthesized.
Colorless Amorphous
¹H-NMR (CDCl₃) δ ppm: 1.42 (t, J=7.0 Hz, 3H), 2.67 (brs, 2H), 3.30-4.18 (m, 7H), 4.18-4.72 (m, 4H), 5.52-5.70 (m, 1H), 6.79-6.97 (m, 2H), 7.18-7.34 (m, 2H), 7.34-7.44 (m, 4H).

Example 2492

Synthesis of 4-(2-{2-[(S)-1-(4-chlorophenyl)-2-methylpropylamino]-3-methoxy-4-oxo-3,5,7,8-tetrahydro-4H-pyrido[4,3-d]pyrimidin-6-yl}-1,1-dimethyl-2-oxo-ethoxy)benzonitrile

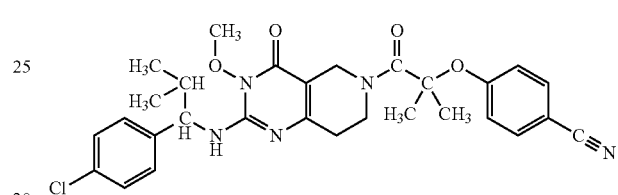

Using an appropriate starting material and following the procedure of Example 1, the object compound was synthesized.
Colorless Amorphous
¹H-NMR (CDCl₃) δ ppm: 0.86 (d, J=6.7 Hz, 3H), 1.03 (d, J=6.7 Hz, 3H), 1.68 (s, 6H), 1.97-2.20 (m, 1H), 2.20-2.52 (m, 2H), 3.35-3.76 (m, 1H), 3.86-4.16 (m, 4H), 4.16-4.39 (m, 1H), 4.43-4.74 (m, 2H), 5.59-5.78 (m, 1H), 6.88 (d, J=8.8 Hz, 2H), 7.18 (d, J=8.3 Hz, 2H), 7.21-7.59 (m, 4H).

Example 2493

Synthesis of 4-{3-(3-butynyl)-4-oxo-2-[(S)-1-(4-trifluoromethylphenyl)ethylamino]-3,5,7,8-tetrahydro-4H-pyrido[4,3-d]pyrimidine-6-carbonyl}benzoic acid methyl ester

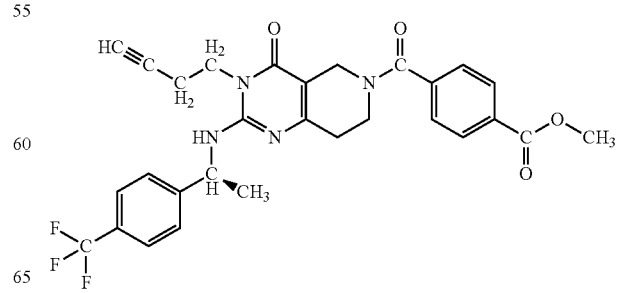

Using an appropriate starting material and following the procedure of Example 1, the object compound was synthesized.

Colorless Amorphous $^1$H-NMR (CDCl$_3$) δ ppm: 1.58 (d, J=6.9 Hz, 3H), 1.98 (s, 1H), 2.28-2.80 (m, 4H), 3.30-3.68 (m, 1H), 3.68-4.37 (m, 7H), 4.37-4.75 (m, 1H), 5.13-5.40 (m, 1H), 5.51 (d, J=5.9 Hz, 1H), 7.49 (d, J=8.2 Hz, 4H), 7.60 (d, J=8.2 Hz, 2H), 8.07 (d, J=7.8 Hz, 2H).

Example 2494

Synthesis of 4-{3-(3-butynyl)-4-oxo-2-[(S)-1-(4-trifluoromethylphenyl)ethylamino]-3,5,7,8-tetrahydro-4H-pyrido[4,3-d]pyrimidine-6-carbonyl}-N,N-dimethylbenzamide

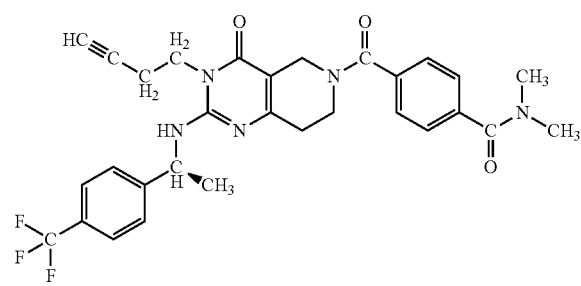 [SMILES: C#CCCn1c(N[C@@H](C)c2ccc(C(F)(F)F)cc2)nc2c(c1=O)CN(C(=O)c1ccc(C(=O)N(C)C)cc1)CC2]

4-{3-(3-Butynyl)-4-oxo-2-[(S)-1-(4-trifluoromethylphenyl)ethylamino]-3,5,7,8-tetrahydro-4H-pyrido[4,3-d]pyrimidine-6-carbonyl}benzoic acid methyl ester (360 mg) was dissolved in MeOH (6 ml), and 5N NaOH solution (0.65 ml) was added. The reaction mixture was stirred at room temperature for 20 hr. The reaction mixture was acidified with aqueous ammonium chloride. The mixture was extracted with methylene chloride and ethyl acetate successively, and the organic layer was dried over sodium sulfate. The organic layer was filtrated and concentrated under reduced pressure to afford the crude acid (0.40 g). The crude acid was suspended in methylene chloride (12 ml), and to the suspension HOBT (0.15 g), WSC (0.19 g), dimethylamine hydrochloride (0.11 g) and triethylamine (0.18 ml) were added. The reaction mixture was stirred at room temperature for 12 hr. The reaction solution was quenched with aqueous NaHCO$_3$, and extracted with ethyl acetate. The organic layer was dried over sodium sulfate, and concentrated under reduced pressure. The residue was purified medium-pressure silica gel column chromatography (solvent; ethyl acetate:hexane=2:3 to 0:100). The titled compound (0.24 g) was obtained as a colorless amorphous substance.

$^1$H-NMR (CDCl$_3$) δ ppm: 1.58 (d, J=6.9 Hz, 3H), 1.98 (s, 1H), 2.27-2.83 (m, 4H), 2.97 (s, 3H), 3.12 (s, 3H), 3.34-3.70 (m, 1H), 3.70-4.70 (m, 5H), 5.18-5.37 (m, 1H), 5.56 (d, J=6.1 Hz, 1H), 7.34-7.56 (m, 6H), 7.60 (d, J=8.2 Hz, 2H).

Example 2495

Synthesis of 2-[(S)-1-(4-chlorophenyl)ethylamino]-3-methoxy-6-(thieno[2,3-b]pyridine-2-carbonyl)-5,6,7,8-tetrahydro-3H-pyrido[4,3-d]pyrimidin-4-one hydrochloride

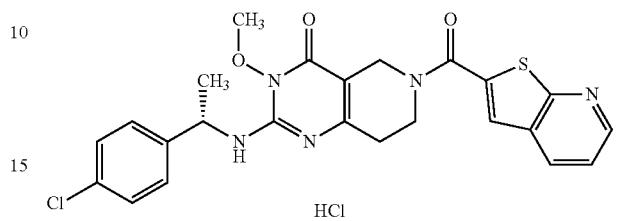

Using an appropriate starting material and following the procedure of Example 11, the object compound was synthesized.

White Powder (Ethanol-Ether)
Melting Point 125-129° C.

Example 2496

Synthesis of 4-(2-{2-[(S)-1-(4-chlorophenyl)ethylamino]-3-methoxy-4-oxo-3,5,7,8-tetrahydro-4H-pyrido[4,3-d]pyrimidin-6-yl}-2-oxoethoxy)-benzonitrile hydrochloride

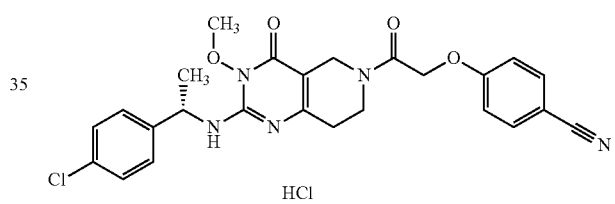

Using an appropriate starting material and following the procedure of Example 11, the object compound was synthesized.

White Powder (Ethanol-Ether)
Melting Point 102-105° C.

Example 2497

Synthesis of 6-(3-chloro-4-methylbenzoyl)-2-[(S)-1-(4-chlorophenyl)ethylamino]-3-methoxy-5,6,7,8-tetrahydro-3H-pyrido[4,3-d]pyrimidin-4-one

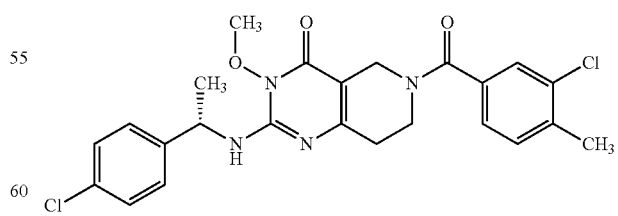

Using an appropriate starting material and following the procedure of Example 11, the object compound was synthesized.

White Powder (Ethanol-Ether)
Melting Point 111-114° C.

Example 2498

Synthesis of 4-[2-(4-chlorobenzylamino)-3-dimethylamino-4-oxo-3,5,7,8-tetrahydro-4H-pyrido[4,3-d]pyrimidine-6-carbonyl]-3-fluorobenzonitrile hydrochloride

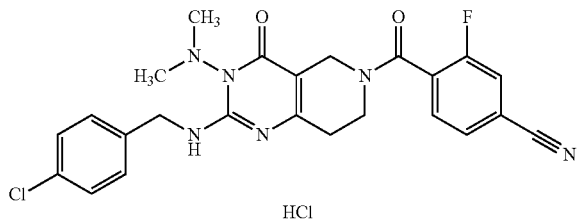 [SMILES: CN(C)n1c(NCc2ccc(Cl)cc2)nc2c(c1=O)CN(C(=O)c1ccc(C#N)cc1F)CC2 ; Cl]

HCl

Using an appropriate starting material and following the procedure of Example 11, the object compound was synthesized.
White Powder (Ethanol-Ether)
Melting Point 128-132° C.

Example 2499

Synthesis of 4-[2-(4-chloro-benzylamino)-3-dimethylamino-4-oxo-3,5,7,8-tetrahydro-4H-pyrido[4,3-d]pyrimidine-6-carbonyl]-benzonitrile hydrochloride

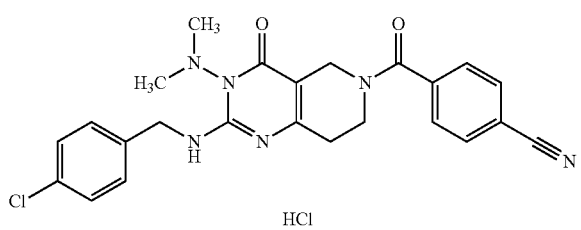 [SMILES: CN(C)n1c(NCc2ccc(Cl)cc2)nc2c(c1=O)CN(C(=O)c1ccc(C#N)cc1)CC2 ; Cl]

HCl

Using an appropriate starting material and following the procedure of Example 11, the object compound was synthesized.
White Powder (Ethanol-Ether)
Melting Point 124-127° C.

Example 2500

Synthesis of 2-[(S)-1-(4-chlorophenyl)ethylamino]-3-dimethylamino-6-(2,4,6-trifluorobenzoyl)-5,6,7,8-tetrahydro-3H-pyrido[4,3-d]pyrimidin-4-one hydrochloride

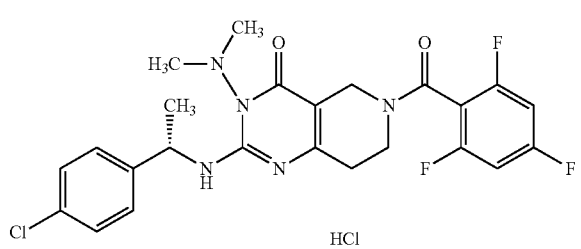 [SMILES: C[C@H](Nc1nc2c(c(=O)n1N(C)C)CN(C(=O)c1c(F)cc(F)cc1F)CC2)c1ccc(Cl)cc1 ; Cl]

HCl

Using an appropriate starting material and following the procedure of Example 11, the object compound was synthesized.
White Powder (Ethanol-Ether)
Melting Point 113-117° C.

Example 2501

Synthesis of 4-{2-[(S)-1-(4-chlorophenyl)ethylamino]-3-dimethylamino-4-oxo-3,5,7,8-tetrahydro-4H-pyrido[4,3-d]pyrimidine-6-carbonyl}-3-fluorobenzonitrile hydrochloride

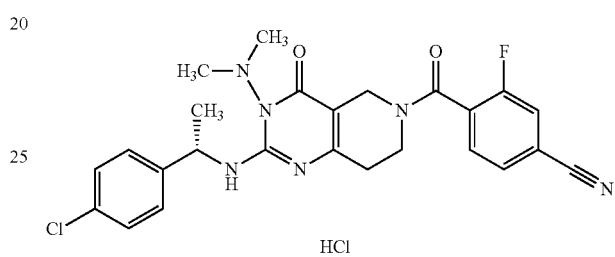

HCl

Using an appropriate starting material and following the procedure of Example 11, the object compound was synthesized.
White Powder (Ethanol-Ether)
Melting Point 122-126° C.

Example 2502

Synthesis of 4-[3-dimethylamino-4-oxo-2-(4-trifluoromethylbenzylamino)-3,5,7,8-tetrahydro-4H-pyrido[4,3-d]pyrimidine-6-carbonyl]-3-fluorobenzonitrile hydrochloride

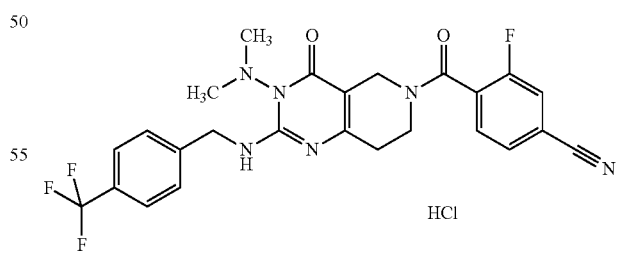

HCl

Using an appropriate starting material and following the procedure of Example 11, the object compound was synthesized.

White Powder (Ethanol-Ether)
Melting Point 127-130° C.

Example 2503

Synthesis of 4-[3-dimethylamino-4-oxo-2-(4-trifluoromethylbenzylamino)-3,5,7,8-tetrahydro-4H-pyrido[4,3-d]pyrimidine-6-carbonyl]benzonitrile hydrochloride

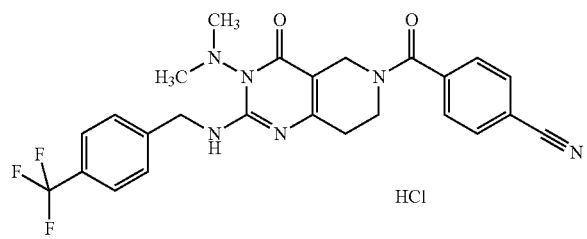 [SMILES: CN(C)n1c(NCc2ccc(C(F)(F)F)cc2)nc2c(c1=O)CN(C(=O)c1ccc(C#N)cc1)CC2 ; Cl]

Using an appropriate starting material and following the procedure of Example 11, the object compound was synthesized.
White Powder (Ethanol-Ether)
Melting Point 127-131° C.

Example 2504

Synthesis of 3-dimethylamino-6-(2,4,6-trifluorobenzoyl)-2-(4-trifluoromethylbenzylamino)-5,6,7,8-tetrahydro-3H-pyrido[4,3-d]pyrimidin-4-one hydrochloride

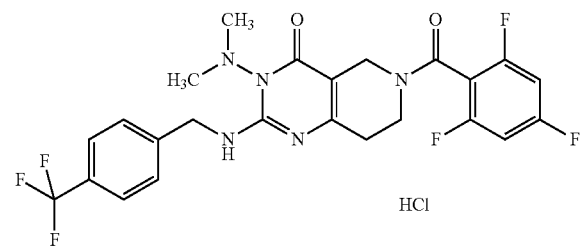 [SMILES: CN(C)n1c(NCc2ccc(C(F)(F)F)cc2)nc2c(c1=O)CN(C(=O)c1c(F)cc(F)cc1F)CC2 ; Cl]

Using an appropriate starting material and following the procedure of Example 11, the object compound was synthesized.
White Powder (Ethanol-Ether)
Melting Point 119-121° C.

Example 2505

Synthesis of 6-(4-chlorobenzoyl)-2-{[(4-chlorophenyl)cyclopropyl-methyl]amino}-3-dimethylamino-5,6,7,8-tetrahydro-3H-pyrido[4,3-d]pyrimidin-4-one hydrochloride

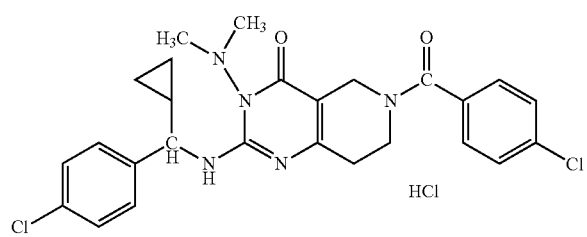 [SMILES: CN(C)n1c(NC(c2ccc(Cl)cc2)C2CC2)nc2c(c1=O)CN(C(=O)c1ccc(Cl)cc1)CC2 ; Cl]

Using an appropriate starting material and following the procedure of Example 4, the object compound was synthesized.
White Powder (Ethanol-Ether)
Melting Point 115-119° C.

Example 2506

Synthesis of 6-(4-chlorobenzoyl)-3-pyrrolidin-1-yl-2-[(S)-1-(4-trifluoromethylphenyl)ethylamino]-5,6,7,8-tetrahydro-3H-pyrido[4,3-d]pyrimidin-4-one hydrochloride

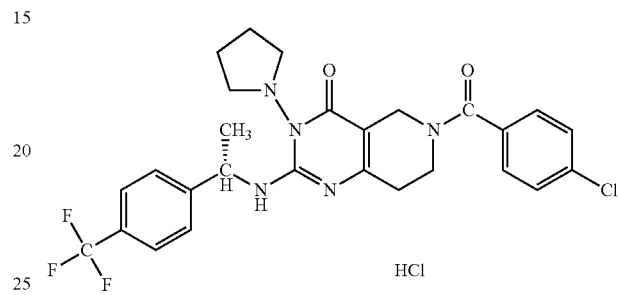

Using an appropriate starting material and following the procedure of Example 4, the object compound was synthesized.
White Powder (Ethanol-Ether)
Melting Point 110-113° C.

Example 2507

Synthesis of 6-(4-chlorobenzoyl)-2-[(S)-1-(4-chlorophenyl)ethylamino]-3-pyrrolidin-1-yl-5,6,7,8-tetrahydro-3H-pyrido[4,3-d]pyrimidin-4-one hydrochloride

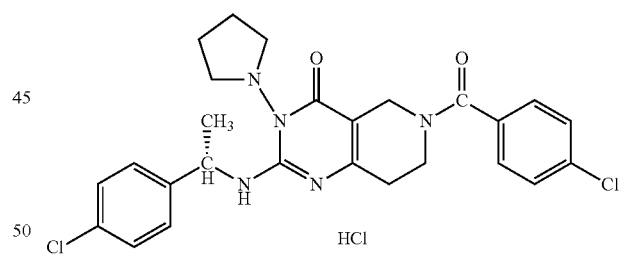

Using an appropriate starting material and following the procedure of Example 4, the object compound was synthesized.
White Powder (Ethanol-Ether)
Melting Point 106-110° C.

Pharmacological Study 1

Inhibitory Activity on Binding of [$^3$H]-PrRP to GPR10

Human GPR10 receptor expressing human embryonic kidney cells, HEK 293 cells, were cultured in Dulbecco's Modified Eagle's medium supplemented with 10% fetal bovine serum and 1% penicilline-streptmycin at 37° C., in 5% carbon dioxide gas conditions. The medium was removed and the cells were recovered in a phosphate buffer to prepare a cell suspension. The cell suspension was homogenated on ice by an ultrasonic cell homogenizer (Microson™ type XL200)

and centrifuged at 40,000 g for 10 minutes at 4° C. After the supernatant was discarded, Buffer A (20 mM HEPES, 10 mM EDTA, 1 µl/ml protease inhibiting cocktail, pH 7.4) was added to the pellet. The pellet was suspended by the ultrasonic cell homogenizer, then the suspension was centrifuged at 40,000 g, for 10 minutes at 4° C. After this operation was repeated once again, the supernatant was discarded, Buffer B (20 mM HEPES, 0.1 mM EDTA, pH 7.4) was added to the pellet, and the pellet was suspended by the ultrasonic homogenizer. This was stored at a freezer of −80° C. as a cell membrane fraction until use in a binding test.

Receptor-expressing HEK 293 cell membrane fraction was analyzed by modifying the methods of C. J. Langmead et al. (see Langmead C J, Szekeres P G; Chambers J K, Ratcliffe S J, Jones D N C, Hirst W D, et al. Characterization of the binding of [$^{125}$I]-human prolactin releasing peptide (PrRP) to GPR10, a novel G protein coupled receptor. Br J Pharmacol 2000; 131: 683-688.). To each well of a 96-well plate, 150 µl of assay buffer (20 mM HEPES, 10 mM EDTA, 1 µl/ml protease inhibiting agent cocktail, pH 7.4), 20 µl of cell membrane fraction, 10 µl of test compound and [$^3$H]-PrRP (final concentration 1 nM) were added and incubated at room temperature for 90 minutes. After completion of the reaction, using a cell harvester, the cell-membrane fraction sample product was filtered under aspiration by a glass fiber filter plate (Unifilter; GF/B) previously treated with 0.5% polyethylene imine. The filter was washed with a 50 mM Tris hydrochloric acid buffer (pH 7.4) three times. After the filter was dried in a dryer (50° C.) for about 3 hours, 40 µl of liquid scintillation cocktail (MicroScint-O) was added to each well and radio activity was measured by a scintillation counter (Packard Topcount). The radio activity in the presence of an excessive amount of non-labeled PrRP (final concentration: 100 nM) was regarded as non-specific binding.

The binding inhibition rate was calculated based on calculating formula:

100−(radio activity when a compound is added−radio activity of non-specific binding)÷(radio activity when a solvent is added−radio activity of non-specific binding)×100.

An IC$_{50}$ value was calculated based on the concentration dependent reaction using a non-linear analysis program and a Ki value was calculated using Cheng-Prussoff formula.

The results are shown in Table 146.

TABLE 146

| Results of pharmacological Test 1 | |
|---|---|
| Test Compounds | Ki value (nM) |
| Compound of Example 1 | 5 |
| Compound of Example 2 | 29 |
| Compound of Example 3 | 42 |
| Compound of Example 5 | 8 |
| Compound of Example 6 | 17 |
| Compound of Example 8 | 25 |
| Compound of Example 9 | 28 |
| Compound of Example 10 | 17 |
| Compound of Example 11 | 15 |
| Compound of Example 63 | 16 |
| Compound of Example 86 | 25 |
| Compound of Example 92 | 11 |
| Compound of Example 95 | 5 |
| Compound of Example 104 | 20 |
| Compound of Example 121 | 17 |
| Compound of Example 163 | 10 |
| Compound of Example 166 | 6 |
| Compound of Example 2386 | 2 |
| Compound of Example 2389 | 8 |

TABLE 146-continued

| Results of pharmacological Test 1 | |
|---|---|
| Test Compounds | Ki value (nM) |
| Compound of Example 2390 | 8 |
| Compound of Example 2391 | 134 |
| Compound of Example 2392 | 12 |
| Compound of Example 2396 | 20 |
| Compound of Example 2402 | 6 |
| Compound of Example 2403 | 12 |
| Compound of Example 2404 | 10 |
| Compound of Example 2405 | 15 |
| Compound of Example 2406 | 2 |
| Compound of Example 2407 | 8 |
| Compound of Example 2409 | 16 |
| Compound of Example 2410 | 10 |
| Compound of Example 2411 | 20 |
| Compound of Example 2412 | 8 |
| Compound of Example 2414 | 18 |
| Compound of Example 2415 | 9 |
| Compound of Example 2416 | 33 |
| Compound of Example 2417 | 17 |
| Compound of Example 2418 | 8 |
| Compound of Example 2419 | 7 |
| Compound of Example 2421 | 44 |
| Compound of Example 2430 | 15 |
| Compound of Example 2431 | 207 |
| Compound of Example 2432 | 36 |
| Compound of Example 2433 | 5 |
| Compound of Example 2434 | 9 |
| Compound of Example 2435 | 2 |
| Compound of Example 2438 | 26 |
| Compound of Example 2441 | 37 |
| Compound of Example 2442 | 140 |
| Compound of Example 2443 | 41 |
| Compound of Example 2444 | 42 |
| Compound of Example 2446 | 28 |
| Compound of Example 2447 | 41 |
| Compound of Example 2448 | 23 |
| Compound of Example 2449 | 24 |
| Compound of Example 2450 | 121 |
| Compound of Example 2451 | 9 |
| Compound of Example 2452 | 4 |
| Compound of Example 2454 | 48 |
| Compound of Example 2456 | 6 |
| Compound of Example 2457 | 8 |
| Compound of Example 2458 | 245 |
| Compound of Example 2459 | 10 |
| Compound of Example 2460 | 14 |
| Compound of Example 2461 | 16 |
| Compound of Example 2462 | 98 |
| Compound of Example 2463 | 3 |
| Compound of Example 2464 | 20 |
| Compound of Example 2465 | 10 |
| Compound of Example 2468 | 6 |
| Compound of Example 2469 | 56 |
| Compound of Example 2470 | 108 |
| Compound of Example 2472 | 61 |
| Compound of Example 2474 | 15 |
| Compound of Example 2475 | 34 |
| Compound of Example 2476 | 9 |
| Compound of Example 2477 | 39 |
| Compound of Example 2478 | 9 |
| Compound of Example 2479 | 42 |
| Compound of Example 2481 | 31 |
| Compound of Example 2482 | 8 |
| Compound of Example 2483 | 13 |
| Compound of Example 2484 | 6 |
| Compound of Example 2487 | 24 |
| Compound of Example 2489 | 26 |
| Compound of Example 2490 | 237 |
| Compound of Example 2494 | 201 |
| Compound of Example 2495 | 3 |

Pharmacological Test 2
Antagonistic Activity on GPR10 Using Human GPR10-Expressing HEK293 Cells.

Antagonistic activity of test compounds on PrRP-induced intracellular calcium mobilization was evaluated using GPR10-expressing HEK293 cells.

HEK293 cells expressing human GPR10 were maintained in Dulbecco's Modified Eagles' medium supplemented with 10% fetal bovine serum, 1% penicillin-streptomycin and 20 mM HEPES at 37° C. in a 5% $CO_2$ incubator. GPR10-expressing HEK293 cells were placed in poly-D-lysine coated 96-well culture plates and cultured for 18-24 hr before the test at a density of $3 \times 10^4$ cells/well. The cells were incubated with 2.5 nM Fluo-8 for 1 hr at room temperature in Recording Buffer containing 1% bovine serum albumin, 0.01% pluronic F-127 and 20 mM HEPES, Hanks Balanced Buffered Saline, pH 7.4. The cells were incubated with test compounds for 15 min at room temperature, and then PrRP (the final concentration, 1 nM) was added into the medium. The changes in intracellular calcium-dependent fluorescence were monitored using a fluorescence imaging plate reader (FDSS3000, Hamamatsu Photonics K.K.). Fluo-8 fluorescence was measured with excitation at 490 nm and emission at 520 nm. The calcium-dependent fluorescence intensity was calculated by subtracting basal intensity (average intensity for 30 sec before agonist stimulation) from peak intensity for 60 sec after PrRP-stimulation, and then $IC_{50}$ values were determined by nonlinear curve-fitting program, GraphPad Prism 5.

The test compounds were proved from the values of $IC_{50}$ that they have the antagonist activity to GPR10 receptor.

The results are shown in Table 147.

TABLE 147

Results of pharmacological Test 2

| Test Compounds | $IC_{50}$(nM) |
|---|---|
| Compound of Example 1 | 42 |
| Compound of Example 2 | 378 |
| Compound of Example 3 | 1722 |
| Compound of Example 5 | 46 |
| Compound of Example 6 | 187 |
| Compound of Example 8 | 253 |
| Compound of Example 9 | 204 |
| Compound of Example 10 | 140 |
| Compound of Example 11 | 34 |
| Compound of Example 63 | 686 |
| Compound of Example 86 | 3710 |
| Compound of Example 92 | 156 |
| Compound of Example 95 | 227 |
| Compound of Example 104 | 158 |
| Compound of Example 121 | 1684 |
| Compound of Example 163 | 648 |
| Compound of Example 166 | 298 |
| Compound of Example 2386 | 140 |
| Compound of Example 2389 | 678 |
| Compound of Example 2390 | 1140 |
| Compound of Example 2391 | 3896 |
| Compound of Example 2392 | 5793 |
| Compound of Example 2396 | 2225 |
| Compound of Example 2402 | 99 |
| Compound of Example 2403 | 824 |
| Compound of Example 2404 | 1128 |
| Compound of Example 2405 | 8793 |
| Compound of Example 2406 | 78 |
| Compound of Example 2407 | 207 |
| Compound of Example 2409 | 2440 |
| Compound of Example 2410 | 665 |
| Compound of Example 2411 | 776 |
| Compound of Example 2412 | 259 |
| Compound of Example 2417 | 780 |
| Compound of Example 2418 | 286 |
| Compound of Example 2419 | 228 |

TABLE 147-continued

Results of pharmacological Test 2

| Test Compounds | $IC_{50}$(nM) |
|---|---|
| Compound of Example 2421 | 1570 |
| Compound of Example 2430 | 1183 |
| Compound of Example 2431 | 3600 |
| Compound of Example 2432 | 238 |
| Compound of Example 2433 | 62 |
| Compound of Example 2435 | 68 |
| Compound of Example 2441 | 4494 |
| Compound of Example 2446 | 2794 |
| Compound of Example 2449 | 3350 |
| Compound of Example 2451 | 1285 |
| Compound of Example 2452 | 1031 |
| Compound of Example 2463 | 187 |
| Compound of Example 2484 | 216 |

Pharmacological Test 3
Inhibition Activity of Restraint Stress-Induced Rat Defecation.

Male Wistar rats (8-10 week old, Japan SLC Co., Ltd.) were used for the test. Rats were housed n several groups, five in each group, under a 12 h light-dark cycle (lights on from 07:00-19:00), with free access to food and water in the house cages. All experiments were carried out in a soundproof room. The rats were transported to a soundproof room for adaptation at least 1 hour before the experiment. Restraint stress-induced defecation test was conducted using a modified method described by K. Miyata et al (Keiji Miyata, Takeshi Kamato, Akito Nishida, Hiroyuki Ito, Hidenobu Yuki, Mayumi Yamano, et al. Role of the serotonin3 receptor in stress-induced defecation. J of Pharmacology and Experimental Therapeutics. 1992; 261 (1); 297-303.). The rats were stressed by placing them in individual compartments of stainless resistant cage (Natsume Seisakusho Co., Ltd.; KN-468, W265×L95×H200 mm) for 1 hr. Test compounds were freshly prepared by suspending in 5% arabic gum/saline using an agate morter, and orally administered (5 mL/kg body weight) 1 or 2 hr prior to resistant stimulus. Fecal pellet induced by restraint stress was collected and counted. The inhibition rate of test compounds (%) was calculated as 1−(stools in test group−average number of stools in vehicle group)×100.

The test compounds were confirmed that they had the inhibition activity for the restraint stress-induced rat defecation.

Pharmacological Test 4
Inhibition Activity of Tail-Pinch Stress-Induced Feeding Behavior in Rat Male Wistar rats (7-9 week old, Japan SLC Co., Ltd.) were used for the test. Rats were housed in several groups, five in each groups, under a 12 h light-dark cycle (lights on from 07:00-19:00), with free access to food and water in the home cages. All experiments were conducted in a soundproof room. The rats were transported to a soundproof room for adaptation at least 1 hour before the experiment. Tail-pinch-induced feeding behavior test was conducted using a partly modified methods described by D. A. Czech et al (D. A. Czech, A. E. Klosterman and K. T. Le Sueur, NG-nitro-L-arginine methyl ester reduces stress-related feeding in the rat tail-pinch model. Pharmacology Biochemistry and Behavior, 60 (1), pp 91-96, 1998). Pre-weighed pelleted foods (Oriental Yeast Co., Ltd., CRF-1) were generously scattered on the floor, and the rats were then gently placed into the center of the cage individually. Tail of the rat was hold with urethane pad, and the tail-pinch stimulus was then applied for 5-10 min with the constant pressure at 3 cm from the tip of the tail by the pressure stimulus control system (Yamashita Technology Science Co., Ltd.).

At the end of the test, the rat was removed from the cage and then all remaining food was weighed. Amount of food intake was calculated by subtracting the food weight from pre-weighed food in each cage.

Test compounds were freshly prepared by suspending in 5% arabic gum/water, and orally administered (5 mL/kg body weight) 1 or 2 hr prior to tail-pinch stimulus.

The test compounds were confirmed that they have the inhibition activity for the tail-pinch stress-induced feeding behavior in rat.

The invention claimed is:

1. A heterocyclic compound represented by general formula (1)

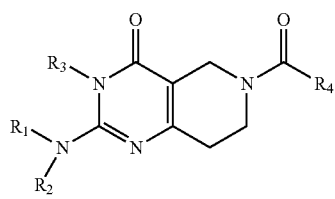

wherein, $R_1$ and $R_2$ each independently represent hydrogen; a phenyl lower alkyl group that may have a substituent(s) selected from the group consisting of a lower alkyl group, a lower alkoxy group, a halogen atom, a halogen-substituted lower alkyl group, a halogen-substituted lower alkoxy group, a cyclo C3-C8 alkyl group and a cyano group, on a benzene ring and/or a lower alkyl group; a cyclo C3-C8 alkyl lower alkyl group; a cyclo C3-C8 alkyl group that may have a halophenyl group(s); or $R_1$ and $R_2$ may form a pyrrolidine ring together with nitrogen adjacent to $R_1$ and $R_2$, and the pyrrolidine ring may have a substituent(s) selected from the group consisting of a halophenyl group and a phenyl group having a halogen-substituted lower alkyl group(s);

$R_3$ represents a lower alkynyl group; an amino group that may have a lower alkyl group(s); or a lower alkoxy group;

$R_4$ represents any one of groups represented by the following (1) to (91):
(1) a phenyl group
(2) a naphthyl group
(3) a dihydroindenyl group
(4) a phenyl lower alkyl group
(5) a pyridyl group
(6) a pyridazinyl group
(7) a triazolyl group
(8) a pyrimidinyl group
(9) an imidazolyl group
(10) a dihydropyridyl group
(11) a quinolyl group
(12) an isoquinolyl group
(13) a tetrahydroquinolyl group
(14) a dihydroquinolyl group
(15) an imidazopyridyl group
(16) a pyrazolopyridyl group
(17) an indolinyl group
(18) a naphthyridinyl group
(19) a benzoimidazolyl group
(20) an indolizinyl group
(21) a thienyl group
(22) a benzothienyl group
(23) a benzodioxolyl group
(24) a benzofuryl group
(25) a thienopyridyl group
(26) a thienopyrrolyl group
(27) a dihydrobenzothiazinyl group
(28) an isoxazolyl group
(29) a tetrahydrobenzoxazepinyl group
(30) an indolyl group
(31) a benzothiazolyl group
(32) a dihydrothienodioxinyl group
(33) a pyrrolidinyl group
(34) a dihydrobenzoxazinyl group
(35) a tetrahydroquinazolinyl group
(36) a tetrahydroquinoxalinyl group
(37) a dihydrobenzodioxinyl group
(38) a chromanyl group
(39) a dihydropyridooxazinyl group
(40) a tetrahydronaphthyl group
(41) a dihydrobenzofuryl group
(42) a dihydrobenzoxazolyl group
(43) a tetrahydrobenzothienyl group
(44) a tetrahydrocyclopentapyrazolyl group
(45) a benzotriazolyl group
(46) a dihydrobenzoimidazolyl group
(47) a dihydrobenzothiazolyl group
(48) an isoindolinyl group
(49) a tetrahydrobenzodiazepinyl group
(50) a dihydrobenzodioxepinyl group
(51) a quinoxalinyl group
(52) an indazolyl group
(53) a cinnolinyl group
(54) a dihydrophthalazinyl group
(55) a dihydronaphthyridinyl group
(56) a hexahydroquinolinyl group
(57) a furopyrrolyl group
(58) a thienopyrazinyl group
(59) an imidazothiazolyl group
(60) a xanthenyl group
(61) a piperidinyl group
(62) a pyrrolyl group
(63) a pyrazolyl group
(64) a thiazolyl group
(65) a furyl group
(66) a pyrazinyl group
(67) a dihydropyrazolyl group
(68) a thiazolidinyl group
(69) a tetrahydrofuranyl group
(70) a tetrahydropyranyl group
(71) a thiadiazolyl group
(72) a dihydropyridazinyl group
(73) a thienyl lower alkyl group
(74) a cyclo C3-C8 alkyl group
(75) a lower alkyl group
(76) a benzodioxolyloxy group
(77) a phenylthio lower alkyl group
(78) a phenylcyclo C3-C8 alkyl group
(79) a phenoxy lower alkyl group
(80) a phenyl lower alkenyl group
(81) a cyclo C3-C8 alkyl lower alkenyl group
(82) a pyridyl lower alkyl group
(83) a benzofuryl lower alkenyl group
(84) a dihydrobenzofuryl lower alkenyl group
(85) a dihydrobenzodioxinyl lower alkenyl group
(86) a dihydrobenzodioxinyloxy lower alkyl group
(87) an oxazolyl group
(88) a dihydroindenyloxy lower alkyl group
(89) a dihydropyrimidinyl group

(90) a pyridyloxy lower alkyl group
(91) a lower alkoxy lower alkyl group;
wherein on the lower alkyl group, cycloalkyl ring, aromatic ring or heterocyclic ring, one or more substituent(s) selected from the following (1-1) to (1-46) may be present:
(1-1) a halogen atom
(1-2) a lower alkyl group
(1-3) a lower alkanoyl group
(1-4) a halogen-substituted lower alkyl group
(1-5) a halogen-substituted lower alkoxy group
(1-6) a cyano group
(1-7) a lower alkoxy group
(1-8) a lower alkylthio group
(1-9) an imidazolyl group that may have a lower alkyl group(s)
(1-10) an oxazolyl group
(1-11) an oxadiazolyl group that may have a lower alkyl group(s)
(1-12) a triazolyl group
(1-13) a benzoyl group
(1-14) a pyridyl group
(1-15) an oxo group
(1-16) a phenyl group that may have a substituent(s) selected from the group consisting of a lower alkyl group, a halogen-substituted lower alkoxy group, a halogen-substituted lower alkyl group and a halogen atom
(1-17) a thienyl group
(1-18) a furyl group
(1-19) a thiazolyl group
(1-20) a triazolyl lower alkyl group
(1-21) a cyclo C3-C8 alkyloxy group
(1-22) a phenyl lower alkyl group
(1-23) a phenoxy group
(1-24) a cyclo C3-C8 alkyl group
(1-25) a pyrazolyl group
(1-26) a pyrrolyl group
(1-27) a lower alkenyl group
(1-28) a pyrrolidinyl group that may have an oxo group(s)
(1-29) a dihydropyrazolyl group that may have a substituent(s) selected from the group consisting of an oxo group and a lower alkyl group
(1-30) a hydroxy group
(1-31) a tetrazolyl group
(1-32) a morpholinyl group
(1-33) a pyrimidinyl group
(1-34) a homo-piperazinyl group that may have a lower alkyl group(s)
(1-35) a lower alkanoylamino group
(1-36) a cyclo C3-C8 alkylcarbonylamino group
(1-37) a phenoxy lower alkyl group
(1-38) a thiomorpholino group
(1-39) a piperidinyl group
(1-40) a lower alkoxy lower alkyl group
(1-41) an amino group that may have a substituent(s) selected from the group consisting of a lower alkyl group, a lower alkanoyl group and a cyclo C3-C8 alkyl group
(1-42) a morpholinyl lower alkyl group
(1-43) a piperidinyl lower alkyl group
(1-44) a lower alkylsulfonyl group
(1-45) an adamantyl lower alkyl group
(1-46) a carbamoyl group that may have a lower alkyl group(s)
or a salt thereof.

2. The heterocyclic compound according to claim 1 represented by general formula (1), wherein, $R_1$ and $R_2$ each independently represent hydrogen; a phenyl lower alkyl group that may have 1 to 3 substituent(s) selected from the group consisting of a lower alkyl group, a lower alkoxy group, a halogen atom, a halogen-substituted lower alkyl group, a halogen-substituted lower alkoxy group, a cyclo C3-C8 alkyl group and a cyano group, on a benzene ring and/or a lower alkyl group; a cyclo C3-C8 alkyl lower alkyl group; a cyclo C3-C8 alkyl group that may have a single halophenyl group; or $R_1$ and $R_2$ may form a pyrrolidine ring together with nitrogen adjacent to $R_1$ and $R_2$, and the pyrrolidine ring may have a single substituent selected from the group consisting of a halophenyl group and a phenyl group having a single halogen-substituted lower alkyl group;

$R_3$ represents a lower alkynyl group; an amino group that may have 1 to 2 lower alkyl group(s); or a lower alkoxy group;

$R_4$ represents any one of groups represented by the following (1) to (91):
(1) a phenyl group
(2) a naphthyl group
(3) a dihydroindenyl group
(4) a phenyl lower alkyl group
(5) a pyridyl group
(6) a pyridazinyl group
(7) a triazolyl group
(8) a pyrimidinyl group
(9) an imidazolyl group
(10) a dihydropyridyl group
(11) a quinolyl group
(12) an isoquinolyl group
(13) a tetrahydroquinolyl group
(14) a dihydroquinolyl group
(15) an imidazopyridyl group
(16) a pyrazolopyridyl group
(17) an indolinyl group
(18) a naphthyridinyl group
(19) a benzoimidazolyl group
(20) an indolizinyl group
(21) a thienyl group
(22) a benzothienyl group
(23) a benzodioxolyl group
(24) a benzofuryl group
(25) a thienopyridyl group
(26) a thienopyrrolyl group
(27) a dihydrobenzothiazinyl group
(28) an isoxazolyl group
(29) a tetrahydrobenzoxazepinyl group
(30) an indolyl group
(31) a benzothiazolyl group
(32) a dihydrothienodioxinyl group
(33) a pyrrolidinyl group
(34) a dihydrobenzoxazinyl group
(35) a tetrahydroquinazolinyl group
(36) a tetrahydroquinoxalinyl group
(37) a dihydrobenzodioxinyl group
(38) a chromanyl group
(39) a dihydropyridooxazinyl group
(40) a tetrahydronaphthyl group
(41) a dihydrobenzofuryl group
(42) a dihydrobenzoxazolyl group
(43) a tetrahydrobenzothienyl group
(44) a tetrahydrocyclopentapyrazolyl group
(45) a benzotriazolyl group
(46) a dihydrobenzoimidazolyl group
(47) a dihydrobenzothiazolyl group
(48) an isoindolinyl group
(49) a tetrahydrobenzodiazepinyl group

(50) a dihydrobenzodioxepinyl group
(51) a quinoxalinyl group
(52) an indazolyl group
(53) a cinnolinyl group
(54) a dihydrophthalazinyl group
(55) a dihydronaphthyridinyl group
(56) a hexahydroquinolinyl group
(57) a furopyrrolyl group
(58) a thienopyrazinyl group
(59) an imidazothiazolyl group
(60) a xanthenyl group
(61) a piperidinyl group
(62) a pyrrolyl group
(63) a pyrazolyl group
(64) a thiazolyl group
(65) a furyl group
(66) a pyrazinyl group
(67) a dihydropyrazolyl group
(68) a thiazolidinyl group
(69) a tetrahydrofuranyl group
(70) a tetrahydropyranyl group
(71) a thiadiazolyl group
(72) a dihydropyridazinyl group
(73) a thienyl lower alkyl group
(74) a cyclo C3-C8 alkyl group
(75) a lower alkyl group
(76) a benzodioxolyloxy group
(77) a phenylthio lower alkyl group
(78) a phenylcyclo C3-C8 alkyl group
(79) a phenoxy lower alkyl group
(80) a phenyl lower alkenyl group
(81) a cyclo C3-C8 alkyl lower alkenyl group
(82) a pyridyl lower alkyl group
(83) a benzofuryl lower alkenyl group
(84) a dihydrobenzofuryl lower alkenyl group
(85) a dihydrobenzodioxinyl lower alkenyl group
(86) a dihydrobenzodioxinyloxy lower alkyl group
(87) an oxazolyl group
(88) a dihydroindenyloxy lower alkyl group
(89) a dihydropyrimidinyl group
(90) a pyridyloxy lower alkyl group
(91) a lower alkoxy lower alkyl group;
wherein, on the lower alkyl group, cycloalkyl ring, aromatic ring or heterocyclic ring, 1 to 4 substituent(s) selected from the following (1-1) to (1-46) may be present:
(1-1) a halogen atom
(1-2) a lower alkyl group
(1-3) a lower alkanoyl group
(1-4) a halogen-substituted lower alkyl group
(1-5) a halogen-substituted lower alkoxy group
(1-6) a cyano group
(1-7) a lower alkoxy group
(1-8) a lower alkylthio group
(1-9) an imidazolyl group that may have a single lower alkyl group
(1-10) an oxazolyl group
(1-11) an oxadiazolyl group that may have a single lower alkyl group
(1-12) a triazolyl group
(1-13) a benzoyl group
(1-14) a pyridyl group
(1-15) an oxo group
(1-16) a phenyl group that may have a single substituent selected from the group consisting of a lower alkyl group, a halogen-substituted lower alkoxy group, a halogen-substituted lower alkyl group and a halogen atom
(1-17) a thienyl group
(1-18) a furyl group
(1-19) a thiazolyl group
(1-20) a triazolyl lower alkyl group
(1-21) a cyclo C3-C8 alkyloxy group
(1-22) a phenyl lower alkyl group
(1-23) a phenoxy group
(1-24) a cyclo C3-C8 alkyl group
(1-25) a pyrazolyl group that may have a single lower alkyl group
(1-26) a pyrrolyl group
(1-27) a lower alkenyl group
(1-28) a pyrrolidinyl group that may have a single oxo group
(1-29) a dihydropyrazolyl group that may have 1 to 2 substituent(s) selected from the group consisting of an oxo group and a lower alkyl group
(1-30) a hydroxy group
(1-31) a tetrazolyl group
(1-32) a morpholinyl group
(1-33) a pyrimidinyl group
(1-34) a homo-piperazinyl group that may have a single lower alkyl group
(1-35) a lower alkanoylamino group
(1-36) a cyclo C3-C8 alkylcarbonylamino group
(1-37) a phenoxy lower alkyl group
(1-38) a thiomorpholino group
(1-39) a piperidinyl group
(1-40) a lower alkoxy lower alkyl group
(1-41) an amino group that may have 1 to 2 substituent(s) selected from the group consisting of a lower alkyl group, a lower alkanoyl group and a cyclo C3-C8 alkyl group
(1-42) a morpholinyl lower alkyl group
(1-43) a piperidinyl lower alkyl group
(1-44) a lower alkylsulfonyl group
(1-45) an adamantyl lower alkyl group
(1-46) a carbamoyl group that may have 1 to 2 lower alkyl group(s)
or a salt thereof.

3. The heterocyclic compound according to claim 2 represented by general formula (1), wherein, $R_1$ and $R_2$ each independently represent hydrogen; a phenyl lower alkyl group that may have 1 to 2 substituent(s) selected from the group consisting of a lower alkoxy group, a halogen atom and a halogen-substituted lower alkyl group on a benzene ring and/or a lower alkyl group; a cyclo C3-C8 alkyl lower alkyl group; a cyclo C3-C8 alkyl group that may have a single monohalophenyl group; or $R_1$ and $R_2$ may form a pyrrolidine ring together with nitrogen adjacent to $R_1$ and $R_2$, and the pyrrolidine ring may have a single substituent selected from the group consisting of a halophenyl group and a phenyl group having a single halogen-substituted lower alkyl group;

$R_3$ represents a lower alkynyl group; an amino group that may have 1 to 2 lower alkyl group(s); a lower alkoxy group;

$R_4$ represents any one of groups represented by the following (1) to (90):
(1) a phenyl group
(4) a phenyl lower alkyl group
(5) a pyridyl group
(11) a quinolyl group
(12) a isoquinolyl group
(13) a tetrahydroquinolyl group
(16) a pyrazolopyridyl group
(19) a benzoimidazolyl group
(21) a thienyl group

(22) a benzothienyl group
(23) a benzodioxolyl group
(24) a benzofuryl group
(25) a thienopyridyl group
(30) an indolyl group
(37) a dihydrobenzodioxinyl group
(40) a tetrahydronaphthyl group
(57) a furopyrrolyl group
(63) a pyrazolyl group
(65) a furyl group
(77) a phenylthio lower alkyl group
(79) a phenoxy lower alkyl group
(80) a phenyl lower alkenyl group
(88) a dihydroindenyloxy lower alkyl group
(90) a pyridyloxy lower alkyl group;
wherein, on the lower alkyl group, cycloalkyl ring, aromatic ring or heterocyclic ring, 1 to 3 substituent(s) selected from the following (1-1) to (1-46) may be present:
(1-1) a halogen atom
(1-2) a lower alkyl group
(1-5) a halogen-substituted lower alkoxy group
(1-6) a cyano group
(1-7) a lower alkoxy group
(1-9) an imidazolyl group that may have a single lower alkyl group
(1-10) an oxazolyl group
(1-15) an oxo group
(1-17) a thienyl group
(1-27) a lower alkenyl group
(1-46) a carbamoyl group that may have 1 to 2 lower alkyl group(s)
or a salt thereof.

4. The heterocyclic compound according to claim 3 represented by general formula (1), wherein, $R_4$ represents any one of groups (1) to (90) below:
(1) a phenyl group that may have 1 to 3 substituent(s) selected from the group consisting of a halogen atom, a lower alkyl group, a halogen-substituted lower alkoxy group, a cyano group, a lower alkoxy group, a lower alkenyl group, an oxazolyl group, a carbamoyl group that may have 1 to 2 lower alkyl group(s) and an imidazolyl group
(4) a phenyl lower alkyl group that may have a single a halogen atom
(5) a pyridyl group that may have 1 to 2 substituent(s) selected from the group consisting of a cyano group and a lower alkoxy group
(11) a quinolyl group that may have a single halogen atom
(13) a tetrahydroquinolyl group that may have 1 to 2 substituent(s) selected from the group consisting of a lower alkyl group and an oxo group
(16) a pyrazolopyridyl group
(19) a benzimidazolyl group that may have 1 to 2 substituent(s) selected from the group consisting of a halogen atom and a lower alkyl group
(21) a thienyl group that may have a single substituent selected from the group consisting of a lower alkyl group, a lower alkoxy group and a halogen atom
(22) a benzothienyl group
(23) a benzodioxolyl group
(24) a benzofuryl group that may have a single substituent selected from the group consisting of a halogen atom and a lower alkoxy group
(25) a thienopyridyl group
(30) an indolyl group that may have 1 to 2 substituent(s) selected from the group consisting of a halogen atom and a lower alkyl group
(37) a dihydrobenzodioxinyl group
(40) a tetrahydronaphthyl group
(57) a furopyrrolyl group that may have a single lower alkyl group
(63) a pyrazolyl group that may have 1 to 2 substituent(s) selected from the group consisting of a thienyl group and a lower alkyl group
(65) a furyl group that may have a single halogen atom
(77) a phenylthio lower alkyl group that may have a single halogen atom
(79) a phenoxy-lower alkyl group that may have 1 to 2 substituent(s) selected from the group consisting of a halogen atom and a cyano group
(80) a phenyl lower alkenyl group that may have a single halogen atom
(88) a dihydroindenyloxy lower alkyl group
(90) a pyridyloxy lower alkyl group
or a salt thereof.

5. A method of manufacturing a pharmaceutical preparation wherein the heterocyclic compound according to any one of claims 1 to 4 represented by general formula (1) or a salt thereof is mixed with a diluent or an excipient to form a pharmaceutical preparation.

6. A pharmaceutical composition comprising the heterocyclic compound according to any one of claims 1 to 4 or a salt thereof as an active ingredient and a pharmaceutically acceptable carrier.

7. The pharmaceutical composition according to claim 6 for treating eating disorder.

8. The heterocyclic compound according to any one of claims 1 to 4 or a salt thereof for treating eating disorder.

9. A method of inhibiting GPR10 in a subject, wherein an effective amount of the heterocyclic compound according to any one of claims 1 to 4 represented by general formula (1) or a salt thereof is administered to the subject.

10. A method of treating eating disorder, comprising administering to a human or animal the heterocyclic compound according to any one of claims 1 to 4 represented by general formula (1) or a salt thereof.

11. A method of producing a pharmaceutical composition, comprising blending the heterocyclic compound according to any one of claims 1 to 4 represented by general formula (1) or a salt thereof and a pharmaceutically acceptable carrier.

12. A method of producing a heterocyclic compound represented by general formula (1)

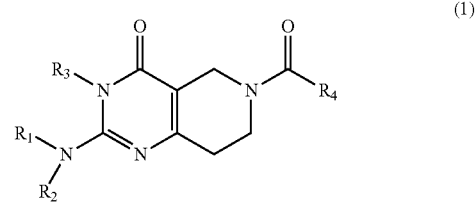

(1)

wherein $R_1$, $R_2$, $R_3$ and $R_4$ are the same as those in formula (1) of claim 1 or a salt thereof, comprising reacting a compound (2) or a reactive derivative thereof represented by general formula (2)

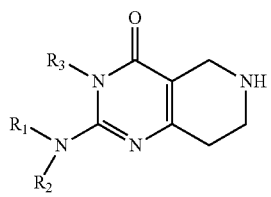

(2)

wherein $R_1$, $R_2$ and $R_3$ are the same as those in formula (1) of claim 1, or a salt thereof with a compound (3) or a reactive derivative thereof represented by general formula (3)

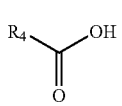

(3)

wherein $R_4$ is the same as that in formula (1) of claim 1, or a salt thereof.

* * * * *